United States Patent
Lu et al.

(10) Patent No.: US 10,265,155 B2
(45) Date of Patent: Apr. 23, 2019

(54) BIOMIMMETIC NANOFIBER SCAFFOLD FOR SOFT TISSUE AND SOFT TISSUE-TO-BONE REPAIR, AUGMENTATION AND REPLACEMENT

(71) Applicants: Helen H. Lu, New York, NY (US); Jeffrey Spalazzi, Staten Island, NY (US); Kristen L. Moffat, Oakmont, PA (US); William N. Levine, New York, NY (US)

(72) Inventors: Helen H. Lu, New York, NY (US); Jeffrey Spalazzi, Staten Island, NY (US); Kristen L. Moffat, Oakmont, PA (US); William N. Levine, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 415 days.

(21) Appl. No.: 14/503,053

(22) Filed: Sep. 30, 2014

(65) Prior Publication Data
US 2015/0100121 A1  Apr. 9, 2015

Related U.S. Application Data

(60) Continuation of application No. 12/806,912, filed on Aug. 24, 2010, now Pat. No. 8,864,843, which is a
(Continued)

(51) Int. Cl.
*A61F 2/08* (2006.01)
*A61K 38/18* (2006.01)
(Continued)

(52) U.S. Cl.
CPC .............. *A61F 2/08* (2013.01); *A61F 2/0811* (2013.01); *A61K 35/32* (2013.01); *A61K 38/18* (2013.01);
(Continued)

(58) Field of Classification Search
CPC ... A61F 2/08; A61F 2/0811; A61F 2002/0858
(Continued)

(56) References Cited

U.S. PATENT DOCUMENTS 3,797,047 A * 3/1974 Pillet .......................... A61F 2/08
128/DIG. 21
3,805,300 A * 4/1974 Tascon-Alonso ......... A61F 2/08
128/DIG. 14
(Continued)

FOREIGN PATENT DOCUMENTS

JP   6-154305   6/1994
JP   6-165817   6/1994
(Continued)

OTHER PUBLICATIONS

U.S. Appl. No. 12/455,765, filed Jun. 6, 2009, Lu et al.
(Continued)

*Primary Examiner* — Alvin Stewart
(74) *Attorney, Agent, or Firm* — John P. White; Gary J. Gershik; Cooper & Dunham LLP

(57) ABSTRACT

An implantable device is provided for soft-tissue or soft tissue-to-bone repair, fixation, augmentation, or replacement that includes a biomimetic and biodegradable nanofiber scaffold. Also provided is a fully synthetic implantable multiphased scaffold which includes, in a single continuous construct, a plurality of phases to mimic the natural anatomy of a tendon or ligament and their insertion sites. Also
(Continued)

Schematic of Scaffold-Mesh Apparatus
Coupled with a Soft Tissue Graft provided are scaffold apparatuses for musculoskeletal tissue engineering.

11 Claims, 102 Drawing Sheets

Specification includes a Sequence Listing.

Related U.S. Application Data division of application No. 12/583,072, filed on Aug. 12, 2009, now Pat. No. 8,753,391, which is a continuation-in-part of application No. PCT/US2008/001889, filed on Feb. 12, 2008, and a continuation-in-part of application No. PCT/US2008/007323, filed on Jun. 11, 2008, and a continuation-in-part of application No. PCT/US2008/007357, filed on Jun. 11, 2008.

(60) Provisional application No. 61/215,085, filed on May 1, 2009, provisional application No. 60/901,047, filed on Feb. 12, 2007, provisional application No. 60/905,649, filed on Mar. 7, 2007, provisional application No. 60/934,198, filed on Jun. 11, 2007, provisional application No. 60/934,182, filed on Jun. 11, 2007.

(51) Int. Cl.
  *B29C 67/04* (2017.01)
  *A61K 45/06* (2006.01)
  *A61K 35/32* (2015.01)
  *A61L 27/18* (2006.01)

(52) U.S. Cl.
  CPC .............. *A61K 45/06* (2013.01); *A61L 27/18* (2013.01); *B29C 67/04* (2013.01); *A61F 2002/0858* (2013.01); *A61F 2210/0004* (2013.01); *A61L 2430/34* (2013.01)

(58) Field of Classification Search
  USPC ............................................ 623/23.72–23.76
  See application file for complete search history.

(56) References Cited

U.S. PATENT DOCUMENTS

| | | | |
|---|---|---|---|
| 4,127,902 A * | 12/1978 | Homsy | A61L 27/14 128/DIG. 14 |
| 4,149,277 A * | 4/1979 | Bokros | A61F 2/08 623/13.2 |
| 4,255,820 A * | 3/1981 | Rothermel | A61F 2/08 623/13.11 |
| 4,400,833 A * | 8/1983 | Kurland | A61B 17/1146 623/1.32 |
| 4,455,690 A * | 6/1984 | Homsy | A61F 2/08 623/13.15 |
| 4,479,271 A | 10/1984 | Bolesky et al. | |
| 4,584,722 A * | 4/1986 | Levy | A61F 2/08 623/13.15 |
| 4,668,233 A * | 5/1987 | Seedhom | A61B 17/1714 623/13.11 |
| 4,731,084 A * | 3/1988 | Dunn | A61F 2/08 623/13.19 |
| 4,744,793 A * | 5/1988 | Parr | A61F 2/0811 623/13.14 |
| 4,917,700 A * | 4/1990 | Aikins | A61F 2/08 623/13.19 |
| 4,946,377 A * | 8/1990 | Kovach | A61F 2/08 623/13.18 |
| 5,002,583 A * | 3/1991 | Pitaru | A61L 27/34 623/11.11 |
| 5,004,474 A * | 4/1991 | Fronk | A61F 2/08 623/13.14 |
| 5,024,669 A | 6/1991 | Peterson et al. | |
| 5,049,155 A * | 9/1991 | Bruchman | A61F 2/08 623/13.2 |
| 5,078,745 A | 1/1992 | Rhenter et al. | |
| 5,084,350 A | 1/1992 | Chang et al. | |
| 5,108,436 A | 4/1992 | Chu et al. | |
| 5,133,755 A | 7/1992 | Brekke | |
| 5,147,400 A * | 9/1992 | Kaplan | A61F 2/06 623/1.38 |
| 5,171,274 A * | 12/1992 | Fluckiger | D04C 1/06 623/13.16 |
| 5,197,983 A * | 3/1993 | Berman | A61F 2/08 623/13.2 |
| 5,217,495 A * | 6/1993 | Kaplan | A61F 2/06 57/225 |
| 5,258,040 A * | 11/1993 | Bruchman | A61F 2/08 57/201 |
| 5,308,701 A | 5/1994 | Cohen et al. | |
| 5,366,508 A | 11/1994 | Brekke | |
| 5,455,041 A | 10/1995 | Genco et al. | |
| 5,456,715 A * | 10/1995 | Liotta | A61M 1/1046 600/16 |
| 5,514,181 A * | 5/1996 | Light | A61B 17/1146 606/229 |
| 5,549,676 A * | 8/1996 | Johnson | A61F 2/08 623/13.13 |
| 5,571,189 A * | 11/1996 | Kuslich | A61F 2/0063 623/17.12 |
| 5,593,441 A * | 1/1997 | Lichtenstein | A61F 2/0063 600/37 |
| 5,607,474 A | 3/1997 | Athanasiou et al. | |
| 5,626,861 A | 5/1997 | Laurencin et al. | |
| 5,656,492 A * | 8/1997 | Glowacki | A61F 2/022 424/425 |
| 5,683,459 A | 11/1997 | Brekke | |
| 5,716,413 A | 2/1998 | Walter et al. | |
| 5,755,792 A | 5/1998 | Brekke | |
| 5,766,618 A | 6/1998 | Laurencin et al. | |
| 5,800,543 A * | 9/1998 | McLeod | A61F 2/08 623/13.19 |
| 5,849,331 A | 12/1998 | Ducheyne et al. | |
| 5,855,610 A | 1/1999 | Vacanti et al. | |
| 5,866,155 A | 2/1999 | Laurencin et al. | |
| 5,885,829 A | 3/1999 | Mooney et al. | |
| 5,904,717 A | 5/1999 | Brekke et al. | |
| 5,922,025 A | 7/1999 | Hubbard | |
| 5,944,754 A | 8/1999 | Vacanti | |
| 5,981,827 A * | 11/1999 | Devlin | C04B 41/85 623/23.51 |
| 5,990,378 A * | 11/1999 | Ellis | A61F 2/0063 606/151 |
| 6,005,161 A | 12/1999 | Brekke et al. | |
| 6,013,591 A | 1/2000 | Ying et al. | |
| 6,027,744 A * | 2/2000 | Vacanti | A61F 2/28 424/426 |
| 6,077,989 A * | 6/2000 | Kandel | A61L 27/12 623/13.17 |
| 6,110,590 A * | 8/2000 | Zarkoob | C07K 14/43586 428/221 |
| 6,143,293 A | 11/2000 | Weiss et al. | |
| 6,179,878 B1 | 1/2001 | Duerig et al. | |
| 6,187,329 B1 | 2/2001 | Agrawal et al. | |
| 6,187,742 B1 | 2/2001 | Wozney et al. | |
| 6,203,572 B1 * | 3/2001 | Johnson | A61F 2/08 606/108 |
| 6,214,047 B1 * | 4/2001 | Melvin | A61F 2/08 623/11.11 |
| 6,235,061 B1 | 5/2001 | Laurencin et al. | |
| 6,291,547 B1 | 9/2001 | Lyles et al. | |
| 6,306,424 B1 | 10/2001 | Vyakarnam et al. | |
| 6,328,765 B1 | 12/2001 | Hardwick et al. | |
| 6,333,029 B1 | 12/2001 | Vyakarnam et al. | |
| 6,365,149 B2 | 4/2002 | Vyakarnam et al. | |
| 6,378,527 B1 | 4/2002 | Hungerford et al. | |
| 6,409,764 B1 | 6/2002 | White et al. | |

(56) References Cited

U.S. PATENT DOCUMENTS

| | | |
|---|---|---|
| 6,432,437 B1 | 8/2002 | Hubbard |
| 6,454,811 B1 | 9/2002 | Sherwood et al. |
| 6,459,948 B1 | 10/2002 | Ateshian et al. |
| 6,534,084 B1 | 3/2003 | Vyakarnam et al. |
| 6,541,022 B1 | 4/2003 | Murphy et al. |
| 6,544,503 B1 | 4/2003 | Vanderhoff et al. |
| 6,558,612 B1 | 5/2003 | Hubbard |
| 6,579,533 B1 | 6/2003 | Tormala et al. |
| 6,592,622 B1 * | 7/2003 | Ferguson ............ A61F 2/0811 623/13.12 |
| 6,602,294 B1 | 8/2003 | Sittinger et al. |
| 6,626,950 B2 | 9/2003 | Brown et al. |
| 6,638,312 B2 * | 10/2003 | Plouhar ............... A61F 2/0063 623/23.72 |
| 6,730,252 B1 | 5/2004 | Teoh et al. |
| 6,733,510 B1 * | 5/2004 | Melvin .............. A61B 17/0401 606/148 |
| 6,737,053 B1 | 5/2004 | Goh et al. |
| 6,746,483 B1 * | 6/2004 | Bojarski ............ A61B 17/0401 623/13.14 |
| 6,773,458 B1 * | 8/2004 | Brauker ................. A61F 2/022 424/422 |
| 6,787,518 B1 | 9/2004 | Kato et al. |
| 6,811,776 B2 | 11/2004 | Kale et al. |
| 6,827,743 B2 * | 12/2004 | Eisermann ............ A61B 17/68 623/23.54 |
| 6,852,330 B2 | 2/2005 | Bowman et al. |
| 6,866,681 B2 * | 3/2005 | Laboureau ................. A61F 2/08 623/13.2 |
| 6,869,445 B1 * | 3/2005 | Johnson ................... A61F 2/28 623/16.11 |
| 6,946,003 B1 * | 9/2005 | Wolowacz ............... A61F 2/08 623/23.72 |
| 6,984,623 B2 | 1/2006 | Celeste et al. |
| 6,995,013 B2 | 2/2006 | Connelly et al. |
| 7,087,200 B2 | 8/2006 | Taboas et al. |
| 7,105,182 B2 | 9/2006 | Szymaitis |
| 7,112,417 B2 | 9/2006 | Vyakarnam et al. |
| 7,163,563 B2 * | 1/2007 | Schwartz ............ A61B 17/064 623/14.12 |
| 7,172,765 B2 | 2/2007 | Chu et al. |
| 7,217,294 B2 | 5/2007 | Kusanagi et al. |
| 7,252,685 B2 | 8/2007 | Bindseil et al. |
| 7,309,232 B2 | 12/2007 | Rutherford et al. |
| 7,319,035 B2 | 1/2008 | Vacanti et al. |
| 7,322,825 B2 | 1/2008 | Szymaitis |
| 7,326,426 B2 | 2/2008 | Nathan et al. |
| 7,351,250 B2 | 4/2008 | Zamierowski |
| 7,390,526 B2 | 6/2008 | Stupp et al. |
| 7,419,681 B2 | 9/2008 | Tormala et al. |
| 7,524,335 B2 | 4/2009 | Slivka et al. |
| 7,531,503 B2 | 5/2009 | Atala et al. |
| 7,674,289 B2 | 3/2010 | Xu |
| 7,704,740 B2 | 4/2010 | Schindler |
| 7,767,221 B2 * | 8/2010 | Lu ...................... A61L 27/3839 424/423 |
| 7,786,086 B2 | 8/2010 | Reches et al. |
| 7,803,574 B2 | 9/2010 | Desai et al. |
| 7,824,447 B2 | 11/2010 | Xu |
| 7,824,701 B2 | 11/2010 | Binette et al. |
| 7,842,737 B2 | 11/2010 | Wang et al. |
| 7,846,213 B2 * | 12/2010 | Lecomte ................... A61F 2/66 623/52 |
| 7,901,461 B2 | 3/2011 | Harmon et al. |
| RE42,526 E * | 7/2011 | Reiser ............... A61B 17/0811 623/13.14 |
| 7,998,221 B2 * | 8/2011 | Lecomte ................... A61F 2/66 623/52 |
| 8,025,699 B2 * | 9/2011 | Lecomte ................... A61F 2/66 623/52 |
| 8,052,753 B2 * | 11/2011 | Melvin .................. A61F 2/0811 623/13.11 |
| 8,070,810 B2 * | 12/2011 | Tarrant ............... A61B 17/1146 623/13.12 |
| 8,142,501 B2 | 3/2012 | Macossay-Torres |
| 8,168,431 B2 | 5/2012 | Brady et al. |
| 8,172,901 B2 * | 5/2012 | Altman .................... A61F 2/08 623/13.11 |
| 8,187,326 B2 | 5/2012 | Hammer et al. |
| 8,226,715 B2 * | 7/2012 | Hwang .................... A61F 2/08 623/13.14 |
| 8,333,803 B2 * | 12/2012 | Park ....................... A61L 27/48 623/13.14 |
| 8,486,143 B2 * | 7/2013 | Laurencin ................. A61F 2/08 623/13.14 |
| 8,486,156 B2 * | 7/2013 | Jonsson .................... A61F 2/66 623/53 |
| 8,679,190 B2 * | 3/2014 | Myung .............. A61F 2/30756 623/13.11 |
| 8,721,684 B2 * | 5/2014 | Denham ............ A61B 17/0401 606/228 |
| 8,753,391 B2 * | 6/2014 | Lu .............................. 623/13.11 |
| 8,802,122 B2 * | 8/2014 | Lu ...................... A61L 27/3839 424/423 |
| 8,864,843 B2 * | 10/2014 | Lu ......................... A61K 38/18 623/23.72 |
| 9,132,022 B2 * | 9/2015 | Lecomte ................... A61F 2/66 |
| 9,277,999 B2 * | 3/2016 | Badylak ................. A61F 2/3099 |
| 9,295,541 B2 * | 3/2016 | Wagner ................... A61F 2/064 |
| 9,339,369 B2 * | 5/2016 | McQuillan .......... A61L 27/3683 |
| 9,339,392 B2 * | 5/2016 | Bagga ................. A61F 2/4601 |
| 9,421,306 B2 * | 8/2016 | Park ....................... A61L 27/48 |
| 9,421,307 B2 | 8/2016 | Amoroso |
| 9,427,495 B2 * | 8/2016 | Lu ...................... A61L 27/3839 |
| 9,451,961 B2 * | 9/2016 | Kubiak .................... A61F 2/08 |
| 2001/0000195 A1 | 4/2001 | Smith et al. |
| 2002/0068974 A1 * | 6/2002 | Kuslich .................. A61B 17/68 623/17.11 |
| 2002/0095213 A1 | 7/2002 | Bakker et al. |
| 2002/0099448 A1 * | 7/2002 | Hiles ..................... A61F 2/0095 623/23.61 |
| 2002/0119177 A1 * | 8/2002 | Bowman ................ A61L 27/44 424/423 |
| 2002/0123750 A1 * | 9/2002 | Eisermann ............ A61B 17/68 606/285 |
| 2002/0127265 A1 | 9/2002 | Bowman et al. |
| 2002/0182241 A1 | 12/2002 | Borenstein et al. |
| 2002/0187104 A1 | 12/2002 | Li et al. |
| 2003/0004578 A1 | 1/2003 | Brown et al. |
| 2003/0012805 A1 * | 1/2003 | Chen ................... A61F 2/30756 424/423 |
| 2003/0023316 A1 * | 1/2003 | Brown .................. A61F 2/0063 623/23.72 |
| 2003/0026860 A1 | 2/2003 | Lasekan et al. |
| 2003/0036797 A1 * | 2/2003 | Malaviya ............ A61B 17/064 623/14.12 |
| 2003/0036801 A1 * | 2/2003 | Schwartz ............. A61F 2/0063 623/23.63 |
| 2003/0071380 A1 | 4/2003 | Wang et al. |
| 2003/0078617 A1 * | 4/2003 | Schwartz ............ A61B 17/064 606/230 |
| 2003/0078659 A1 * | 4/2003 | Yang ........................ A61F 2/08 623/13.17 |
| 2003/0114936 A1 | 6/2003 | Sherwood et al. |
| 2003/0137083 A1 * | 7/2003 | Ko ....................... D01D 5/0038 264/449 |
| 2003/0147935 A1 | 8/2003 | Binette et al. |
| 2003/0168756 A1 * | 9/2003 | Balkus, Jr. .............. B82Y 30/00 264/10 |
| 2003/0175257 A1 | 9/2003 | Song et al. |
| 2003/0198615 A1 | 10/2003 | Chaput et al. |
| 2003/0225458 A1 | 12/2003 | Hammer et al. |
| 2004/0010320 A1 | 1/2004 | Huckle et al. |
| 2004/0024456 A1 * | 2/2004 | Brown, Jr. .......... A61B 17/0401 623/13.15 |
| 2004/0033214 A1 | 2/2004 | Young et al. |
| 2004/0078090 A1 | 4/2004 | Binette et al. |
| 2004/0109845 A1 | 6/2004 | Terkeltaub |
| 2004/0122209 A1 | 6/2004 | Poole |

(56) References Cited

U.S. PATENT DOCUMENTS

| | | | |
|---|---|---|---|
| 2004/0137225 A1* | 7/2004 | Balkus, Jr. | B82Y 30/00 428/364 |
| 2004/0243235 A1* | 12/2004 | Goh | A61F 2/08 623/13.17 |
| 2004/0267362 A1* | 12/2004 | Hwang | A61F 2/08 623/13.15 |
| 2005/0008675 A1 | 1/2005 | Bhatia et al. | |
| 2005/0095695 A1 | 5/2005 | Shindler et al. | |
| 2005/0118236 A1 | 6/2005 | Qiu et al. | |
| 2005/0192622 A1* | 9/2005 | Bowlin | A61F 2/01 606/200 |
| 2005/0196425 A1 | 9/2005 | Zamora et al. | |
| 2005/0205498 A1 | 9/2005 | Sowemimo-Coker et al. | |
| 2005/0255583 A1 | 11/2005 | Depaola et al. | |
| 2006/0036331 A1 | 2/2006 | Lu et al. | |
| 2006/0067969 A1* | 3/2006 | Lu | A61L 27/3839 424/423 |
| 2006/0085063 A1* | 4/2006 | Shastri | A61F 2/02 623/1.41 |
| 2006/0136071 A1* | 6/2006 | Maspero | A61L 27/3847 623/23.76 |
| 2006/0165663 A1 | 7/2006 | Tanaka et al. | |
| 2006/0204738 A1 | 9/2006 | Dubrow et al. | |
| 2006/0273279 A1 | 12/2006 | Kaplan et al. | |
| 2007/0071728 A1 | 3/2007 | Ko et al. | |
| 2007/0129811 A1* | 6/2007 | Plouhar | A61F 2/0063 623/23.75 |
| 2007/0162121 A1* | 7/2007 | Tarrant | A61B 17/1146 623/13.12 |
| 2007/0231275 A1 | 10/2007 | Ueda | |
| 2007/0244484 A1 | 10/2007 | Luginbuehl | |
| 2007/0269481 A1 | 11/2007 | Li et al. | |
| 2008/0026419 A1 | 1/2008 | Bottlang et al. | |
| 2008/0027542 A1* | 1/2008 | McQuillan | A61L 27/3683 623/13.11 |
| 2008/0044900 A1 | 2/2008 | Mooney et al. | |
| 2008/0051888 A1 | 2/2008 | Ratcliffe | A61F 2/08 623/13.18 |
| 2008/0085292 A1 | 4/2008 | Rezania et al. | |
| 2008/0170982 A1* | 7/2008 | Zhang | B82Y 10/00 423/447.3 |
| 2008/0273206 A1 | 11/2008 | Genge et al. | |
| 2008/0274185 A1 | 11/2008 | Mao | |
| 2008/0274545 A1 | 11/2008 | Kuo et al. | |
| 2009/0148486 A1 | 6/2009 | Lu et al. | |
| 2009/0162643 A1 | 6/2009 | Dubrow et al. | |
| 2009/0196901 A1 | 8/2009 | Guilak et al. | |
| 2009/0317446 A1 | 12/2009 | Tan et al. | |
| 2009/0319049 A1* | 12/2009 | Shah | A61F 2/38 623/20.31 |
| 2010/0047309 A1 | 2/2010 | Lu et al. | |
| 2010/0093093 A1* | 4/2010 | Leong | A61L 27/3847 435/396 |
| 2010/0114547 A1 | 5/2010 | Boyden et al. | |
| 2010/0143439 A1 | 6/2010 | Jayasuriya et al. | |
| 2010/0168771 A1 | 7/2010 | Guldberg et al. | |
| 2010/0172952 A1 | 7/2010 | Srouji et al. | |
| 2010/0179659 A1 | 7/2010 | Li et al. | |
| 2010/0191332 A1* | 7/2010 | Euteneuer | A61F 2/0063 623/13.15 |
| 2010/0234955 A1 | 9/2010 | Santerre et al. | |
| 2010/0288343 A1* | 11/2010 | Sotzing | B82Y 10/00 136/252 |
| 2010/0291178 A1 | 11/2010 | Lu et al. | |
| 2010/0292791 A1* | 11/2010 | Lu | A61K 38/18 623/13.12 |
| 2010/0298937 A1* | 11/2010 | Laurencin | A61F 2/08 623/13.14 |
| 2010/0303881 A1 | 12/2010 | Hoke et al. | |
| 2010/0331979 A1 | 12/2010 | McDade et al. | |
| 2011/0009963 A1 | 1/2011 | Binnette et al. | |
| 2011/0020917 A1* | 1/2011 | Wen | A61L 27/50 435/283.1 |
| 2011/0029078 A1* | 2/2011 | Ratcliffe | A61F 2/08 623/13.2 |
| 2011/0038871 A1 | 2/2011 | Wen et al. | |
| 2011/0046734 A1 | 2/2011 | Tobis et al. | |
| 2011/0066242 A1 | 3/2011 | Lu et al. | |
| 2011/0097406 A1 | 4/2011 | Bryant et al. | |
| 2011/0171607 A1 | 7/2011 | Mao et al. | |
| 2011/0184227 A1* | 7/2011 | Altman | A61F 2/08 600/37 |
| 2011/0201984 A1 | 8/2011 | Dubrow et al. | |
| 2011/0293685 A1* | 12/2011 | Kuo | A61L 27/3604 424/422 |
| 2011/0307059 A1* | 12/2011 | Young | A61L 27/3662 623/13.17 |
| 2011/0313538 A1* | 12/2011 | Oh | A61L 27/56 623/23.61 |
| 2012/0020011 A1 | 1/2012 | Seliktar et al. | |
| 2012/0029653 A1 | 2/2012 | Evans et al. | |
| 2012/0046758 A1 | 2/2012 | Evans et al. | |
| 2012/0226295 A1* | 9/2012 | Jabbari | A61L 27/44 606/151 |
| 2012/0239145 A1* | 9/2012 | Peterson | A61F 2/08 623/13.14 |
| 2013/0030340 A1* | 1/2013 | Vincent | B01D 39/163 602/42 |
| 2013/0122248 A1* | 5/2013 | Haselby | D04H 1/728 428/131 |
| 2014/0037708 A1* | 2/2014 | Tan | A61K 47/34 424/426 |
| 2014/0039620 A1* | 2/2014 | Cantournet | A61F 2/08 623/13.14 |
| 2014/0172096 A1* | 6/2014 | Koob | A61F 2/08 623/13.19 |
| 2014/0309738 A1* | 10/2014 | Harley | A61F 2/08 623/13.11 |
| 2015/0150681 A1* | 6/2015 | Ricci | A61L 27/54 623/23.51 |
| 2015/0374514 A1* | 12/2015 | Clausen | A61F 2/66 623/53 |
| 2016/0262894 A1* | 9/2016 | Cronstein | A61F 2/28 |
| 2016/0374820 A1* | 12/2016 | Khandaker | A61F 2/441 623/17.12 |

FOREIGN PATENT DOCUMENTS

| | | |
|---|---|---|
| WO | WO 1998/22041 | 5/1998 |
| WO | WO/1999/07777 | 2/1999 |
| WO | WO/1999/33415 | 7/1999 |
| WO | WO 1999/055252 A2 | 11/1999 |
| WO | WO 2001/34060 | 5/2001 |
| WO | WO 2005/042048 A2 | 5/2005 |
| WO | WO/2005/086706 | 9/2005 |
| WO | WO/2005/089127 | 9/2005 |
| WO | WO 2006/116530 A2 | 11/2006 |
| WO | WO/2008/070186 | 6/2008 |
| WO | WO 2008/091391 | 7/2008 |
| WO | WO/2008/100534 | 8/2008 |
| WO | WO 2008/128304 | 10/2008 |
| WO | WO/2008/154030 | 12/2008 |
| WO | WO/2008/154035 | 12/2008 |
| WO | WO/2008/154035 A1 | 12/2008 |
| WO | WO/2008/156725 | 12/2008 |
| WO | WO/2009/038808 | 3/2009 |
| WO | WO 2009/055609 A1 | 4/2009 |
| WO | WO 2009/102967 | 8/2009 |
| WO | WO 2010/144992 | 12/2010 |
| WO | WO 2011/163328 | 12/2011 |
| WO | WO 2012/009341 | 1/2012 |
| WO | WO 2012/021885 | 2/2012 |
| WO | WO 2014/169236 A1 | 10/2014 |
| WO | WO 2014/169249 A1 | 10/2014 |

OTHER PUBLICATIONS

U.S. Appl. No. 12/655,193, filed Dec. 22, 2009, Lu et al.
Office Action dated Oct. 4, 2007 by the U.S. Patent and Trademark Office in connection with U.S. Appl. No. 11/073,275.

(56) References Cited

OTHER PUBLICATIONS

Office Action dated Apr. 17, 2008 by the U.S. Patent and Trademark Office in connection with U.S. Appl. No. 11/073,275.
Final Office Action dated Nov. 13, 2008 by the U.S. Patent and Trademark Office in connection with U.S. Appl. No. 11/073,275.
Notice of Allowance dated May 14, 2009 by the U.S. Patent and Trademark Office in connection with U.S. Appl. No. 11/073,275.
Notice of Allowance dated Sep. 24, 2009 by the U.S. Patent and Trademark Office in connection with U.S. Appl. No. 11/073,275.
Office Action dated Oct. 18, 2007 by the U.S. Patent and Trademark Office in connection with U.S. Appl. No. 11/073,261.
Final Office Action dated Apr. 30, 2008 by the U.S. Patent and Trademark Office in connection with U.S. Appl. No. 11/073,261.
Office Action dated Aug. 28, 2008 by the U.S. Patent and Trademark Office in connection with U.S. Appl. No. 11/073,261.
Final Office Action dated Mar. 6, 2009 by the U.S. Patent and Trademark Office in connection with U.S. Appl. No. 11/073,261.
PCT International Preliminary Report on Patentability dated Dec. 11, 2009 in connection with PCT/US2008/007323, international filing date Jun. 11, 2008.
PCT International Preliminary Report on Patentability dated Dec. 11, 2009 in connection with PCT/US2008/007357, international filing date Jun. 11, 2008.
PCT International Preliminary Report on Patentability dated Feb. 24, 2009 in connection with PCT/US2005/007010, international filing date Mar. 4, 2005.
PCT International Preliminary Report on Patentability dated Jun. 10, 2009 in connection with PCT/US2007/025127, international filing date Dec. 6, 2007.
PCT International Preliminary Report on Patentability dated Sep. 5, 2006 in connection with PCT/US2005/007129, international filing date Mar. 4, 2005.
PCT International Search Report dated Dec. 8, 2008 in connection with PCT Application No. PCT/US2008/007323, international filing date Jun. 11, 2008.
PCT International Search Report dated Feb. 14, 2006 in connection with PCT Application No. PCT/US2005/007129, international filing date Mar. 4, 2005.
PCT International Search Report dated Feb. 17, 2010 in connection with PCT Application No. PCT/US2009/06453, international filing date Dec. 8, 2009.
PCT International Search Report dated Jan. 6, 2009 in connection with PCT Application No. PCT/US2008/010985, international filing date Sep. 22, 2008.
PCT International Search Report dated Jul. 14, 2008 in connection with PCT Application No. PCT/US05/07010, international filing date Mar. 4, 2005.
PCT International Search Report dated Jul. 19, 2008 in connection with PCT Application No. PCT/US08/01889, international filing date Feb. 12, 2008.
Communication Pursuant to Rule 161 and 162 EPC dated Jan. 20, 2010 in connection with European Application No. 08768402.3, international filing date Jun. 11, 2008.
Brooks, Peter (2002) "Impact of Osteoarthritis on Individuals and Society: How Much Disability? Social Consequences and . . . " Curr. Opin. In Rheumatology. 14(5):573-577.
Lu et al. (2001) "Polymer-bioactive glass . . . " BED 50:693-694 (American Society of Mechanical Engineers Proceedings of the Bioengineering Conference, 2001).
Lu et al. (2003) "Three-dimensional, bioactive, biodegradable, polymer-bioactive glass composite scaffolds . . . " J. Biomed. Matls. Res. Part A 64(3):465-474.
Mikos, et al. (2006) "Engineering Complex Tissues" Tissue Engineering 12 (12):3307-3339.
Sherwood et al. (2002) "A three-dimensional osteocondral composite scaffold for articular cartilage repair." Biomaterials 23: 4739-4751.
Spalazzi et al. (2003) "Osteoblast and Chondrocyte Interactions during . . . " IEEE Engineering in Medicine and Biology Magazine Sep./Oct. 2003: 27-34.

Spalazzi, et al. (2006) "Development of Controlled Matrix Heterogeneity on a Triphasic Scaffold for Orthopedic Interface Tissue Engineering" Tissue Eng. 12(12):3497-508.
Spalazzi JP, et al. (2008) "Mechanoactive Scaffold Induces Tendon Remodeling and Expression of Fibrocartilage Markers" clin orthop relat res 466:1938-1948.
Stys, PK (2005) "General mechanisms of axonal damage and its prevention." J. Neurol. Sci. 233:3-13.
PCT International Search Report dated Jan. 5, 2012 in connection with PCT Application No. PCT/US11/47739, international filing date Aug. 15, 2011.
PCT International Search Report dated Jan. 9, 2012 in connection with PCT Application No. PCT/US11/41391, international filing date Jun. 22, 2011.
PCT International Search Report dated Jan. 9, 2012 in connection with PCT Application No. PCT/US11/43687, international filing date Jul. 12, 2011.
Written Opinion of the International Search Authority dated Jan. 5, 2012, in connection with International Application No. PCT/US11/47739.
Written Opinion of the International Search Authority dated Jan. 9, 2012, in connection with International Application No. PCT/US11/41391.
Written Opinion of the International Search Authority dated Jan. 9, 2012, in connection with International Application No. PCT/US11/43687.
Office Action issued Dec. 15, 2011 in connection with Canadian Application No. 2,557,231, national stage of PCT International Application No. PCT/US2005/007129, filed.
Communication Pursuant to Article 94(3) EPC dated Nov. 18, 2011 in connection with European Application No. 05724636.5, filed Mar. 4, 2005.
Mar. 23, 2012 Response to Communication Pursuant to Article 94(3) EPC dated Nov. 18, 2011 in connection with European Application No. 05724636.5, filed Mar. 4, 2005.
Extended European Search Report dated Oct. 18, 2012 in connection with European Application No. 08768402.3.
Dec. 3, 2012 Amendment in Response to Aug. 3, 2012 Office Action filed in connection with U.S. Appl. No. 12/806,912.
Mar. 16, 2012 Office Action issued in connection with U.S. Appl. No. 12/583,072.
Jun. 18, 2012 Amendment in Response to Mar. 16, 2012 Office Action filed in connection with U.S. Appl. No. 12/583,072.
Nov. 9, 2012 Final Office Action issued in connection with U.S. Appl. No. 12/583,072.
Apr. 9, 2013 Amendment and Request for Continued Examineation (RCE) filed in response to Nov. 9, 2012 Final Office Action which was issued in connection with U.S. Ser.
Apr. 29, 2013 Office Action issued in connection with U.S. Appl. No. 12/583,072.
Jul. 29, 2013 Amendment in Response to Apr. 29, 2013 Office Action filed in connection with U.S. Appl. No. 12/583,072.
Mar. 11, 2013 Response to Nov. 9, 2012 Final Office Action filed in connection with U.S. Appl. No. 12/583,072.
Mar. 25, 2013 Advisory Action issued in connection with U.S. Appl. No. 12/583,072.
Jan. 24, 2012 Office Action issued in connection with U.S. Appl. No. 12/806,912.
May 9, 2012 Amendment in Response to Jan. 24, 2012 Office Action filed in connection with U.S. Appl. No. 12/806,912.
Aug. 3, 2012 Office Action issued in connection with U.S. Appl. No. 12/806,912.
Feb. 5, 2013 Final Office Action issued in connection with U.S. Appl. No. 12/806,912.
Apr. 5, 2013 Amendment in Response to Feb. 5, 2013 Final Office Action filed in connection with U.S. Appl. No. 12/806,912.
Apr. 12, 2013 Advisory Action issued in connection with U.S. Appl. No. 12/806,912.
May 3, 2013 Amendment in Response to Feb. 5, 2013 Final Office Action filed in connection with U.S. Appl. No. 12/806,912.
Jul. 18, 2013 Office Action issued in connection with U.S. Appl. No. 12/806,912.

(56) References Cited

OTHER PUBLICATIONS

Oct. 18, 2013 Amendment in Response to Jul. 18, 2013 Office Action filed in connection with U.S. Appl. No. 12/806,912.
Dec. 24, 2013 Final Office Action issued in connection with U.S. Appl. No. 12/806,912.
Apr. 14, 2014 Amendment in Response to Dec. 24, 2013 Final Office Action filed in connection with U.S. Appl. No. 12/806,912.
Notice of Allowance dated May 22, 2014 by the U.S. Patent and Trademark Office in connection with U.S. Appl. No. 12/806,912.
Amendment Communication dated Jun. 7, 2011 In Response to Apr. 18, 2011 Office Action issued in connection with U.S. Appl. No. 12/455,765.
Office Action dated Sep. 8, 2011 in connection with U.S. Appl. No. 12/455,765.
Amendment Communication dated Feb. 4, 2012 In Response to Sep. 8, 2011 Office Action issued in connection with U.S. Appl. No. 12/455,765.
Office Action dated Apr. 23, 2012 in connection with U.S. Serial No. 12/455,765.
Amendment Communication dated Oct. 23, 2012 In Response to Apr. 23, 2012 Office Action issued in connection with U.S. Appl. No. 12/455,765.
50. Office Action dated Nov. 26, 2014 in connection with U.S. Appl. No. 12/455,765.
Amendment Communication dated Mar. 26, 2015 In Response to Nov. 26, 2014 Office Action issued in connection with U.S. Appl. No. 12/455,765.
Office Action dated Jul. 31, 2015 in connection with U.S. Appl. No. 12/455,765.
Amendment Communication dated Oct. 30, 2015 In Response to Jul. 31, 2015 Office Action issued in connection with U.S. Appl. No. 17/455,765.
Office Action dated Feb. 10, 2016 in connection with U.S. Appl. No. 12/455,765.
Office Action dated Sep. 13, 2012 in connection with U.S. Appl. No. 12/655,191, filed Dec. 22, 2009.
Amendment communication dated Dec. 13, 2012 In Response to Sep. 13, 2012 Office Action issued in connection with U.S. Appl. No. 12/655,193.
Office Action dated Jan. 4, 2013 in connection with U.S. Appl. No. 12/655,193, filed Dec. 22, 2009.
Amendment communication dated May 6, 2013 In Response to Jan. 4, 2013 Office Action issued in connection with U.S. Appl. No. 12/655,193.
Office Action dated Aug. 12, 2013 in connection with U.S. Appl. No. 12/655,193, filed Dec. 22, 2009.
Amendment communication dated Jan. 13, 2014 In Response to Aug. 12, 2013 Office Action issued in connection with U.S. Appl. No. 12/655,193.
Advisory Action dated Jan. 22, 2014 in connection with. U.S. U.S. Appl. No. 12/555,193, filed Dec. 22, 2009.
Supplemental Amendment communication Jan. 30, 2014 in Response to Aug. 12, 2013 Office Action issued in connection with. U.S. Appl. No. 12/655,193.
Notice of Allowance dated Feb. 19, 2014 in connection with U.S. Appl. No. 12/655,153.
PCT International Preliminary Report on Patentability dated Dec. 28, 2012 in connection with PCT Application No. PCT/US2011/041391, international filing date Jun. 22, 2011.
PCT international Search Report dated Aug. 29, 2014 in connection with PCT Application No. PCT/US2014/033843, international filing date Apr. 11, 2014.
PCT International Search Report dated Oct. 16, 2007 in connection with PCT Application No. PCT/US2006/015860, international filing date Apr. 28, 2006.
PCT International Search Report dated Jan. 2, 2009 in connection with PCT Application No. PCT/US2008/081011, international filing date Oct. 23, 2008.
PCT international Search Report dated Aug. 29, 2014 in connection with PCT Application No. PCT/US2014/033866 international filing date Apr. 11, 2014.
PCT International Preliminary Report on Patentability dated Jan. 15, 2013 in connection with PCT Application No. PCT/US2011/043687, international filing date Jul. 12, 2011.
PCT International Preliminary Report on Patentability dated Oct. 13, 2015 in connection with PCT Application No. PCT/US2014/033843, international filing date Apr. 11, 2014.
Written Opinion of the International Search Authority dated Oct. 16, 2007, in connection with International Application No. PCT/US2006/015860.
Written Opinion of the International Search Authority dated Jan. 2, 2009, in connection with International Application No. PCT/US2008/081011, international filing date Oct. 23, 2008.
Written Opinion of the International Search Authority dated Aug. 29, 2014, in connection with International Application No. PCT/US2014/033866, international filing date Apr. 11, 2014.
Supplemental European Search Report dated Oct. 11, 2012 in connection with European Application No. 08768402.
Extended European Search Report dated Aug. 29, 2013 in connection with European Application No. 08841018.8.
Briggs, P.F.A. et al., "Evidence-based dentistry: endodontic failure—how should it be managed?," Br. Dent. J. 183:159-164 (1997).
Brock, D.P. et al., "Alpha-smooth-muscle actin in and contraction of porcine dental pulp cells," J. Dent. Res. 81:203-208(2002).
Buurma, B., et al., "Transplantation of human pulpal and gingival fibroblasts attached to synthetic scaffolds," Eur. J. Oral Sci. 107:282-289(1999).
Cheung, G.S.: "Endodontic failures—changing the approach," Inter. Dent. J. 46:131-138(1996).
Cho, B.C. et al., "The bone regenerative effect of chitosan microsphere-encapsulated growth hormone on bony consolidation in mandibular distraction osteogenesis in a dog model," J. Craniofac. Surg. 15(2):299-311(2004).
Choi, S.H. et al., "Effect of recombinant human bone morphogenetic protein-2/absorbable collagen sponge (rhBMP-2/ACS) on healing in 3-wall intrabony defects in dogs," J. Periodontol. 73(1):63-72(2002).
Clark et al., "Porous implants as drug delivery vehicles to augment host tissue integration," FASEB J. 22(6):1684-93(2008).
Couble, M.L., Farges, J.C., Bleicher, F., Perrat-Mabillon, B., Boudeulle, M., Magloire, H.; "Odontoblast differentiation of human dental pulp cells in explant cultures," Calcif. Tissue Int. 66:129-138(2000).
Cox, C.F., et al., "Tunnel defects in dentin bridges: their formation following direct pulp capping," Oper. Dent. 21(1): 4-11(1996).
Cvek, M., et al., "Pulp revascularization in reimplanted immature monkey incisors predictability and the effect of antibiotic systemic prophylaxis," Endod. Dent. Traumatol. 6:157-169 (1990).
Cvek, M., et al., "Effect of topical application of Doxycycline on pulp revascularization and periodontal Healing in reimplanted monkey incisors," Endod. Dent. Traumatol. 6:170-176(1990).
Cvek, M.: "A clinical report on partial pulpotomy and capping with calcium hydroxide in permanent incisors with complicated crown fracture," J. Endod. 4:232-237(1978).
D'Aquino, R., Graziano, A., Sampaolesi, M., Laino, G., Pirozzi, G., De, R. A., Papaccio, G; "Human postnatal dental pulp cells co-differentiate into osteoblasts and endotheliocytes: a pivotal synergy leading to adult bone tissue formation," Cell Death. Differ. 14(6):1162-1171(2007).
Dahlen G., Haapasalo, M; "Microbiology of apical periodontisis. In Essential Endodontology: Prevention and Treatment of Apical Periodontitis", Orstavik, D., Pitt Ford, T.R., Eds.; Blackwell Science: Oxford, pp. 106-130(1998).
Das, S., Das, A.K., and Murphy, R.A.; "Experimental apexigenesis in baboons," Endod. Dent. Traumatol. 13:31-35(1997).
Derringer, K.A., Linden, R.W.; "Angiogenic growth factors released in human dental pulp following orthodontic force," Arch. Oral Biol. 48(4):285-291(2003).
Derringer, K.A., Linden, R.W.; "Enhanced angiogenesis induced by diffusible angiogenic growth factors released from human dental pulp explants of orthodontically moved teeth." Eur. J. Orthod. 20(4):357-367(1998).

(56) References Cited

OTHER PUBLICATIONS

Derringer, K.A. Linden, R. W.; "Vascular endothelial growth factor, fibroblast growth factor 2, platelet derived growth factor and transforming growth factor beta released in human dental pulp following orthodontic force," Arch. Oral Biol. 49(8):631-641 (2004).

Dikovsky, D., Bianco-Peled, H., Seliktar, D.; "The effect of structural alterations of PEG-fibrinogen hydrogel scaffolds on 3-D cellular morphology and cellular migration," Biomaterials. 27(8):1496-1506 (2006).

Edwards et al.; "Gene-enhanced tissue engineering for dental hard tissue regeneration: (2) dentin-pulp and periodontal regeneration," Head Face Med. 2:1-9(2006).

Elbert, D.L., Hubbell, J. A.; "Conjugate addition reactions combined with free-radical cross-linking for the design of materials for tissue engineering." Biomacromolecules. 2(2):430-441(2000).

Elisseeff, J., Mcintosh, W., Anseth, K., Riley, S., Ragan, P., Langer, R.; "Photoencapsulation of chondrocytes in poly(ethylene oxide)-based semi-interpenetrating networks," J. Biomed. Mater. Res. 51(2):164-171(2000).

Etienne, O. et al.; "Degradability of polysaccharides multilayer films in the oral environment: an in vitro and in vivo study," Biomacromolecules. 6(2):726-733(2005).

Fong et al.; "The Crowning Achievement: Getting to the Root of the Problem, Journal of Dental Education," 69(5):555-570(2005).

Friedman, S.; "Treatment outcome and prognosis of endodontic therapy," In Orstavik, D. and Pitt Ford, T.R., (eds.): Essential Endodontology: Prevention and Treatment of Apical Periodontitis. Oxford, Blackwell Science, pp. 367-401 (1998).

Fuks, A.B., et al.; "Pulp response to collagen and glutaraldehyde in pulpotomized primary teeth of baboons," Pediatr. Dent. 13:142-150(1991).

Fuks, A.B., Michaeli, Y., Sofer-Saks, B., Shoshan, S.; "Enriched collagen solution as a pulp dressing in pulpotomized teeth in monkeys," Pediatr. Dent. 6:243-247(1984).

Goldberg, M., Smith, A. J.; "Cells and extracellular matrices of dentin and pulp: A biological basis for repair and tissue engineering," Crit. Rev. Oral Biol. Med. 15(1):13-27(2004).

Grando, M. L., Westphalen, B. L., de Figueiredo, J. A., Nor, J. E., de Araujo, F. B., Fossati, A. C.; "Vascular endothelial growth factor and its relationship with the dental pulp," J. Endod. 33(5):524-530(2007).

Gronthos, S., Brahim, J., Li, W., Fisher, L. W., Gherman, N., Boyde, A., DenBesten, P., Robey, P. G., Shi, S.; "Stem cell properties of human dental pulp stem cells," J. Dent. Res. 81:531-535(2002).

Gronthos, S., Mankani, M., Brahim, J., Robey, P.G., Shi, S.; "Postnatal human dental pulp stem cells (DPSCs) in vitro and in vivo," PNAS 97:13625-13630 (2000).

Hao, J. et al.; "Mineralized nodule formation by human dental papilla cells in culture," Eur. J. Oral Sci. 105:318-324(1997).

Hargreaves, K.M., Goodis, H.E.; Seltzer and Bender's: Dental Pulp. Chicago, Quintessence Publishing Co. Inc., 2002.

Hasselgren G., Larsson A., Rundquist L.; "Pulpal status following autogenous transplantation of fully developed maxillary canines," Oral Surg. 44:106-112 (1977).

Herrick, S., Blanc-Brude, O., Gray, A., Laurent, G.; "Fibrinogen," Int. J. Biochem. Cell Biol. 31(7):741-746(1999).

Horsted P., Sandergaard B., Thylstrup A., El Attar K., Fejerskov O.; "A retrospective study of direct pulp capping with calcium hydroxide compounds," Endo. Dent. Traumatol. 1:29-34(1985).

Iohara et al., "Dentin Regeneration by Dental Pulp Stem Cell Therapy with Recombinant Human Bone Morphogenetic Protein 2," J. Dental Res., 83(8):590-595(2004).

Jepsen, S., Albers, H.K., Fleiner, B., Tucker, M., Rueger, D.; "Recombinant human osteogenic protein-1 induces dentin formation: an experimental study in miniature swine," J. Endod. 23:378(1997).

Kaigler, D. et al.; "Tissue engineering's impact on Dentistry," J. Dent. Educ. 65:456-462 (2001).

About, I. et al.; "Influence of resinous monomers on the differentiation in vitro of human pulp cells into odontoblasts," J. Biomed. Mater. Res. (Appl. Biomater.) 63:418-423, (2002).

About, I. et al.; "Human dentin production in vitro," Exp. Cell Res. 258: 33-41 (2000).

ADA. Survey of Dental Practice. 5S99. 1999. American Dental Association. Survey of Dental Services. (Generic).

Almany, L. et al.; "Biosynthetic hydrodel scaffolds made from fibrinogen and polyethylene glycol for 3D cell cultures," Biomaterials, 26 (15), 2467-2477 (2005).

Almushayt, A. et al.; "The in-vivo role of DMP2 in the cytodifferentiation of undifferentiated mesenchymal pulp cells into odontoblast-like cells," Presented at IADR. (Generic), J. Dent. Research, 81 (Spec. lss. A), A-278 (2002).

Andreasen, J.O. et al.; "Replantation of 400 avulsed permanent incisors. 1. Diagnosis of healing complications," Endod. Dent. Traumatol. 11 :51-58(1995).

Andreasen, J.O. et al.; "Replantation of 400 avulsed permanent incisors. 2. Factors related to pulp healing," Endod. Dent. Traumatol. 11 :59-68(1995).

Andreasen, J.O., et al.; "Replantation of 400 avulsed permanent incisors. 3. Factors related to root growth," Endod. Dent. Traumatol. 11 :69-75(1995).

Anitua, E.; "Autologous preparations rich in growth factors promote proliferation and induce VEGF and HGF production by human tendon cells in culture," J. Orthop. Res., 23 (2), 281-286 (2005).

Banes, A.J.; "Mechanoreception at the cellular level: the detection, interpretation, and diversity of responses to mechanical sianals," Biochem. Cell Bio. 73:349-365 (1995).

Barkhordar RA, et al.; "Interleukin-1 B Activity and Collagen Synthesis in Human Dental Pulp Fibroblasts," Journal of Endodontics 28:157-159(2002).

Barthel et al.; "Pulp Capping of Carious Exposures: Treatment Outcome after 5 and 10 Years: A Retrospective Study," J. Endod. 26:525-528(2000).

Baumgartner, J. C., Hargreaves, K. M., Goodis, H. E., Eds.; "Pulpal infections including caries. In Seltzer and Bender's: Dental Pulp," Quintessence Publishing Co, Inc: Chicago, pp. 281-307 (2002).

Bimstein, E. et al.; "Enhanced healing of tooth-pulp wounds in the dog by enriched collagen solution as a capping agent," Arch. Oral Biol. 26:97-101 (1981).

Bohl et al.; "Role of synthetic extracellular matrix in development of engineered dental pulp," J. Biomater. Sci. Polym. Ed 9:749-764 (1998).

Bouhadir et al.; "Promoting Angiogenesis in Engineered Tissues," J. Drug Target 9:397-406 (2001).

Bouvier, Met al.; "In vitro mineralization of a three-dimensional collagen matrix by human dental pulp cells in the presence of chondroitin sulphate," Arch. Oral Biol. 35:301-309 (1990).

Katti et al.; "Bioresorbable Nanofiber-Based Systems for Wound Healing and Drug Delivery: Optimization of Fabrication Parameters," J. Biomed. Mater. Res. B. Appl. Biomater. 70:286-296 (2004).

Kishi, Y., Takahashi, K.; "Change of Vascular Architecture of Dental Pulp with Growth" in Dynamic Aspects of Dental Pulp, lnoki, R., Kudo, T., Olgart, L., Eds.; Chapman and Hall: London, pp. 97-129(1995).

Kling, M., Cvek, M., and Mejare, I.; "Rate and predictability of pulp revascularization in therapeutically reimplanted permanent incisors," Endod. Dent. Traumatol. 2:83-89(1986).

Klokkevold, P.R., Fukayama, H., Sung, E.C., Bertolami, C.N.; "The effect of chitosan (poly-N-acetyl glucosamine) on lingual hemostasis in heparinized rabbits," J. Oral Maxillofac. Surg. 57(1):49-52(1999).

Knezevic V., Sim A.J., Borg T.K., Holmes J.W.; "Isotonic biaxial loading of fibroblast-populated collagen gels: a versatile, low-cost system for the study of mechanobiology." Biomech. Model Mechanobiol. 1(1):59-67(2002).

Koran et al.; "Apparent viscosity of materials used for making edentulous impressions," J. Amer. Dent. Assoc. 95:75-79(1977).

Landesberg R., Roy M., Glickman R.S.; "Quantification of growth factor levels using a simplified method of platelet-rich plasma gel preparation," J. Oral Maxillofac. Surg. 58(3):297-300(2000).

(56) References Cited

OTHER PUBLICATIONS

Lu, H. et al.; "In vitro bone formation using muscle-derived cells: a new paradigm for bone tissue engineering using polymer-bone morphogenetic protein matrices," Biochem. Biophys. Res. Commun. 305(4):882-889(2003).
Lu, H., Jiang, S., Tang, A., Hung, C. T., Guo, X.E.; "Development of Controlled Heterogeneity an a Polymer-Ceramic Hydrogel Scaffold for Osteochondral Repair," Bioceramics. 17(Key Engineering Materials vols. 284-286),607-610(2005).
Lutolf, M.P., Hubbell, J.A.; "Synthesis and physiochemical characterization of end-linked poly(ethylene glycol)-co-peptide hydrogels formed by Michael-type addition," Biomacromolecules. 4(3):713-722(2003).
Ma, L., Gao, C., Mao, Z., Zhou, J., Shen, J., Hu, X., Han, C.; "Collagen/chitosan porous scaffolds with improved biostability for skin tissue engineering," Biomaterials. 24(26):4833-4841(2003).
Magloire H., Joffre A., Bleicher F.; "An in vitro model of human dental pulp repair," J Dent. Res. 75(12):1971-8(1996).
Mathieu, S., El-Battari, A., Dejou, J., About, I.; "Role of injured endothelial cells in the recruitment of human pulp cells," Arch. Oral Biol. 50(2):109-113(2005).
Mauck, R.L. et al.; "Functional tissue engineering of articular cartilage through dynamic loading of chondrocyte-seeded agarose gels," J. Biomech. Eng. 122:252-260(2000).
Mejare, I. and Cvek, M.; "Partial pulpotomy in young permanent teeth with deep carious lesions," Endod. Dent. Traumatol. 9:238-242(1993).
Mesaros, S.V. and Trope, M.; "Revascularization of traumatized teeth assessed by laser Doppler flowmetry: case report," Endod. Dent. Traumatol. 13:24-30(1997).
Mjor, I.A., Heyeraas, K.J.; "Pulp-Dentin and Periodontal Anatomy and Physiology," In Essential Endodontology, Orstavik, D., Pitt Ford, T.R., Eds.; Blackwell Science: New York, pp. 9-41(1998).
Mooney, D.J., et al.; "Engineering dental pulp-like tissue in vitro," Biotechnol. Prog. 12:865-868(1996).
Mori, T., Okumura, M., Matsuura, M., Ueno K., Tokura, S., Okamoto, Y., Minami, S., Fujinaga, T.; "Effects of chitin and its derivatives on the proliferation and cytokine production of fibroblasts in vitro," Biomaterials. 18(13):947-951(1997).
Murray et al.; "Analysis of Pulpal Reactions to Restorative Procedures, Materials, Pulp Capping, and Future Therapies," Crit. Rev. Oral. Biol. Med. 13(6):509-520(2002).
Murray, M.M., Spindler, K.P., Ballard, P., Welch, T.P., Zurakowski, D., Nanney, L.B.; "Enhanced histologic repair in a central wound in the anterior cruciate ligament with a collagen-platelet-rich plasma scaffold," J. Orthop. Res. 25(8):1007-17(2007).
Murray, M.M., Spindler, K.P., Devin, C., Snyder, B.S., Muller, J., Takahashi, M., Ballard, P., Nanney, L.B., Zurakowski, D.; "Use of a collagen-platelet rich plasma scaffold to stimulate healing of a central defect in the canine ACL," J. Orthop. Res. 24(4):820-830(2006).
Muzzarelli, et al.; "Osteoconduction exerted by methylpyrrolidinone chitosan used in dental surgery," Biomaterials. 14(1):39-43(1993).
Muzzarelli, R., Biagini, G., Pugnaloni, A., Filippini, O., Baldassarre, V., Castaldini, C., Rizzoli, C.; "Reconstruction of parodontal tissue with chitosan," Biomaterials. 10(9):598-603(1989).
Myers, W.C. and Fountain, S.B.; "Dental pulp regeneration aided by blood and blood substitutes after experimentally induced periapical infection," Oral Surg. 37:441-450(1974).
Nakashima, M.; "Establishment of primary cultures of pulp cells from bovine permanent incisors," Arch. Oral Biol. 36:655-663 (1991).
Nakashima, M.; "Induction of dentine in amputated pulp of dogs by recombinant human bone morphogenetic proteins-2 and -4 with collagen matrix," Arch. Oral Biol. 39:1085-1089(1994).
Nakashima, M., et al.; "Induction of dental pulp stem cell differentiation into odontoblasts by electroporation-mediated gene delivery of growth/differentiation factor 11 (Gdf11)," Gene Ther. 9:814-818(2002).

Nevins, A., Finkelstein, F., Laporta, R., and Borden, B.G.: "Induction of hard tissue into pulpless open-apex teeth using collagen-calcium phosphate gel," J. Endod. 4:76-81(1978).
Nevins, A., Finkelstein, F., Laporta, R., Borden, B.G., and Moodnik, R.; "Formation of mineralized scar tissue induced by implants containing collagen-calcium phosphate gel," J. Endod. 1:303-309(1975).
Nevins, A.J., Finkelstein, F., Borden, B.G., and Laporta, R.: "Revitalization of pulpless open apex teeth in rhesus monkeys, using collagen-calcium phosphate gel," J. Endod. 2:159-16(1976).
Nevins, A.J., LaPorta, F.F., Borden, B.G., and Spangberg, L.S.; "Pulpotomy and partial pulpectomy procedures in monkey teeth using cross-linked collagen-calcium phosphate gel," Oral Surg. Oral Med. Oral Pathol. 49:360-365(1980).
Nguyen, K.T., West, J.L.; "Photopolymerizabie hydrogels for tissue engineering applications," Biomaterials. 23(22):4307-4314(2002).
Nishimura, K., Nishimura, S., Seo, H., Nishi, N., Tokura, S., Azuma, I.; "Effect of multiporous microspheres derived from chitin and partially deacetylated chitin on the activation of mouse peritoneal macrophages," Vaccine. 5:(2)136-140(1987).
Nyborg, H.; "Healing processes in the pulp on capping; a morphologic study; experiments on surgical lesions of the pulp in dog and man," Acta Odontol. Scand. 13(suppl.16):1-130(1995).
Okiji, T.; "Pulp as a connective tissue," In Hargreaves, K.M. and Goodis, H.E., (eds.): Seltzer and Bender's: Dental Pulp. Chicago, Quintessence Publishing Co, Inc., 2002.
Ozawa M., Ikeda H., Suda. H.; "The effect of pulpward pressure on the response to 50% lidocaine (lignocaine) applied to exposed dentine in cats," Arch. Oral Biol. 47(4):333-6(2002).
Park, D.S., Choi, B.H., Zhu, S.J. Huh, J.Y., Kim, B.Y., Lee, S.H.; "Injectable bone using chitosanalginate gel/Mesenchymal stem cells/BMP-2 composites," J. Craniomaxillofac. Surg. 33(1): 50-4(2005).
Park, J.S., Choi, S.H., Moon, I.S., Cho, K.S., Chai, J.K., Kim, C.K.; "Eight-week histological analysis on the effect of chitosan on surgically created one-wall intrabony defects in beagle dogs," J. Clin. Periodontol. 30(5):443-453(2003).
Peters et al.; "Engineering vascular networks in porous polymer matrices," J. Biomed. Mater. Res. 60(4):668-678(2002).
Rabea, E.I., Badawy, M.E., Stevens, C.V., Smagghe G., Steurbaut, W.; "Chitosan as antimicrobial agent: Applications and mode of action," Biomacromolecules. 4(6):1457-1465(2003).
Ranly D.M. and Garcia-Godoy, F.; "Current and potential pulp therapies for primary and young permanent teeth," J. Dent. 28(3):153-61(2000).
Reisbick, M.H.; "Effect of Viscosity on the Accuracy and Stability of Elastic Impression Materials," J. Dent. Res. 52:407-411(1973).
Khanarian et al.; "A functional agarose-hydroxyapatite scaffold for osteochondral interface regeneration", Biomaterials, Jul. 1, 2012, vol. 33, No. 21, pp. 5247-5258.
Richardson et al.; "Polymeric system for dual growth factor delivery," Nat. Biotechnol. 19:1029-1034(2001).
Roeder, B.A., Kokini, K., Sturgis, J.E., Robinson, J.P., and Voytik-Harbin, S.L.; "Tensile mechanical properties of three-dimensional type I collagen extracellular matrices with varied microstructure," J. Biomed. Eng. 124:214-222(2002).
Rungvechvuttivittaya, S., et al.; "Responses of macrophage-associated antigen-expressing cells in the dental pulp of rat molars to experimental tooth replantation," Arch. Oral Biol. 43:701-710(1998).
Rutherford, B. et al.; "A new biological approach to vital pulp therapy," Crit. Rev. Oral Biol. Med. 6:218-229(1995).
Rutherford, R.B. et al.; "Treatment of inflamed ferret dental pulps with recombinant bone morphogenetic protein-7," Eur. J. Oral Sci. 108:202-206(2000).
Rutherford, R.B.; "BMP-7 gene to inflamed ferret dental pulps," Eur. J. Oral Sci. 109:427-424(2001).
Salani, D., Taraboletti, G., Rosano, L., Di, C., V, Barsotti, P., Giavazzi, R., Bagnato, A.; "Endothelin-1 induces an angiogenic phenotype in cultured endothelial cells and stimulates neovascularization in vivo," Am. J. Pathol. 157(5):1703-1711(2000).
Sapelli, P., Baldassare, V., Muzzarelli, R., Emanuelli, M.; "Chitosan in Dentistry," In Chitin in Nature and Technology, pp. 507-512, 1986.

(56) References Cited

OTHER PUBLICATIONS

Sarasam, A., Madihaliv, S.V.; "Characterization of chitosan-polycaprolactone blends for tissue engineering applications," Biomaterials. 26(7):5500-5508(2005).
Seliktar, D.; "Extracellular stimulation in tissue engineering," Ann. N.Y. Acad. Sci. 1047:386-394(2005).
Six, N. et al.; "Osteogenic proteins (bone sialoprotein and bone morphogenetic protein-7) and dental pulp mineralization," J. Mater. Sci. Mater. Med. 13:225-232(2002).
Six, N. et al.; "Differential repair responses in the coronal and radicular areas of the exposed rat molar pulp induced by recombinant human bone morphogenetic protein 7 (osteogenic protein 1)," Arch. Oral Biol. 47:177-187(2002).
Sjogren, U., Hagglund, B., Sundqvist, G., and Wing, K.; "Factors affecting the long-term results of endodontic treatment," J. Eondod. 16:498-504(1990).
Skoglund, A. and Hasselgren, G.; "Tissue changes in immature dog teeth autotransplanted to surgically prepared sockets," Oral Surg. Oral Med. Oral Pathol. 74:789-95(1992).
Skoglund, A. and Tronstad, L.; "Pulpal changes in replanted and autotransplanted immature teeth of dogs," J. Endod. 7(7):309-316(1981).
Skoglund, A., Tronstad, L., and Wallenius, K.; "A microangiographic study of vascular changes in replanted and autotransplanted teeth of young dogs," Oral Surg. 44:17-28(1978).
Skoglund, A., Tronstad, L., and Wallenius, K.; "Pulpal survival in replanted and auto-transplanted apicoectomized mature teeth of dogs with prepared nutritional canals," Int. J. Oral Surg. 12:31-38(1983).
Skoglund, A.; "Pulpal changes in replanted and autotransplanted apicoectomized mature teeth of dogs," Int. J. Oral Surg. 10:111-121(1981).
Skoglund, A.; "Vascular changes in replanted and autotransplanted apicoectomized mature teeth of dogs," Int. J. Oral Surg. 10:100-110(1981).
Smith, C.S., Setchell, D.J., and Harty, F.J.; "Factors influencing the success of conventional root canal therapy—a five-year retrospective study," Int. Endod. J. 26:321-333(1993).
Suda, H., Ikeda, H.; "The Circulation of the Pulp," In Seltzer and Bender's Dental Pulp, pp. 123-150(2002).
Suh, J.K.; Matthew, H.W.; "Application of chitosan-based polysaccharide biomaterials in cartilage tissue engineering: a review," Biomaterials. 21(24):2589-2598(2000).
Temenoff, J.S., Athanasiou, K.A., LeBaron, R.G., Mikos, A.G.; "Effect of poly( ethylene glycol) molecular weigh on tensile and swelling properties of oligo(poly(ethylene glycol) fumarate) hydrogels for cartilage tissue engineering," J. Biomed. Mater. Res. 59(3):429-437(2002).
Teng J., et al.; "Human Pulpal Fibroblasts Cultured in Type I Collagen Gel For Dental Pulp Tissue Engineering," Proceedings of the Society for Biomaterials, 30th Annual meeting, p. 188 (2005).
Thresher et al.; "The stress analysis of human teeth," J. Biomech. 6:443-449(1973).
Toparli, M., Gokay, N., and Aksoy, T.; "Analysis of a restored maxillary second premolar tooth by using three-dimensional finite element method," J. Oral Rehab. 26:157(1999).
Tran-Hung L., Mathieu, S., About, I.; "Role of human pulp fibroblasts in angiogenesis," J. Dent. Res. 85(9):819-823(2006).
Tsay, R.C., Vo, J., Burke, A., Eisig, S.B., Lu, H.H., Landesberg, R.; "Differential growth factor retention by platelet-rich plasma composites," J. Oral Maxillofac. Surg. 63(4):521-528(2005).
Tziafas, D., Smith, A.J., and Leso, H.; "Designing new treatment strategies in vital pulp therapy," J. Dent. 28:77-92(2000).
Van Amerongen, J.P. et al.; "The concentration, extractability and characterization of collagen in human dental pulp," Arch. Oral Biol. 28:339-345(1983).
Vermilyea et al.; "Rotational Viscometry of a Zinc Phosphate and a Zinc Polyacrylate Cement," J. Dent. Res. 56:762-767 (1977).
Vongsavan, N., Matthews, B.; "The vascularity of dental pulp in cats," J. Dent. Res. 71(12):1913-1915(1992).
Weiger, R., Axmann-Krcmar, D., and Lost, C.; "Prognosis of conventional root canal treatment reconsidered," Endod. Dent. Traumatol. 14:1-9(1998).
Williams et al.; "Orthodontic tooth movement analysed by the Finite Element Method," Biomaterials. 5:347-351(1984).
Yanpiset, K. and Trope, M.; "Pulp revascularization of replanted immature dog teeth after different treatment methods," Endod. Dent. Traumatol. 16:211-217(2000).
Yanpiset, K., et al.; "Efficacy of laser Doppler flowmetry for the diagnosis of revascularization of reimplanted immature dog teeth," Dent. Traumatol. 17:63-70(2001).
Young et al.; "Tissue-Engineered Hybrid Tooth and Bone," Tissue Eng. 11(9-10):1599-610(2005).
Young, C.S.; "Tissue engineering of complex tooth structures on biodegradable polymer scaffolds," J. Dent. Res. 81:695-700(2002).
Zhang, J.Q., Nagata, K., Iijima, T.; "Scanning electron microscopy and immunohistochemical observations of the vascular nerve plexuses in the dental pulp of rat incisor," Anal. Rec. 251(2):214-220(1998).
Zheng-Ming Huang et al.; "A review on polymer nanofibers by electrospinning and their applications in nanocomposites," Comp. Sci.Tech. 63:2223-2253 (2003).
Zhu, W., Mow, V.C., Koob, T.J., Eyre, D.R.; "Viscoelastic shear properties of articular cartilage and the effects of glycosidase mammalian cell encapsulation," Biomaterials. 15(13):1049-1056(1994).
Zielinski, B.A., Aebischer, P.; "Chitosan as a matrix for mammalian cell encapsulation," Biomaterials. 15(13):1049-1056 (1994).
Zilberman, U., Mass, E., and Sarnat, H.; "Partial pulpotomy in carious permanent molars," Am. J. Dent. 2:147-150(1989).
Albander, J.M.; "Epidemiology and Risk Factors of Periodontal Diseases" The Dental Clinics of North America 2005, 49:517-532.
Alhadlaq et al.; "Tissue-engineered Neogenesis of Human-shaped Mandibular Condyle from Rat Mesenchymal Stem Cells," J. Dent. Res., 2003, DD. 951-956, vol. 62, No. 12.
Anderson, H.C.; "Electron Microscope Studies of Induced Cartilage Development and Calcification" The Journal of Cell Biology 1967 35:81-101.
Anderson, H.C.; "Molecular Biology of Matrix Vesicles" Clinical Orthopaedics and Related Research 1995 314:266-280.
Anderson, H.C.; "Vesicles Associated with Calcification in the Matrix of Epiphyseal Cartilage" The Journal of Cell Biology 1969 41:59-72.
Baker et al.; "The Relationship between the Mechanical Properties and Cell Behavior on PLGA and PCL Scaffolds for Bladder Tissue Engineering" Biomaterials 2009 30:1321-1328.
Bartold, P.M., Narayanan, A.S.; "Molecular and Cell Biology of Healthy and Diseased Periodontal Tissues" Periodontology 2006 40:29-49.
Benjamin, M., Ralphs, J.R.; "Entheses—the Bony Attachments of Tendons and Ligaments" Italian Journal of Anatomy and Embryology 2001 106(2 Suppl 1) :151-157 (Abstract only).
Bernard, G.W., Pease, D.C.; "An Electron Microscopic Study of Initial Intramembranous Osteogenesis" American Journal of Anatomy 1969 125:271-290.
Berrey et al.; "Fractures of Allografts" The Journal of Bone and Joint Surgery 1990 72-A(6) :825-833.
Blandford et al.; "Modeling of Matrix Vesicle Biomineralization Using Large Unilamellar Vesicles" Journal of Inorganic Biochemistry 2003 94:14-27.
Boskey et al.; "Matrix Vesicles Promote Mineralizatlon in a Gelatin Gel" Calcified Tissue International 1997 60:309-315.
Boskey et al.; "Persistence of Complexed Acidic Phospholipids in Rapidly Mineralizing Tissues is Due to Affinity for Mineral and Resistance to Hydrolytic Attack: In Vitro Data" Calcified Tissue International 1996 58:45-51.
Brennan et al.; "The Impact of Oral Disease and Nonsurgical Treatment on Bacteremia in Children," J Am. Dent. Assoc., 2007, pp. 80-85, vol. 138.
Brogi et al.; "Distinct Patterns of Expression of Fibroblast Growth Factors and Their Receptors in Human Atheroma and Nonatherosclerotic Arteries". The American Society for Clinical Investigation, Inc. vol. 92, Nov. 1993, 2408-2418.

(56) References Cited

OTHER PUBLICATIONS

Bruneau et al.; "Anterior Cervical Interbody Fusion with Hydroxyapatite Graft and Plate System" Neurosurgical Focus 2001 10(4):1-6.
Buehler, M.J.; "Molecular Nanomechanics of Nascent Bone: Fibrillar Toughening by Mineralization" Nanotechnology 2007 18:295102(9pp).
Camolezi et al.; "Construction of an Alkaline Phosphatase-Liposome System: A Tool for Biomineralization Study" The International Journal of Biochemistry & Cell Biology 2002 34:1091-1101.
Chesnutt et al.; "Composite Chitosan/Nano-Hydroxyapatite Scaffolds Induce Osteocalcin Production by Osteoblasts In Vitro and Support Bone Formation In Vivo" Tissue Engineering: Part A 2009 15 (9): 2571-2579.
Chew et al.; "Sustained Release of Proteins from Electrospun Biodegradable Fibers" Biomacromolecules 2005 6:2017-2024.
Christensen et al.; "Immunocytochemical demonstration of nerve growth factor receptor (NGF-R) in developing human fetal teeth," Anat and Embryol, 1993, pp. 247-55, vol. 188, No. 3.
Cook, J.J., Cook, E.A.; "Bioscaffolds and the Reconstruction of Ligaments and Tendons in the Foot and Ankle" Clinics in Podiatric Medicine and Surgery 26:535-543(2009).
Costa et al.; "Creating Alignment and Anisotropy in Engineered Heart Tissue: Role of Boundary Conditions in a Model Three Dimensional Culture System" Tissue Engineering 2003 9 (4): 567-577.
Eanes et al.; "Calcium Phosphate Formation in Aqueous Suspensions of Multilamellar Liposomes" Calcified Tissue International 1984 36:421-430.
Eanes, E.D., Hailer, A.W.; "Liposome-Mediated Calcium Phosphate Formation in Metastable Solutions" Calcified Tissue International 1985 37:390-394.
Eanes, E.D.; "Mixed Phospholipid Liposome Calcification" Bone and Mineral 1992 17:269-272.
Elisseeff et al.; "Transdermal photopolymerization for minimally invasive implantation," Proc. Natl. Acad. Sci. USA, 1999, pp. 3104-3107, vol. 96.
Ettel et al.; "Porous Hydroxyapatite Grafts in Chronic Subcrestal Periodontal Defects in Rhesus Monkeys: A Histological Investigation" Journal of Periodontology 1989 60 (6): 342-351.
Fan et al.; "Enhanced Differentiation of Mesenchymal Stem Cells Co-Cultured with Ligament Fibroblasts on Gelatin/Silk Fibroin Hybrid Scaffold" Biomaterials 29:1017-1027 (2008).
Gao et al.; "Anterior Cruciate Ligament Reconstruction with LARS Artificial Ligament: A Multicenter Study with 3- to 5-Year Follow-up" Arthroscopy: The Journal of Arthroscopic and Related Surgery 26(4):515-523 (2010).
Gay et al.; "Ultrastructure of Matrix Vesicles and Mineral in Unfixed Embryonic Bone" Metabolic Bone Disease & Related Research 1978 1:105-108.
Giannoudis et al.; "Bone Substitutes: An Update" Injury, International Journal of the Care of the Injured 2005 36S:S20-S27.
Guven, G., Altun, C., Gunhan, O., Gurbuz, T., Basak, F., Akbulut, E., Cehreli, Z. C.; "Co-expression of cyclooxygenase-2 and vascular endothelial growth factor in inflamed human pulp: an immunohistochemical study." J. Endod. 2007, 33 (1), 18-20.
He et al.; "Biocompatibility and Osteogenic Capacity of Periodontal Ligament Stem Cells on nHAC/PLA and HA/TCP Scaffolds" Journal of Biomaterials Science 2011 22:179-194.
Henneman et al.; "Mechanobiology of Tooth Movement" European Journal of Orthodontics 2008 30:299-306.
Ho et al.; "The Biomechanical Characteristics of the Bone-Periodontal Ligament-Cementum Complex" Biomaterials 2010 31(25):6635-6646.
Ho et al.; "The Tooth Attachment Mechanism Defined by Structure, Chemical Composition and Mechanical Properties of Collagen Fibers in the Periodontium" Biomaterials 2007 28 (35): 5235-5245.
Hong et al.; "Tissue-engineered Rabbit Cranial Suture from Autologous Fibroblasts and BMP2," J Dent Res, 2004, pp. 751-756, vol. 83, No. 10.
Horiuchi et al.; "Identification and Characterization of a Novel Protein, Periostin, with Restricted Expression to Periosteum and Periodontal Ligament and Increased Expression by Transforming Growth Factor β" Journal of Bone and Mineral Research 1999 14(7):1239-1249.
Huang et al.; "Effect of Liposomes on Mineralization in Rat Osteoblast-Enriched Cultures" The Kaohsiung Journal of Medical Sciences 1999 15 (4). : 187-194 (Abstract only).
Huang et al.; "The Effect of Tetracycline Embedded Liposomes on the Mineralization of Rat Osteoblast-Enriched Cultures" The IADR/AADR/CADR 8 oth General Session 2002 Abstract.
Huang et al.; "A review on polymer nanofibers by electrospinning and their applications in nanocomposites," Composites Science and Technology, 2003, pp. 2223-2253, vol. 53.
Ierardi et al.; "Erythrocyte Ghost Cell-Alkaline Phosphatase: Construction and Characterization of a Vesicular System for Use in Biomineralization Studies" Biochimica et Biophysica Acta 2002 1567:183-192.
Jackson, I.T., Yavuzer, R.; "Hydroxyapatite Cement: An Alternative for Craniof acial Skeletal Contour Refinements" British Journal of Plastic Surgery 2000 53:24-29.
Kay, M.I., Young, R.A.; "Crystal Structure of Hydroxyapatite" Nature 1964 204:1050-1052 (Abstract only).
Kim et al.; "Extracellular Signal-Regulated Kinsases Regulate Dendritic Growth in Rat Sympathetic Neurons". The Journal of Neuroscience, Mar. 31, 2004. 24 (13):3304-3312.
Kirsch et al.; "The Roles of Annexins and Types II and X Collagen in Matrix Vesicle-Mediated Mineralization of Growth Plate Cartilage" The Journal of Biological Chemistry 2000 27 5 (45): 35577-35583.
Klein et al.; "Loss of Sprouty2 or Sprouty4 Leads to Development of Supernumerary Teeth by Modulating FGF Signaling, COST Action B23 Oral Facial Development and Regeneration," Joint Meeting of the Working Group 1-4 and the Management Committee, 2006, p. 13, vol. 47, No. 2.
Kontonasaki et al.; "Attachment and Proliferation of Human Periodontal Ligament Fibroblasts on Bioactive Glass Modified Ceramics" Journal of Oral Rehabilitation 2007 34:57-67.
Lalani et al.; "Spatial and Temporal Localization of FGF-2 and VEGF in Healing Tooth Extraction Sockets in a Rabbit Model," J. Oral Maxillofacial Surg., 2005, pp. 1500-1508, vol. 63.
Langer, R., Vacanti, J.P.; "Tissue Engineering" Science 1993 260:920-926.
Laurencin et al.; "Tissue Engineering: Orthopedic Applications" Annual Review of Biomedical Engineering 1999 1:19-46.
Li et al.; "Hydroxyapatite Coating Enhances Polyethylene Terephthalate Artificial Ligament Graft Osteointegration in the Bone Tunnel" International Orthopaedics 35:1561-1567(2011).
Liao et al.; "A Novel Bioactive Three-Dimensional β-Tricalcium Phosphate/Chitosan Scaffold for Periodontal Tissue Engineering" Journal of Materials Science: Materials in Medicine 2010 21:489-496.
Liao et al.; "Hierarchically Biomimetic Bone Scaffold Materials: Nano-HA/Collagen/PLA Composite" Journal of Biomedical Materials Research Part B: Applied Biomaterials 2004 69B:158-165.
Liao et al.; "Processing Nanoengineered Scaffolds through Electrospinning and Mineralization Suitable for Biomimetic Bone Tissue Engineering" Journal of the Mechanical Behavior of Biomedical Materials 2008 1:252-260.
Lovschall et al.; Pulp-capping with Recombinant Human Insulin-Like Growth Factor I (rhIGF-1) in Rat Molars, Adv. Dent Res., 2001, pp. 108-112, vol. 15.
Lynch et al.; "At Combination of platelet-derived and insulin-like growth factors enhances periodontal regeneration," Clin Periodont, 1989, pp. 545-548, vol. 16.
Ma et al.; "Grafting of Gelatin on Electrospun Poly (caprolactone) Nanofibers to Improve Endothelial Cell Spreading and Proliferation and to Control Cell Orientation" Tissue Engineering 2005 11 (7/8) :1149-1158.
Majeska, R.J., Wuthier, R.E.; "Studies on Matrix Vesicles Isolated from Chick Epiphyseal Cartilage" Biochimica et Biophysica Acta 1975 391:51-60.

(56) References Cited

OTHER PUBLICATIONS

Mao et al.; Craniofacial Tissue Engineering by Stem Cells, J. Dent Res., 2006, pp. 966-979, vol. 85, No. 11.
Mattuella et al.; Vascular Endothelial Growth Factor and Its Relationship With the Dental Pulp, JOE, 2007, pp. 524-530, vol. 33, No. 5.
Messersmith et al.; "Preparation of Calcium-Loaded Liposomes and Their Use in Calcium Phosphate Formation" Chemistry of Materials 1998 10:109-116.
Messersmith, P.B., Starke, S.; "Thermally Triggered Calcium Phosphate Formation from Calcium-Loaded Liposomes" Chemistry of Materials 1998 10:117-124.
Michel et al.; "Giant Liposome Microreactors for Controlled Production of Calcium Phosphate Crystals" Langmuir 2004 20:6127-6133.
Moioli et al.; "Sustained Release of TGFf33 from PLGA Microspheres and Its Effect on Early Osteogenic Differentiation of Human Mesenchymal Stem Cells," Tissue Engineering, 2006, pp. 537-546, vol. 12, No. 3.
Moreau et al.; "Sequential Biochemical and Mechanical Stimulation in the Development of Tissue-Engineered Ligaments" Tissue Engineering: Part A 14(7):1161-1172(2008).
Murphy et al.; "Sustained Release of Vascular Endothelial Growth Factor from Mineralized Poly(lactide-co-glycolide) Scaffolds for Tissue Engineering" Biomaterials 2000 21:2521-2527 (Exhibit 10).
Murphy, W.L., Messersmith, P.B.; "Compartmental Control of Mineral Formation: Adaptation of a Biomineralization Strategy for Biomedical Use" Polyhedron 2000 19: 357-363(Exhibit 11).
Nakamura et al.; "Temporal and Spatial Expression Profiles of BMP Receptors and Noggin during BMP-2-Induced Ectopic Bone Formation" Journal of Bone and Mineral Research 2003 18(10) :1854-1862(Exhibit 12).
Nakashima et al.; "The application of bone morphogenetic proteins to dental tissue engineering," Nat. Biotechnol., 2003, pp. 1025-1032, vol. 21, No. 9. (Exhibit 13).
Nakashima et al.; "The Application of Tissue Engineering to Regeneration of Pulp and Dentin in Endodontics," J Endod., 2005, pp. 711-718, vol. 31, No. 10.
Osborn, J.F., Newesely, H.; "The Material Science of Calcium Phosphate Ceramics" Biomaterials 1980 1:108-111.
Park et al.; "Delivery of TGF-J31 and chondrocytes via injectable, biodegradable hydrogels for cartilage tissue engineering applications," Biomaterials, 2005, pp. 7095-7103, vol. 26.
Reddy, G.K., Enwemeka, C.S.; "A Simplified Method for the Analysis of Hydroxyproline in Biological Tissues" Clinical Biochemistry 1996 29 (3) :225-229.
Register et al.; "Roles of Alkaline Phosphatase and Labile Internal Mineral in Matrix Vesicle-Mediated Calcification" The Journal of Biological Chemistry 1986 261(20):9354-9360.
Reneker, D.R., Chun, I.; "Nanometre Diameter Fibres of Polymer, Produced by Electrospinning" Nanotechnology 1996 7:216-223.
Rodan et al.; "Characterization of a Human Osteosarcoma Cell Line (Saos-2) with Osteoblastic Properties" Cancer Research 1987 47:4961-4966.
Salvi et al.; "Clinical evaluation of root filled teeth restored with or without post-and-core systems in a specialist practice setting," Int Endod J., 2007, pp. 209-215, vol. 40, No. 3.
Sarig-Nadir et al.; "Laser Photoablation of Guidance Microchannels into Hydrogels Directs Cell Growth in Three Dimensions," Biophysical Journal 96(11 ), pp. 4 743-4 752 (2009).
Sarraf et al.; "In vitro Mesenchymal Stem Cell Differentiation After Mechanical Stimulation" Cell Proliferation 44:99-108(2011).
Seo et al.; "Investigation of Multipotent Postnatal Stem Cells from Human Periodontal Ligament" Lancet 2004 364:149-155.
Shao et al.; "Designing a Three-Dimensional Expanded Polytetrafluoroethylene-Poly(lactic-co-glyconic acid) Scaffold for Tissue Engineering" Artificial Organs 33(4):309-317(2009).
Shay; "Infectious Complications of Dental and Periodontal Diseases in the Elderly Population," Clin Infect. Dis., 2002, pp. 1215-1223, vol. 34, No. 9.
Shor et al.; "Fabrication of Three-Dimensional Polycaprolactone/Hydroxyapatite Tissue Scaffolds and Osteoblast-Scaffold Interactions In Vitro" Biomaterials 2007 28:5291-5297.
Spoerke et al.; "A Bioactive Titanium Foam Scaffold for Bone Repair" Acta Biomaterialia 2005 1(5):523-533 (Abstract only).
Stemgent; Product Specification Sheet, Stemfactor TM FGF-basic, Human Recombinant, 2012, 2 pages.
Stosich et al.; "Adipose Tissue Engineering from Human Adult Stem Cells: Clinical Implications in Plastic and Reconstructive Surgeries," Plast. Reconstr. Surg., 2007, pp. 71-83, vol. 119.
Tsai, J. and Kam, L.; "Rigidity-Dependent Cross Talk between Intgrin and Cadherin Signaling" Biophysical Journal 2009 96:L39-L41.
Vaquette et al. "Aligned Poly(L-lactic-co-ecaprolactone) Electrospun Microfibers and Knitted Structure: A Novel Composite Scaffold for Ligament Tissue Engineering" Journal of Biomedical Materials Research Part A 94A:1270-1282 (2010).
Varghese et al.; "Chondroitin Sulfate Based Niches for Chondrogenic Differentiation of Mesenchymal Stem Cells" Matrix Biology 27:12-21(2008).
Venugopal et al.; "Nanobioengineered Electrospun Composite Nanofibers and Osteoblasts for Bone Regeneration" Artificial Organs 2008 32 (5): 388-397.
Verret et al.; "Hydroxyapatite Cement in Craniofacial Reconstruction" Otolaryngology—Head and Neck Surgery 2005 133:897-899.
Vunjak-Noyakovic et al.; "Tissue Engineering of Ligaments" Annual Review of Biomedical Engineering 2004 6:131-156.
Wang et al.; "Effects of BMP-7 on Mouse Tooth Mesenchyme and Chick Mandibular Mesenchyme, Developmental Dynamics," 1999, oo. 320-335, vol. 216, No. 4/5.
Wang et al.; "Multifunctional Chondroitin Sulphate for Cartilage Tissue-Biomaterial Integration" Nature Materials 6:385-392(2007).
Weissman et al.; "Hydroxyapatite Cement to Repair Skull Base Defects: Radiologic Appearance" American Journal of Neuroradiology 1996 17:1569-1574.
Wu, W., Nancollas, G.H.; "Kinetics of Heterogeneous Nucleation of Calcium Phosphates on Anatase and Rutile Surfaces" "Journal of Colloid and Interface Science 1998 199:206-211."
PCT International Search Report dated Jun. 17, 2008 in connection with PCT Application No. PCT/US2007/025127, international filing date Dec. 6, 2007.
PCT International Search Report dated Mar. 3, 2009 in connection with PCT Application No. PCT/US2008/007485, international filing date Jun. 11, 2008.
PCT International Search Report dated Oct. 14, 2008 in connection with PCT Application No. PCT/US2008/07357, international filing date Jun. 11, 2008.
Written Opinion of the International Search Authority dated Feb. 14, 2006, in connection with PCT/US2005/007129, international filing date Mar. 4, 2005.
Written Opinion of the International Search Authority dated Feb. 17, 2010, in connection with PCT/US2009/06453, international filing date Dec. 8, 2009.
Written Opinion of the International Search Authority dated Jan. 6, 2009, in connection with PCT/US2008/010985, international filing date Sep. 22, 2008.
Written Opinion of the International Search Authority dated Jan. 2, 2009, in connection with PCT/US2008/007323, international filing date Jun. 11, 2008.
Written Opinion of the International Search Authority dated Jul. 14, 2008 in connection with International Application No. PCT/US05/07010, international filing date Mar. 4, 2005.
Written Opinion of the International Search Authority dated Jun. 17, 2008 in connection with PCT/US2007/025127, international filing date Mar. 4, 2005.
Written Opinion of the International Search Authority dated Oct. 14, 2008 in connection with PCT/US2008/07357, international filing date Jun. 11, 2008.
Xie J, et al. (2006) "Mechano-active scaffold design based on microporous poly(L-lactide-co-epsilon-caprolactone) . . . " Tissue Eng. 12(3):449-458.

(56) References Cited

OTHER PUBLICATIONS

Yoshimoto et al. (2003) "A biodegradable nanofiber scaffold by electrospinning and its potential for bone tissue engineering." Biomaterials 24: 2077-2082.
Kwei, et al. (2010) "Nanofiber Alignment Regulates Adhesion and . . . " Bioengineering Conference—Proceedings of the 2010 IEEE 36th Annual Northeast. Mar. 26-28, 2010, pp. 1-2.
Leong, et al. (2006) "Polymer-Ceramic Composite Scaffold Induces Osteogenic . . . " Proceedings of the 28th IEEE EMBS Annual International Conference. Aug. 30-Sep. 3, pp. 2651-26.
Thibault, et al. (2010) "Osteogenic Differentation of Mesenchymal Stem Cells on . . . " Tissue Engineering: Part A. 16(2):431-440.
Yin et al. (2009) "The Regulation of Tendon Stem Cell Differentation by the Alignment of Nanofibers" Biomaterials. 31:2163-2175.

* cited by examiner

Figure 1
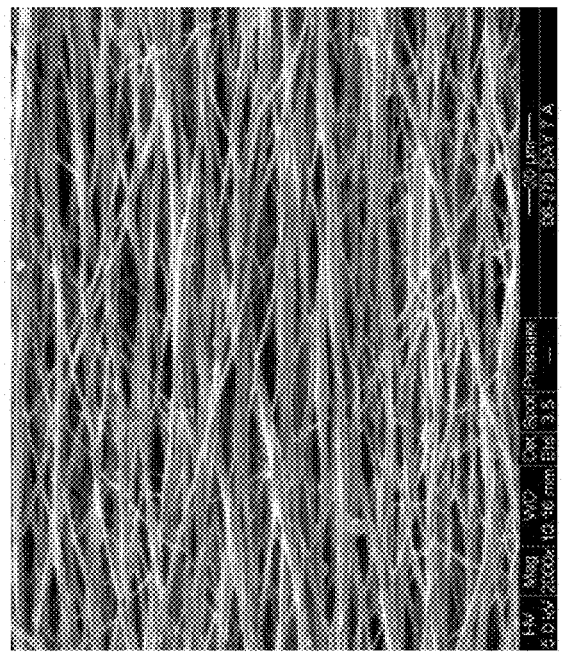
Figure 1B
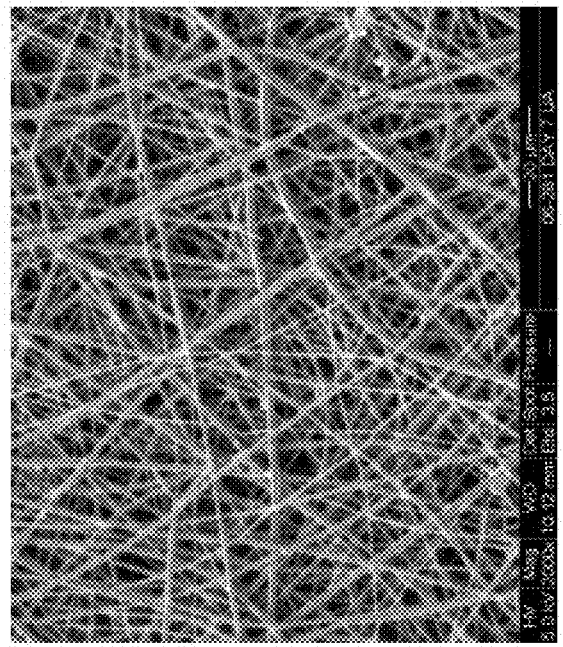
Figure 1A

FIGURE 5A
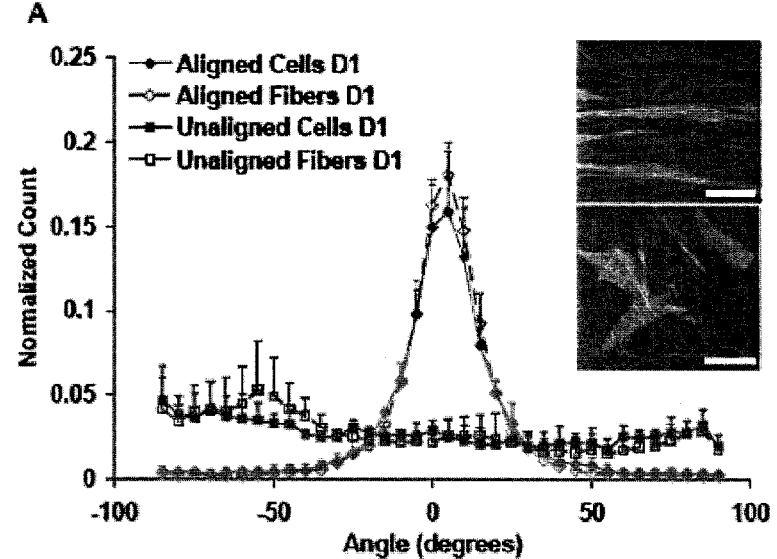
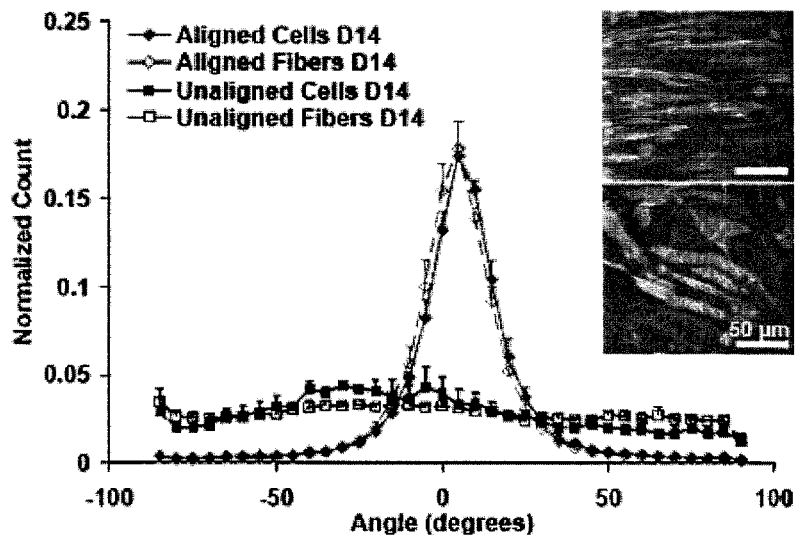

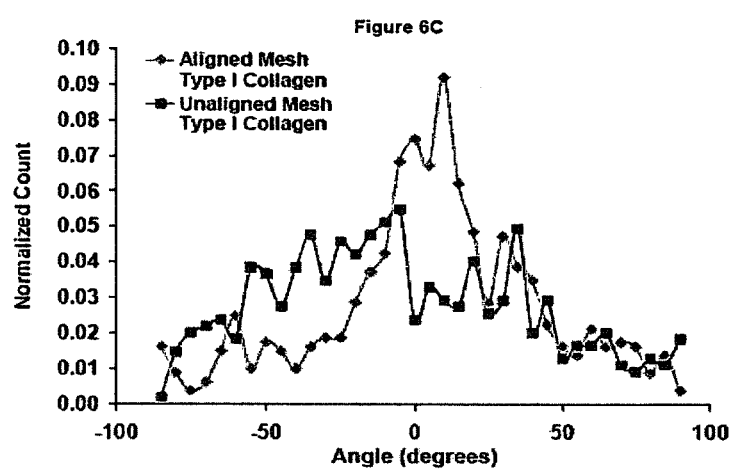

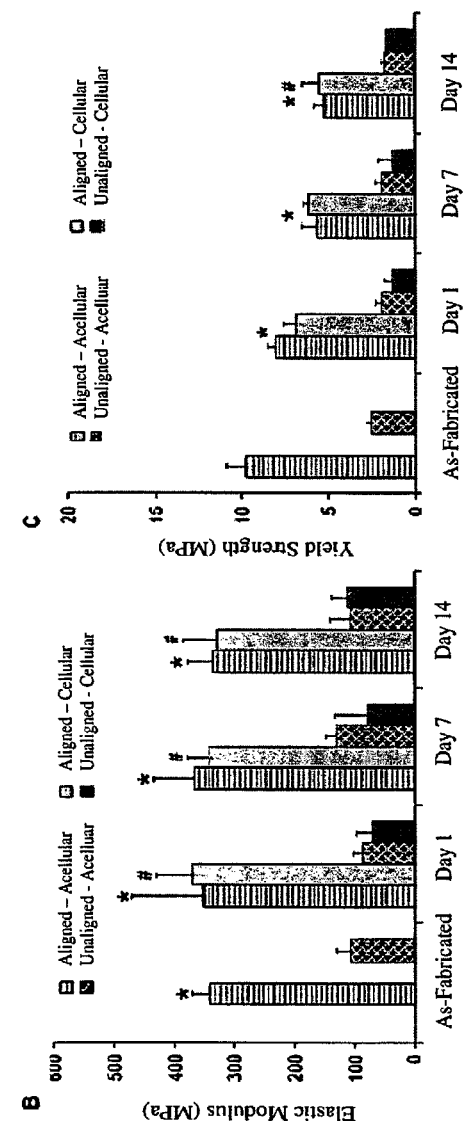

FIGURE 9
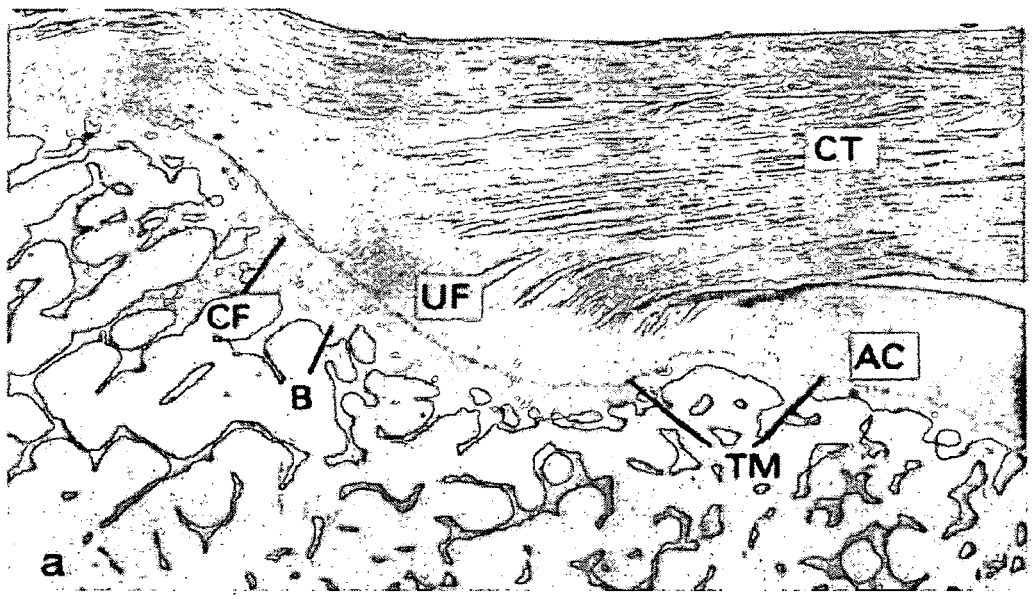
Figure 9A
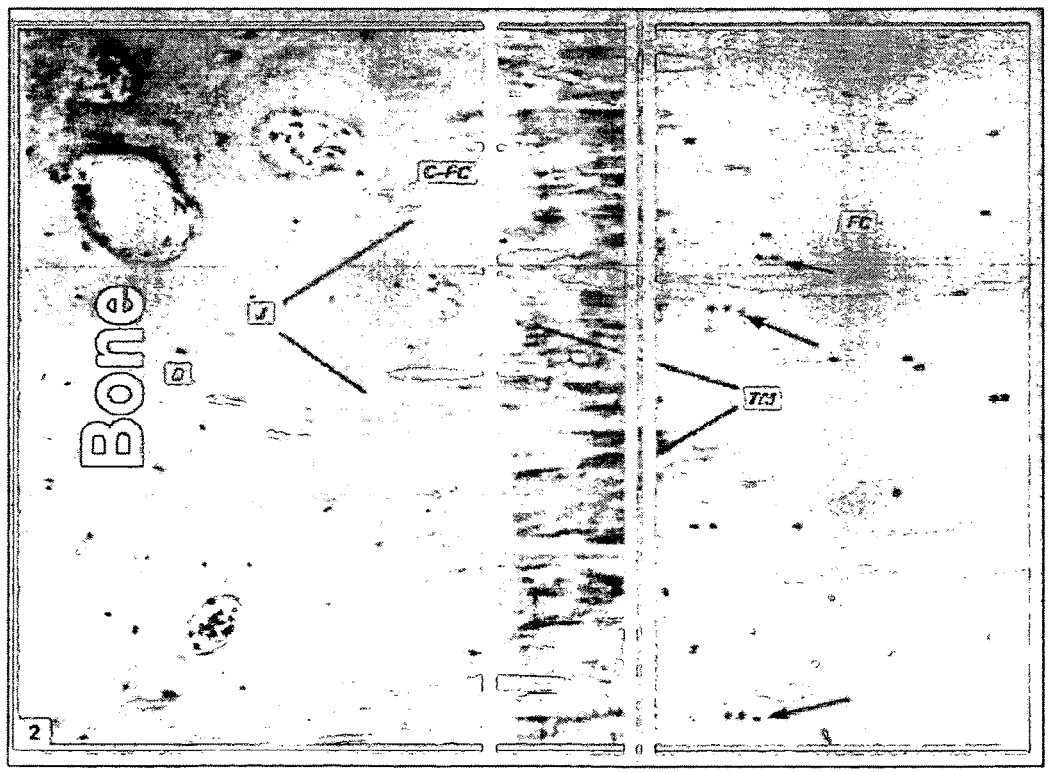
Figure 9B

FIGURE 12
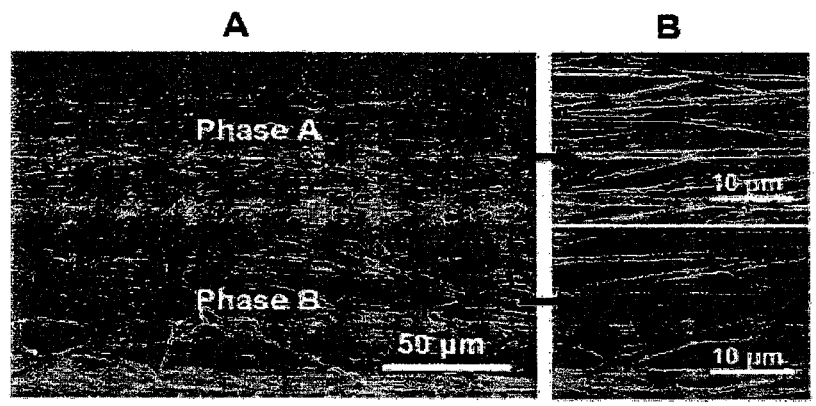
Figure 12A        Figure 12B
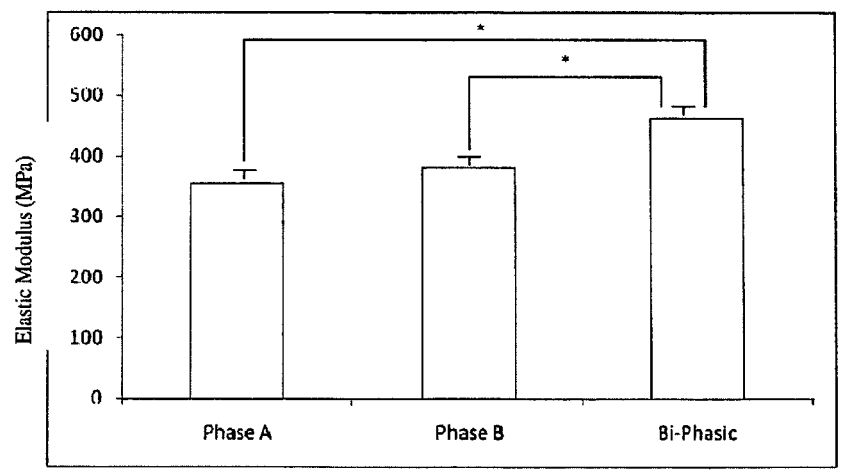
Figure 12C

FIGURE 14
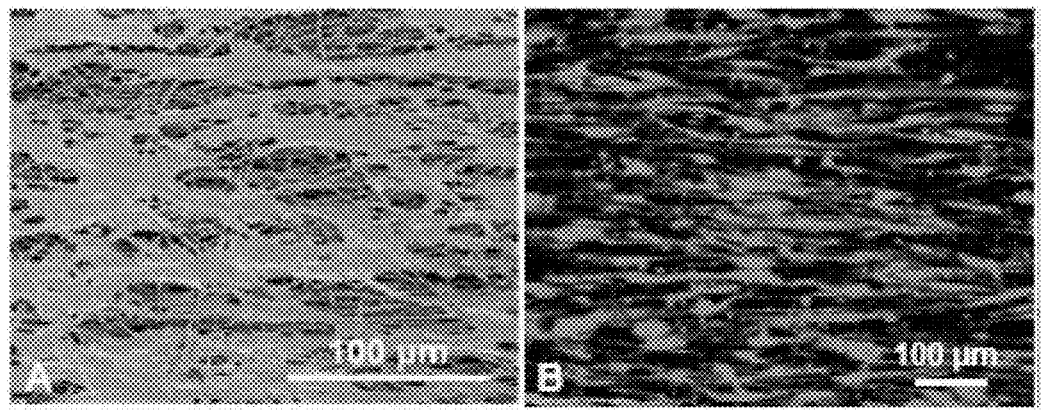
Figure 14A                    Figure 14B
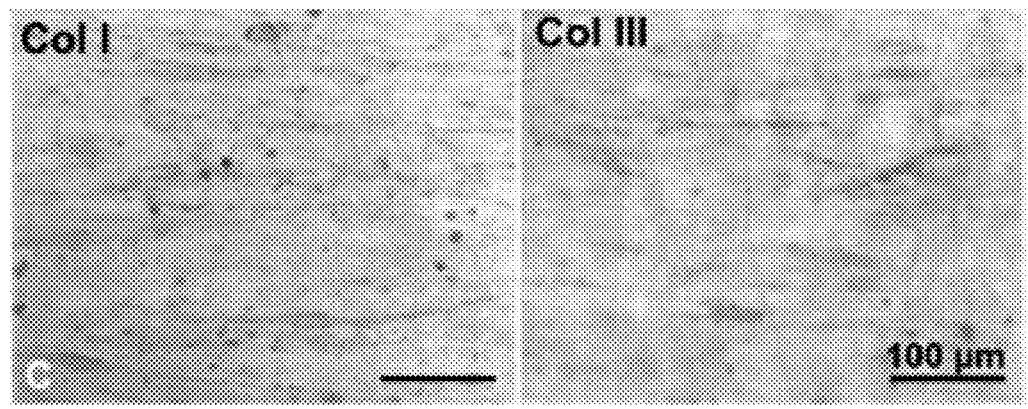
Figure 14C

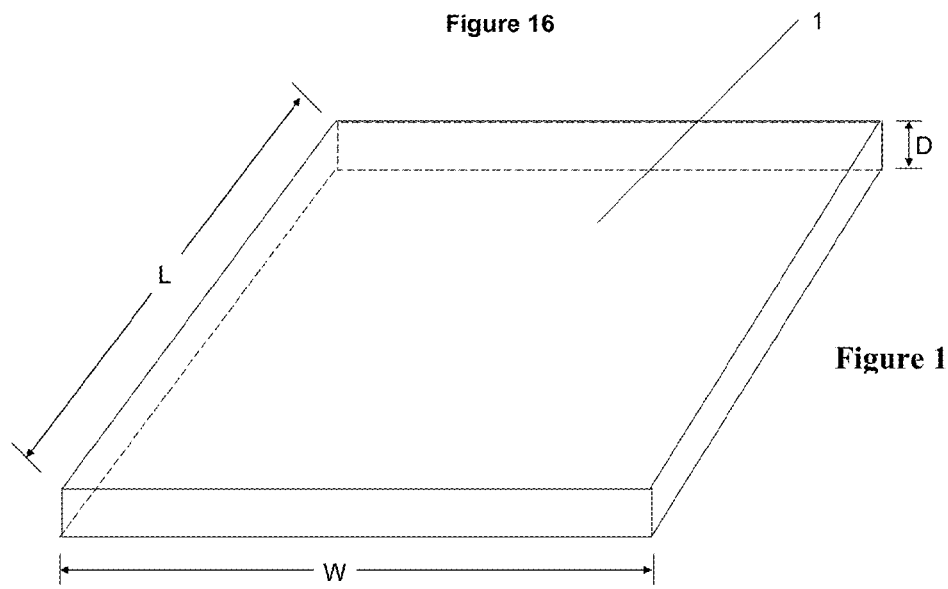
Figure 16
Figure 16A
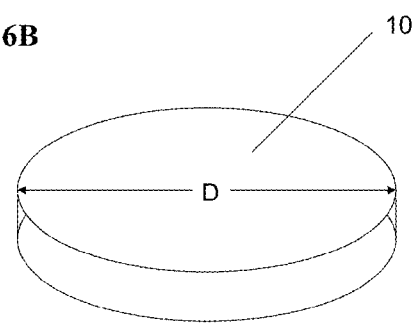
Figure 16B

Fiber Orientation and Alignment

FIGURE 21
Figure 21A
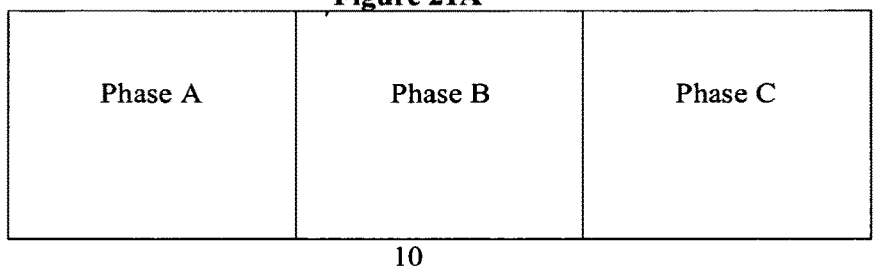
10
Figure 21B
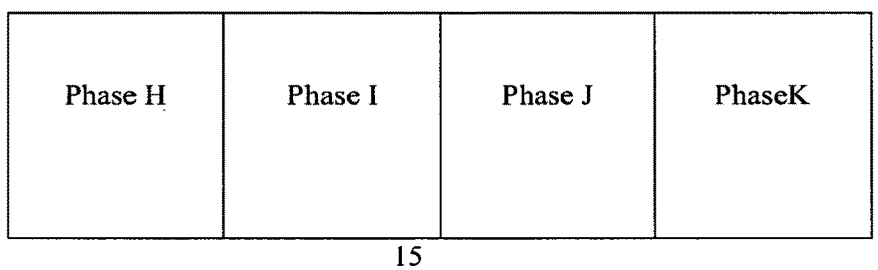
15
Figure 21C
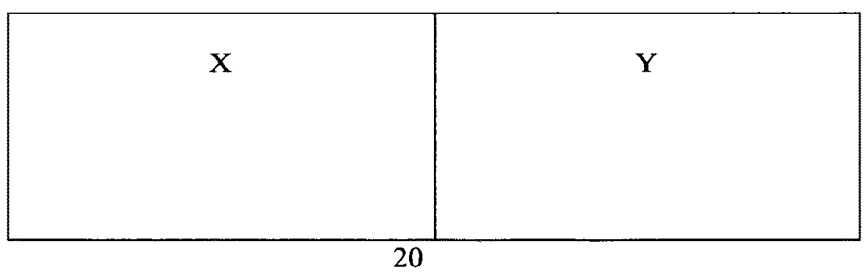
20

FIGURE 22
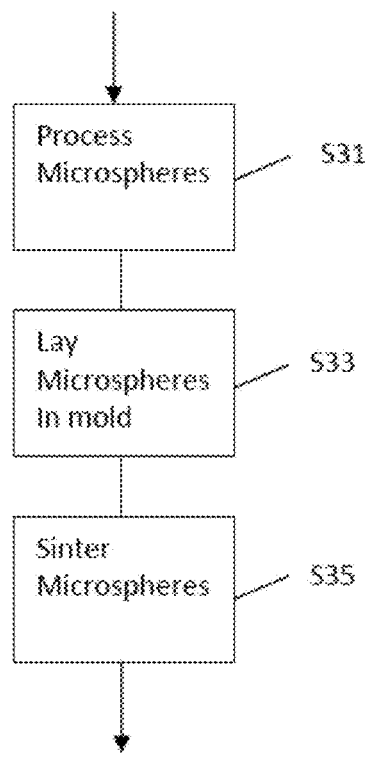
Figure 22A
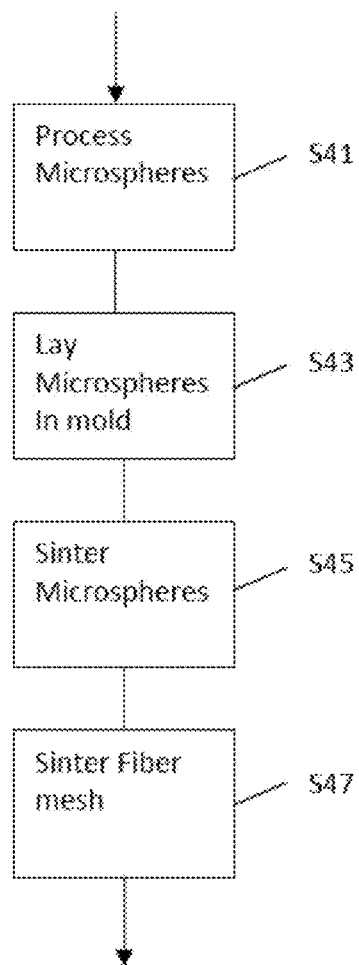
Figure 22B

FIGURE 23
FIG. 23A
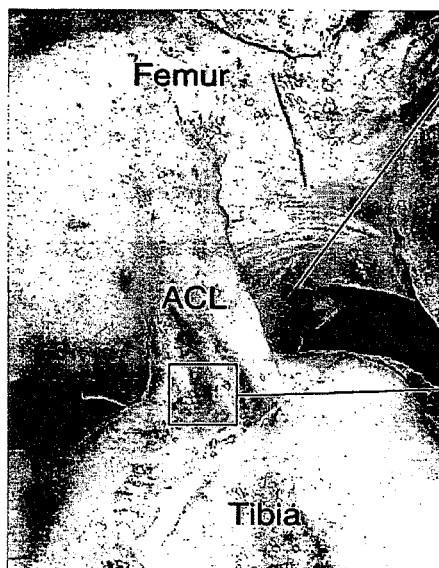
FIG. 23B
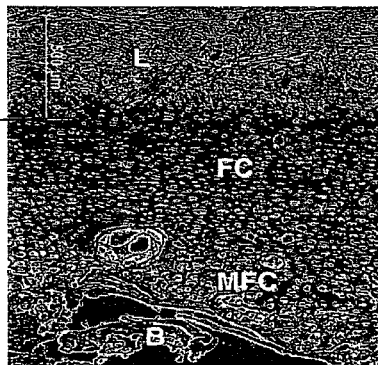
FIG. 23C

FIGURE 24
Figure 24A
Figure 24B

FIGURE 25
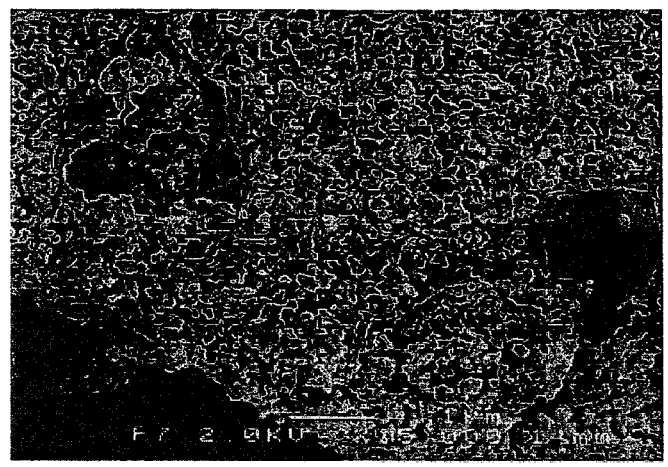
Figure 25A
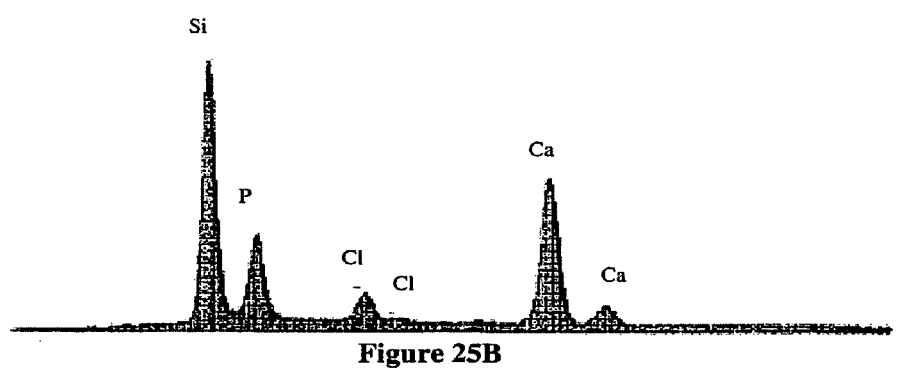
Figure 25B

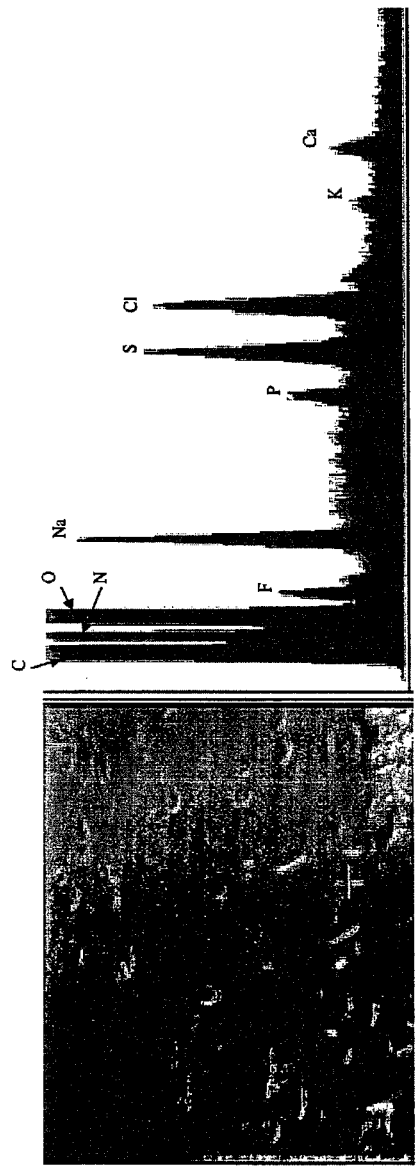

FIGURE 30
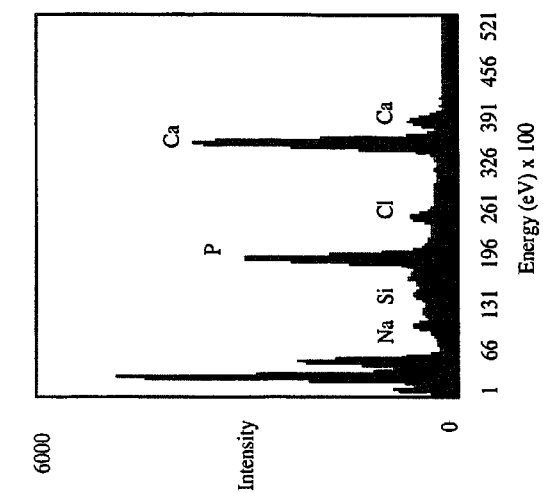
Figure 30B
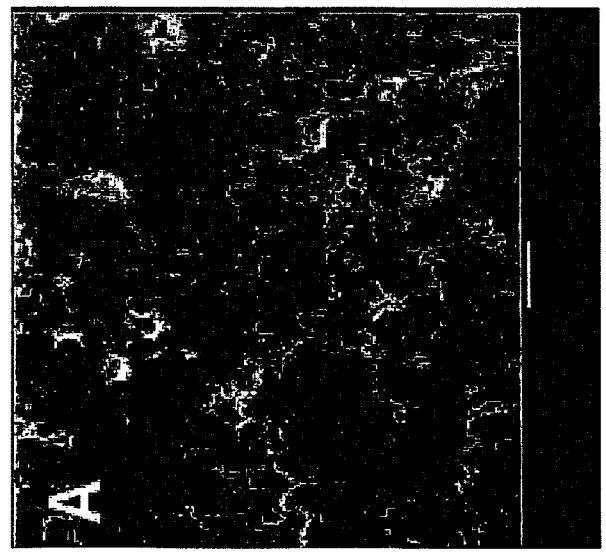
Figure 30A

FIGURE 33

FIGURE 37
Figure 37A
Figure 37B
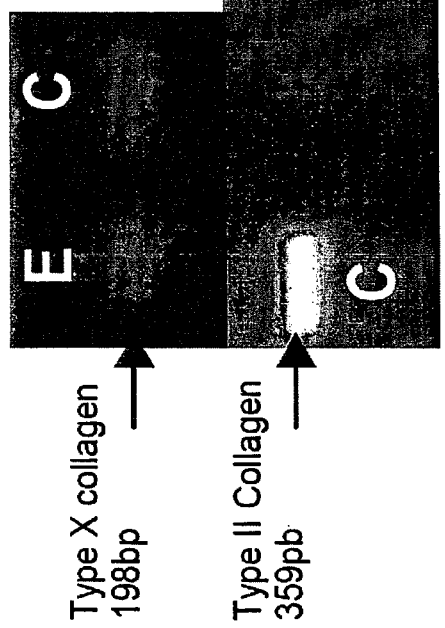
Type X collagen 198bp
Type II Collagen 359pb

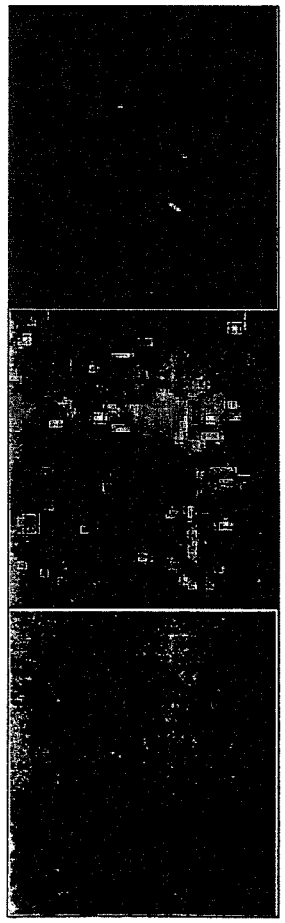
FIGURE 42
Figure 42A  Figure 42B  Figure 42C  Figure 42D  Figure 42E

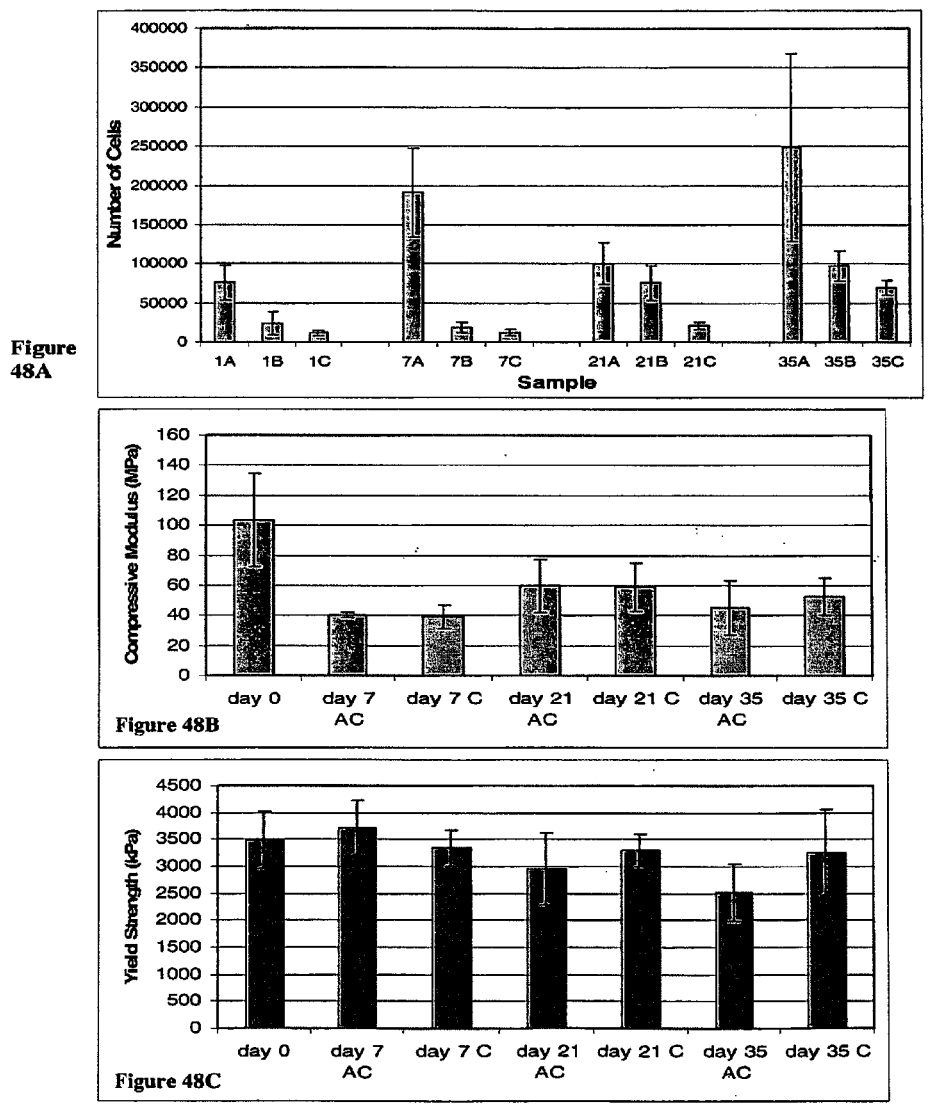

Figure 51A
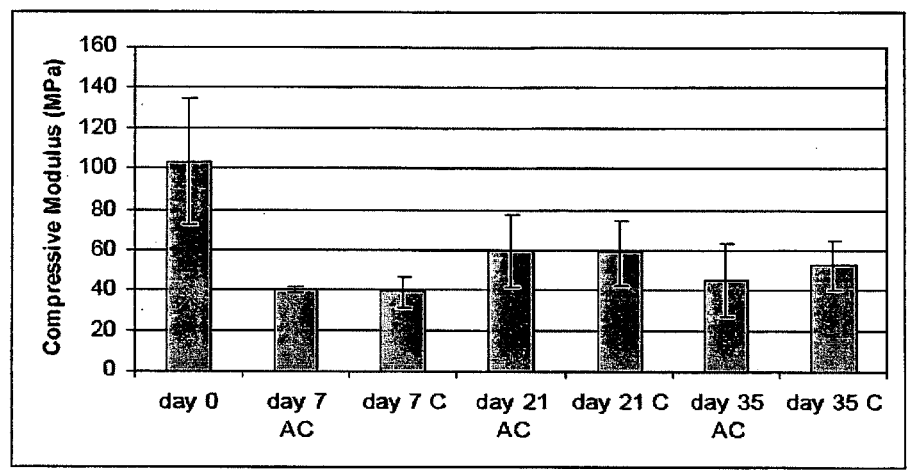
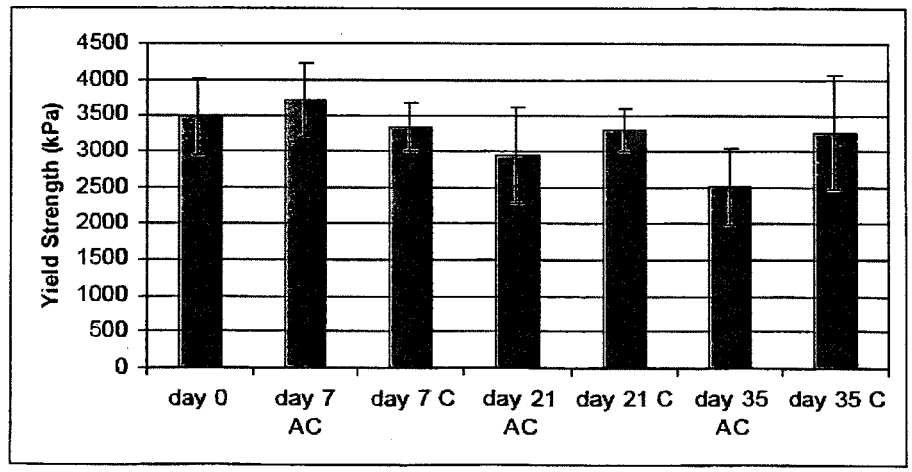
Figure 51B

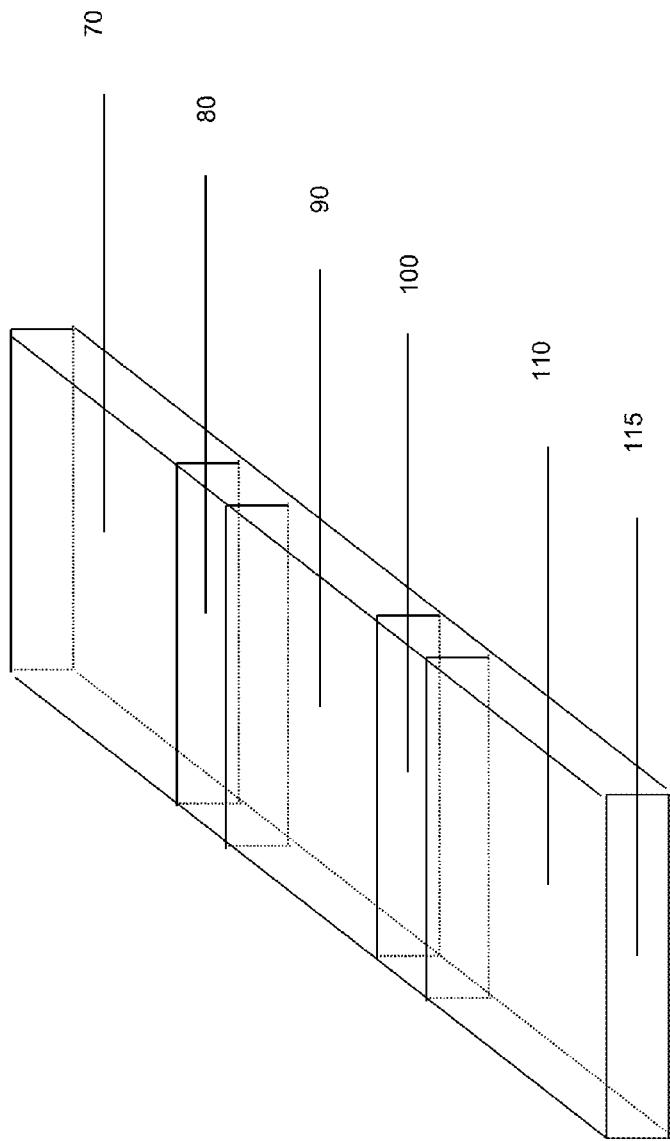

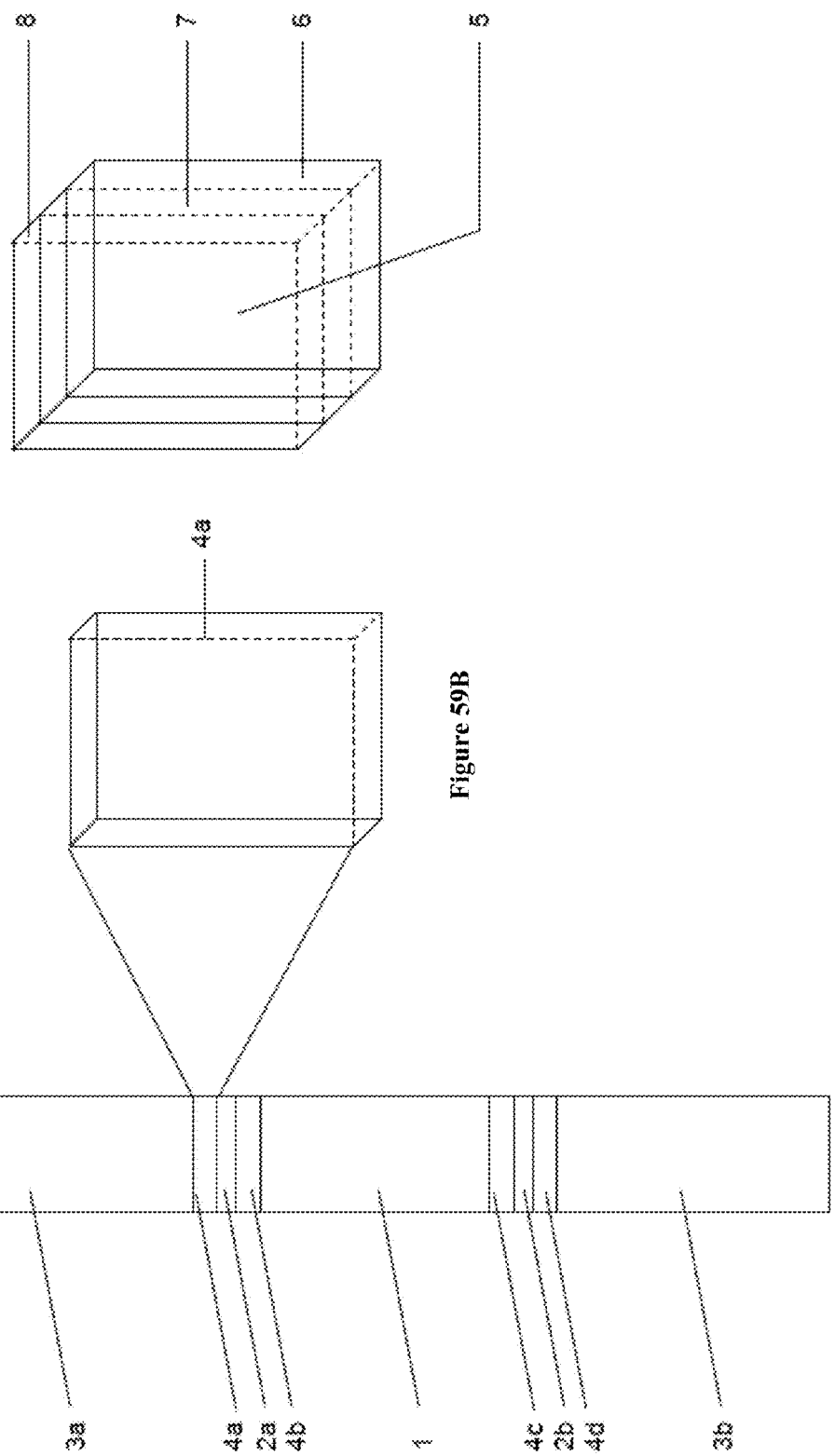

Schematic of Triphasic Scaffold with
Degraded Cell Barrier Inserted Between the Adjacent Phases Schematic of Triphasic Scaffold Coupled to a Synthetic Graft for a Ligament Schematic of Scaffold-Mesh Apparatus
Coupled with a Soft Tissue Graft

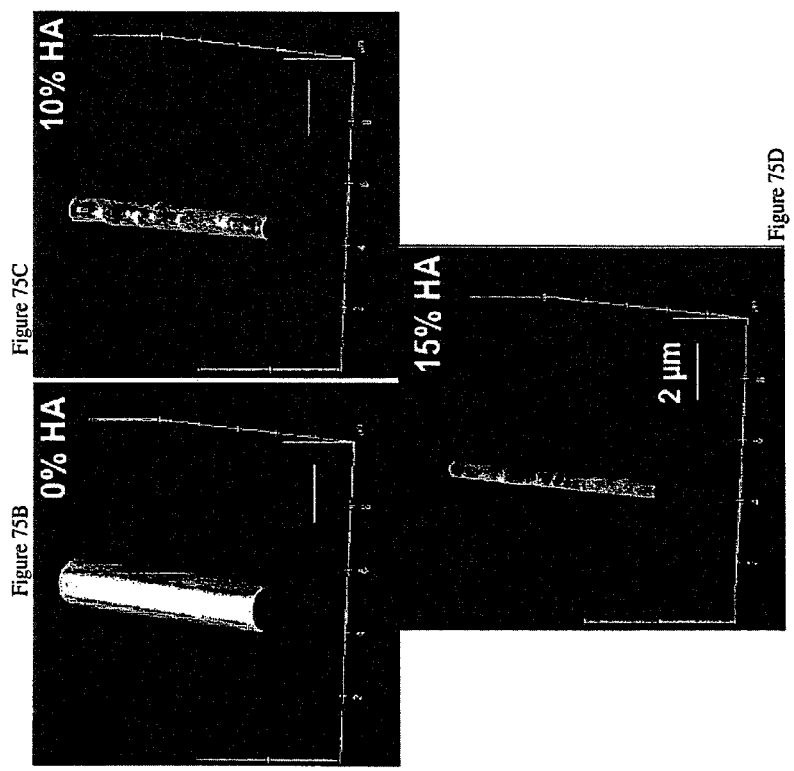

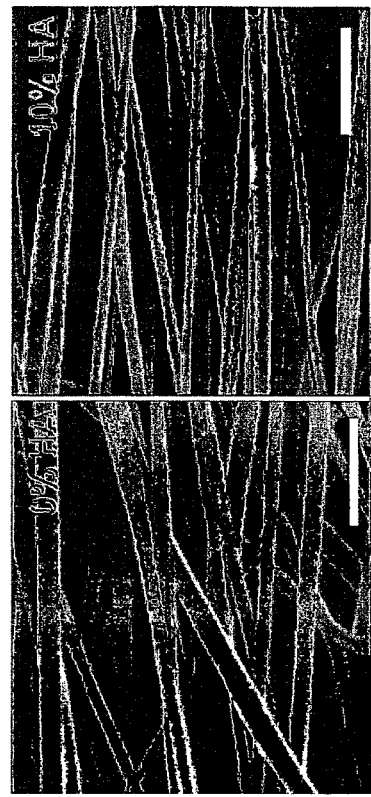
Figure 76B
Figure 76C
Figure 76D

Alcian Blue
20x
bar = 100 um

BIOMIMMETIC NANOFIBER SCAFFOLD FOR SOFT TISSUE AND SOFT TISSUE-TO-BONE REPAIR, AUGMENTATION AND REPLACEMENT

This application is a continuation of U.S. Ser. No. 12/806,912, filed Aug. 24, 2010, now allowed, which is a divisional of U.S. Ser. No. 12/583,072, filed Aug. 12, 2009, now U.S. Pat. No. 8,753,391, issued Jun. 17, 2014, which is a continuation-in-part of and claims the benefit of (a) PCT International Application No. PCT/US2008/001889, filed Feb. 12, 2008 which in turn claimed priority of U.S. Provisional Applications Nos. 60/901,047 and 60/905,649, filed Feb. 12, 2007 and Mar. 7, 2007, respectively; (b) PCT International Application No. PCT/US2008/007323, filed Jun. 11, 2008 which in turn claimed priority of U.S. Provisional Application No. 60/934,198, filed Jun. 11, 2007 and (c) PCT International Application No. PCT/US2008/007357, filed Jun. 11, 2008 which in turn claimed priority of U.S. Provisional Application No. 60/934,182, filed Jun. 11, 2007. This application also claims the benefit of (d) U.S. Provisional Application No. 61/215,085, filed May 1, 2009. The entire contents of each of (a) through (d) are hereby incorporated by reference herein.

This invention was made with government support under NSF Graduate Fellowship (GK-12 0338329) awarded by the National Science Foundation and Grant Numbers R21 AR052402-01A1, R01 AR056459-01 and R21 AR055280-01 awarded by the National Institutes of Health. The government may have certain rights in the invention.

BACKGROUND

Throughout this application, certain publications are referenced. Full citations for these publications, as well as additional related references, may be found immediately preceding the claims. The disclosures of these publications are hereby incorporated by reference into this application in order to more fully describe the state of the art as of the date of the invention described and claimed herein.

This application relates to musculoskeletal tissue engineering. For example, a scaffold apparatus is discussed below which can serve as a functional interface between multiple tissue types. Methods for preparing a multi-phase scaffold are also discussed. Some exemplary embodiments which include a soft tissue-bone interface are discussed.

As examples of soft tissue-bone interface, the human rotator cuff and anterior cruciate ligament (ACL) are described below. The rotator cuff, the ACL and the ACL-bone interface are used in the following discussion as examples to aid in understanding the description of the methods and apparatuses of this application. This discussion, however, is not intended to, and should not be construed to, limit the claims of this application.

The Rotator Cuff

The rotator cuff consists of a group of four muscles and tendons, including the supraspinatus, infraspinatus, teres minor, and subscapularis, which function in synchrony to stabilize the glenohumeral joint as well as to actively control shoulder kinematics. The supraspinatus tendon inserts into the humeral head via a direct insertion exhibiting region-dependent matrix heterogeneity and mineral content.

Four distinct yet continuous tissue regions are observed at the tendon-bone junction (FIG. 9A): tendon proper, non-mineralized fibrocartilage, mineralized fibrocartilage and bone (Benjamin, 1986; Benjamin, 2002; Woo, 1988). The tendon proper consists of fibroblasts found between aligned collagen fibers in a matrix rich in collagen I, with small amounts of collagen III and proteoglycans (Blevins, 1997). The non-mineralized fibrocartilage region is composed of fibrochondrocytes in a matrix of collagen I, II, and III with fibers oriented perpendicular to the calcified interface region (Kumagai, 1994). The mineralized fibrocartilage region consists of hypertrophic fibrochondrocytes within a matrix of collagen I and II (Kumagai, 1994) as well as collagen X (Thomopoulos, 2003). The last region of the insertion site is bone which consists of osteoblasts, osteoclasts, and osteocytes in a mineralized matrix rich in type I collagen. This controlled matrix heterogeneity exhibited by the tendon-bone interface serves to minimize stress concentrations and to mediate load transfer between two distinct tissue types (Thomopoulos, 2003; woo, 1988). Due to its functional significance, interface regeneration is a pre-requisite for biological fixation.

Rotator cuff tears are among the most common injuries afflicting the shoulder, with greater than 75,000 repair procedures performed annually in the United States alone (Vitale, 2007). Clinical intervention is required because injuries to the rotator cuff do not heal, largely due to the complex anatomy noted above and the extended range of motion of the shoulder joint, as well as the relative weakening and hypovascularization of the cuff tendons (Codman, 1934; Yamanaka, 1994; Dejardin, 2001). Moreover, chronic degeneration increases both the frequency and size of cuff tears with age (Tempelhof, 1999) and is considered the main contributing factor in the pathogenesis of rotator cuff tendon tears (Dejardin, 2001; Soslowsky, 2000). Early primary anatomic repair followed by carefully controlled rehabilitation is currently the treatment of choice for symptomatic rotator cuff tears (Dejardin, 2001).

Rotator cuff repair has evolved from traditional open repair to "mini-open" to primarily arthroscopic (Gartsman, 2001; Galatz, 2004; Willaims, 2004; Mazzocca, 2005; Cole 2007). This transition has occurred due to advances in surgical techniques and fixation methods, with the current technique being a double row "suture-bridge" technique which simulates the compression afforded by transosseous sutures previously used in open and mini-open repairs (Park, 2007). These methods have been shown to improve mechanical strength and graft stability (Park, 2005). The focus in the field now centers on how to address the challenge of achieving functional rotator cuff healing and/or augmentation, which is essential for long term clinical success.

Currently, a significant demand exists for a functional tendon grafting system which can augment and promote rotator cuff healing post surgical repair, due to the relatively high failure rates associated with current repair procedures as well as the clinical need to treat large tears and chronic degeneration of the rotator cuff tendons. For example, failure rates as high as 90% have been reported after primary repair of chronic rotator cuff injuries (Galatz, 2004), generally attributed to factors such as osteoporotic bone, degenerative and poorly vascularized tendons, severe tendon weakening, muscle atrophy, and size of the original defect (Gazielly, 1994; Gartsman, 1997; Mansat, 1997; Rokito, 1996; Romeo, 1999). Moreover, the primary repair of chronic degenerative cuff injuries often results in excessive tension on the cuff tissues and at the repair site (Dejardin, 2001; DeOrio, 1984; Gerber, 1999). To improve healing, synthetic grafts (Post, 1985; Ozaki, 1986) have been designed to reconstruct large rotator cuff defects. See also, e.g., U.S. Pat. No. 7,112,417. However, these devices are suboptimal due to concerns of biocompatibility as well as their inability to meet the functional demand of the native tendon.

Recently, biological matrices such as acellularized allogeneic and xenogeneic extracellular matrix scaffolds have emerged as promising grafts for rotator cuff repair and augmentation (Dejardin, 2001; Schlpegel, 2006). Both collagen-rich dermis and small intestinal submucosa (SIS) (Badylak, 2002) have been marketed commercially as graft patches for reinforcing soft tissue repair following rotator cuff surgery (Derwin, 2006; Lannotti, 2006). See also, e.g., U.S. Pat. Nos. 6,638,312 and 7,160,333. SIS is particularly attractive as it exhibits a biomimetic, collagen nanofiber-based architecture and alignment, thus it can be readily remodeled by host cells while encouraging angiogenesis and neo-collagen production (Badylak, 2002).

Highly promising results have been reported for SIS in several animal models (Dejardin, 2001; Schlegel, 2006), but unfortunately suboptimal outcomes were observed in human trials (Lannotti, 2006; Sclamberg, 2004), in which augmentation with SIS did not improve the rate of tendon healing or clinical outcome scores. Similar outcomes have been reported for other biological grafts used in rotator cuff repair (Sclamberg, 2004; Coons, 2006).

The suboptimal results of biologically-derived grafts may be attributed to mismatch in mechanical properties and the rapid matrix remodeling experienced in the physiologically demanding and often diseased shoulder joint. Utilizing a canine model, Derwin et al. (Derwin, 2006) performed a systematic comparison of the biomechanical properties of commercially available extracellular matrices for rotator cuff augmentation. A mismatch in mechanical properties with the canine infraspinatus tendon was observed for all types of extracellular matrix tested.

Moreover, it has been reported that the mechanical properties of SIS decreased as resorption occurred prematurely (Derwin, 2006). Thus the mismatch in the kinetics of graft remodeling and neo-collagen formation compromised the clinical outcome. Therefore, the debilitating effect of rotator cuff tears coupled with the high incidence of failure associated with existing graft choices emphasize the clinical need for functional rotator graft augmentation solutions.

The Anterior Cruciate Ligament (ACL)

The ACL consists of a band of regularly oriented, dense connective tissue that spans the junction between the femur and tibia. It participates in knee motion control and acts as a joint stabilizer, serving as the primary restraint to anterior tibial translation. The natural ACL-bone interface consists of three regions: ligament, fibrocartilage (non-mineralized and mineralized) and bone. The natural ligament to bone interface is arranged linearly from ligament to fibrocartilage and to bone. The transition results in varying cellular, chemical, and mechanical properties across the interface, and acts to minimize stress concentrations from soft tissue to bone.

The ACL is the most often injured ligament of the knee. Due to its inherently poor healing potential and limited vascularization, ACL ruptures do not heal effectively upon injury, and surgical intervention is typically needed to restore normal function to the knee.

Clinically, autogenous grafts based on either bone-patellar tendon-bone (BPTB) or hamstring-tendon (HST) grafts are often a preferred grafting system for ACL reconstruction, primarily due to a lack of alternative grafting solutions. Current ACL grafts are limited by donor site morbidity, tendonitis and arthritis. Synthetic grafts may exhibit good short term results but encounter clinical failure in long-term follow-ups, since they are unable to duplicate the mechanical strength and structural properties of human ACL tissue. ACL tears and ruptures are currently commonly repaired using semitendinosus grafts. Although semitendinosus autografts are superior, they often fail at the insertion site between the graft and the bone tunnel. One of the major causes of failure in this type of reconstruction grafts is its inability to regenerate the soft-tissue to bone interface.

Despite their distinct advantages over synthetic substitutes, autogenous grafts have a relatively high failure rate. A primary cause for the high failure rate is the lack of consistent graft integration with the subchondral bone within bone tunnels. The site of graft contact in femoral or tibial tunnels represents the weakest point mechanically in the early post-operative healing period. Therefore, success of ACL reconstructive surgery depends heavily on the extent of graft integration with bone.

ACL reconstruction based on autografts often results in loss of functional strength from an initial implantation time, followed by a gradual increase in strength that does not typically reach the original magnitude. Despite its clinical success, long term performance of autogenous ligament substitutes is dependent on a variety of factors, including structural and material properties of the graft, initial graft tension, intrarticular position of the graft, as well as fixation of the graft. These grafts typically do not achieve normal restoration of ACL morphology and knee stability.

There is often a lack of graft integration with host tissue, in particular at bony tunnels, which contributes to suboptimal clinical outcome of these grafts. The fixation sites at the tibial and femoral tunnels, instead of the isolated strength of the graft material, have been identified as mechanically weak points in the reconstructed ACL. Poor graft integration may lead to enlargement of the bone tunnels, and in turn may compromise the long term stability of the graft.

Increased emphasis has been placed on graft fixation, as post surgery rehabilitation protocols require the immediate ability to exercise full range of motion, reestablish neuromuscular function and weight bearing. During ACL reconstruction, the bone-patellar tendon-bone or hamstring-tendon graft is fixed into the tibial and femoral tunnels using a variety of fixation techniques. Fixation devices include, for example, staples, screw and washer, press fit EndoButton® devices, and interference screws. In many instances, EndoButton® devices or Mitek® Anchor devices are utilized for fixation of femoral insertions. Staples, interference screws, or interference screws combined with washers can be used to fix the graft to the tibial region.

Recently, interference screws have emerged as a standard device for graft fixation. The interference screw, about 9 mm in diameter and at least 20 mm in length, is used routinely to secure tendon to bone and bone to bone in ligament reconstruction. Surgically, the knee is flexed and the screw is inserted from the para-patellar incision into the tibial socket, and the tibial screw is inserted just underneath the joint surface. After tension is applied to the femoral graft and the knee is fully flexed, the femoral tunnel screw is inserted. This procedure has been reported to result in stiffness and fixation strength levels which are adequate for daily activities and progressive rehabilitation programs.

While the use of interference screws have improved the fixation of ACL grafts, mechanical considerations and biomaterial-related issues associated with existing screw systems have limited the long term functionality of the ligament substitutes. Screw-related laceration of either the ligament substitute or bone plug suture has been reported. In some cases, tibial screw removal was necessary to reduce the pain suffered by the patient. Stress relaxation, distortion of magnetic resonance imaging, and corrosion of metallic screws have provided motivation for development of biodegradable screws based on poly-α-hydroxy acids. While lower incidence of graft laceration was reported for biodegradable screws, the highest interference fixation strength of the grafts to bone is reported to be 475 N, which is significantly lower than the attachment strength of ACL to bone. When tendon-to-bone fixation with polylactic acid-based interference screws was examined in a sheep model, intraligamentous failure was reported by 6 weeks. In addition, fixation strength is dependent on quality of bone (mineral density) and bone compression.

Two insertion zones can be found in the ACL, one at the femoral end and another located at the tibial attachment site. The ACL can attach to mineralized tissue through insertion of collagen fibrils, and there exists a gradual transition from soft tissue to bone. The femoral attachment area in the human ACL was measured to be $113\pm27$ mm$^2$ and $136\pm33$ mm$^2$ for the tibia insertion. With the exception of the mode of collagen insertion into the subchondral bone, the transition from ACL to bone is histologically similar for the femoral and tibial insertion sites.

The insertion site is comprised of four different zones: ligament, non-mineralized fibrocartilage, mineralized fibrocartilage, and bone. The first zone, which is the ligament proper, is composed of solitary, spindle-shaped fibroblasts aligned in rows, and embedded in parallel collagen fibril bundles of 70-150 μm in diameter. Primarily type I collagen makes up the extracellular matrix, and type III collagen, which are small reticular fibers, are located between the collagen I fibril bundles. The second zone, which is fibrocartilaginous in nature, is composed of ovoid-shaped chondrocyte-like cells. The cells do not lie solitarily, but are aligned in rows of 3-15 cells per row. Collagen fibril bundles are not strictly parallel and much larger than those found in zone 1. Type II collagen is now found within the pericellular matrix of the chondrocytes, with the matrix still made up predominantly of type I collagen. This zone is primarily avascular, and the primary sulfated proteoglycan is aggrecan. The next zone is mineralized fibrocartilage. In this zone, chondrocytes appear more circular and hypertrophic, surrounded by larger pericellular matrix distal from the ACL. Type X collagen, a specific marker for hypertrophic chondrocytes and subsequent mineralization, is detected and found only within this zone. The interface between mineralized fibrocartilage and subjacent bone is characterized by deep inter-digitations. Increasing number of deep inter-digitations is positively correlated to increased resistance to shear and tensile forces during development of rabbit ligament insertions. The last zone is the subchondral bone and the cells present are osteoblasts, osteocytes and osteoclasts. The predominant collagen is type I and fibrocartilage-specific markers such as type II collagen are no longer present.

For bone-patellar tendon-bone grafts, bone-to-bone integration with the aid of interference screws is the primary mechanism facilitating graft fixation. Several groups have examined the process of tendon-to-bone healing.

Blickenstaff et al. (1997) evaluated the histological and biomechanical changes during the healing of a semitendinosus autograft for ACL reconstruction in a rabbit model. Graft integration occurred by the formation of an indirect tendon insertion to bone at 26 weeks. However, large differences in graft strength and stiffness remained between the normal semitendinosus tendon and anterior cruciate ligament after 52 weeks of implantation.

In a similar model, Grana et al. (1994) reported that graft integration within the bone tunnel occurs by an intertwining of graft and connective tissue and anchoring of connective tissue to bone by collagenous fibers and bone formation in the tunnels. The collagenous fibers have the appearance of Sharpey's fibers seen in an indirect tendon insertion.

Rodeo et al. (1993) examined tendon-to-bone healing in a canine model by transplanting digital extensor tendon into a bone tunnel within the proximal tibial metaphysis. A layer of cellular, fibrous tissue was found between the tendon and bone, and this fibrous layer matured and reorganized during the healing process. As the tendon integrated with bone through Sharpey's fibers, the strength of the interface increased between the second and the twelfth week after surgery. The progressive increase in strength was correlated with the degree of bone in growth, mineralization, and maturation of the healing tissue.

In most cases, tendon-to-bone healing with and without interference fixation does not result in the complete re-establishment of the normal transition zones of the native ACL-bone insertions. This inability to fully reproduce these structurally and functionally different regions at the junction between graft and bone is detrimental to the ability of the graft to transmit mechanical stress across the graft proper and leads to sites of stress concentration at the junction between soft tissue and bone.

Zonal variations front soft to hard tissue at the interface facilitate a gradual change in stiffness and can prevent build up of stress concentrations at the attachment sites.

The insertion zone is dominated by non-mineralized and mineralized fibrocartilage, which are tissues adept at transmitting compressive loads. Mechanical factors may be responsible for the development and maintenance of the fibrocartilagenous zone found at many of the interfaces between soft tissue and bone. The fibrocartilage zone with its expected gradual increase in stiffness appears less prone to failure.

Benjamin et al. (1991) suggested that the amount of calcified tissue in the insertion may be positively correlated to the force transmitted across the calcified zone.

Using simple histomorphometry techniques, Gao et al. determined that the thickness of the calcified fibrocartilage zone was $0.22\pm0.7$ mm and that this was not statistically different from the tibial insertion zone. While the ligament proper is primarily subjected to tensile and torsional loads, the load profile and stress distribution at the insertion zone is more complex.

Matyas et al. (1995) combined histomorphometry with a finite element model (FEM) to correlate tissue phenotype with stress state at the medial collateral ligament (MCL) femoral insertion zone. The FEM model predicted that when the MCL is under tension, the MCl, midsubstance is subjected to tension and the highest principal compressive stress is found at the interface between ligament and bone.

Calcium phosphates have been shown to modulate cell morphology, proliferation and differentiation. Calcium ions can serve as a substrate for $Ca^{2+}$-binding proteins, and modulate the function of cytoskeleton proteins involved in cell shape maintenance.

Gregiore et al. (1987) examined human gingival fibroblasts and osteoblasts and reported that these cells underwent changes in morphology, cellular activity, and proliferation as a function of hydroxyapatite particle sizes. Culture distribution varied from a homogenous confluent monolayer to dense, asymmetric, and multi-layers as particle size varied from less than 5 μg to greater than 50 μg, and proliferation changes correlated with hydroxyapatite particles size.

Cheung et al. (1985) further observed that fibroblast mitosis is stimulated with various types of calcium-containing complexes in a concentration-dependent fashion.

Chondrocytes are also dependent on both calcium and phosphates for their function and matrix mineralization. Wuthier et al. (1993) reported that matrix vesicles in fibrocartilage consist of calcium-acidic phospholipids-phosphate complex, which are formed from actively acquired calcium ions and an elevated cytosolic phosphate concentration.

Phosphate ions have been reported to enhance matrix mineralization without regulation of protein production or cell proliferation, likely because phosphate concentration is often the limiting step in mineralization. It has been demonstrated that human foreskin fibroblasts when grown in micromass cultures and under the stimulation of lactic acid can dedifferentiate into chondrocytes and produce type II collagen.

Cheung at al. (1985) found a direct relationship between β-glycerophosphate concentrations and mineralization by both osteoblasts and fibroblasts. Increased mineralization by ligament fibroblasts is observed with increasing concentration of β-glycerophosphate, a media additive commonly used in osteoblast cultures. These reports strongly suggest the plasticity of the fibroblast response and that the dedifferentiation of ligament fibroblasts is a function of mineral content in vitro.

Progressing through the four different zones which make up the native ACL insertion zone, several cell types are identified: ligament fibroblasts, chondrocytes, hypertrophic chondrocytes and osteoblasts, osteoclasts, and osteocytes. The development of in vitro multi-cell type culture systems facilitates the formation of the transition zones.

No reported studies on either the co-culture of ligament fibroblasts with osteoblasts, nor on the in vitro and in vivo regeneration of the bone-ligament interface are known.

No reported studies which examine the potential of multi-phased scaffolds in facilitating the fixation of ligament or tendon to bone are known. As the interface between graft and bone is the weakest point during the initial healing period, recent research efforts in ACL tissue engineering have concentrated on design of multi-phased scaffolds in order to promote graft integration.

Goulet at al. (2000) developed a bio-engineered ligament model, where ACL fibroblasts were added to the structure and bone plugs were used to anchor the bioengineered tissue. Fibroblasts isolated from human ACL were grown on bovine type I collagen, and the bony plugs were used to promote the anchoring of the implant within the bone tunnels.

Cooper et al. (2000) and Lu et al. (2001) developed a tissue engineered ACL scaffold using biodegradable polymer fibers braided into a 3-D scaffold. This scaffold has been shown to promote the attachment and growth of rabbit ACL cells in vitro and in vivo. However, no multiphased scaffolds for human ligament-to-bone interface are known.

SUMMARY

This application describes scaffold apparatuses for musculoskeletal tissue engineering.

While the mechanism for interface regeneration is not known, knowledge of the structure-function relationship at the tendon-bone insertion (Thomopoulos, 2003; Thomopoulos, 2006) provides invaluable clues in biomimetic nanofiber scaffold design for interface regeneration. Combining biomechanical testing with the quasi-linear viscoelastic model (QLV) (Fung, 1972), Thomopoulos et al. (Thomopoulos, 2003) determined the mechanical properties of the rat supraspinatus tendon insertion sites and later related it to collagen orientation using a finite element model (Thomopoulos, 2006). It was found that controlled collagen organization plays an important role in reducing stress concentration at the tendon-bone insertion (Thomopoulos, 2006). Specifically, the average collagen fiber angle varied from 83-98° in the non-mineralized and 86-103° in the mineralized fibrocartilage region, indicating that the interface fiber architecture deviated minimally from the tendon proper.

In addition to collagen alignment, another intrinsic parameter of the interface is the region-dependent mineral distribution across the insertion site (Benjamin, 1986; Woo, 1988). Calcium phosphate is a prime modulator of both the biochemical milieu and the nature of mechanical stimuli presented to cells. Moreover, the spatial variation in mineral content at the interface is mechanically relevant, as increased mineral content has been associated with higher mechanical properties (Currey, 1998; Ferguson, 2003; Moffat, 2006; Radhakrishnan, 2004). For example, Ferguson et al. found a positive correlation between indentation modulus and hardness with mineralization in calcified human articular cartilage. Moffat et al. reported that increases in compressive modulus of the mineralized fibrocartilage region at the ligament-bone insertion corresponded to the presence of minerals (Moffat, 2006). These observations collectively suggest that both collagen alignment and mineral content are critical design parameters for interface tissue engineering.

Accordingly, one embodiment of the present invention is an implantable device for soft-tissue or soft tissue-to-bone fixation, repair, augmentation, or replacement comprising a biomimetic and biodegradable nanofiber scaffold, which scaffold comprises one or more continuous phases.

Another embodiment of the invention is an implantable biphasic biomimetic and biodegradable nanofiber device for soft tissue or soft tissue-to-bone interface fixation, repair, augmentation, or replacement. This device comprises a first phase comprising nanofibers made from a biodegradable polymer and a second phase coupled to the first phase, which second phase comprises nanofibers made from a biodegradable polymer and a biocompatible ceramic, wherein the first and second phases are continuous.

A further embodiment of the invention is an implantable device for fixation, repair, augmentation, or replacement of a rotator cuff or a tendon-to-bone interface thereof. This devices comprises a biphasic, biomimetic, and biodegradable nanofiber scaffold having a first phase comprising nanofibers whose anisotropy mimics that of a tendon and non-mineralized fibrocartilage, which nanofibers are made from a biodegradable polymer and a second phase coupled to the first phase, which second phase comprises nanofibers whose anisotropy mimics that of mineralized fibrocartilage and bone, which nanofibers are made from a biodegradable polymer and a biocompatible ceramic, wherein the first and second phases are continuous.

Another embodiment of the present invention is a method for fixation of, repairing, augmenting, or replacing a damaged soft tissue or soft tissue-to-bone interface in a patient. This method comprises affixing a biomimetic, biodegradable, continuous multi-phasic nanofiber scaffold to a surgically relevant site in order to fixate; repair, augment, or replace the damaged soft tissue or soft tissue-to-bone interface.

Yet another embodiment of the present invention is a method for fixating, repairing, augmenting, or replacing a damaged rotator cuff in a patient. This method comprises affixing a biomimetic and biodegradable continuous multi-phase nanofiber scaffold to a surgically relevant site in order to repair, augment, or replace the damaged rotator cuff.

This application further discloses a fully synthetic scaffold for, e.g., musculoskeletal tissue engineering.

One embodiment of the present invention is a fully synthetic implantable multi-phased scaffold. This scaffold comprises, in a single continuous construct, a plurality of phases designed to mimic the natural anatomy of a tendon or a ligament.

Another embodiment is a fully synthetic implantable multi-phased scaffold for ligament repair. This scaffold for ligament repair comprises (i) a first phase comprising a synthetic graft material suitable for implantation into a mammal, the synthetic graft material dimensioned to have a body with first and second ends; (ii) two second phases, each second phase comprising microspheres or mesh and having a body and first and second ends, the first end of the respective second phases disposed at each end of the first phase; and (iii) two third phases, each third phase comprising a body and first and second ends, the first end of the respective third phases disposed at the second end of each respective second phase, such that the first phase is separated from the respective third phases by each of the second phases, the third phases comprising a material suitable for anchoring the scaffold to bone.

A further embodiment is a fully synthetic implantable multi-phased scaffold for tendon repair. This scaffold for tendon repair comprises (i) a first phase comprising a synthetic graft material suitable for implantation into a mammal, the synthetic graft material dimensioned to have a body with first and second ends; (ii) two second phases, each second phase comprising microspheres or mesh and having a body and first and second ends, the first end of the respective second phases disposed at each end of the first phase; and (iii) two third phases, each third phase comprising a body and first and second ends, the first end of the respective third phases disposed at the second end of each respective second phase, such that the first phase is separated from the respective third phases by each of the second phases, the third phases comprising a material suitable for anchoring the scaffold to bone.

An additional embodiment is a fully synthetic implantable multi-phased scaffold for anterior cruciate ligament repair. This scaffold for anterior cruciate ligament repair comprises a first phase comprising a synthetic graft material suitable for implantation into a mammal, the synthetic graft material dimensioned to have a body with first and second ends; (ii) two second phases, each second phase comprising microspheres or mesh and having a body and first and second ends, the first end of the respective second phases disposed at each end of the first phase; and (iii) two third phases, each third phase comprising a body and first and second ends, the first end of the respective third phases disposed at the second end of each respective second phase, such that the first phase is separated from the respective third phases by each of the second phases, the third phases comprising a material suitable for anchoring the scaffold to bone.

This application further describes multiphasic apparatuses for musculoskeletal tissue engineering.

A scaffold apparatus, according to one preferred embodiment, is multi-phasic and can support growth, maintenance and differentiation of multiple tissue and cell types. The multi-phasic scaffold apparatus is biomimetic, biodegradable and/or osteointegrative.

This application also provides a scaffold apparatus for fixing musculoskeletal soft tissue to bone in a subject, said apparatus comprising two portions, wherein each portion comprises a scaffold, including first through third phases, wherein (i) the first phase comprises a material which promotes growth and proliferation of fibroblasts, (ii) the second phase adjacent to the first phase comprises a material which promotes growth and proliferation of chondroblasts, and (iii) the third phase adjacent to the second phase comprises a material which promotes the growth and proliferation of osteoblasts.

This application further provides a scaffold apparatus for fixing musculoskeletal soft tissue to bone in a subject, said scaffold apparatus comprising (i) a first phase comprising a material which promotes growth and proliferation of fibroblasts, (ii) a second phase adjacent to the first phase comprising a material which promotes growth and proliferation of chondroblasts, and (iii) a third phase adjacent to the second phase comprising a material which promotes the growth and proliferation of osteoblasts, wherein a degradable cell barrier is inserted between the adjacent phases.

This application further provides a scaffold apparatus for fixing musculoskeletal soft tissue to bone in a subject, said scaffold apparatus comprising (i) a first phase comprising a material which promotes growth and proliferation of fibroblasts, (ii) a second phase adjacent to the first phase comprising a material which promotes growth and proliferation of chondroblasts, and (iii) a third phase adjacent to the second phase comprising a material which promotes the growth and proliferation of osteoblasts, wherein said first phase of the apparatus is coupled to a soft tissue graft.

This application further provides a scaffold apparatus for fixing musculoskeletal soft tissue to bone in a subject, said scaffold apparatus comprising (i) a graft collar and (ii) a polymer-fiber mesh coupled to the graft collar to apply compressive mechanical loading to the graft collar.

BRIEF DESCRIPTION OF THE FIGURES

FIG. 1 shows the structural properties of the aligned and unaligned nanofiber scaffolds. Scanning electron micrographs of FIG. 1A aligned and FIG. 1B unaligned nanofiber scaffolds are shown A(2000×, bar=20 μm)

FIGS. 5A-5B show quantitative analysis of fibroblast response on aligned and unaligned nanofiber scaffolds at day 1 and day 14 post-plating. Nanofiber organization guided cell attachment and was analyzed based on analysis of FIG. 5A Mean Vector Angle (0-horizontally aligned) and FIG. 5B Mean Vector Length (0-random, 1=aligned, *:p<0.05). The inserted pictures in FIG. 5A shows confocal images of cell on aligned (top) and unaligned (bottom) nanofibres (60×, bar=50 μm).

FIG. 6C demonstrates that matrix production on the nanofiber scaffolds was also guided by nanofiber organization, with an aligned collagen I matrix found on the aligned anofiber scaffolds (Day 7, mean angle analysis).

FIG. 7B shows elastic modulus, *:p<0.05 vs. unaligned, and #:p<0.05 vs. unaligned cellular scaffolds; FIG. 7C shows yield strength, *:p<0.05 for aligned vs. as fabricated aligned nanofiber scaffolds, and #:p<0.05 day 1 vs. day 14.

FIG. 9A shows a supraspinatus tendon-to-bone insertion site (100) CT: Tendon, OF: Uncalcified Fibrocartilage, CF: Calcified Fibrocartilage, B: Bone.

FIG. 9B shows another view of the supraspinatus tendon-to-bone insertion site with the interface regions (calcified and non-calified) highlighted.

FIG. 12 shows a biphasic nanofiber scaffold according to the present invention at different magnifications (FIGS. 12A and 12B) under scanning electron microscopy. The nanofiber scaffold was fabricated with Phase A consisting of PLGA with 0% HA and Phase B containing 5% HA. The phases (FIGS. 12A and 12B) of FIG. 12 are continuous. When tested in tension (FIG. 12C), the elastic modulus of the biphasic constructs (n=3) was found to be significantly greater than either Phase A or Phase B alone (n=5).

FIG. 14 shows that (FIG. 14A) matrix and (FIG. 14B) cellular morphology corresponded to fiber alignment on PLGA-HA (5%) nanofiber meshes at day 21 as shown by SEM and confocal fluorescence microscopy, respectively. (FIG. 14C) Extracellular matrix consisted of both type I and type II collagen as shown by immunohistochemistry.

FIGS. 16A and 16B show top-side views of two embodiments of the present invention.

FIG. 18 C shows an expanded view of an embodiment where one of the phases is comprised of multiple layers.

FIG. 21A shows a schematic diagram of a scaffold apparatus; FIG. 21B shows a schematic diagram of another scaffold apparatus; FIG. 21C shows a schematic diagram of a multi-phased scaffold apparatus.

FIG. 22A shows a flow chart for a method for preparing a scaffold; FIG. 22B shows a flowchart for another method for preparing a multi-phased scaffold.

FIG. 23A shows a posterior view of an intact bovine anterior cruciate ligament (ACL) connecting the femur to the tibia (left); FIG. 23B shows an environmental scanning electron microscope (ESEM) image of transition from ligament (L) to fibrocartilage (FC) to bone (B) at the ACL insertion (upper right); FIG. 23C shows a histological micrograph of similar ACL to bone interface additionally showing mineralized fibrocartilage (MFC) zone (lower right).

FIGS. 24A-24B show Bovine tibial-femoral joint after ACL and insertion site extraction (right), ACL and insertion sites after excision.

FIG. 26B: 500×).

FIG. 27A shows a SEM image of the cross section of the femoral insertion zone, 1000×; FIG. 27B shows an EDAX spectrum of the femoral insertion zone. The peak intensities of Ca, P are higher compared to those in ligament region.

FIG. 29B shows the formation of Ca—P over time.

FIG. 30A shows an SEM image of a PLAGA-BG scaffold; FIG. 30B shows an EDAX spectrum of PLAGA-BG immersed in SBF for 14 days.

FIG. 33A shows Alizarin Red (ALZ) stain of ACF fibroblasts, 14 days, 20×; FIG. 33B shows ALZ stain of interface of ACL fibroblasts and osteoblasts, 14 days, 20×; FIG. 33C shows ALZ stain of ACL osteoblasts, 14 days, 20×; FIG. 33D shows Alkaline Phophatase (ALP) stain of ACL fibroblasts, 7 days, 32×; FIG. 33E shows ALP and 4',5-diamidino-2-phenylindole (DAPI) stain of co-culture of osteoblasts and fibroblasts, 7 days, 32×; and FIG. 33F shows APL stain of osteoblasts, 7 days, 32×.

FIG. 35A and FIG. 35B show images of the same scaffold; FIG. 35C is a schematic of scaffold design depicting the three layers.

FIG. 36A shows cells stained with hematoxylin and eosin (H&E) stain; FIG. 36B shows cells stained with Alcian blue; FIG. 36C shows the location of Type I collagen; FIG. 36D shows the location of Type II collagen (green) and nucleic acids (red).

FIG. 37A and FIG. 37B show reverse transcriptase PCR (RT-PCR) gels for day 7 micromass samples. FIG. 37A shows Type X collagen expression. FIG. 37B shows Type II collgen expression (C: control micromass sample; E: experimental osteoblast-chondrocyte co-culture sample).

FIG. 38A shows chondrocyte control (2000×); FIG. 38B shows co-culture of osteoblasts and chondrocytes (1500×).

FIG. 38C shows chondocyte control, day (500×); FIG. 38D shows co-culture of osteoblasts and chondrocytes, day 1 (500×); FIG. 38E shows co-culture of osteoblasts and chondrocytes, day 7 (750×).

FIGS. 42A-42C show fluorescence microscopy images (day 28, ×10) for Phases A through C, respectively.

FIGS. 42D-42E are images showing extracellular matrix production for Phases B and C, respectively.

FIG. 43A) Phase C, Day 0-×1000;
FIG. 43B) Phase C, Day 28-×1000;
FIG. 43C) Phase A, Day 28-×1000;
and
FIG. 43D) Phase B, Day 28-×70.

FIG. 44A) Phase A, Day 0, ×10;
FIG. 44B) Phase B, Day 0, ×10;
FIG. 44C) Phase C, Day 0, ×10;
FIG. 44D) Phase A, Day 28, ×10;
FIG. 44E) Phase B, Day 28, ×10; and
FIG. 44F) Phase C, Day 28, ×10.

FIGS. 46A-46F show images of osteoblast and fibroblast in culture, in another set of experiments:
FIG. 46A) Day 0, 5×;
FIG. 46B) Day 0, 5×;
FIG. 46C) Day 1, 5×;
FIG. 46D) Day 2, 5×;
FIG. 46E) Day 1, 32× (cell contact); and
FIG. 46F) Day 1, 32×.

FIG. 46G) Live-dead stain of 1 hour sample, 5×;
FIG. 46H) ALP stain of osteoblast and fibroblast, day 2, 20×;
and
FIG. 46I) Collagen I staining, day 6, 20×.

FIG. 48A shows a graph which demonstrates cell proliferation in Phases A, B, and C during 35 days of human hamstring tendon fibroblast and osteoblast co-culture on multiphased scaffolds.

FIGS. 46B-48C graphically show mechanical testing data for multiphased scaffolds seeded with human hamstring tendon fibroblasts and human osteoblasts over 35 days of culture (n=4).

FIG. 51A-B: show graphically mechanical testing data for multiphased scaffolds seeded with human hamstring tendon fibroblasts and human osteoblasts over 35 days of culture (n=4). Scaffolds were tested in uniaxial compression. Compressive modulus (FIG. 51A) and yield strength (FIG. 51B) were calculated from the resulting stress-strain curves. Both cell seeded (FIG. 51C) and acellular (AC) scaffolds were examined at days 0, 7, 21, and 35. Scaffold compressive modulus was significantly greater at day 0 than for all subsequent time points and groups (p<0.05).

FIGS. 52A-52D show SEMs of electrospun meshes spun at:

FIG. 52A) $1^{st}$ gear, 7.4 m/s;

FIG. 52B) $2^{nd}$ gear, 9.4 m/s;

FIG. 52C) $3^{rd}$ gear, 15 m/s; and

FIG. 52D) $4^{th}$ gear, 20 m/s.

FIGS. 52E-52F show scanning electron microscopy (SEM) images of a multiphased scaffold, with 85:15 PLAGA electrospun mesh joined with PLAGA:BG composite microspheres.

FIG. 56A-568 show a top-down view of a fully synthetic implantable multiphase scaffold according to the present invention. FIG. 56B shows an exploded side view of the scaffold of FIG. 56A.

FIG. 58A-58B show an elevated side view of an embodiment of a fully synthetic implantable multi-phase scaffold according to the present invention having a single layer. FIG. 58A shows an elevated side view of an embodiment of a fully synthetic implantable multi-phase scaffold according to the present invention having multiple layers.

FIG. 59A-59C show a top-down view of another embodiment of a fully synthetic implantable multi-phase scaffold according to the present invention having the same phases of FIG. 56, but with mesh dividers between each phase. FIG. 59B shows an exploded elevated side view of a mesh located in between adjacent phases of the scaffold of FIG. 59A. FIG. 59C shows an elevated side view of a mesh of a fully synthetic implantable multi-phase scaffold according to the present invention having multiple layers.

FIG. 67 shows Experimental design for tracking the three types of implanted cell populations in vivo and determining their presence over a 4-week implantation period.

FIGS. 75B-75D show fiber diameter of the 0% HA, 10% HA and the 15% HA nanofiber-based scaffold in Example 1.6.

FIGS. 76A-76D show the fiber diameter decreasing with increasing mineral content in Example 1.6.

DETAILED DESCRIPTION

Figure 2:
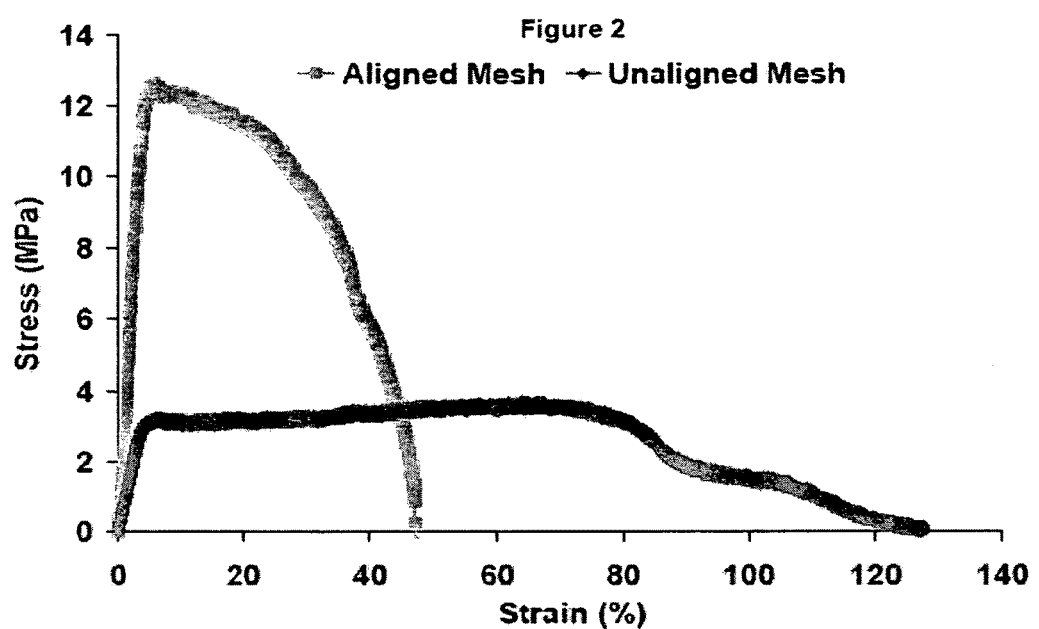
FIG. 2 shows mechanical properties of aligned and unaligned nanofiber scaffolds. A representative stress-strain curve for aligned and unaligned nanofiber scaffolds tested in uniaxial tension is shown.

In order to facilitate an understanding of the material which follows, one may refer to Freshney, R. Ian. *Culture of Animal Cells—A Manual of Basic Technique* (New York:

Wiley-Liss, 2000) for certain frequently occurring methodologies and/or terms which are described therein.

Terms

The following references provide one of skill with a general definition of many of the terms used in this invention: Singleton et al., Dictionary of Microbiology and Molecular Biology (2nd Ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991).

Unless defined otherwise, all technical and scientific terms used herein have the meaning commonly understood by a person skilled in the art to which this invention belongs. However, except as otherwise expressly provided herein, each of the following terms, as used in this application, shall have the meaning set forth below.

As used herein, "a single continuous construct" means that each phase is "continuous" with the phase adjacent to it. Thus, in the present fully synthetic implantable multiphased scaffolds, the interface between one phase and the next is designed, e.g., by sintering and other means described in more detail below, to mimic the natural anatomical structure, e.g., of a tendon or of a ligament, particularly the insertion sites thereof. In the present invention, the scaffold may have more than one phase, depending on the anatomical architecture of the ligament or tendon to be repaired, fixed, augmented, or replaced. An exemplary number of phases is from about 1 to about 10, such as for example, from about 2 to about 4, preferably 3 or 4. As noted above, in such multiphasic embodiments, each phase of the scaffold is continuous from phase-to-phase.

As used herein, "aligned fibers" shall mean groups of fibers which are oriented along the same directional axis. Examples of aligned fibers include, but are not limited to, groups of parallel fibers.

As used herein, "bioactive" shall include a quality of a material such that the material has an osteointegrative potential, or in other words the ability to bond with bone. Generally, materials that are bioactive develop an adherent interface with tissues that resist substantial mechanical forces.

As used herein, a "biocompatible" material is a synthetic or natural material used to replace part of a living system or to function in intimate contact with living tissue. Biocompatible materials are intended to interface with biological systems to evaluate, treat, augment or replace any tissue, organ or function of the body. The biocompatible material has the ability to perform with an appropriate host response in a specific application and does not have toxic or injurious effects on biological systems. One example of a biocompatible material can be a biocompatible ceramic.

As used herein, "biodegradable" means that the scaffold, once implanted into a host, will begin to degrade. The implantable devices of the present invention may be used in open surgical procedures, so-called "mini-open" procedures, and arthroscopic procedures as may be required and determined by a surgeon. Preferably, the implantable devices of the present invention are used in arthroscopic procedures. The nanofiber scaffold of the implantable device is biomimetic and biodegradable. The rate of biodegradation may be engineered into the nanofiber scaffold based on the polymers used, the ratio of copolymers used, and other parameters well known to those of skill in the art. Moreover, in certain embodiments of the present invention, when the nanofiber scaffold is a multiphasic nanofiber scaffold, the rate of biodegradation of each phase may be separately engineered according to the needs of the particular surgery to be performed.

As used herein, "biomimetic" shall mean a resemblance of a synthesized material to a substance that occurs naturally in a human body and which is not rejected by (e.g., does not cause an adverse reaction in) the human body. When used in connection with the "nanofiber scaffold", biomimetic means that the nanofiber scaffold is biologically inert (i.e., will not cause an immune response/rejection) and is designed to resemble a structure (e.g., soft tissue anatomy) that occurs naturally in a mammalian, e.g., human, body and that promotes healing when implanted into the body.

As used herein, "chondrocyte" shall mean a differentiated cell responsible for secretion of extracellular matrix of cartilage. Preferably the cells are from a compatible human donor. More preferably, the cells are from the patient (i.e., autologous cells).

As used herein, "fibroblast" shall mean a cell of connective tissue that secretes proteins and molecular collagen including fibrillar procollagen, fibronectin and collagenase, from which an extracellular fibrillar matrix of connective tissue may be formed. Fibroblasts synthesize and maintain the extracellular matrix of many tissues, including but not limited to connective tissue. The fibroblast cell may be mesodermally derived, and secrete proteins and molecular collagen including fibrillar procollagen, fibronectin and collagenase, from which an extracellular fibrillar matrix of connective tissue may be formed. A "fibroblast-like cell" means a cell that shares certain characteristics with a fibroblast (such as expression of certain proteins).

As used herein, "fully synthetic" scaffold means that the scaffold is composed of man-made material, such as synthetic polymer, or a polymer-ceramic composite, but it does not preclude further treatment with material of biological or natural origin, such as seeding with appropriate cell types, e.g., seeding with osteoblasts, osteoblast-like cells, and/or stem cells, or treating with a medicament, e.g., anti-infectives, antibiotics, bisphosphonate, hormones, analgesics, antiinflammatory agents, growth factors, angiogenic factors, chemotherapeutic agents, anti-rejection agents, and RGD peptides.

As used herein, "functional" shall mean affecting physiological or psychological functions but not organic structure.

As used herein, "glass transition temperature" means the temperature at which, upon cooling, a noncrystalline ceramic or polymer transforms from a supercooled liquid into a rigid glass. The noncrystalline ceramic or polymer may be of multiple form and composition, and may be formed as microspheres. In the context of a sintering process, such as discussed in this application, the polymer chains from adjacent microspheres typically entangle, effectively forming a bond between the microspheres upon cooling. As the polymer is heated above its glass transition temperature, long range polymer chain motion begins.

As used herein, "hydrogel" shall mean any colloid in which the particles are in the external or dispersion phase and water is in the internal or dispersed phase.

As used herein, "graft fixation device" means a device for fixation of a graft, including but not limited to staples, interference screws with or without washers, press fit EndoButton® devices and Mitek® anchor devices.

As used herein, "graft" shall mean the device to be implanted during medical grafting, which is a surgical procedure to transplant tissue without a blood supply, including but not limited to soft tissue graft, synthetic grafts, and the like. As used herein, "imparted" means treated, including but not limited to application of medicament on the surface of the scaffold, integration of medicament within the scaffold, or a combination of the two. At least one of the first, second, or third phases of the synthetic implantable multi-phased scaffold may also be imparted with a medicament, such as anti-infectives, antibiotics, bisphosphonate, hormones, analgesics, anti-inflammatory agents, growth factors, angiogenic factors, chemotherapeutic agents, anti-rejection agents, or RGD peptides. Preferably, at least one of the first, second, or third phases of the synthetic implantable multi-phased scaffold is imparted with growth factors. In this way, delivery of medicaments, particularly growth factors to, e.g., specific anatomic regions is achievable.

As used herein, "implantable device" according to the present invention is a surgically appropriate, e.g., biocompatible, apparatus having the design and physical properties set forth in more detail below. Preferably, the implantable device is designed and dimensioned to function in the surgical repair, augmentation, or replacement of damaged soft tissue, such as, e.g., a rotator cuff, including fixation of tendon-to-bone. More particularly, the implantable device comprises a "nanofiber scaffold".

As used herein, "implantable" or "suitable for implantation" means surgically appropriate for insertion into the body of a host, e.g., biocompatible, or having the design and physical properties set forth in more detail below.

As used herein, "interference screw" means a device indicated for soft tissue-bone fixation, specifically, a type of graft fixation device which anchors a flexible transplant like a tendon or a ligament in an opening in a bone. The screw generally has a screw body, a head at one end of said screw body and a penetrating end at an opposite end of said screw body. The device may be used in, for example, anterior cruciate ligament surgery. The device may be metallic or bioabsorbable and may include, but is not limited to, titanium cannulated interference screws, Poly-L-Lactide (PLLA) interference screws, etc.

As used herein, "matrix" shall mean a three-dimensional structure fabricated from biomaterials. The biomaterials can be biologically-derived or synthetic.

As used herein, "mesh" means a network of material. The mesh of the second phase may be woven synthetic fibers, non-woven synthetic fibers, and nanofibers suitable for implantation into a mammal, e.g., a human. The woven and non-woven fibers may be made according to well known techniques. The nanofiber mesh may be made according to techniques known in the art and those disclosed in, e.g., co-owned international application no. PCT/US2008/001889 filed on Feb. 12, 2008 to Lu et al., which application is incorporated by reference as if recited in full herein.

As used herein, "microspheres", i.e., the microspheres of the second phase, mean microbeads, which are suitable, e.g., for cell attachment and adhesion. The microspheres of the second phase may be made from polymers such as aliphatic polyesters, poly(amino acids), copoly(ether-esters), polyalkylenes oxalates, polyamides, poly(iminocarbonates), polyorthoesters, polyoxaesters, polyamidoesters, poly($\varepsilon$-caprolactone)s, polyanhydrides, polyarylates, polyphosphazenes, polyhydroxyalkanoates, polysaccharides, or biopolymers, or a blend of two or more of the preceding polymers. Preferably, the polymer comprises at least one of the following materials: poly(lactide-co-glycolide), poly(lactide) or poly(glycolide). More preferably, the polymer is poly(lactide-co-glycolide) (PLGA).

As used herein, "nanofiber mesh" shall mean a flexible netting of nanofibers, oriented such that at least some of the nanofibers are not parallel to others of the nanofibers.

As used herein, "nanofiber scaffold" is constructed of "nanofibers." As used herein, "nanofiber" shall mean fibers with diameters no more than 1000 nanometers. In the present invention, a "nanofiber" is a biodegradable polymer that is electrospun into a fiber as described in more detail herein below. The nanofibers of the scaffold are oriented in such a way (i.e., aligned or unaligned) so as to mimic the natural architecture of the soft tissue to be repaired. Moreover, the nanofibers and the subsequently formed nanofiber scaffold are controlled with respect to their physical properties, such as for example, fiber diameter, pore diameter, and porosity so that the mechanical properties of the nanofibers and nanofiber scaffold are similar to the native tissue to be repaired, augmented or replaced. Thus, in the case of a rotator cuff repair, the nanofiber scaffold is able to regenerate the native insertion of tendon-to-bone through interface tissue engineering and promote tendon-to-bone integration and biological fixation. In the present invention, such a nanofiber scaffold may be multiphasic, such as e.g., biphasic. One aspect of such multiphasic nanofiber scaffolds is that each phase is "continuous" with the phase adjacent to it. Thus, in the present nanofiber scaffolds, the interface between one phase and the next is designed, e.g., by electrospinning and other means described in more detail below, to mimic the natural anatomical transition between, e.g., tendon and bone at a tendon-to-bone interface. By designing the nanofiber scaffolds of the present invention so that the phases are continuous, improved fixation and function is achieved by minimizing stress concentrations and mediating load transfer between tendon and bone compared to prior systems. In the present invention, the nanofiber scaffold may be engineered to remain in place for as long as the treating physician deems necessary. Typically, the nanofiber scaffold will be engineered to have biodegraded between 6-18 months after implantation, such as for example 12 months.

As used herein, "osteoblast" shall mean a bone-forming cell which forms an osseous matrix in which it becomes enclosed as an osteocyte. It may be derived from mesenchymal osteoprogenitor cells. The term may also be used broadly to encompass osteoblast-like, and related, cells, such as osteocytes and osteoclasts. An "osteoblast-like cell" means a cell that shares certain characteristics with an osteoblast (such as expression of certain proteins unique to bones), but is not an osteoblast. "Osteoblast-like cells" include preosteoblasts and osteoprogenitor cells. Preferably the cells are from a compatible human donor. More preferably, the cells are from the patient (i.e., autologous cells).

As used herein, "osteointegrative" means having the ability to chemically bond to bone.

As used herein, "particle reinforcement" means a process for forming a composite with a higher strength than the original material (for example, a polymer) by adding particles of a reinforcing material with a higher strength (for example, a ceramic).

As used herein, "polymer" means a chemical compound or mixture of compounds formed by polymerization and including repeating structural units. Polymers may be constructed in multiple forms and compositions or combinations of compositions.

As used herein, "porosity" means the ratio of the volume of interstices of a material to a volume of a mass of the material.

As used herein, "sintering" shall mean densification of a particulate polymer compact involving a removal of pores between particles (which may be accompanied by equivalent shrinkage) combined with coalescence and strong bonding between adjacent particles. The particles may include particles of varying size and composition, or a combination of sizes and compositions.

As used herein, "soft tissue graft" shall mean a graft which is not synthetic, and can include autologous grafts, syngeneic grafts, allogeneic grafts, and xenogeneic graft.

As used herein, "soft tissue" includes, as the context may dictate, tendon and ligament, as well as the bone to which such structures may be attached. Preferably, "soft tissue" refers to tendon- or ligament-bone insertion sites requiring surgical repair, such as for example tendon-to-bone fixation.

As used herein, "stem cell" e.g., a mesenchymal stem cell, means an unspecialized cell that has the potential to develop into many different cell types in the body, such as mesenchymal osteoprogenitor cells, osteoblasts, osteocytes, osteoclasts, chondrocytes, and chondrocyte progenitor cells. Preferably the cells are from a compatible human donor. More preferably, the cells are from the patient (i.e., autologous cells).

As used herein, "synthetic graft material", i.e., first phase, means man-made material that is intended for insertion into a host body. The synthetic graft material used in the first phase may be made from aliphatic polyesters, poly(amino acids), copoly(ether-esters), polyalkylenes oxalates, polyamides, poly(iminocarbonates), polyorthoesters, polyoxaesters, polyamidoesters, poly(ε-caprolactone)s, polyanhydrides, polyarylates, polyphosphazenes, polyhydroxyalkanoates, polysaccharides, degradable polyurethanes, or biopolymers, or a blend of two or more of the preceding polymers. Preferably, the synthetic graft material used in the first phase is poly(lactide-co-glycolide), poly(lactide) or poly(glycolide).

As used herein, "synthetic" shall mean that the material is not of a human or animal origin.

As used herein, all numerical ranges provided are intended to expressly include at least the endpoints and all numbers that fall between the endpoints of ranges.

The following examples are provided to further illustrate the devices and methods of the present invention. These examples are illustrative only and are not intended to limit the scope of the invention in any way.

EMBODIMENTS

The Biomimetic Nanofiber Scaffold for Soft Tissue and Soft Tissue-to-Bone Repair, Augmentation and Replacement The ideal nanofiber scaffold for rotator cuff tendon repair must be able to meet the functional demand of the native tendon by matching its mechanical properties as well as promoting host cell-mediated healing by mimicking the ultrastructure organization of the native tendon. In addition to being biomimetic and able to promote cell attachment and growth, the nanofiber scaffold must be biodegradable so it can be gradually replaced by new tissue without compromising graft mechanical properties. To this end, the present invention is directed to a nanofiber scaffold for, inter alia, rotator cuff repair, augmentation, or replacement, including fixation of tendon-to-bone. These nanofiber scaffolds are highly advantageous for orthopedic tissue engineering due to their superior biomimetic potential and physiological relevance because they exhibit high aspect ratio, surface area, porosity and closely mimic the native extracellular matrix (Ma, 2005; Christenson, 2007; Pham, 2006; Li, 2007; Murgan, 2007). The biomimetic design of the nanofiber-based scaffold include fiber diameter mimicking collagen fibrils, fiber organization guides cell and ECM alignment, controlled mechanical properties which mimic the native matrix, and high porosity and surfe area-to-volume ratio.

Nanofiber scaffolds have been investigated for bone (34 Yoshimoto, 2003; Garreta, 2007; Fujihara, 2005; Badmi, 2006), meniscus (38), intervertebral disk (Nerukar, 2007), cartilage (Li, 2003; Li, 2005), ligament (Lee, 2005; Bashur, 2006) as well as tendon tissue engineering (Sahoo, 2006), and they are likely to be a promising solution for the functional augmentation of rotator cuff repairs. Moreover, nanofiber organization and alignment can be readily modulated during fabrication (Murugan, 2007; Matthews, 2002; Yang, 2005; Pham, 2006). See also, e.g., U.S. Pat. No. 6,689,166. Thus, nanofiber scaffold systems exhibit significant versatility in their ability to tailor structural and material properties to meet the functional demands of, e.g., the rotator cuff.

Accordingly, one embodiment of the present invention is an implantable device for soft-tissue or soft tissue-to-bone fixation, repair, augmentation, or replacement. The device comprises a biomimetic and biodegradable nanofiber scaffold, which scaffold comprises one or more continuous phases. The present invention is well suited for soft-tissue repairs in mammals, particularly humans. More particularly, the implantable device comprises a "nanofiber scaffold".

The implantable devices of the present invention may be used in open surgical procedures, so-called "mini-open" procedures, and arthroscopic procedures as may be required and determined by a surgeon. Preferably, the implantable devices of the present invention are used in arthroscopic procedures.

The nanofiber scaffold of the implantable device is biomimetic and biodegradable. The rate of biodegradation may be engineered into the nanofiber scaffold based on the polymers used, the ratio of copolymers used, and other parameters well known to those of skill in the art. Moreover, in certain embodiments of the present invention, when the nanofiber scaffold is a multiphasic nanofiber scaffold, the rate of biodegradation of each phase may be separately engineered according to the needs of the particular surgery to be performed.

In the present invention, the nanofiber scaffold may be engineered to remain in place for as long as the treating physician deems necessary. Typically, the nanofiber scaffold will be engineered to have biodegraded between 6-18 months after implantation, such as for example 12 months. As used herein, all numerical ranges provided are intended to expressly include at least the endpoints and all numbers that fall between the endpoints of ranges.

In one embodiment of the present invention, the nanofiber scaffold comprises a plurality of nanofibers that are made from a biodegradable polymer. In the present invention, the biodegradable polymer may be selected from biodegradable polymer is selected from the group consisting of aliphatic polyesters, poly(amino acids), modified proteins, polydepsipeptides, copoly(ether-esters), polyurethanes, polyalkylenes oxalates, polyamides, poly(iminocarbonates), polyorthoesters, polyoxaesters, polyamidoesters, poly(ε-caprolactone)s, polyanhydrides, polyarylates, polyphosphazenes, polyhydroxyalkanoates, polysaccharides, modified polysaccharides, polycarbonates, polytyrosinecarbonates, polyorthocarbonates, poly(trimethylene carbonate), poly(phosphoester)s, polyglycolide, polylactides, polyhydroxybutyrates, polyhydroxyvalerates, polydioxanones, polyalkylene oxalates, polyalkylene succinates, poly(malic acid), poly(maleic anhydride), polyvinylalcohol, polyesteramides, polycyanoacrylates, polyfumarates, poly (ethylene glycol), polyoxaesters containing amine groups, poly(lactide-co-glycolides), poly(lactic acid)s, poly(glycolic acid)s, poly(dioxanone)s, poly(alkylene alkylate)s, biopolymers, collagen, silk, chitosan, alginate, and a blend of two or more of the preceding polymers.

Preferably, the polymer comprises at least one of poly (lactide-co-glycolide), poly(lactide), and poly(glycolide). More preferably, the polymer is a copolymer, such as for example a poly(D,L-lactide-co-glycolide) (PLGA). The advantages of the PLGA nanofiber scaffold include that it is 1) biomimetic and guides tendon regeneration, 2) biodegradable and replaced by host tissue, 3) exhibit physiologically relevant mechanical properties, and 4) enable biological fixation of tendon-to-bone.

As noted above, the ratio of polymers may be varied in the biocompatible polymer of the nanofibers in order to achieve certain desired physical properties, including e.g., strength, ease of fabrication, degradability, and biocompatibility. Preferably, the ratio of polymers in the biocompatible polymer, e.g., the PLGA copolymer, is between about 25:75 to about 95:5. More preferably, the ratio of polymers in the biocompatible polymer, e.g., the PLGA copolymer, is between about 85:15. Generally, a ratio of about 25:75 in the PLGA copolymer will equate to a degradation time of about six months, a ratio of about 50:50 in the PLGA copolymer will equate to a degradation time of about twelve months, and a ratio of about 85:15 in the PLGA copolymer will equate to a degradation time of about eighteen months.

As noted above, the anisotropy of the nanofibers in the nanofiber scaffold may be controlled. In the present invention, the anisotropy of the nanofibers in the nanofiber scaffold may be varied between substantially aligned to substantially unaligned, depending on the anatomical structure of the soft tissue or soft tissue-to-bone interface to be repaired, augmented, fixated, or replaced. For example, the nanofiber alignment and orientation may be designed with reference to the alignment and orientation of various extracellular matrix components, such as collagen, which as noted above, has an average fiber angle of 83-98° (non-mineralized) and 86-103° (mineralized and fibrocartilage) depending on the region measured (Thomopoulos, 2006). In one aspect of the invention, it is preferred that the nanofibers are aligned. In another aspect, the nanofibers are unaligned. In a further aspect, the nanofiber scaffold may contain regions where the orientation of the nanofibers varies from substantially aligned to substantially unaligned. Thus, in one embodiment, the nanofiber scaffold comprises both aligned and unaligned nano fibers.

As noted above, the nanofiber alignment and orientation mimics the anatomy of the soft-tissue or soft tissue-to-bone interface to be repaired, augmented, fixated, or replaced. Mimicking the anatomy of soft tissue or soft tissue-to-bone interface means having structure and design mimicking that of the native soft tissue or soft tissue-to-bone interface. Preferably, the soft tissue to be repaired, augmented, or replaced is a ligament or tendon. More preferably, the soft tissue is a rotator cuff. For example, the nanofiber alignment and orientation mimics the anatomy of a tendon-to-bone interface, such as, e.g., a rotator cuff tendon-to-bone interface. (shown in FIG. 9) Thus, in one aspect, the nanofiber scaffold is designed to mimic soft tissue and comprises a preformed interface region. Other soft tissue and soft tissue-to-bone interfaces in a mammal, particularly a human, are well known to those of skill in the art and are contemplated herein.

In the present invention, the nanofiber scaffold may have one or more phases, depending on the anatomical architecture of the soft tissue or soft tissue-to-bone interface to be repaired, fixated, augmented, or replaced. An exemplary number of phases is from about 1 to about 10, such as for example, from about 2 to about 4. In one aspect of the invention, phases may be adjacent to each other in a single sheet (FIG. 18 A (biphasic, with phases 70 and 80) and B (triphasic, with phases 90, 100, and 110). In this embodiment, each phase is aligned along a horizontal axis (x). In another aspect, the phases may be layered, one over another (FIGS. 17 A (two layers, 20, 30) and B (three layers (40, 50, and 60)). In this embodiment, the phases are aligned/layered along a vertical axis (y). In another embodiment, at least two phases are layered along a vertical axis and at least two phases are aligned along a horizontal axis. In another aspect, at least one of the phases comprises more than one layer, e.g., from about 2 to about 20 layers (see, e.g., FIG. 18 C insert showing a phase (80) comprised of an exemplary three layers (120, 130, and 140)), and each layer may be composed of the same or different nanofiber polymer and/or biocompatible ceramic, nanofiber alignment and orientation, and coating. For example, in one biphasic embodiment, a first phase may contain two layers: a first layer having nanofibers aligned in a parallel arrangement and a second layer having the nanofibers arranged in an unaligned manner. Similarly, in another biphasic embodiment, a first phase may contain two layers: a first layer having nanofibers aligned in a perpendicular arrangement and a second layer having the nanofibers arranged in an unaligned manner. Thus, depending on the physical properties desired in the overall scaffold, one or more layers of nanofibers may be arranged, wherein each layer has the same or different alignment (e.g., parallel, perpendicular, unaligned (or any variation therebetween)). Thus, different properties, particularly viscoelastic responses that mimic the natural architecture of a native soft tissue or soft tissue-to-bone interface, may be engineered into the scaffold by, e.g., varying the number and alignment of each layer within a particular phase.

Preferably, the nanofiber scaffold is multiphasic, such as for example biphasic. As noted above, in such multiphasic embodiments, each phase of the scaffold is continuous from phase-to-phase.

Figure 17A:
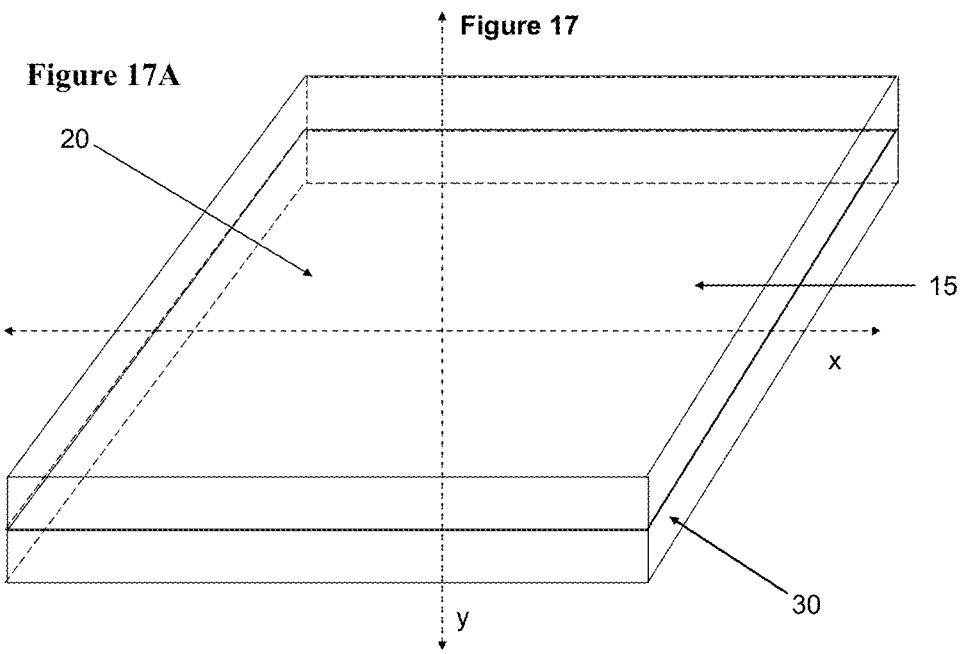
FIG. 17 shows top-side views of multiphasic embodiments of the invention that are layered-biphasic (FIG. 17A) and triphasic (FIG. 17B). In these embodiments, the phases are layered along a vertical axis (y).
Figure 17B:
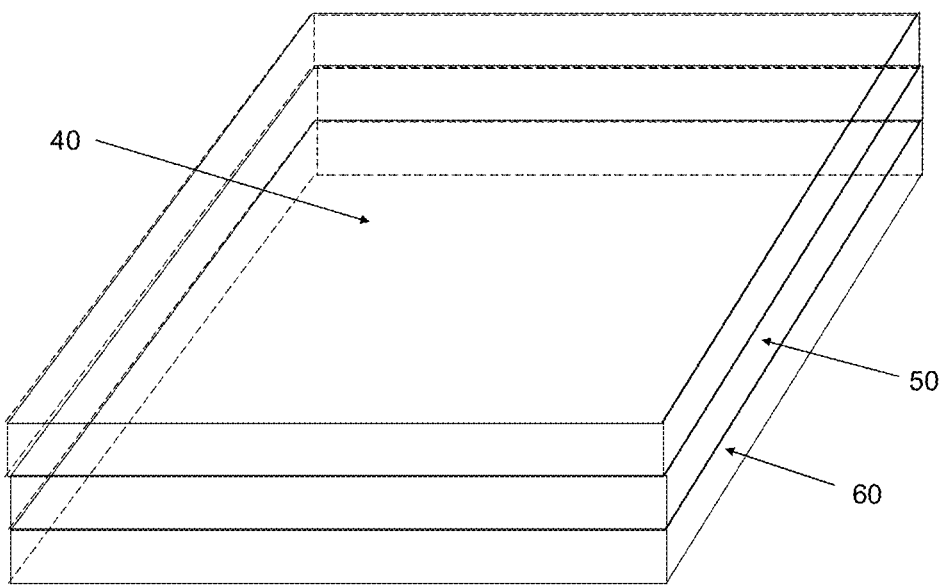
Figures 18, 18A:
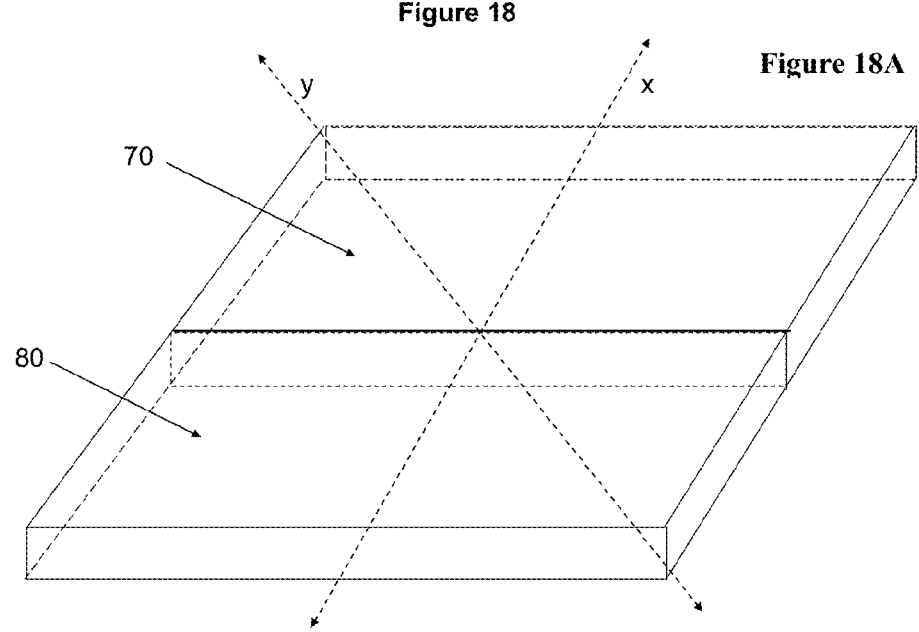
FIG. 18 shows top-side views of multiphasic embodiments of the invention that are aligned along a horizontal axis (x)-biphasic (FIG. 18A) and triphasic (FIG. 18B).
Figure 18B:
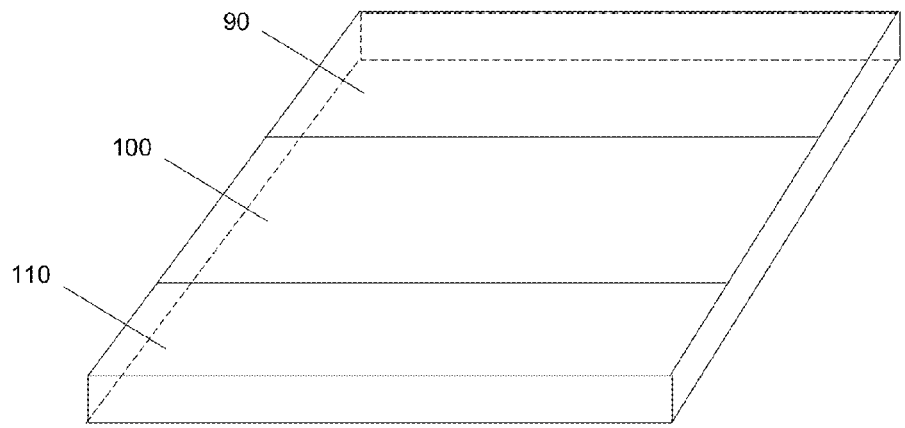
Figure 18C:
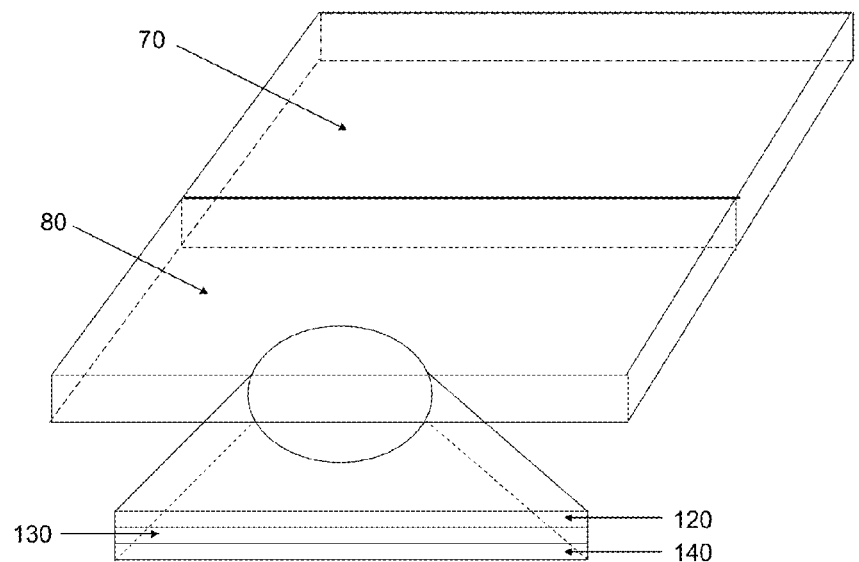

Referring now to FIG. 17, in one embodiment of the biphasic design, the implantable device (15) includes a first phase (20) comprising nanofibers made from a biodegradable polymer. The implantable device includes a second phase (30), which is coupled to the first phase. In the present invention, the phases are coupled to each other using standard techniques, such as those disclosed in more detail in the examples. The second phase comprises nanofibers made from a biodegradable polymer and a biocompatible ceramic. In this embodiment, the first phase is continuous with the second phase.

In this embodiment, the biocompatible ceramic may be incorporated into the biodegradable polymer by any conventional means. For example, the biocompatible ceramic may be incorporated into the biodegradable polymer to form a composite nanofiber by solution immersion (Lu, 2003; Lu, 2005), liposome delivery, or electrospinning (Wutticharoenmongkol, 2006; Sui, 2007) as described in more details in the Examples. Preferably, the biocompatible ceramic is incorporated into the nanofibers of the second phase by electrospinning.

The biocompatible ceramic may be selected from any ceramic material that is biologically inert (or substantially inert), is incorporatable into the nanofiber scaffold, and will enhance the nanofiber scaffold's mimicry of mineralized and non-mineralized anatomy in a soft tissue or soft tissue-to-bone interface to be repaired, fixated, augmented, or replaced. For example, the biocompatible ceramic may be selected from silicon nitride-based ceramics, Pseudowollastonite ceramics ($\beta$-CaSiO$_3$), bredigite (Ca$_7$MgSi$_4$O$_{16}$) ceramics, mono-phase ceramics of monticellite (CaNgSiO (4)), akermanite ceramics (Ca$_2$MgSi$_2$O$_7$), tricalcium silicate (Ca(3)SiO(5)), hydroxyapatite, bio-active glass, calcium phosphate, dense calcium sulfate (DCaS), porous silicated calcium phosphate (Si—CaP), tricalcium phosphate (TCP), calcium pyrophosphate (CPP), and combinations thereof. Preferably, the biocompatible ceramic is hydroxyapatite or bio-active glass, such as, e.g., 45S5® bioglass (Novabone, Alachua, Fla.).

The biocompatible ceramic may be incorporated into the nanofibers of the scaffold at any convenient concentration based on the method of incorporation used and the desired physical properties of the scaffold. By way of example, in a composite nanofiber scaffold design according to the present invention, nanofibers that range from 0 to about 25% biocompatible ceramic may be electrospun. For example, nanofibers containing about 1%, about 5%, about 15%, and about 25% hydroxyapatite may be electrospun.

In another aspect of the invention, a bioactive agent may be incorporated into the nanofiber scaffold of the implantable device. In the present invention, the "bioactive agent" may be any pharmaceutically acceptable entity that does not deleteriously affect the structure or function of the nanofiber scaffold and which may provide an added benefit to the patient.

The bioactive agent may be incorporated into a portion or the entirety of one or more phases (or layers) of the nanofiber scaffolds of the present invention. One or more bio-active agents may be distributed throughout a nanofiber scaffold. In another aspect of the invention, one or more bioactive agents may be incorporated into a first phase of a multiphasic nanofiber scaffold and one or more other bioactive agents (the same or different from those incorporated into the first phase) may be incorporated into another phase of the multiphasic nanofiber scaffold. For example, in the case of a biphasic nanofiber scaffold for a rotator cuff repair, a growth factor that promotes growth of tendon fibroblasts may be incorporated into the first phase, which is attached to the tendon and a growth factor that promotes the growth of osteoblasts may be incorporated into the second phase, which is attached to bone.

The bioactive agents may be incorporated into the nanofiber scaffold using procedures well known in the art, including, e.g., immersion, impregnation, vacuum suction, spraying, and the like.

Non-limiting representative examples of suitable bioactive agents according to the present invention include an anti-infective, an extracellular matrix component, an antibiotic, bisphosphonate, a hormone, an analgesic, an anti-inflammatory agent, a growth factor, an angiogenic factor, a chemotherapeutic agent, an anti-rejection agent, an RGD peptide, and combinations thereof.

Non-limiting representative examples of suitable growth factors according to the present invention include a member of the Transforming Growth Factor (TGF) super family, a vascular endothelial growth factor (VEGF), a platelet-derived growth factor (PDGF)$_1$ an insulin-derived growth factor (IGF), a modulator of a growth factor, and combinations thereof. In one aspect of this embodiment, a member of the TGF super family is selected from TGF-$\beta$, bone morphogenetic proteins (BMPs), growth differentiation factors (GDFs), Activin A and Activin B, Inhibin A, Inhibin B, anti-mullerian hormone, Nodal, and combinations thereof.

In another aspect of this embodiment, the TGF-$\beta$ is selected from TGF-$\beta$1, TGF-$\beta$2, TGF-$\beta$3, and combinations thereof. In a further aspect of this embodiment, the BMP is selected from the group consisting of BMP1-20 and combinations thereof. In yet another aspect of this embodiment, the GDFs are selected from GDF1-15 and combinations thereof. In a further aspect of this embodiment, the IGF is selected from IGF1, IGF2, insulin growth factor binding proteins 1-6 (IGFBP1-6), and combinations thereof. In a further aspect of this embodiment, a modulator of a growth factor is a SMAD (small mothers against decapentaplegic) selected from SMAD1-9 and combinations thereof.

The nanofiber scaffold may be treated with other materials to enhance or provide other additional biological benefits as desired. For example, the nanofiber scaffold may further contain a hydrogel disposed on all or a portion of the scaffold. In a multiphasic nanofiber scaffold, such as for example, the biphasic nanofiber scaffold, the hydrogel may be disposed on at least a portion of one or both of the phases (or one or more layers of a phase).

The hydrogel may be disposed/incorporated into the nanofiber scaffold using procedures well known in the art, including immersion, impregnation, vacuum suction, spraying, and the like.

Non-limiting representative examples of suitable hydrogels according to the present invention are composed of a material selected from agarose, carrageenan, polyethylene oxide, polyethylene glycol, tetraethylene glycol, triethylene glycol, trimethylolpropane ethoxylate, pentaerythritol ethoxylate, hyaluronic acid, thiosulfonate polymer derivatives, polyvinylpyrrolidone-polyethylene glycol-agar, collagen, dextran, heparin, hydroxyalkyl cellulose, chondroitin sulfate, dermatan sulfate, heparan sulfate, keratan sulfate, dextran sulfate, pentosan polysulfate, chitosan, alginates, pectins, agars, glucomannans, galactomannans, maltodextrin, amylose, polyalditol, alginate-based gels cross-linked with calcium, polymeric chains of methoxypoly(ethylene glycol)monomethacrylate, chitin, poly(hydroxyalkyl methacrylate), poly(electrolyte complexes), poly(vinylacetate) cross-linked with hydrolysable bonds, water-swellable N-vinyl lactams, carbomer resins, starch graft copolymers, acrylate polymers, polyacrylamides, polyacrylic acid, ester cross-linked polyglucans, and derivatives and combinations thereof.

In the present invention, hydrogels may contain mammalian cells, such as, e.g., human cells, in order to promote tissue repair. Non-limiting representative examples of suitable cells that may be incorporated into the hydrogel and subsequently the nanofiber scaffold include fibroblasts, chondrocytes, osteoblasts, osteoblast-like cells, stem cells, and combinations thereof. Preferably the cells are from a compatible human donor. More preferably, the cells are from the patient (i.e., autologous cells). The cells may be incorporated into a portion or the entirety of one or more phases (or one or more layers of a phase) of the nanofiber scaffolds of the present invention, with or without use of a hydrogel. Moreover, one or more cell types may be distributed throughout a nanofiber scaffold. In another aspect of the invention, one or more cell types may be incorporated into a first phase of a multiphasic nanofiber scaffold and one or more other cell types (the same or different from those incorporated into the first phase) may be incorporated into another phase of the multiphasic nanofiber scaffold. For example, in the case of a biphasic nanofiber scaffold for a rotator cuff repair, tendon fibroblasts may be incorporated into the first phase, which is attached to the tendon and osteoblasts may be incorporated into the second phase, which is attached to bone.

In another aspect of the invention, fibroblasts, stem cells, chondrocytes, or combinations thereof are disposed on at least a portion of the first phase of a biphasic nanofiber scaffold. In a further aspect, chondrocytes, osteoblasts, osteoblast-like cells, stem cells, or combinations thereof are disposed on at least a portion of the second phase of a biphasic nanofiber scaffold. In yet another aspect of this embodiment, fibroblasts stem cells, and chondrocytes are disposed on at least a portion of the first phase of a nanofiber scaffold and chondrocytes, osteoblasts, osteoblast-like cells, stem cells, or combinations thereof are disposed on at least a portion of the second phase of the nanofiber scaffold.

In one aspect of these embodiments, the stem cells are undifferentiated prior to disposition on the implantable device. In another aspect, the stem cells are pre-differentiated prior to disposition on the implantable device. The pre-differentiated stem cells may be selected for lineages that are specific for the type of repair to be carried out. For example, stem cells that will differentiate into osteoblasts and/or osteoclasts lineages in the case of a tendon-to-bone interface may be incorporated into the phase of the implantable device that will be fixated to bone. Whereas, stem cells that will differentiate into, e.g., fibroblasts, chondrocytes, and the like may be disposed on the phase of the implantable device that will be attached to the tendon.

As disclosed above, the nanofibers and the nanofiber scaffold of the implantable device are designed to mimic the anatomic architecture of the soft tissue or soft tissue-to-bone interface to be repaired, fixated, augmented, or replaced. Thus, the physical and mechanical properties of the nanofibers and nanofiber scaffold must approximate those of the soft tissue or soft tissue-to-bone interface to be repaired, fixated, augmented, or replaced. In the case of rotator cuff repair, implantable devices of the present invention that are biphasic and biomimetic have been designed and made. As discussed in more detail below, these nanofiber scaffolds have physical properties that are the same as or substantially the same as the in vivo architecture.

For example, a single layer of a scaffold composed of aligned nanofibers according to the present invention may have a yield strength of about 9.8±1.1 MPa, an elastic modulus of about 341±30 MPa, and an ultimate stress of about 12.0±1.5 MPa. In the case of a scaffold composed of non-aligned nanofibers, a single layer of such a nanofiber scaffold may have a yield strength of about 2.5±0.4 MPa, an elastic modulus of about 107±23 MPa, and an ultimate stress of about 3.7±0.2 MPa.

Moreover, in one implantable device according to the present invention, the nanofiber scaffold is composed of nanofibers with a fiber diameter of between about 568 to about 615 nm, a pore diameter of about 4.2 to about 4.9 µm, a porosity of about 80.7 to about 81.8%, and a permeability of about 5.7 to about $7.9 \times 10^{12}$ m$^4$/N s. As will be understood by one skilled in the art, the nanofiber scaffolds may be designed having the physical properties of the soft tissue or soft tissue-to-bone interface to be repaired. Thus, the parameters of each physical characteristic (e.g., yield strength, elastic modulus, ultimate stress, fiber diameter, pore diameter, and permeability) will be designed according to the repair to be carried out. The specific values for these characteristics may be determined from the literature and/or are readily measured using conventional techniques.

As discussed in more detail below, each of these physical properties can be modified, as desired, to approximate the natural architecture of the soft tissue to be repaired, augmented, or replaced by making the appropriate selection of polymer and/or polymer ratio, by modifying the electrospinning process, and by the selection of biocompatible ceramic materials and/or hydrogel for incorporation into the nanofiber scaffold.

Figure 20:
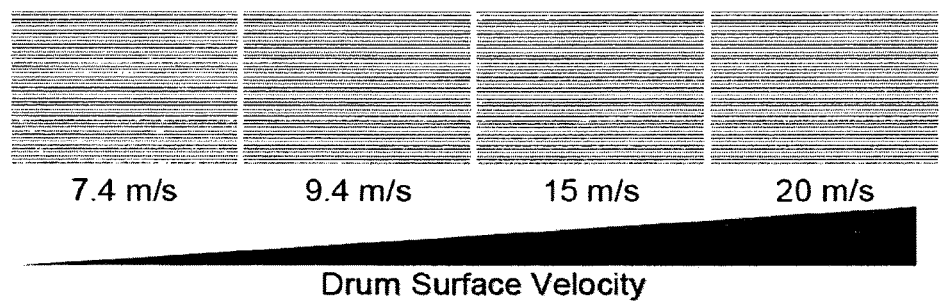
FIG. 20 is a series of micrographs showing how nanofiber orientation and alignment change with the drum surface velocity during electrospinning.

For example, the orientation and alignment of the nanofibers may be modified based on whether the nanofibers are spun onto a static surface, which produces fibers of decreased orientation and alignment or whether the nanofibers are spun onto a rotating drum. As shown in FIG. 20 and described in more detail in Example 1, increasing drum surface velocity increases the degree of fiber alignment and orientation.

In another embodiment of the present invention, there is provided an implantable biphasic biomimetic and biodegradable nanofiber device for soft-tissue or soft tissue-to-bone interface fixation, repair, augmentation, or replacement. This device comprises a first phase comprising nanofibers made from a biodegradable polymer and a second phase coupled to the first phase, which second phase comprises nanofibers made from a biodegradable polymer and a biocompatible ceramic, wherein the first and second phases are continuous. In a further embodiment of the present invention, there is provided an implantable device for fixation, repair, augmentation, or replacement of a rotator cuff or a tendon-to-bone interface thereof. This device comprises a biphasic, biomimetic, and biodegradable nanofiber scaffold that mimics a tendon-to-bone interface. This device has a first phase comprising nanofibers whose anisotropy mimics that of a tendon and non-mineralized fibrocartilage, which nanofibers are made from a biodegradable polymer and a second phase coupled to the first phase, which second phase comprises nanofibers whose anisotropy mimics that of mineralized fibrocartilage and bone, which nanofibers are made from a biodegradable polymer and a biocompatible ceramic, wherein the first and second phases are continuous.

In these last two embodiments, the biodegradable polymer is selected from the group consisting of aliphatic polyesters, poly(amino acids), modified proteins, polydepsipeptides, copoly(ether-esters), polyurethanes, polyalkylenes oxalates, polyamides, poly(iminocarbonates), polyorthoesters, polyoxaesters, polyamidoesters, poly(ε-caprolactone)s, polyanhydrides, polyarylates, polyphosphazenes, polyhydroxyalkanoates, polysaccharides, modified polysaccharides, polycarbonates, polytyrosinecarbonates, polyorthocarbonates, poly(trimethylene carbonate), poly(phosphoester)s, polyglycolide, polylactides, polyhydroxybutyrates, polyhydroxy valerates, polydioxanones, polyalkylene oxalates, polyalkylene succinates, poly(malic, acid), poly(maleic anhydride), polyvinylalcohol, polyesteramides, polycyanoacrylates, polyfumarates, poly(ethylene glycol), polyoxaesters containing amine groups, poly(lactide-co-glycolides), poly(lactic acid)s, poly(glycolic acid)s, poly(dioxanone)s, poly(alkylene alkylate)s, biopolymers, collagen, silk, chitosan, alginate, and a blend of two or more of the preceding polymers.

In these last two embodiments, the biocompatible ceramic is selected from silicon nitride-based ceramics, Pseudowollastonite ceramics ($\beta$-CaSi$\theta_3$), bredigite (Ca$_7$MgSi$_4$OiS) ceramics, mono-phase ceramics of monticellite (CaMgSiO(4)), akermanite ceramics (Ca$_2$MgSi$_2$O$_7$), tricalcium silicate (Ca(3)SiO(5)), hydroxyapatite, bio-active glass, calcium phosphate, dense calcium sulfate (DCaS), porous silicated calcium phosphate (Si—CaP), tricalcium phosphate (TCP), calcium pyrophosphate (CPP), and combinations thereof.

In another aspect of these embodiments, at least one of the phases further comprises a bioactive agent selected from an anti-infective, an extracellular matrix component, an antibiotic, bisphosphonate, a hormone, an analgesic, an antiinflammatory agent, a growth factor, an angiogenic factor, a chemotherapeutic agent, an anti-rejection agent, an RGD peptide, and combinations thereof.

In these last two embodiments, non-limiting representative examples of suitable growth factors according to the present invention include a member of the Transforming Growth Factor (TGF) super family, a vascular endothelial growth factor (VEGF), a platelet-derived growth factor (PDGF), an insulin-derived growth factor (IGF), a modulator of a growth factor, and combinations thereof. In one aspect of these embodiments, a member of the TGF super family is selected from TGF-β, bone morphogenetic proteins (BMPs), growth differentiation factors (GDFs), Activin A and Activin B, lnhibin A, lnhibin B, anti-mullerian hormone, Nodal, and combinations thereof.

In another aspect of these embodiments, the TGF-β is selected from TGF-β1, TGF-β2, TGF-β3, and combinations thereof. In a further aspect of this embodiment, the BMP is selected from the group consisting of BMP1-20 and combinations thereof. In yet another aspect of these embodiments, the GDFs are selected from GDF1-15 and combinations thereof. In a further aspect of these embodiments, the IGF is selected from IGF1, IGF2, insulin growth factor binding proteins 1-6 (IGFBP1-6), and combinations thereof. In a further aspect of these embodiments, a modulator of a growth factor is a SMAD (small mothers against decapentaplegic) selected from SMAD1-9 and combinations thereof.

In these last two embodiments, the implantable device may further comprise a hydrogel disposed on at least a portion of one or both of the phases (or one or more layers of a phase). In this aspect, the hydrogel is composed of a material selected from agarose, carrageenan, polyethylene oxide, polyethylene glycol, tetraethylene glycol, triethylene glycol, trimethylolpropane ethoxylate, pentaerythritol ethoxylate, hyaluronic acid, thiosulfonate polymer derivatives, polyvinylpyrrolidone-polyethylene glycol-agar, collagen, dextran, heparin, hydroxyalkyl cellulose, chondroitin sulfate, dermatan sulfate, heparan sulfate, keratan sulfate, dextran sulfate, pentosan polysulfate, chitosan, alginates, pectins, agars, glucomannans, galactomannans, maltodextrin, amylose, polyalditol, alginate-based gels cross-linked with calcium, polymeric chains of methoxypoly(ethylene glycol)monomethacrylate, chitin, poly(hydroxyalkyl methacrylate), poly(electrolyte complexes), poly(vinylacetate) cross-linked with hydrolysable bonds, water-swellable N-vinyl lactams, carbomer resins, starch graft copolymers, acrylate polymers, polyacrylamides, polyacrylic acid, ester cross-linked polyglucans, and derivatives and combinations thereof.

In these embodiments, the implantable device may further comprise fibroblasts, chondrocytes, osteoblasts, osteoblast-like cells, stem cells, or combinations thereof. In this aspect, fibroblasts, stem cells, chondrocytes, or combinations thereof are disposed on at least a portion of the first phase.

In another aspect, chondrocytes, osteoblasts, osteoblast-like cells, stem cells, or combinations thereof are disposed on at least a portion of the second phase. In a further aspect, fibroblasts, stem cells, and chondrocytes are disposed on at least a portion of the first phase and chondrocytes, osteoblasts, osteoblast-like cells, stem cells, or combinations thereof are disposed on the second phase.

In one aspect of these embodiments, the stem cells are undifferentiated prior to disposition on the implantable device. In another aspect, the stem cells are pre-differentiated prior to disposition on the implantable device. The pre-differentiated stem cells may be selected for lineages that are specific for the type of repair to be carried out. For example, stem cells that will differentiate into osteoblasts and/or osteoclasts lineages in the case of a tendon-to-bone interface may be incorporated into the phase of the implantable device that will be fixated to bone. Whereas, stem cells that will differentiate into, e.g., fibroblasts, chondrocytes, and the like may be disposed on the phase of the implantable device that will be attached to the tendon.

In the present invention, the nanofiber scaffolds of the implantable device may be manufactured in manner that is convenient for surgical delivery. Preferably, the nanofiber scaffolds are manufactured in a manner that closely mimics the architectural anatomy to be repaired, fixated, augmented, or replaced. Thus, to a certain degree, the soft tissue or soft tissue-to-bone interface to be repaired will drive the dimensions of the nanofiber scaffolds.

Referring now to FIG. 16 A, and by way of example, for a rotator cuff, the implantable device (1) will be about 0.2 to about 2.0 mm thick (D). The shape of the implantable device is not critical, but should be informed by surgeon preference. Typically, the implantable device (1) may be about 5.0 cm long (p) and about 5.0 cm wide (W). Alternatively, referring to FIG. 16 B, the implantable device (10) may be about 10.0 cm in diameter (D). Preferably, the implantable device will be dimensioned so that it is larger than required for the repair, fixation, augmentation, or replacement, so that the surgeon may adjust the dimensions to fit the particular anatomy of the patient.

Another embodiment of the invention is a method for fixation of, repairing, augmenting, or replacing a damaged soft tissue or soft tissue-to-bone interface in a patient. This method comprises affixing a biomimetic, biodegradable continuous multiphasic nanofiber scaffold according to the present invention to a surgically relevant site in order to repair, fixate, augment, or replace the damaged soft tissue or soft tissue-to-bone interface.

A further embodiment of the present invention is a method for fixating, repairing, augmenting, or replacing a damaged rotator cuff in a patient. This method comprises affixing a biomimetic and biodegradable continuous multiphase nanofiber scaffold according to the present invention to a surgically relevant site in order to repair, augment, or replace the damaged rotator cuff.

In sum, the present invention relates to a biodegradable polymer-based nanofiber scaffold designed for repair, fixation, augmentation, or replacement of tendon-to-bone insertion site damage, such as, for example, rotator cuff repair. Data disclosed herein include human rotator cuff fibroblast response on the degradable nanofiber scaffolds as well as the effects of nanofiber organization (aligned vs. unaligned fibers) on cell attachment and matrix deposition. The novel nanofiber scaffold of the present invention has been designed to match the structural and mechanical properties of the rotator cuff tendon. Although not wishing to be bound by a particular theory, it is believed that fibroblast attachment, morphology and matrix elaboration will be guided by the underlying organization of nanofiber scaffolds.

The Fully Synthetic Implantable Multiphased Scaffold

One embodiment of the present invention is a fully synthetic implantable multi-phased scaffold. This scaffold comprises, in a single continuous construct, a plurality of phases designed to mimic the natural anatomy of a tendon or a ligament. Natrual anatomy of the tendon or ligament means the native structure and design of the tendon or ligament, both in terms of macroscopic anatomy and microscopic anatomy.

In the present invention, the scaffold may have more than one phase, depending on the anatomical architecture of the ligament or tendon to be repaired, fixed, augmented, or replaced. An exemplary number of phases is from about 1 to about 10, such as for example, from about 2 to about 4, preferably 3 or 4. As noted above, in such multiphasic embodiments, each phase of the scaffold is continuous from phase-to-phase.

In one aspect, the composition of each phase of the fully synthetic implantable multi-phased scaffold is selected to promote growth and maintenance of soft tissue and/or soft tissue-to-bone interfaces.

In another aspect, the fully synthetic implantable multi-phased scaffold is biodegradable.

In the present invention, the polymer may be selected from aliphatic polyesters, poly(amino acids), modified proteins, polydepsipeptides, copoly(ether-esters), polyurethanes, polyalkylenes oxalates, polyamides, Poly(iminocarbonates), polyorthoesters, polyoxaesters, polyamidoesters, Poly($\varepsilon$-caprolactone)s, polyanhydrides, polyarylates, polyphosphazenes, polyhydroxyalkanoates, polysaccharides, modified polysaccharides, polycarbonates, polytyrosinecarbonates, polyorthocarbonates, poly(trimethylene carbonate)s, poly(phosphoester)s, polyglycolide, polylactides, polyhydroxybutyrates, polyhydroxyvalerates, polydioxanones, polyalkylene oxalates, polyalkylene succinates, poly(malic acid), poly(maleic anhydride), polyvinylalcohol, polyesteramides, polycyanoacrylates, polyfumarates, poly(ethylene glycol), polyoxaesters containing amine groups, poly(lactide-co-glycolides), poly(lactic acid)s, poly(glycolic acid)s, poly(dioxanone)s, poly(alkylene alkylate)s, biopolymers, or a blend of two or more of the preceding polymers.

Figure 55:
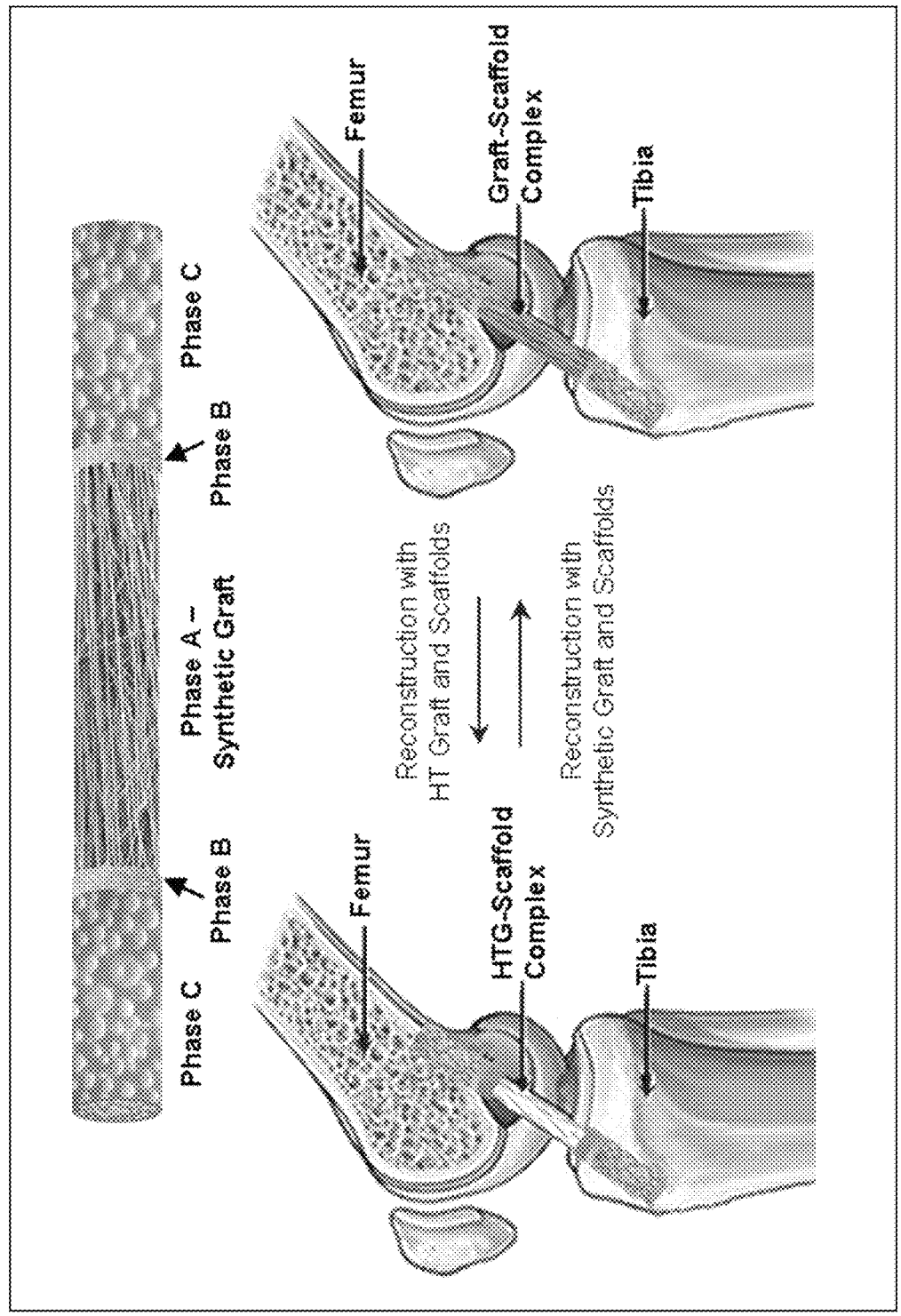
FIG. 55 shows a comparison of a prior HTG scaffold complex utilizing graft material from a natural source and a fully synthetic implantable scaffold according to the present invention. As shown, the fully synthetic implantable scaffold has three phases—Phase A is a synthetic graft, Phase B disposed on either side of Phase A is made from microspheres, and Phase C, disposed on either side of the respective Phase B material, is made from a composite material.
Figure 56:
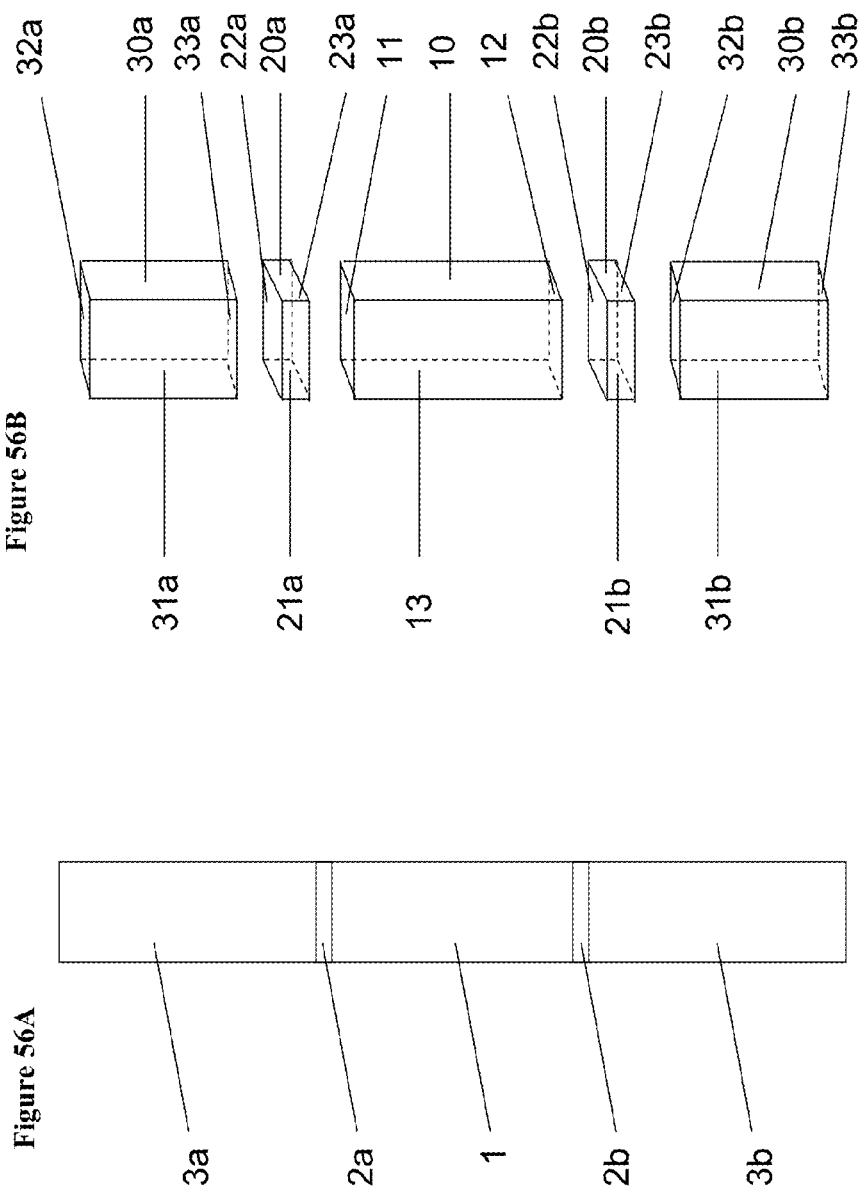

Referring now to FIGS. 56A and B, in a further aspect of the fully synthetic implantable multi-phased scaffold, the scaffold comprises (i) a first phase (1, 10) comprising a synthetic graft material suitable for implantation into a mammal, such as, e.g., a human, the synthetic graft material is dimensioned to have a body (13) with first and second ends (11, 12); (ii) two second phases (2*a*, 2*b*; 20*a*, 20*b*), each second phase comprising microspheres or mesh and having a body (21*a*, 21*b*) and first (22*a*, 22*b*) and second (23*a*, 23*b*) ends, the ends (23*a*, 22*b*) of the respective second phases disposed at each end of the first phase (11, 12); and (iii) two third phases (3*a*, 3*b*; 30*a*, 30*b*), each third phase having a body (31*a*, 31*b*) and first and second ends (32*a*, 33*a*; 32*b*, 33*b*). The first end of the respective third phases (3*a*, 3*b*; 30*a*, 30*b*) is disposed at an end of each respective second phase (22*a*, 23*b*), such that the first phase (1, 10) is separated from the respective third phases (3*a*, 3*b*; 30*a*, 30*b*) by each of the second phases (2*a*, 2*b*; 20*a*, 20*b*), the third phases (3*a*, 3*b*; 30*a*, 30*b*) comprising a material suitable for anchoring the scaffold to bone. FIG. 55 is a graphic rendering of such a scaffold with phases A, S, and C corresponding to phases 1, 2*a*, *b*, and 3*a*, *b* (and 10, 20*a*, *b*, and 30*a*, *b*), respectively of FIG. 56.

Figure 57:
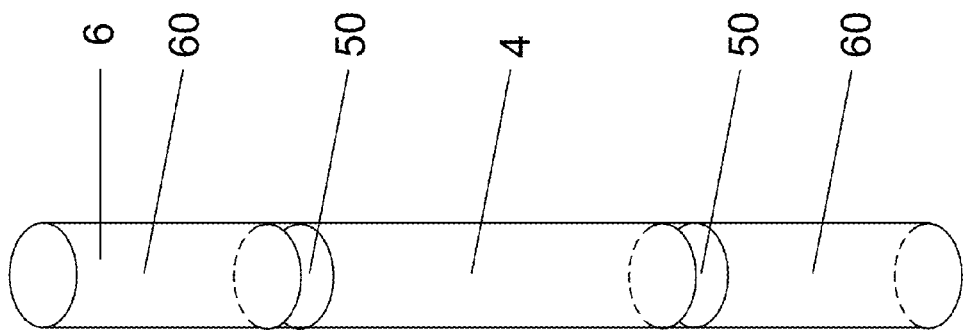
FIG. 57 shows an elevated side view of another embodiment of a fully synthetic implantable multi-phase scaffold according to the present invention.

The shape of the scaffold is not critical, but should be informed by surgeon preference and the type of procedure. Thus, as shown in FIGS. 55 and 57, the scaffold may be cylindrical or, as shown in FIGS. 56 and 58, the scaffold may be rectangular. Such shapes are only exemplary and are not intended to limit the shape of the scaffold in any way. Preferably, the scaffold will be dimensioned so that it is larger than is required for the specific procedure so that the surgeon may adjust the dimensions to fit the particular anatomy of the patient.

With reference to FIG. 57, a cylindrical embodiment of the scaffold of the present invention (65) is shown. The scaffold comprises (i) a first phase (40) comprising a synthetic graft material suitable for implantation into a mammal, such as, e.g., a human, the synthetic graft material is dimensioned to have a body with first and second ends; (ii) two second phases (50*a*, 50*b*), each second phase comprising microspheres or mesh and having a body and first and second ends, the first end of the respective second phases disposed at each end of the first phase; and (iii) two third phases (60*a*, 60*b*), each third phase disposed at the second end of each respective second phase, such that the first phase (40) is separated from the respective third phases (60*a*, 60*b*) by each of the second phases (50*a*, 50*b*), the third phases comprising a material suitable for anchoring the scaffold to bone and/or to soft tissue.

In the present invention, the fully synthetic scaffold may have multiple phases and layers, which are designed to mimic the natural architecture of the repair site. Thus, in the present invention, the scaffold may have, e.g., from 1 to 10 phases and from 1 to 10 layers. In the present invention, when a numerical range is provided, all members of the range are intended, including the endpoints. By way of example only, FIG. 58A shows a fully synthetic multiphasic scaffold (115) having multiple phases (70, 80, 90, 100, and 110). Each phase is designed to mimic a specific architecture at a repair site. In this embodiment, phase (90) corresponds to a synthetic graft material. Phases (80) and (100) may be the same or different and may be made of microspheres or mesh. Phases (70) and (110) may be the same or different and may be made of a material suitable for anchoring the scaffold to bone and/or to soft tissue.

Figure 58B:
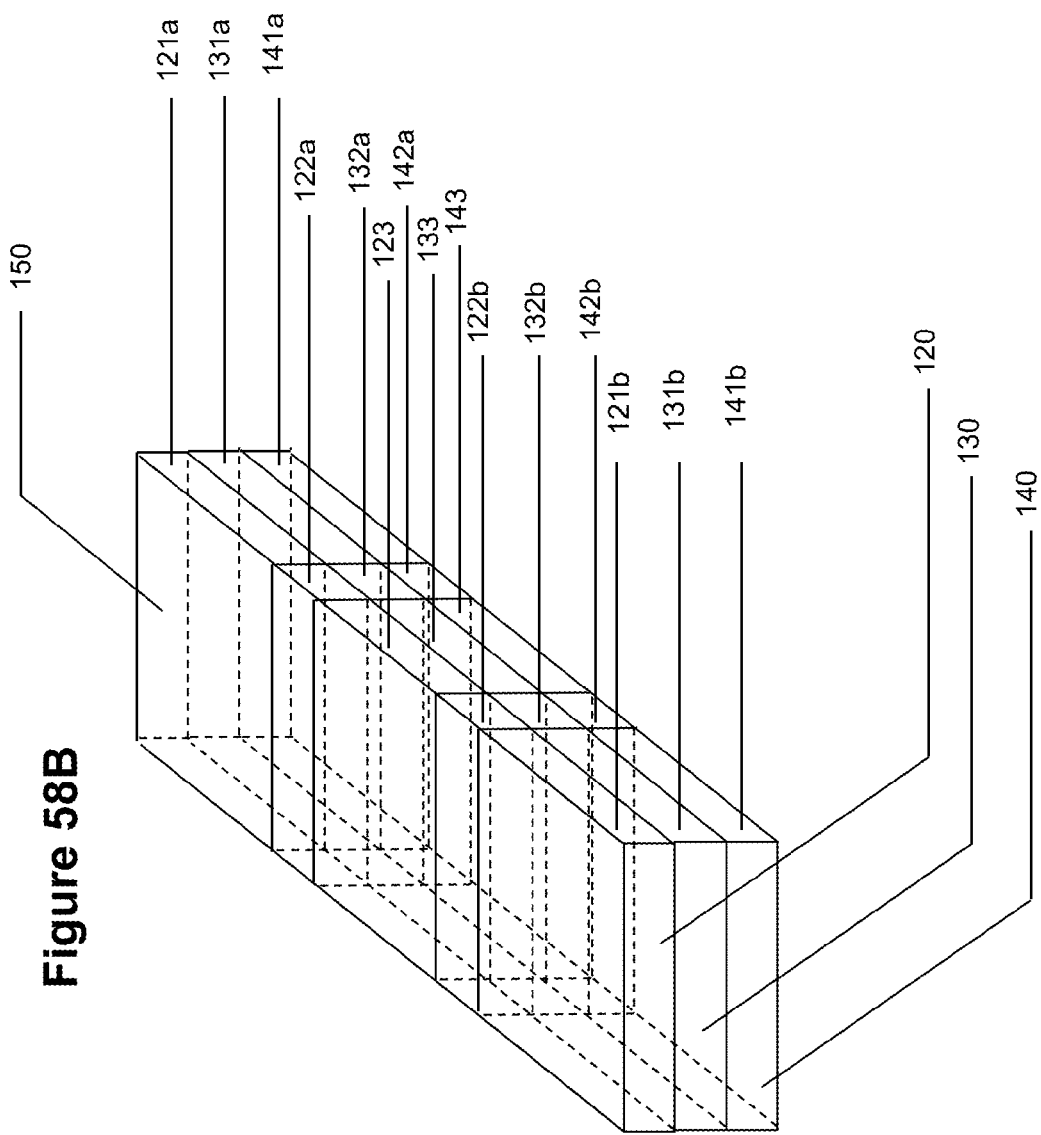

Now referring to FIG. 58B, a fully synthetic scaffold (150) according to the present invention is exemplified having three layers (120, 130, and 140, respectively). Each layer of the scaffold may be the same (i.e., contain the same phases in the same order) or different (i.e., contain the same phases in a different order) depending on the requirements of the surgery. Moreover, the dimensions of each phase may be the same or different and may be the same or different from layer to layer. As shown, layer 120 is comprised of phases 121*a*, *b*, 122*a*, *b*, 123; layer 130 is comprised of phases 131*a*, *b*, 132*a*, *b*, 133; and layer 140 is comprised of phases 141*a*, *b*, 142*a*, *b*, 143.

Figure 60:
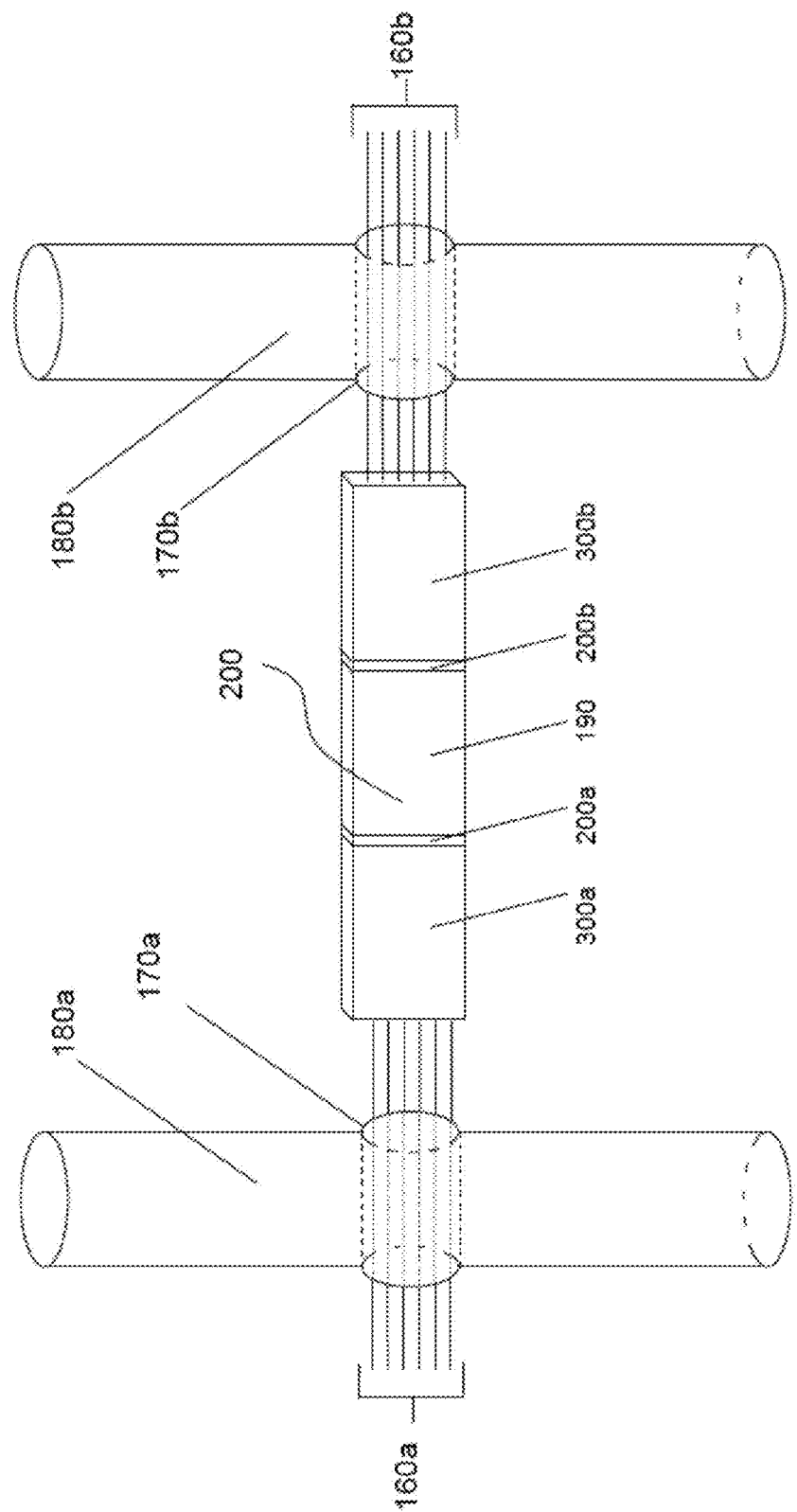
FIG. 60 shows an elevated side view of a fully synthetic implantable multi-phase scaffold according to the present invention in which a fourth phase is shown for fixation to a bone.
Figure 61:
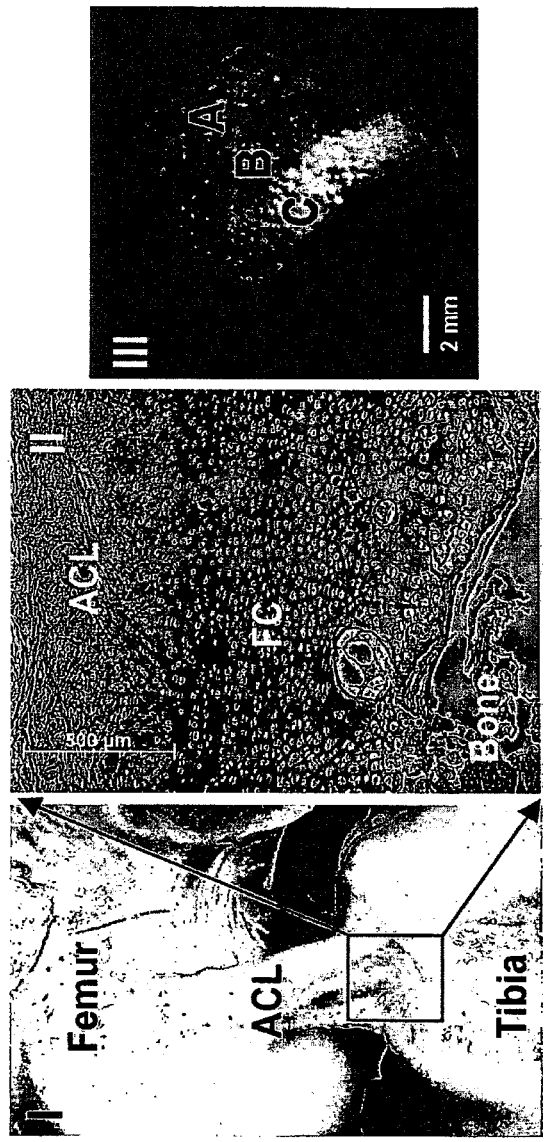
FIG. 61: I and II: ACL-to-bone insertion (Trichrome, 5×) III: Biomimetic Triphasic scaffold (Ø 7.5×6.5 mm).

Now referring to FIG. 60, another embodiment of the present invention is shown. In this embodiment, a fully synthetic multiphasic scaffold (200) having four phases (190; 200*a* and 200*b*; 300*a* and 300*b*; and 160*a* and 160*b*). Each phase is designed to mimic a specific architecture at a repair site. In this embodiment, the first phase (190) corresponds to a synthetic graft material as described herein. The second phase (200*a*) and (200*b*) may be the same or different and may be made of microspheres or mesh as described herein. The third phase (300*a*) and (300*b*) may be the same or different as described herein. The fourth phase (160*a* and 160*b*, respectively) is disposed on either side of the third phase (300*a* and 300*b*, respectively). As shown, the respective first ends of the fourth phase are disposed adjacent to the respective second ends of the third phase. The fourth phase is made of a material that is dimensioned and suitable for mechanical fixation of each respective fourth phase to bone.

The third phase may be made from a polymer-ceramic composite. The polymer of the composite may be selected from polyesters, poly(amino acids), copoly(ether-esters), polyalkylenes oxalates, polyamides, poly(iminocarbonates), polyorthoesters, polyoxaesters, polyamidoesters, poly(ε-caprolactone)s, polyanhydrides, polyarylates, polyphosphazenes, polyhydroxyalkanoates, polysaccharides, or biopolymers, or a blend of two or more of the preceding polymers. The ceramic of the composite may be selected from bioactive glass, calcium phosphate, hydroxyapatite, or beta tricalcium phosphate. Preferably, the polymer is poly(lactide-co-glycolide) and the ceramic is bio-active glass.

The material used in the fourth phase may be made from aliphatic polyesters, poly(amino acids), copoly(ether-esters), polyalkylenes oxalates, polyamides, poly(iminocarbonates), polyorthoesters, polyoxaesters, polyamidoesters, poly(ε-caprolactone)s, polyanhydrides, polyarylates, polyphosphazenes, polyhydroxyalkanoates, polysaccharides, degradable polyurethanes, or biopolymers, or a blend of two or more of the preceding polymers. Preferably, the synthetic graft material used in the fourth phase is poly(lactide-co-glycolide), poly(lactide) or poly(glycolide).

The fourth phase is suitably dimensioned for fixation to bone using conventionally known surgical techniques for mechanical fixation to bone. As shown in FIG. 60, for example, the fibrous ends of the fourth phase (160a, 160b) may be threaded through a hole (170a, 170b) in bone (180a, 180b), e.g., a femur and tibia in the case of an ACL repair, and may be secured thereto by e.g., tying, screws, nails, and other similar fixation devices and/or techniques. Ideally, each respective fourth phase is longer than required in order to allow the surgeon to trim it as necessary based on the selected fixation method.

The first phase of the synthetic implantable multi-phased scaffold may be joined to the respective second phases by sintering or solvent evaporation, and the third phases may be joined to the second phases by sintering or solvent evaporation. Additionally, the fourth phases may be joined to the third phases by sintering or solvent evaporation. Other methods known in the art for forming a continuous construct are also within the scope of the invention.

In one aspect, at least one of the third phase of the synthetic implantable multi-phased scaffold is adapted to support growth and maintenance of bone. Accordingly, the scaffold may be adapted for use in ligament repair or replacement, e.g., repair or replacement of anterior-cruciate ligaments, medial collateral ligaments, lateral collateral ligaments, posterior cruciate ligaments, cricothyroid ligaments, periodontal ligaments, anterior sacroiliac ligaments, posterior sacroiliac ligaments, sacrotuberous ligaments, inferior pubic ligaments, superior pubic ligaments, suspensory ligaments of the penis, suspensory ligaments of the breast, volar radiocarpal ligaments, dorsal radiocarpal ligaments, ulnar collateral ligaments, or radial collateral ligaments.

The first phase may be seeded with at least one of fibroblasts, fibroblast-like cells, and stem cells. At least one second phase may be seeded with at least one of chondrocytes, fibroblasts, and stem cells. At least one third phase may be seeded with at least one of osteoblasts, osteoblast-like cells, and stem cells.

At least one of the first, second, or third phases of the synthetic implantable multi-phased scaffold may also be imparted with a medicament, such as anti-infectives, antibiotics, bisphosphonate, hormones, analgesics, anti-inflammatory agents, growth factors, angiogenic factors, chemotherapeutic agents, anti-rejection agents, or RGD peptides.

In another aspect, the fully synthetic implantable multi-phased scaffold may be adapted for use in tendon repair or replacement, e.g., repair or replacement of rotator cuff tendons, elbow tendons, wrist tendons, hamstring tendons, patellar tendons, ankle tendons, foot tendons, supra-spinatus tendon, the Achilles tendon, or the patellar tendon.

Another embodiment is a fully synthetic implantable multi-phased scaffold for ligament repair. This scaffold for ligament repair comprises (i) a first phase comprising a synthetic graft material suitable for implantation into a mammal, the synthetic graft material dimensioned to have a body with first and second ends; (ii) two second phases, each second phase comprising microspheres or mesh and having a body and first and second ends, the first end of the respective second phases disposed at each end of the first phase; and (iii) two third phases, each third phase comprising a body and first and second ends, the first end of the respective third phases disposed at the second end of each respective second phase, such that the first phase is separated from the respective third phases by each of the second phases, the third phases comprising a material suitable for anchoring the scaffold to bone.

In one aspect, this scaffold further comprises two fourth phases, each fourth phase disposed at the second end of each respective third phase, the fourth phases comprising a material dimensioned and suitable for mechanical fixation of each respective fourth phase to bone.

In this embodiment, the compositions of each of the phases, as well as preferred compositions of these phases, are as previously disclosed herein. In one aspect, the first phase may be joined to the respective second phases by sintering or solvent evaporation and the respective third phases are joined to the respective second phases by sintering or solvent evaporation. Additionally, the fourth phases are joined to the third phases by sintering or solvent evaporation.

A further embodiment is a fully synthetic implantable multi-phased scaffold for tendon repair. This scaffold for tendon repair comprises (i) a first phase comprising a synthetic graft material suitable for implantation into a mammal, the synthetic graft material dimensioned to have a body with first and second ends; (ii) two second phases, each second phase comprising microspheres or mesh and having a body and first and second ends, the first end of the respective second phases disposed at each end of the first phase; and (iii) two third phases, each third phase comprising a body and first and second ends, the first end of the respective third phases disposed at the second end of each respective second phase, such that the first phase is separated from the respective third phases by each of the second phases, the third phases comprising a material suitable for anchoring the scaffold to bone.

In one aspect, this scaffold further comprises two fourth phases, each fourth phase disposed at the second end of each respective third phase, the fourth phases comprising a material dimensioned and suitable for mechanical fixation of each respective fourth phase to bone.

In this embodiment, the compositions of each of the phases, as well as preferred compositions of these phases, are as previously disclosed herein. In one aspect of this embodiment, the first phase may be joined to the respective second phases by sintering or solvent evaporation and the respective third phases are joined to the respective second phases by sintering or solvent evaporation. Additionally, the fourth phases are joined to the third phases by sintering or solvent evaporation.

An additional embodiment is a fully synthetic implantable multi-phased scaffold for anterior cruciate ligament repair. This scaffold for anterior cruciate ligament repair comprises a first phase comprising a synthetic graft material suitable for implantation into a mammal, the synthetic graft material dimensioned to have a body with first and second ends; (ii) two second phases, each second phase comprising microspheres or mesh and having a body and first and second ends, the first end of the respective second phases disposed at each end of the first phase; and (iii) two third phases, each third phase comprising a body and first and second ends, the first end of the respective third phases disposed at the second end of each respective second phase, such that the first phase is separated from the respective third phases by each of the second phases, the third phases comprising a material suitable for anchoring the scaffold to bone.

In one aspect, this scaffold further comprises two fourth phases, each fourth phase disposed at the second end of each respective third phase, the fourth phases comprising a material dimensioned and suitable for mechanical fixation of each respective fourth phase to bone.

In this embodiment, the compositions of each of the phases, as well as preferred compositions of these phases, are as previously disclosed herein. In one aspect, the first phase may be joined to the respective second phases by sintering or solvent evaporation and the respective third phases are joined to the respective second phases by sintering or solvent evaporation. Additionally, the fourth phases are joined to the third phases by sintering or solvent evaporation.

The fully synthetic implantable multi-phased scaffold of the present invention, as previously disclosed, may further comprise a mesh disposed between adjacent phases. The mesh may be made from woven fibers, non-woven fibers, and nanofibers. Additionally, the mesh may be comprised of one or more layers.

Now referring to FIG. 59A, a fully synthetic scaffold according to the present invention is exemplified having mesh (4b, 4c, 4a, and 4d respectively) between adjacent phases of the scaffold (i.e., phases 1 and 2a; 1 and 2b; 2a and 3a; and 2b and 3b, respectively). FIG. 59B shows an exploded elevated side view of a mesh (4a) located in between phases (2a and 3a of FIG. 59A). FIG. 59C shows a mesh (5) having three layers (6, 7, and 8, respectively), but the present invention contemplates from about 1 to about 10 layers for a mesh divider. When the mesh is made of electrospun nanofibers, the alignment and orientation of each mesh layer may be varied as described in, e.g., Lu et al. international application no PCT/US2008/001889. Each layer of the mesh may be the same (i.e., contain the same mesh in the same order) or different (i.e., contain the same mesh in a different order) depending on the requirements of the surgery. Moreover, the dimensions of each mesh may be the same or different and may be the same or different from layer to layer.

The present invention may optionally include other variations in the phases or scaffolds as set forth below. For example, the scaffolds may have a gradient of properties (such as structural properties, pore diameter, chemical properties, mechanical properties, etc.), for the repair of musculoskeletal tissue. Such scaffolds are preferably multi-phased, biodegradable, and osteointegrative.

A scaffold apparatus, according to one preferred embodiment, is multiphasic, including first, second and third phases, and preferably can support growth, maintenance and differentiation of multiple tissue and cell types.

The first phase comprises a first material adapted for integration and growth (for example, by including one or more osteogenic agents, osteogenic materials, osteoinductive agents, osteoinductive materials, osteoconductive agents, osteoconductive materials, growth factors, chemical factors, etc.) of a first tissue type and is seeded with a first type of cells (for example, osteoblasts, osteoblast-like cells, stem cells, etc.). The material of the first phase may include, but are not limited to, microspheres, foams, sponges and any other three dimensional (3-D) scaffold construct consisting of polymer and/or ceramic. Polymers may include, but are not restricted to, any biodegradable polymer such as any of the poly-(α-hydroxy acids), or natural polymers such as silk, collagen, or chitosan. Ceramics may include but are not limited to bioactive glass, hydroxyapatite, beta tricalcium phosphate, or any other calcium phosphate material.

The third phase comprises a second material adapted for integration and growth of a second tissue type seeded with a second type of cells (for example, fibroblasts, chondrocytes, stem cells, etc.). The third phase may include a composite of materials, including, but not limited to, microspheres, a fiber mesh, degradable polymers, etc.

The second phase is an interfacial zone between the first and third phases.

The multiphasic scaffold apparatus preferably has a gradient of calcium phosphate content across the phases, and is preferably biomimetic, biodegradable (that is, each phase is degradable) and/or osteointegrative.

A scaffold apparatus for musculoskeletal tissue engineering, according to another embodiment, may include microspheres of selected sizes and/or composition. The microspheres may be layered to have a gradient of microsphere sizes and/or compositions. The scaffold may provide a functional interface between multiple tissue types (for example, soft tissue and bone).

FIG. 21A shows schematically a multi-phased scaffold apparatus 10 comprising phase A, phase B, and phase C. Phases A-C have a gradient of properties. The gradient of properties across phases A-C of the scaffold may include mineral content (for example, Ca—P), mechanical properties, chemical properties, structural properties, porosity, geometry, etc. It should be apparent to one skilled in the art that although apparatus 10 has three phases, the apparatus can be integrated in a scaffold with four or more phases.

For example, the multi-phased scaffold may contain a gradient of Ca—P concentrations. Phase A may be constructed of fiber mesh with aligned fibers and with no Ca—P, phase C may be constructed of polymer-ceramic composite with high Ca—P, and phase B may be constructed of polymer-ceramic composite with lower Ca—P than phase C.

The scaffold apparatus can promote growth and maintenance of multiple tissue types. The scaffold may support growth, maintenance and differentiation of multiple tissue and cell types. The multi-phased scaffold may mimic the inhomogeneous properties of the insertion zone between soft tissue and bone, resulting in desired growth, phenotypic expression, and interactions between relevant cell types.

The phases of the scaffold may be inhomogeneous in properties. The phases may have zonal differences in mineral content and matrix morphology designed to mimic the tissue-bone interface and to facilitate the growth and maintenance of different tissues. The phases may differ in morphology. For example, phase A can include a porous fibrous mesh, while phases B and C include microspheres. According to another embodiment, the scaffold may include a composite of microspheres and a fiber mesh.

The scaffold preferably includes multiple phases. According to one embodiment, one phase (for example, phase A) supports growth and maintenance of soft tissue, another phase (for example, phase C) supports growth and maintenance of bone, and a third phase is an interfacial zone between the first and second phases. The first phase for supporting growth and maintenance of the soft tissue may be seeded with at least one of fibroblasts, chondrocytes and stem cells. The second phase for supporting growth and maintenance of the bone may be seeded with at least one of osteoblasts, osteoblast-like cells and stem cells. The second phase can contain at least one of osteogenic agents, osteogenic materials, osteoinductive agents, osteoinductive materials, osteoconductive agents, osteoconductive materials, growth factors and chemical factors.

Further, at least one of said first phase and said second phase may be seeded with one or more agents by using a microfluidic system.

The third phase may include some of the microspheres. The third phase can include a gradient of microsphere sizes and/or a gradient of microsphere compositions. The microspheres in the third phase may be joined by sintering in at least one stage.

The second phase may include additional microspheres. The second phase can comprise one of polymeric and composite microspheres including a range of diameters or a gradient of diameter. At least some of the microspheres of the third phase may be in a first range of sizes, and the additional microspheres of the second phase may be in a second range of sizes lower than the first range of sizes.

The second phase can comprise polymeric hydrogels of one of polyethylene glycol and hydroxyethyl methacrylate. The hydrogel may comprise one or more of poly(ethylene glycol), agarose, alginate, 2-hydroxyethyl methacrylate and polyacrylamide. The second phase can comprise collagen gels with varied mineral content.

The scaffold may include a composite of microspheres and a fiber mesh. The fiber mesh may be a degradable polymer. For example, the first phase may include a fiber mesh. The fiber mesh of the first phase and the microspheres of the third phase may be sintered together. The fiber mesh may be electrospun.

The mesh can include one or more desired agents and/or compound. For example, at least one of bioactive agents and peptides may coat the surface of the mesh. The bioactive agents and peptides can enhance differentiation, proliferation and attachment of cells and specific cell types. Also or alternatively, at least one of bioactive agents and peptides can directly be incorporated into the mesh.

According to one embodiment, the scaffold may include multiple phases joined by a gradient of properties. The multiple phases joined by the gradient of properties may be processed through one or more sintering stages. The gradient of properties across the multiple phases of the scaffold can include mechanical properties, chemical properties, mineral content, structural properties, porosity and/or geometry.

The scaffold apparatus can include plural phases of microspheres. For example, a first phase of the microspheres can comprise polymer and a second phase of the microspheres can comprise one of bioactive glass and calcium phosphate. Varying concentrations of calcium phosphate can be incorporated into the microspheres. The calcium phosphate can be selected from a group comprising tricalcium phosphate, hydroxyapatite, and a combination thereof. The polymer can be selected from a group comprising aliphatic polyesters, poly(amino acids), copoly(ether-esters), polyalkylenes oxalates, polyamides, poly(iminocarbonates), polyorthoesters, polyoxaesters, polyamidoesters, poly(c-caprolactone)s, polyanhydrides, polyarylates, polyphosphazenes, polyhydroxyalkanoates, polysaccharides, and biopolymers, and a blend of two or more of the preceding polymers. The polymer can comprise at least one of poly(lactide-co-glycolide), poly(lactide) and poly(glycolide).

The microspheres may comprise one or more of CaP, bioactive glass, polymer, etc. The microspheres may be processed through one or more sintering stages.

The microspheres may comprise one or more desired agents or compounds. For example, at least one of bioactive agents and peptides may coat the surface of at least some of the microspheres. The bioactive agents and peptides can enhance at least one of differentiation, proliferation and attachment of cells and specific cell types. Also or alternatively, at least one of bioactive agents and peptides can directly be incorporated into at least some of the microspheres. The microspheres can additionally include one or more agents selected from a group comprising antiinfectives, hormones, analgesics, anti-inflammatory agents, growth factors, chemotherapeutic agents, anti-rejection agents and RGD peptides.

The apparatus is preferably biomimetic, biodegradable and/or osteointegrative.

According to one exemplary embodiment, the apparatus may be integrated in a graft fixation device. The graft fixation device may be used, for example, for graft fixation at the bone tunnels during anterior cruciate ligament reconstruction. According to another embodiment, the apparatus may be integrated in an interference screw.

In addition, the scaffold apparatus, according to another exemplary embodiment, may be integrated in a graft collar. The graft collar has many applications. For example, the graft collar may be adapted for hamstring tendon-to-bone healing. As another example, the graft collar can be adapted for peridontal ligament repair. Further, the graft collar may be adapted for spinal repair.

A scaffold apparatus for soft tissue-to-bone interface tissue engineering, according to another exemplary embodiment, is shown schematically in FIG. 21B. Apparatus 15 includes a first region H, a second region I which is joined to region H, a third region J which is joined to region I, and a fourth region K which is joined to region J.

Region H comprises composite microspheres of a first size and composition optimized to promote growth, proliferation, and differentiation of a first cell type for integration and growth of a first tissue type. The composite microspheres of region H can include a range of sizes.

Region I comprises at least one of microspheres and a fibrous mesh having a second size and a second composition. The microspheres and/or fibrous mesh of region I can include a range or gradient of sizes, and/or a gradient of compositions.

Region J comprises at least one of a microsphere and a fibrous mesh having a third size and a third composition. Regions I and J are optimized to promote growth, proliferation and differentiation of a second cell type for integration and formation of a second tissue type. The microspheres and/or fibrous mesh of region J can include a range or gradient of sizes, and/or a gradient of compositions.

Region K comprises at least one of a microsphere and a fibrous mesh having a composition adapted to promote growth, proliferation, and differentiation of a third cell type for integration and growth of a third tissue The regions H—K can be joined together through one of a solid state sintering process and a solvent aggregation process, in which selected growth factors or bioactive agents are incorporated into each region to promote formation, growth and integration of said first, second and third types of tissues. The scaffold apparatus may be integrated in a graft collar.

A multi-phased scaffold apparatus for providing a functional interface between bone and soft tissue, according to an embodiment schematically shown in FIG. 21C, includes microspheres as one phase, and a mesh as another phase. The microspheres and the mesh may be sintered together.

FIG. 21C shows schematically a multi-phased scaffold apparatus 20 comprising phase X and phase Y. Microspheres may be one phase of the scaffold and a mesh may be another phase of the scaffold. The microspheres and the mesh may be sintered together. The apparatus 20 may be integrated in a scaffold which includes multiple phases (for example, three or more).

The microsphere and mesh structure of the scaffold may be geometrically heterogeneous, including a fiber mesh for culturing fibroblasts and an open-pore structure for osteoblasts. At least one zone of hydrogels or open-pore structure for chondrocytes may also be included. The microsphere and mesh components may be incorporated into the scaffold to allow for the co-culturing of multiple cell types to mimic the multitude of cell types found at native tissue interfaces. The mesh can be electrospun.

The scaffold may be modified to achieve specific cell culture parameters, for example, by including microspheres of varying diameters to vary the porosity of the scaffold in different regions. Furthermore, the scaffold may be fabricated in a variety of geometries. For example, the scaffold apparatus can be integrated in a graft collar.

This application also describes methods for preparing a scaffold for musculoskeletal tissue engineering. A method, according to one embodiment (FIG. 22A), includes (a) processing a plurality of microspheres (step S31), including incorporating calcium phosphate into the microspheres, (b) laying the processed microspheres in a mold (step S33), the microspheres in the mold presenting a gradient of microsphere sizes and/or compositions, and (c) sintering together the microspheres in the mold above a glass transition temperature (step S35).

Additional steps may optionally be added to the method to impart additional scaffold features or characteristics. For example, the method may further include sintering a fiber mesh onto the microsphere construct to provide a functional interface between multiple tissue types. Further, the method may further comprise electrospinning said fiber mesh prior to attaching the electrospun fiber mesh onto the microsphere construct.

Varying concentrations of calcium phosphate may be incorporated into the microspheres. The calcium phosphate incorporated into the microspheres may include hydroxyapatite, tricalcium phosphate, etc.

The particulate phase of the microspheres may include bioactive glass. Varying porosity or concentrations of bioactive glass may be incorporated into the microspheres.

The method may further include applying a particle reinforcement process to the microspheres. The method may further include incorporating particulates in the microspheres prior to the sintering step to strengthen the microspheres.

A method for preparing a multi-phase scaffold for musculoskeletal tissue engineering, according to an exemplary embodiment (FIG. 22B), includes (a) processing a plurality of microspheres (step S41), including incorporating calcium phosphate into the microspheres, (b) laying the processed microspheres in a mold (step S43), wherein the microspheres in the mold presenting a gradient of microsphere sizes for a first phase and a second phase of the multi-phase scaffold, with microspheres of the first phase being in a first range of sizes, and with microspheres of the second phase being in a second range of sizes larger than the first range of sizes, (c) sintering together the microspheres in the mold above a glass transition temperature (step S45), and (d) sintering a fiber mesh, as a third phase of the multi-phase scaffold, onto the microsphere construct prepared in (c) (step S47).

Additional steps may optionally be included. For example, the method may further include seeding the third phase with at least one of fibroblasts (for example, human hamstring tendon fibroblasts), chondrocytes and stem cells. The seeding of the third phase supports growth and maintenance of soft tissue. Also, the method can include seeding the first phase with at least one of osteoblasts and stem cells. The seeding of the first phase supports growth and maintenance of bone. The method may further include seeding the second phase with at least one of chondrocytes and stem cells. Seeding of the second phase can support growth and maintenance of fibrocartilage.

The first phase may support growth and maintenance of bone. The third phase may support growth and maintenance of soft tissue. The second phase may serve at least as an interfacial zone between the first phase and the third phase.

For example, the method may further comprise seeding the first phase with first cells, for supporting growth and maintenance of the bone, seeding the third phase with second cells for supporting growth and maintenance of the soft tissue, and allowing at least some of said first cells and said second cells to migrate to the second phase.

In addition, the method may further comprise seeding at least one of said first, second and third phases with one or more agents by using a microfluidic system.

Further, the method may further comprise electrospinning said fiber mesh prior to attaching the fiber mesh onto the microsphere construct.

This application also provides methods for producing polymer/ceramic composite microspheres. The composite microspheres can be formed by applying an emulsion and solvent evaporation process. The composite microspheres can comprise a degradable polymer and one of bioactive glass and calcium phosphate ceramics. The degradable polymer can be dissolved in a solvent. The bioactive glass and/or calcium phosphate ceramics can be mixed into the polymer solution. A suspension of the bioactive glass and/or calcium phosphate ceramics in the polymer solution can be poured into a stirring surfactant solution.

Calcium phosphate and/or bioactive glass particles may be encapsulated in the microspheres during emulsion.

Figure 54:
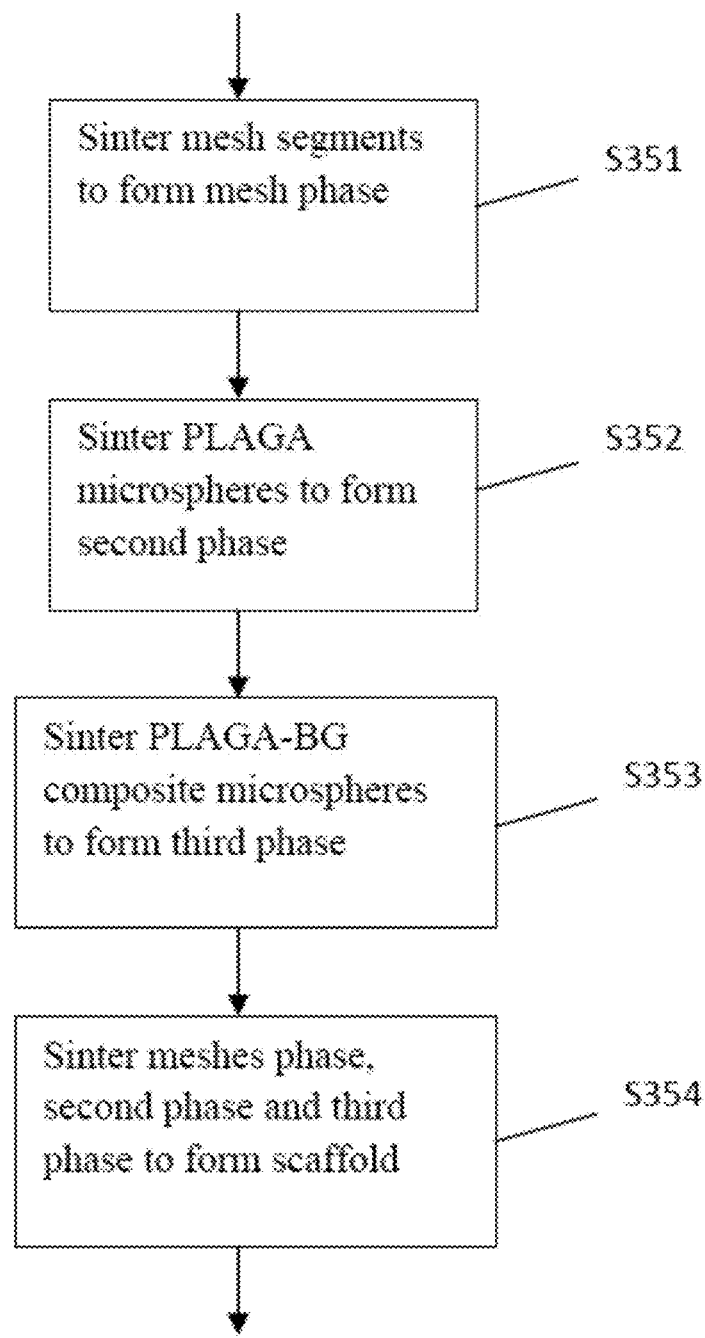
FIG. 54 shows a flow chart for another method for preparing a scaffold.

A method, according to another exemplary embodiment (FIG. 54), for preparing a multi-phase scaffold for musculoskeletal tissue engineering, can comprise the steps of (a) forming a mesh scaffold by sintering together a plurality of mesh segments as a first phase of the multi-phase scaffold (step S351), (b) forming a second scaffold by sintering together a plurality of poly-lactide-co-glycolide microspheres as a second phase of the multi-phase scaffold (step S352), (c) forming a third scaffold by sintering together a plurality of microspheres formed of a composite of poly-lactide-co-glycolide and bioactive glass as a third phase of the multi-phase scaffold (step S353), and (d) sintering together said mesh scaffold, said second scaffold and said third scaffold (step S354). Steps S351 through S353 may be performed in any order.

The Triphasic Scaffold for Use as Graft Collar or Interference Screw

In an exemplary embodiment (FIG. 62), a scaffold apparatus for fixing musculoskeletal soft tissue to bone in a subject, comprises two portions, each portion including first through third phases, wherein (i) the first phase of the scaffold comprises a material which promotes growth and proliferation of fibroblasts, (ii) the second phase adjacent to the first phase comprises a material which promotes growth and proliferation of chondroblasts, and (iii) the third phase adjacent to the second phase comprises a material which promotes the growth and proliferation of osteoblasts.

Figure 62:
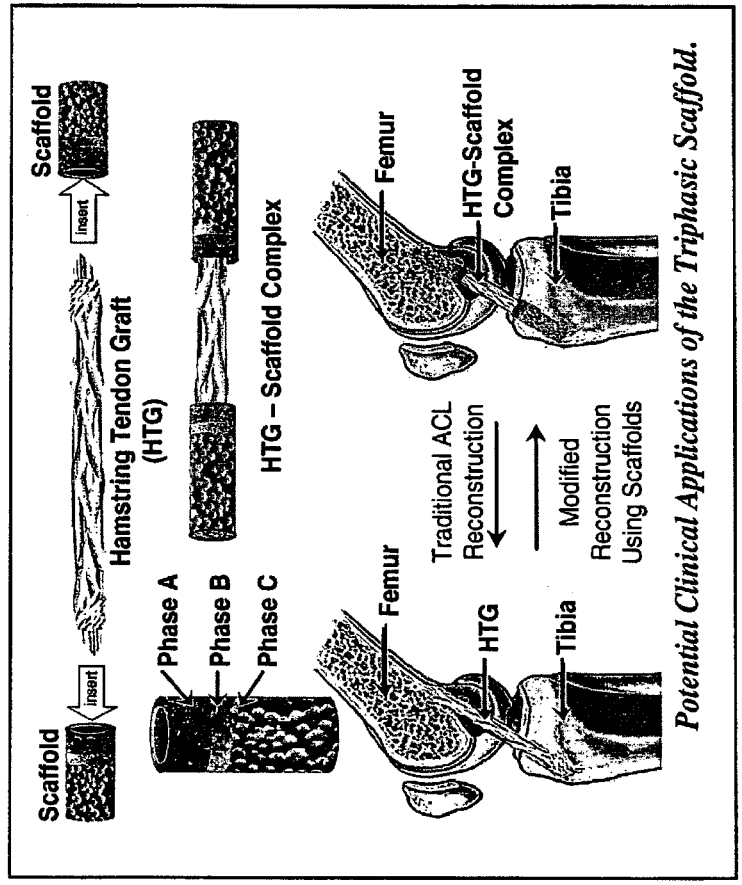
FIG. 62 shows potential clinical applications of the triphasic scaffold.

In the exemplary embodiment of FIG. 62, the two portions (for example, portions 31 and 32) encase respective portions of a soft tissue graft on all sides (for example, halves 31a and 31b) of the scaffold apparatus.

In another embodiment (FIG. 63), two portions combine to encase a portion (35) of a soft tissue graft on all sides.

In another embodiment (for example, FIG. 62), the first phase is exposed to the joint cavity. In another embodiment (for example FIG. 62) the second phase contacts articular cartilage. In another embodiment (for example, FIG. 62), the third phase is encased in bone. In another embodiment, the interference screw is biomimetic. In another embodiment, the interference screw is biodegradable. In another embodiment, the interference screw is osteointegrative. In another embodiment, a degradable cell barrier is inserted between the adjacent phases. In another embodiment, the degradable cell barrier comprises a nanofiber mesh. In another embodiment, the nanofiber mesh comprises polylactide-co-glycolide (PLGA). In another embodiment, the nanofiber mesh is electrospun.

The application further provides an interference apparatus comprising a scaffold apparatus for fixing musculoskeletal soft tissue to bone in a subject, said apparatus comprising two portions, wherein each portion comprises a scaffold, including first through third phases, wherein (i) the first phase comprises a material which promotes growth and proliferation of fibroblasts, (ii) the second phase adjacent to the first phase comprises a material which promotes growth and proliferation of chondroblasts, and (iii) the third phase adjacent to the second phase comprises a material which promotes the growth and proliferation of osteoblasts. In one embodiment, the interference apparatus is an interference screw.

Figure 69:
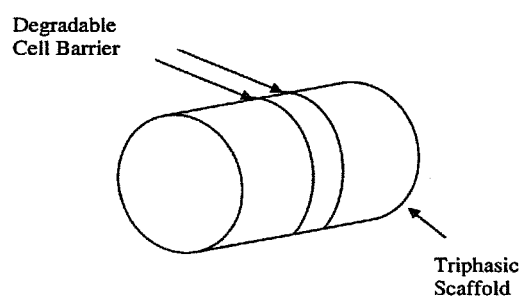
FIG. 69 shows a schematic view of a triphasic scaffold with degradable cell barrier inserted between adjacent phases.
Figure 70:
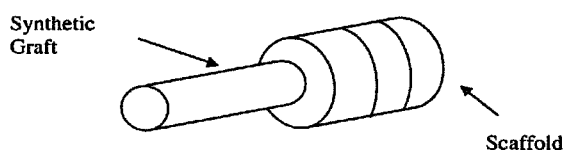
FIG. 70 shows a schematic view of a triphasic scaffold coupled to a synthetic graft for a ligament.

In another exemplary embodiment (FIG. 69), a scaffold apparatus for fixing musculoskeletal soft tissue to bone in a subject, comprises (i) a first phase (91) comprising a material which promotes growth and proliferation of fibroblasts, (ii) a second phase (92) adjacent to the first phase comprising a material which promotes growth and proliferation of chondroblasts, and (iii) a third phase (93) adjacent to the second phase (92) comprising a material which promotes the growth and proliferation of osteoblasts, wherein a degradable cell barrier (94a, 94b) is inserted between adjacent phases of the scaffold apparatus.

In one embodiment, the first phase is for supporting growth and maintenance of soft tissue, the second phase is for supporting the growth and maintenance of fibrocartilage, and the third phase is for supporting the growth and maintenance of bone tissue. In another embodiment, the first phase is seeded with at least one of fibroblasts and stem cells. In another embodiment, the stem cells are mesenchymal stem cells. In another embodiment, the first phase includes fiber mesh. In another embodiment, the fiber mesh is electrospun.

In another embodiment, the second phase is seeded with at least one of chondrocytes and stem cells. In another embodiment, the stem cells are mesenchymal stem cells.

In another embodiment, the third phase is seeded with at least one of osteoblasts, osteoblast-like cells, and stem cells. In another embodiment, the stem cells are mesenchymal stem cells.

In another embodiment, said third phase contains at least one of osteogenic agents, osteogenic materials, osteoinductive agents, osteoinductive materials, osteoconductive agents, osteoconductive materials, growth factors and chemical factors.

In one embodiment, said scaffold apparatus is integrated in a graft collar. In another embodiment, said graft collar is adapted for hamstring tendon-to-bone healing. In another embodiment, said first phase is seeded with human hamstring tendon fibroblasts. In another embodiment, said graft collar is adapted for peridontal ligament repair. In another embodiment, said graft collar is adapted for spinal repair. In another embodiment, at least one of said first phase and said third phase is seeded with one or more agents by using a microfluidic system.

In one embodiment, the scaffold has multiple phases joined by a gradient of properties. In another embodiment, the multiple phases of the scaffold are processed through one or more sintering stages. In another embodiment, the gradient of properties across the multiple phases of the scaffold includes mechanical properties. In another embodiment, the gradient of properties across the multiple phases of the scaffold includes chemical properties. In another embodiment, the gradient of properties across the multiple phases of the scaffold includes mineral content. In another embodiment, the gradient of properties across the multiple phases of the scaffold includes structural properties. In another embodiment, the gradient of properties across the multiple phases of the scaffold includes porosity. In another embodiment, the gradient of properties across the multiple phases of the scaffold includes geometry.

In one embodiment, the first phase comprises polymer and the third phase comprises one of bioactive glass and calcium phosphate. In another embodiment, the calcium phosphate is selected from a group comprising tricalcium phosphate, hydroxyapatite, and a combination thereof. In another embodiment, the polymer is selected from a group comprising aliphatic polyesters, poly(amino acids), copoly (ether-esters), polyalkylenes oxalates, polyamides, poly (iminocarbonates), polyorthoesters, polyoxaesters, polyamidoesters, poly(ε-caprolactone)s, polyanhydrides, polyarylates, polyphosphazenes, polyhydroxyalkanoates, polysaccharides, and biopolymers, and a blend of two or more of the preceding polymers. In another embodiment, the polymer comprises at least one of poly(lactide-co-glycolide), poly(lactide) and poly(glycolide).

In one embodiment, the apparatus is biomimetic. In another embodiment, the apparatus is biodegradable. In another embodiment, the apparatus is osteointegrative.

In one embodiment, the apparatus additionally include one or more agents selected from a group comprising antiinfectives, hormones, analgesics, anti-inflammatory agents, growth factors, chemotherapeutic agents, anti-rejection agents and RGD peptides.

In one embodiment, the degradable cell barrier is a nanofiber mesh. In another embodiment, the nanofiber mesh comprises polylactide-co-glycolide (PLGA). In another embodiment, the nanofiber mesh is electrospun.

In another exemplary embodiment, a scaffold apparatus for fixing musculoskeletal soft tissue to bone in a subject, comprises (i) a first phase (101) comprising a material which promotes growth and proliferation of fibroblasts, (ii) a second phase (102) adjacent to the first phase comprising a material which promotes growth and proliferation of chondroblasts, and (iii) a third phase (103) adjacent to the second phase comprising a material which promotes the growth and proliferation of osteoblasts, wherein said first phase (101) of the apparatus is coupled to a soft tissue graft (104). In one embodiment, the soft tissue graft is a graft of a ligament and the ligament is an anterior cruciate ligament.

A scaffold apparatus, according to one preferred embodiment, is multiphasic, including phases A, B, and C, and preferably can support growth, maintenance and differentiation of multiple tissue and cell types.

The Phase A comprises a first material adapted for integration and growth of a second tissue type seeded with a second type of cells (for example, fibroblasts, chondrocytes, stem cells, etc.). Phase A may include a composite of materials, including, but not limited to, microspheres, a fiber mesh, degradable polymers, etc.

Phase C comprises a second material adapted for integration and growth (for example, by including one or more osteogenic agents, osteogenic materials, osteoinductive agents, osteoinductive materials, osteoconductive agents, osteoconductive materials, growth factors, chemical factors, etc.) of a first tissue type and is seeded with a first type of cells (for example, osteoblasts, osteoblast-like cells, stem cells, etc.). The material of the first phase may include, but is not limited to, microspheres, foams, sponges and any other three dimensional (3-D) scaffold construct consisting of polymer and/or ceramic. Polymers may include, but is not restricted to, any biodegradable polymer Such as any of the poly-(α-hydroxy acids), or natural polymers such as silk, collagen, or chitosan. Ceramics may include but are not limited to bioactive glass, hydroxyapatite, beta tricalcium phosphate, or any other calcium phosphate material.

Phase B is an interfacial zone between the first and third phases. In one embodiment, Phase B is seeded with chondrocytes, such that a fibrocartilage interface can be formed and maintained with interactions between these three cell types.

The multiphasic scaffold apparatus preferably is preferably biomimetic, biodegradable (that is, each phase is degradable) and/or osteointegrative.

The scaffold may provide a functional interface between multiple tissue types (for example, soft tissue and bone).

FIG. 62 shows an example of a multi-phased scaffold apparatus in the form of a graft collar comprising phase A, phase B, and phase C. It should be apparent to one skilled in the art that although the apparatus shown in FIG. 62 has three phases, the apparatus can be integrated in a scaffold with four or more phases.

The scaffold apparatus can promote growth and maintenance of multiple tissue types. The scaffold may support growth, maintenance and differentiation of multiple tissue and cell types. The multi-phased scaffold may mimic the inhomogeneous properties of the insertion zone between soft tissue and bone, resulting in desired growth, phenotypic expression, and interactions between relevant cell types.

The phases of the scaffold may be inhomogeneous in properties. The phases may have zonal differences in mineral content and matrix morphology designed to mimic the tissue-bone interface and to facilitate the growth and maintenance of different tissues. The phases may differ in morphology. For example, phase A can include a porous fibrous mesh, while phases B and C include microspheres. According to another embodiment, the scaffold may include a composite of microspheres and a fiber mesh.

The scaffold preferably includes multiple phases. According to one embodiment, one phase (for example, phase A) supports growth and maintenance of soft tissue, another phase (for example, Phase B) is an interfacial zone between the first and second phases and another phase (for example, phase C) supports growth and maintenance of bone. Phase A for supporting growth and maintenance of the soft tissue may be seeded with at least one of fibroblasts, chondrocytes and stem cells. Phase C for supporting growth and maintenance of the bone may be seeded with at least one of osteoblasts, osteoblast-like cells and stem cells. Phase C can contain at least one of osteogenic agents, osteogenic materials, osteoinductive agents, osteoinductive materials, osteoconductive agents, osteoconductive materials, growth factors and chemical factors.

Further, at least one of said Phase A and Phase C may be seeded with one or more agents by using a microfluidic system.

The scaffold may include a composite of microspheres and a fiber mesh. The fiber mesh may be a degradable polymer. For example, the first phase may include a fiber mesh. The fiber mesh of the first phase and the microspheres of the third phase may be sintered together. The fiber mesh may be electrospun.

The mesh can include one or more desired agents and/or compound. For example, at least one of bioactive agents and peptides may coat the surface of the mesh. The bioactive agents and peptides can enhance differentiation, proliferation and attachment of cells and specific cell types. Also or alternatively, at least one of bioactive agents and peptides can directly be incorporated into the mesh.

According to one embodiment, the scaffold may include multiple phases joined by a gradient of properties. The multiple phases joined by the gradient of properties may be processed through one or more sintering stages. The gradient of properties across the multiple phases of the scaffold can include mechanical properties, chemical properties, mineral content, structural properties, porosity and/or geometry.

The scaffold apparatus can include plural phases of microspheres. For example, Phase A of the microspheres can comprise polymer and Phase C of the microspheres can comprise one of bioactive glass and calcium phosphate. Varying concentrations of calcium phosphate can be incorporated into the microspheres. The calcium phosphate can be selected from a group comprising tricalcium phosphate, hydroxyapatite, and a combination thereof. The polymer can be selected from a group comprising aliphatic polyesters, poly(amino acids), copoly(ether-esters), polyalkylenes oxalates, polyamides, poly(iminocarbonates), polyorthoesters, polyoxaesters, polyamidoesters, poly(ε-caprolactone)s, polyanhydrides, polyarylates, polyphosphazenes, polyhydroxyalkanoates, polysaccharides, and biopolymers, and a blend of two or more of the preceding polymers. The polymer can comprise at least one of poly(lactide-co-glycolide), poly(lactide) and poly(glycolide).

The microspheres may comprise one or more of CaP, bioactive glass, polymer, etc. The microspheres may be processed through one or more sintering stages.

The microspheres may comprise one or more desired agents or compounds. For example, at least one of bioactive agents and peptides may coat the surface of at least some of the microspheres. The bioactive agents and peptides can enhance at least one of differentiation, proliferation and attachment of cells and specific cell types. Also or alternatively, at least one of bioactive agents and peptides can directly be incorporated into at least some of the microspheres. The microspheres can additionally include one or more agents selected from a group comprising anti-infectives, hormones, analgesics, anti-inflammatory agents, growth factors, chemotherapeutic agents, anti-rejection agents and RGD peptides.

The apparatus is preferably biomimetic, biodegradable and/or osteointegrative.

According to one exemplary embodiment, the apparatus may be integrated in a graft fixation device. The graft fixation device may be used, for example, for graft fixation at the bone tunnels during anterior cruciate ligament reconstruction.

According to another embodiment, the apparatus may be integrated in an interference screw.

In addition, the scaffold apparatus, according to another exemplary embodiment, may be integrated in a graft collar.

The graft collar has many applications. For example, the graft collar may be adapted for hamstring tendon-to-bone healing. As another example, the graft collar can be adapted for peridontal ligament repair. Further, the graft collar may be adapted for spinal repair.

This application further provides a scaffold apparatus for fixing musculoskeletal soft tissue to bone in a subject, said scaffold apparatus comprising (i) a graft collar and (ii) a polymer-fiber mesh coupled to the graft collar to apply compressive mechanical loading to the graft collar.

Figure 71:
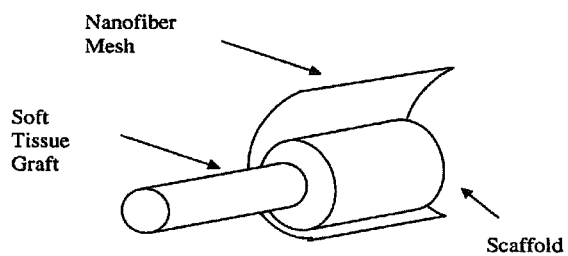
FIG. 71 shows a schematic view of a scaffold-mesh apparatus coupled with a soft tissue graft.

In one embodiment, the polymer-fiber mesh wraps around the graft collar. In another embodiment, the surface of the graft collar is wrapped in its entirety. (FIG. 71)

In one embodiment, the graft collar is biphasic. In another embodiment, the polymer-fiber mesh comprises nanofibers. In yet another embodiment, the nanofiber mesh comprises polylactide-co-glycolide (PLGA). In yet another embodiment, the nanofiber mesh is electrospun.

According to one embodiment, the scaffold apparatus is coupled to a soft tissue graft. (FIG. 71) According to another embodiment, the soft tissue graft is graft for a ligament. In another embodiment, the ligament is an anterior cruciate ligament.

In another exemplary embodiment (FIG. 71), an interference apparatus comprising a scaffold apparatus is provided for fixing musculoskeletal soft tissue to bone in a subject, said scaffold apparatus comprising (i) a graft collar 101 and (ii) a polymer-fiber mesh (105) coupled to the graft collar to apply compressive mechanical loading to the graft collar. In one embodiment, the interference apparatus is an interference screw.

In one embodiment, the polymer-fiber mesh wraps around the graft collar. In another embodiment, an outer surface of the graft collar is wrapped in its entirety by the polymer-fiber mesh.

In one embodiment, the graft collar is biphasic. In another embodiment, the biphasic graft collar includes a first phase comprising a material which promotes growth and proliferation of fibroblasts, and a second phase adjacent to the first phase comprising a material which promotes the growth and proliferation of osteoblasts.

In another embodiment, the polymer-fiber mesh comprises nanofibers. In yet another embodiment, the nanofiber mesh comprises polylactide-co-glycolide (PLGA). In yet another embodiment, the nanofiber mesh is electrospun.

In one embodiment, the scaffold apparatus is coupled to a soft tissue graft. In another embodiment, the soft tissue graft is a graft for a ligament of the subject. In yet another embodiment, the ligament is an anterior cruciate ligament of the subject.

This application further provides a graft-fixation apparatus comprising a scaffold apparatus for fixing musculoskeletal soft tissue to bone in a subject comprising (i) a graft collar and (ii) a polymer-fiber mesh coupled to the graft collar to apply compressive mechanical loading to the graft collar.

In an exemplary embodiment, the graft fixation apparatus is an interference screw.

This application further provides a scaffold apparatus for fixing musculoskeletal soft tissue to bone, said scaffold apparatus being configured to apply mechanical loading to a soft tissue graft to promote regeneration of a fibrocartilage interface between said soft tissue and said bone.

In one embodiment, the scaffold apparatus comprises a nanofiber mesh configured to apply said mechanical loading to said soft tissue graft.

In another embodiment, mechanical loading is applied by said scaffold apparatus dynamically or intermittently to said soft tissue graft.

In another embodiment, mechanical loading is applied by said scaffold apparatus statically to promote regeneration of a fibrocartilage interface between said soft tissue and said bone in a subject.

In another embodiment, the scaffold apparatus comprises a material that promotes growth and proliferation of chondroblasts.

In another embodiment, the scaffold apparatus comprises first and second phases, wherein (i) the first phase comprises a material that promotes growth and proliferation of chondroblasts, (ii) the second phase adjacent to the first phase comprises a material that promotes growth and proliferation of osteoblasts.

In yet another embodiment, the scaffold apparatus comprises first, second and third phases, wherein (i) the first phase comprises a material that promotes growth and proliferation of fibroblasts, (ii) the second phase adjacent to the first phase comprises a material that promotes growth and proliferation of chondroblasts, and (iii) the third phase adjacent to the second phase comprises a material that promotes the growth and proliferation of osteoblasts.

The specific embodiments and examples described herein are illustrative, and many variations can be introduced on these embodiments and examples without departing from the spirit of the disclosure or from the scope of the appended claims. Elements and/or features of different illustrative embodiments and/or examples may be combined with each other and/or substituted for each other within the scope of this disclosure and appended claims.

Further non-limiting details are described in the following Experimental Details section which is set forth to aid in an understanding of the subject matter but is not intended to, and should not be construed to, limit in any way the claims which follow thereafter.

EXPERIMENTAL DETAILS

Example 1: Nanofiber Scaffolds and Human Rotator Cuff Cells on Nanofiber Scaffolds Characterization of the Aligned and Unaligned Nanofiber Scaffolds Both aligned and unaligned PLGA nanofiber scaffolds were successfully fabricated and characterized. Structural properties of aligned and unaligned nanofiber scaffolds are summarized in Table 1.

TABLE 1

Structural Properties of Unaligned and Aligned Nanofiber Scaffolds

|  | Scaffold Thickness (mm) | Fiber Diameter (nm) | Pore Diameter (μm) | Porosity (%) | Permeability (m4/N · s) |
|---|---|---|---|---|---|
| Aligned (n = 5) | 0.22 ± 0.02 | 615 ± 152.4 | 228 ± 1.056 | 80.745 ± 2.966 | $(7.87 \pm 2.47) \times 10^{-12}$ |
| Unaligned (n = 5) | 0.19 ± 0.02 | 568 ± 147 | 4.914 ± 0.777 | 81.760 ± 3.929 | $(5.72 \pm 0.637) \times 10^{-12}$ |

The average nanofiber diameter for the aligned nanofiber scaffolds was 615±152 nm, while fiber diameter of the unaligned group measured 568±147 nm. No significant difference was found between the two groups. Similarly, nanofiber scaffold porosity, pore diameter and permeability were also found to be comparable between the aligned and unaligned nanofiber scaffolds (Table 1).

In contrast, the mechanical properties of the as-fabricated aligned and unaligned nanofiber scaffolds differed significantly ($p<0.05$). As shown in FIG. 2, the aligned nanofiber scaffold exhibited a markedly different stress-strain profile when compared to the unaligned nanofiber scaffold, with a significantly higher tensile modulus, yield stress as well as ultimate tensile stress. Table 2 summarizes the mechanical properties of aligned and unaligned nanofiber scaffolds, with significantly higher mechanical properties found in the aligned nanofiber scaffolds (*: $p<0.05$).

TABLE 2

Mechanical Properties of Aligned and Unaligned Scaffolds

|  | Elastic Modulus (Mpa) | Yield Strength (Mpa) | Ultimate Stress (Mpa) |
|---|---|---|---|
| Aligned (n = 5) | 341 ± 30* | 9.8 ± 1.1* | 12.0 ± 1.5* |
| Unaligned (n = 5) | 107 ± 23 | 2.5 ± 0.4 | 3.7 ± 0.2 |

(*p < 0.05)

Specifically, the aligned nanofiber scaffold exhibited a three-fold higher elastic modulus, and nearly four-fold higher yield strength and ultimate tensile strength when compared to the unaligned nanofiber scaffolds. It is emphasized here that the nanofiber scaffold structural properties (porosity, permeability) are similar to values reported for soft tissue (Weiss, 2006; Yin, 2004; O'Brien, 2007; LeRoux, 2002; Joshi, 1995; Kwan, 1989; Latridis, 1998; Drost, 1995) and the mechanical properties of the aligned nanofiber scaffolds are within range of those reported for human supraspinatus tendon (Itoi, 1995).

Effects of Nanofiber Organization on Fibroblast Attachment and Alignment

1. Cell Attachment Morphology

Figure 3:
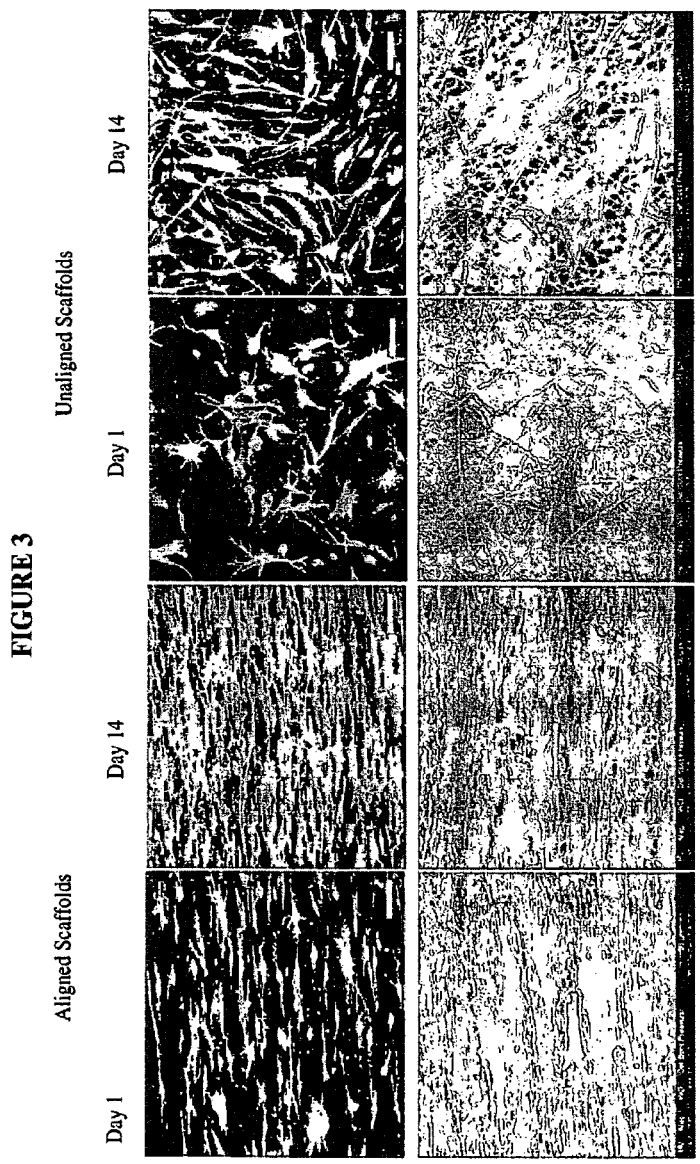
FIG. 3 shows the effects of nanofiber organization on cell morphology. The top panel shows confocal microscopy of human rotator cuff fibroblasts at day 1 and day 14 (20×, bar=100 μm). The bottom panel shows scanning electron micrographs of cells grown on aligned and unaligned nanofiber scaffolds at day 1, and day 14 (1000×, bar=50 μm). The fibroblasts remained viable and grew on both types of substrate over time, with the rotator cuff cells exhibiting phenotypic elongated morphology on the aligned nanofiber scaffolds.

The attachment morphology and growth of human rotator cuff fibroblasts on aligned and unaligned nanofiber scaffolds were visualized via both electron and confocal microscopy. As shown in FIG. 3, the fibroblasts attached to the nanofiber scaffold but assumed distinct morphologies on the two types of nanofiber scaffolds. Specifically, the cells grown on the aligned fibers adopted a phenotypic elongated morphology and oriented in the direction of the long axis of the fiber. In contrast, fibroblasts seeded on the unaligned mesh exhibited a polygonal morphology without preferential orientation. Moreover, while the human fibroblasts proliferated on both types of substrates over time, these morphological differences were maintained over the two-week culturing period (FIG. 3).

2. Gene Expression

Figure 4:
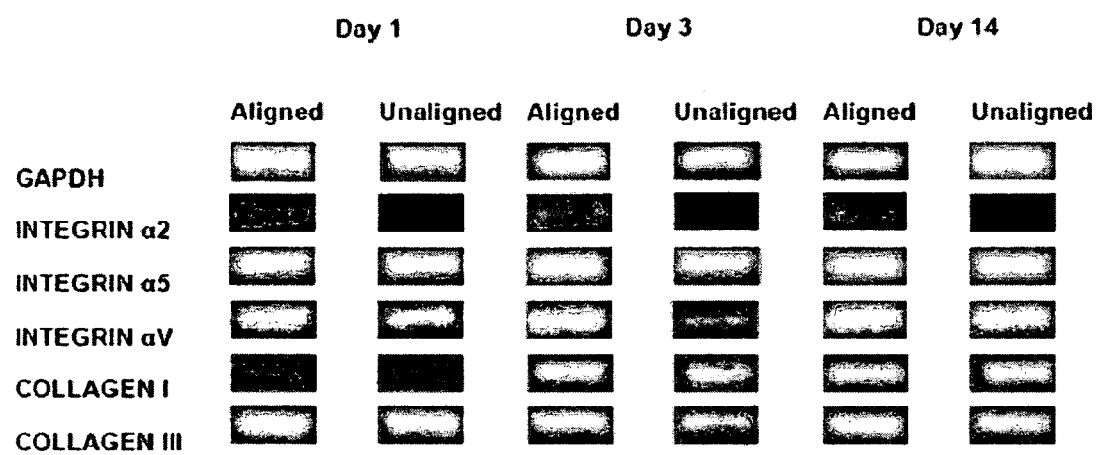
FIG. 4 shows gene expression on aligned and unaligned nanofbier scaffolds over time. Integrin expression differed between the aligned and unaligned groups while types I and III collagen expression were maintained on both anaofiber scaffold types. The α2 expression was detected on the unaligned nanofiber scaffolds at all time points evaluated.

Fibroblast gene expression was compared over time on aligned and unaligned nanofiber scaffolds (FIG. 4). All groups expressed the housekeeping gene GAPDH at all time points. It was observed that integrin expression differed between the aligned and unaligned nanofiber scaffolds while the cells expressed both types I and III collagen on the nanofiber scaffolds. The expression of α2 integrin was observed on the aligned nanofiber scaffolds at days 1, 3 and 14, while no α2 expression was seen on the unaligned nanofiber scaffolds. All genes evaluated were expressed at all time points on the monolayer control (data not shown).

3. Quantitative Analysis of Cell Attachment and Alignment

Figure 5B:
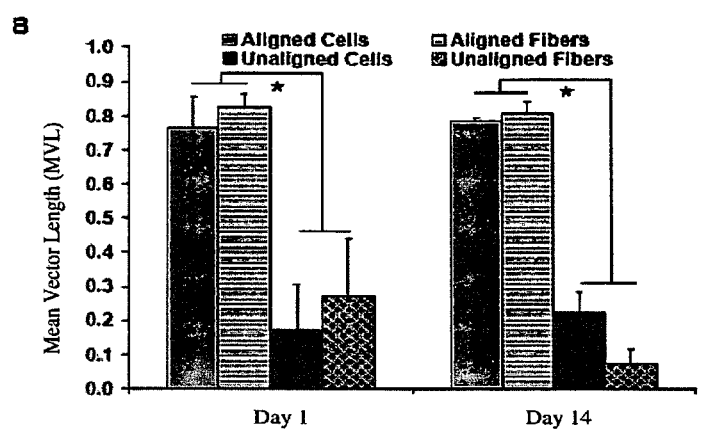

The attachment response of human rotator cuff fibroblasts to the inherent organization of the nanofiber scaffolds (aligned vs. unaligned) was further analyzed using quantitative circular statistical analysis (58, 67). Specifically, cell alignment and orientation over time were compared to those of the underlying nanofiber substrate, focusing on mean vector angle (FIG. 5A) and angular deviation as well as mean vector length (FIG. 5B). Table 3 summarizes the alignment analysis results.

TABLE 3

Summary of Cell and Fiber Orientation

| Day 1 (n = 3) | Mean Angle ± Angular Deviation (°) |
|---|---|
| Aligned Cells | 4.24 ± 19.73 |
| Aligned Fibers | 4.32 ± 17.00 |
| Unaligned Cells | −63.46 ± 37.70 |
| Unaligned Fibers | −55.69 ± 35.97 |
| Aligned Cells | 6.19 ± 18.74 |
| Aligned Fibers | 4.62 ± 17.78 |
| Unaligned Cells | −19.45 ± 35.93 |
| Unaligned Fibers | −20.84 ± 38.14 |

At day 1, fibroblast attachment on the aligned nanofiber scaffolds was significantly more aligned than on unaligned nanofiber scaffolds. As shown in FIG. 5A, analysis of cell and fiber orientation and alignment at day 1 revealed that cells grown on the aligned nanofiber scaffolds are oriented horizontally, exhibiting a similar mean angle distribution and narrow angular deviation as that of the aligned nanofibers on which the cells are seeded. Interestingly, fibroblasts on unaligned nanofiber scaffolds also conformed to matrix organization at day 1, demonstrating a similar random orientation with a wide angular deviation approximating those of the unaligned nanofiber scaffold matrix (FIG. 5A, Table 3).

At day 14, fibroblast growth and morphology continued to be dictated by the underlying nanofiber organization, with significantly higher alignment measured for fibroblasts cultured on the aligned nanofiber scaffolds compared to those found on the unaligned nanofiber scaffolds ($p<0.05$). However, within each nanofiber scaffold type (aligned or unaligned), circular statistical analysis of fibroblast growth revealed no significant change in alignment parameters when compared to day 1 results. Specifically, the mean angle (FIG. 5A) and angular deviation (Table 3), as well as the mean vector length (FIG. 5B) values of both cell and nanofiber scaffold samples at day 14 did not differ significantly from those found at days 1.

Effects of Nanofiber Organization on Fibroblast Growth and Matrix Deposition

Figures 6, 6A:
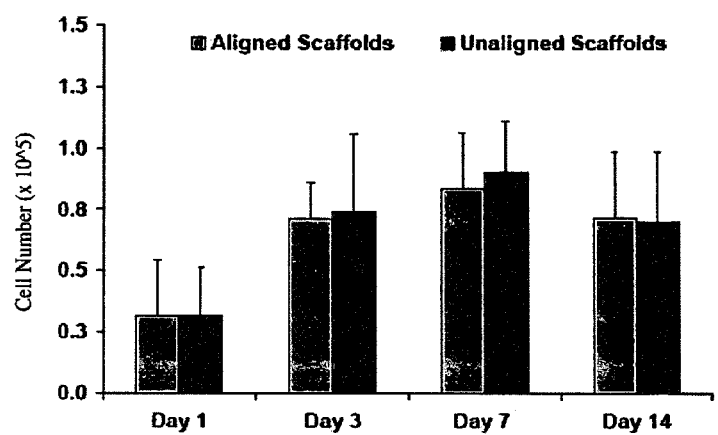
FIG. 6 shows cell proliferation and matrix elaboration on aligned and unaligned nanofiber scaffolds.
FIG. 6A shows that cells grew on both types of nanofiber scaffolds independent of fiber alignment.
Figure 6B:
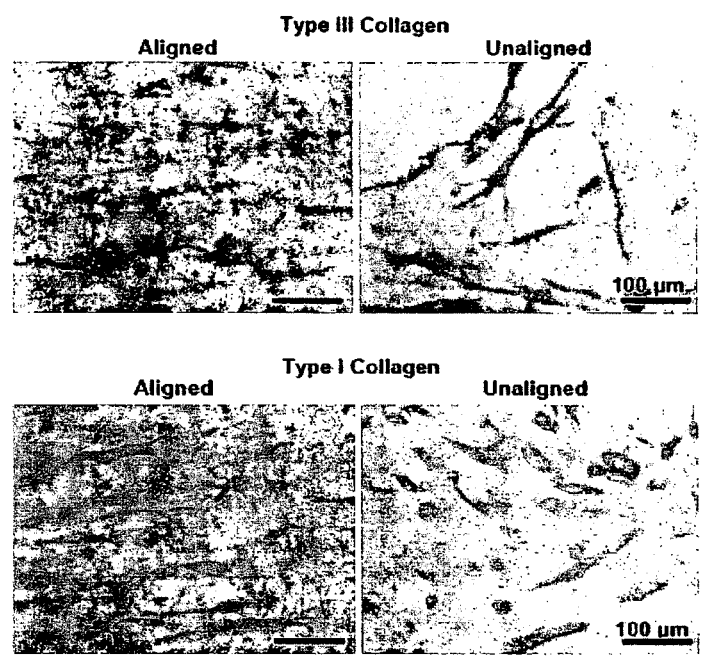
FIG. 6B shows immunohistochemical staining for types I and III collagen (Day 7, 20×, bar=100 μm).

The human tendon fibroblasts proliferated on the nanofiber scaffolds over the two week period, with no significant difference in cell proliferation found between the aligned and unaligned groups (FIG. 6A). Matrix deposition by human fibroblasts on nanofiber scaffolds was also evaluated over time, and the cells produced a collagen-rich matrix containing both type I and type III collagen (FIG. 6B). Additionally, circular statistical analysis of the immunohistochemistry images revealed that collagen matrix deposition was also guided by nanofiber organization, with an aligned type I collagen matrix found only when the fibroblasts were cultured on the aligned nanofiber scaffold (FIG. 6C).

Effects of In Vitro Culture on Nanofiber Scaffold Mechanical Properties

Figures 7, 7A:
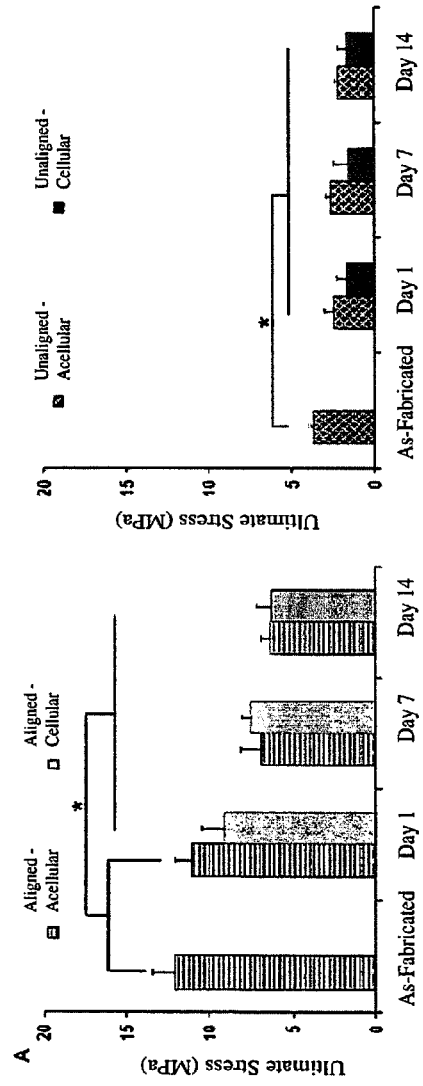
FIG. 7 shows the effects of in vitro culture on nanofiber scaffold mechanical properties. Mechanical properties decreased due to polymer degradation, and aligned nanofiberscaffolds were significantly stronger than unaligned nanofiber scaffolds.
FIG. 7A shows ultimate tensile strength; *:p<0.05.

The mechanical properties of fibroblast-seeded PLGA nanofiber scaffolds were also determined over time and compared as a function of in vitro culture (cellular vs. acellular nanofiber scaffolds) as well as nanofiber organization (aligned vs. unaligned). As expected for PLGA, in vitro culture decreased nanofiber scaffold mechanical properties over time, with a significantly lower ultimate tensile stress and yield strength found over time for both aligned and unaligned nanofiber scaffolds when compared to the as-fabricated nanofiber scaffolds (FIGS. 7A,C; $p<0.05$). In contrast, in vitro culture has no significant effect on nanofiber scaffold elastic modulus (FIG. 7B). When compared to the acellular controls, the ultimate tensile stress, elastic modulus and the yield strength of the fibroblast-seeded nanofiber scaffolds did not vary significantly over time (FIG. 7).

At all examined time points and culture conditions, the elastic modulus, ultimate tensile stress, and yield strength of the aligned nanofiber scaffolds were significantly greater than those of the unaligned nanofiber scaffolds ($p<0.05$), and this trend was consistently observed in both cellular and acellular groups. Interestingly, a significant decrease in ultimate tensile stress was detected at day 1 for the unaligned nanofiber scaffold, while such a decrease was not found until a week later for the aligned group (FIG. 7A, day 7). For yield strength, a significant decrease was measured for aligned nanofiber scaffolds at day 1 compared to the as-fabricated group (FIG. 7C, $p<0.05$), and the yield strength of the day 14 aligned nanofiber scaffolds was significantly lower compared to day 1 ($p<0.05$). In contrast, no significant decrease was observed for the aligned nanofiber scaffolds at any time point.

By controlling nanofiber organization (aligned vs. unaligned), nanofiber scaffolds with controlled matrix anisotropy mimicking those of any muscle-to-bone insertion site, e.g., a rotator cuff, may be engineered. In the present invention, the effects of nanofiber organization on the resultant nanofiber scaffold structural and mechanical properties, as well as the response of primary cells derived from the human rotator cuff tendons were systematically investigated. Additionally, the effects of fibroblast culture and duration on the ability of the nanofiber scaffold to maintain stable mechanical properties were also evaluated. It was found that nanofiber organization controls nanofiber scaffold mechanical properties and is the primary factor guiding the attachment morphology, alignment, gene expression as well as matrix deposition by human rotator cuff fibroblasts. Moreover, while in vitro culture resulted in an expected decrease in nanofiber scaffold mechanical properties with polymer degradation, these changes were modulated by nanofiber organization. Based on these observations, it is clear that nanofiber organization exerts significant control over cell response as well as nanofiber scaffold properties, and it is a critical parameter in nanofiber scaffold design for functional muscle-to-bone repair, e.g., rotator cuff repair.

In addition to possessing a fiber diameter approximating that of collagen fibers present in the tendon extracellular matrix, the nanofiber scaffolds of the present invention exhibit structural properties that are optimal for soft tissue repair, including its over 80% porosity and high permeability which can facilitate nutrient transport as well as promote cell viability and tissue growth in vitro and in vivo. Additionally, the permeability of the nanofiber scaffold is within range of those reported for musculoskeletal tissues (Weiss, 2006; Yin, 2004; O'Brien, 2002; Joshi, 1995; Kwan, 1989; Latridis, 1998; Drost, 1995). For the unaligned and aligned nanofiber scaffolds of the present invention, tensile (elastic) modulus varied from 107 MPa to 341 MPa and the ultimate tensile stress from 3.7 MPa to 12.0 MPa, respectively. While the elastic modulus of the nanofiber scaffold was unaffected by in vitro culture, both yield strength and ultimate tensile stress decreased significantly over time. However, the magnitude of nanofiber scaffold mechanical properties remained within the range of those reported for human rotator cuff tendons (Itoi, 1995). Moreover, the mechanical properties of the nanofiber scaffolds of the present invention can be further tailored by varying, e.g., either the average molecular weight or co-polymer ratio of the degradable polymers (Lu, 2005).

The observed differences in mechanical properties between the aligned and unaligned nanofiber scaffolds are similar to those seen in other types of nanofiber scaffolds (Li, 2007; Baker, 2007; Lee, 2005; Courtney, 2006; Stankus, 2006). These reports collectively highlight another distinct advantage of the nanofiber scaffold in that by varying nanofiber organization and alignment, matrix anisotropy can be pre-engineered into nanofiber scaffold design. This is especially desirable for tendon repair or regeneration, as nanofiber scaffolds with controlled matrix anisotropy can be fabricated to recapitulate the inherent structure-function relationship of, e.g., rotator cuff tendons.

When Itoi et al. evaluated the tensile mechanical properties of the human supraspinatus tendon at the anterior, middle and posterior regions of the tendon; it was found that both the elastic modulus and ultimate tensile stress varied as a function of tendon region. Specifically, the elastic modulus values ranged from 50 MPa to 170 MPa when progressing from the posterior to the superficial region, while the ultimate tensile stress spanned from 4.1 MPa to 16.5 MPa from the posterior to the superficial tendon region. Moreover, Thomopoulos et al. (Thomopoulos, 2003) reported that collagen organization and alignment play an important role in reducing stress concentration at the supraspinatus tendon-to-bone insertion (Thomopoulos, 2006). By controlling nanofiber organization (alignment or layering) and/or other nanofiber scaffold parameters such as polymer composition or molecular weight, nanofiber scaffolds with biomimetic collagen alignment and region-dependent mechanical properties can be readily engineered and utilized for, e.g., rotator cuff repair, augmentation and regeneration.

Nanofiber organization also exerted profound effects on cellular response. The nanofiber scaffolds of the present invention were pre-designed with similar structural properties (nanofiber diameter, porosity, pore size, permeability). Thus, any observed differences in cell response can be primarily attributed to differences in nanofiber organization (aligned vs. unaligned).

Human rotator cuff fibroblast attachment and matrix production were guided by the organization of nanofibers of the aligned or unaligned nanofiber scaffolds. Both qualitative and quantitative analyses revealed that the cells exhibited phenotypic morphology and attached preferentially along the fiber axis of the aligned nanofiber scaffolds, while random cell attachment was found on the unaligned nanofiber scaffold. These differences were maintained over time and more importantly, subsequent cell-mediated matrix production also conformed to scaffold nanofiber organization. This contact guidance phenomena, in which surface topography of the biomaterial substrate regulates the spatial distribution of focal contacts and the direction of cell spreading (Singhvi, 1994; Curtis, 1997; Glass-Brudzinski, 2002; Teixeira, 2003; Wang, 2003; Engelmayer, 2006), is similar to those reported for connective tissue cells cultured on synthetic or natural polymer-based nanofiber scaffolds (Li, 2007; Baker, 2007; Li, 2003; Lee, 2005; Bashur, 2006; Li, 2002; Stankus, 2006; Zhong, 2006). As discussed above, these observed differences in cell response on aligned or unaligned nanofiber scaffolds and the resultant matrix properties can be readily exploited for, e.g., functional repair of rotator cuff injuries as well as the formation of complex tissues.

Interestingly, the data presented herein suggest that the human rotator cuff fibroblasts may detect differences in nanofiber alignment during initial attachment as well as post-adhesion matrix synthesis. It was identified here that while the expression of integrins such as $\alpha 5$ and $\alpha V$ were consistently observed on both aligned and unaligned nanofiber scaffolds, $\alpha 2$ expression was only detectable on the aligned nanofiber scaffolds (FIG. 4). Li at al. (Li, 2003) compared fetal bovine chondrocytes response in monolayer culture to those seeded on an unaligned Poly($\epsilon$-caprolactone) nanofiber scaffold, and found that $\alpha 2$ expression was suppressed when compared to monolayer controls. It has been reported that $\alpha 2$ is a key integrin that mediates cell attachment to collagenous matrix (Hynes, 1992; Loeser, 2000; Hynes, 2002; Garcia, 2005; Delon, 2007). Thus, expression of $\alpha 2$ integrin by rotator cuff fibroblasts on the aligned nanofiber scaffold suggests that matrix fiber alignment may also regulate integrin expression. Moreover, compared to the unaligned nanofibers, the aligned nanofiber scaffold may better mimic the native extracellular matrix produced by the rotator cuff fibroblasts.

Fibroblasts proliferated on both aligned and unaligned nanofiber scaffolds of the present invention over time, with no significant difference observed between groups at all time points. These results are in agreement with previous studies which also reported minimal effect on cell proliferation due to nanofiber organization (Baker, 2007; Lee, 2005). Additionally, no apparent differences in types I and III collagen deposition were observed between the aligned and unaligned groups in immunohistochemical staining. While collagen production was not quantified in this study, Baker and Mauck (Baker, 2007) reported that fiber architecture has little effect on normalized collagen content for both bovine mesenchymal stem cells and meniscal fibrochondrocytes cultured on aligned and unaligned poly(s-caprolactone) nanofiber scaffolds. Interestingly, Lee et al. (Lee, 2005) reported significantly higher total collagen synthesis by human ligament fibroblasts grown on aligned polyurethane nanofiber scaffolds subjected to mechanical loading. These results collectively indicate that mechanical stimulation and fiber organization may be coupled to promote overall collagen production over time, and in turn improve cuff healing and long term clinical response.

The intended application of the novel nanofiber scaffold system presented here is to improve, e.g., the repair and/or augmentation of tears in muscle-to-bone insertion sites, such as, e.g., rotator cuff tendons, specifically by providing a biomimetic substrate with physiologically relevant mechanical properties that will enable functional and stable repair or augmentation of the damaged area, e.g., rotator cuff. Therefore, it is important to characterize whether nanofiber scaffold mechanical properties will be maintained during in vitro culture and if cell-mediated matrix production will compensate for changes in mechanical properties due to nanofiber degradation.

As expected, nanofiber scaffold mechanical properties decreased due to hydrolytic degradation of the PLGA nanofibers (Lu, 2005). Interestingly, the aligned PLGA nanofiber scaffolds maintained the as-fabricated tensile mechanical properties longer than the unaligned group. The ultimate tensile stress of the unaligned nanofiber scaffold decreased significantly by day 1, while no such change was detected for the aligned nanofiber scaffolds until day 7. These observations also suggest that degradation kinetics of the nanofiber scaffolds and associated changes in mechanical properties are dependent on fiber organization. No significant increase in nanofiber scaffold mechanical properties due to fibroblast culture was observed, which is likely due to the relatively short culturing time evaluated, as reported significant increases in mechanical properties in cell-seeded nanofiber scaffolds are not found until day 70 of in vitro culture (Baker, 2007).

Effects of Co-Culture on Osteoblast and Ligament Fibroblast Phenotypes

We propose that heterotypic cellular interactions are important in the maintenance and repair of the tendon-to-bone interface. When damage to the interface region during rotator cuff injury or subsequent repair results in non-physiologic exposure of normally segregated tissue types (e.g., bone and tendon), heterotypic cellular interactions (osteoblast-fibroblast) may initiate repair and direct the regeneration of a neo-interface between these two tissues.

It is well documented that in post anterior cruciate ligament reconstruction using soft tissue-based grafts, tendon-bone healing within the bone tunnel results in the formation of a fibrocartilage-like interface (Rodeo, 1993). Using a rabbit model, Koike et al. (Koike, 2005) evaluated tendon-bone healing and found that after resection of the enthesis, the reattachment of the supraspinatus tendon to the greater tuberosity of the humerus led to the regeneration of a new fibrocartilage-like interface. Interestingly, chondrocytes were not observed until two weeks post reattachment and their number increased to the level of the positive control by week six. In vitro co-culture of ligament fibroblast and osteoblast have shown that their interaction regulates cell phenotype (Wang, 2007) and results in the expression of fibrocartilage-like markers such as aggrecan, cartilage oligomeric matrix protein and collagen II. These observations suggest that the fibrocartilage interface can be formed when the tendon is juxtaposed with bone, and fibroblast-osteoblast interactions may be critical in initiating this interface regeneration process.

Biphasic Nanofiber Scaffold for Tendon-to-Bone Interface Tissue Engineering

Nanofiber scaffolds represent promising matrices for interface tissue engineering due to their superior biomimetic potential and physiological relevance because they exhibit high aspect ratio, surface area, porosity and closely mimic the extracellular matrix (Ma, 2005; Christenson, 2007; Pham, 2006; Li, 2007; Murugan, 2007). These nanofiber scaffolds have been investigated for bone (Garrets, 2007; Fujihara, 2005; Badami, 2006; Yoshimoto, 2003), meniscus (Baker, 2007), intervertebral disc (Nerukar, 2007), cartilage (Li, 2003; Li, 2005), ligament (Lee, 2005; Bashur, 2006) as well as tendon tissue engineering (Sahoo, 2006).

Figure 10:
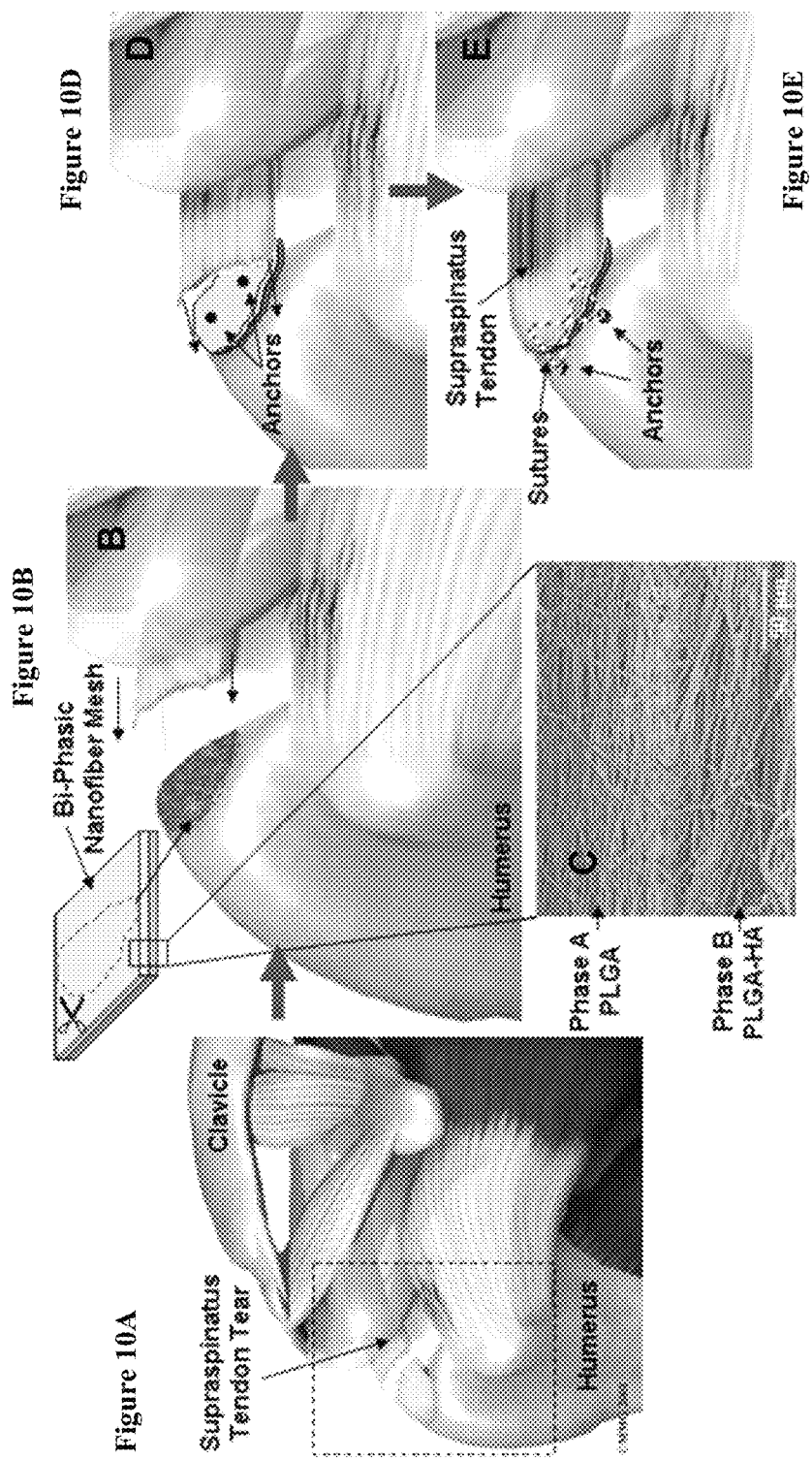
FIGS. 10A-10E show one embodiment of a clinical application of a biphasic nanofiber scaffold according to the present invention.

Inspired by the structure and organization of the tendon-bone insertion site, and focusing on mimicking collagen alignment and exercising spatial control in mineral content, we have developed a nanofiber-based biphasic nanofiber scaffold. In this biphasic design, Phase A consists of nanofibers of biodegradable polymer, such as, e.g., polylactide-co-glycolide (PLGA) (representing the non-calcified interface), while Phase B is of composite nanofibers of a biocompatible ceramic, such as, e.g., hydroxyapatite (HA) nanoparticles and a biodegradable polymer, such as, e.g., PLGA (FIGS. 10 and 17) (representing the calcified interface). It is expected that this novel nanofiber scaffold will provide the necessary structural and mechanical properties as well as mineral distribution to guide the regeneration of the complex heterogeneous tendon-to-bone interface. Additionally, by implementing nanofibers that mimic the alignment of collagen fibers at the insertion site, the biphasic nanofiber scaffold provides the foundation for guided matrix deposition and tendon-bone healing. Moreover, the biphasic nanofiber scaffold exhibits tensile mechanical properties similar to those reported for human supraspinatus tendon (Itoi, 1995), and supports, e.g., fibroblast, osteoblast culture in preliminary studies. The nanofiber scaffolds of the present invention may be fabricated into a multiphasic, e.g., a biphasic patch for, e.g., rotator cuff repair (FIG. 10). The nanofiber scaffold can be sutured onto the tendon during cuff repair and will integrate with bone through the PLGA-HA phase.

Fibroblast Response on PLGA-HA Nanofiber Scaffolds

Figure 13:
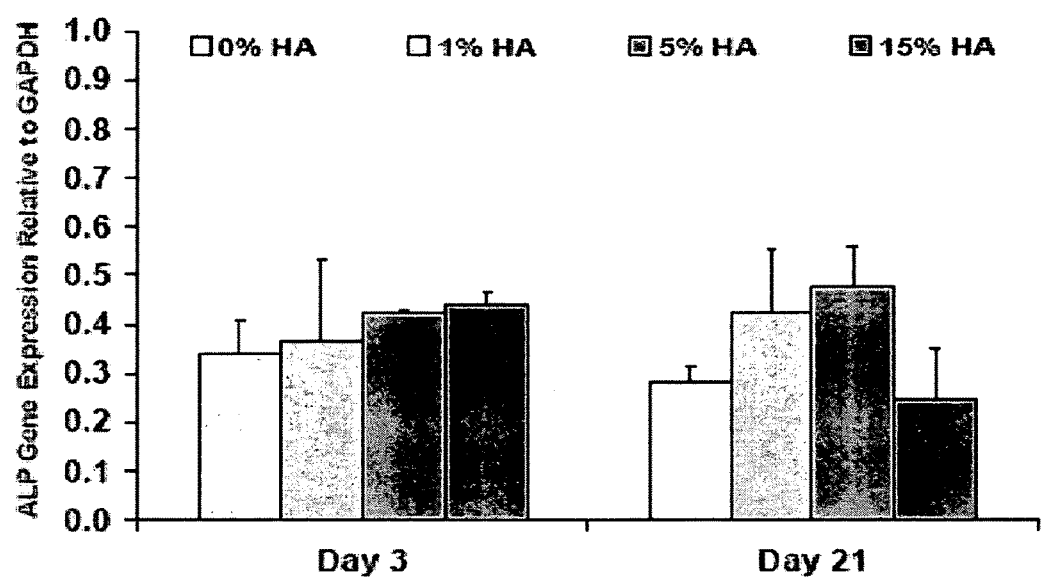
FIG. 13 shows that increasing HA content in PLGA nanofiber meshes had no significant effect on alkaline phosphatase gene expression at days 3 and 21 as indicated by semiquantitative analysis of PCR band intensities (n=2).

A preliminary evaluation was carried out of the mineralization potential of human rotator cuff tendon fibroblasts as a function of HA content (0, 1, 5, 15 wt %) in Phase B. Briefly, fibroblasts derived from explant cultures of human tissue (male, aged 49-79 yrs) were seeded on a PLGA-HA nanofiber scaffold according to the present invention (3.14× $10^4$ cells/$cm^2$). It was found that fibroblasts remained viable (FIG. 14) and proliferated on all substrates. The cells were elongated and aligned along the long axis of the fibers. Gene expression for alkaline phosphatase (ALP) was similar among all groups at both days 3 and 21, and only basal ALP activity levels were measured in these cultures (FIG. 13). Collagen I & III deposition was maintained on the PLGA-HA nanofiber scaffolds, with no observable differences found between groups (FIG. 14). These results suggest that increased HA content had no adverse effect on fibroblast phenotype and does not appear to induce ectopic mineralization.

Co-Culture on the Biphasic Nanofiber Scaffold (Phases A & B)

Figure 15:
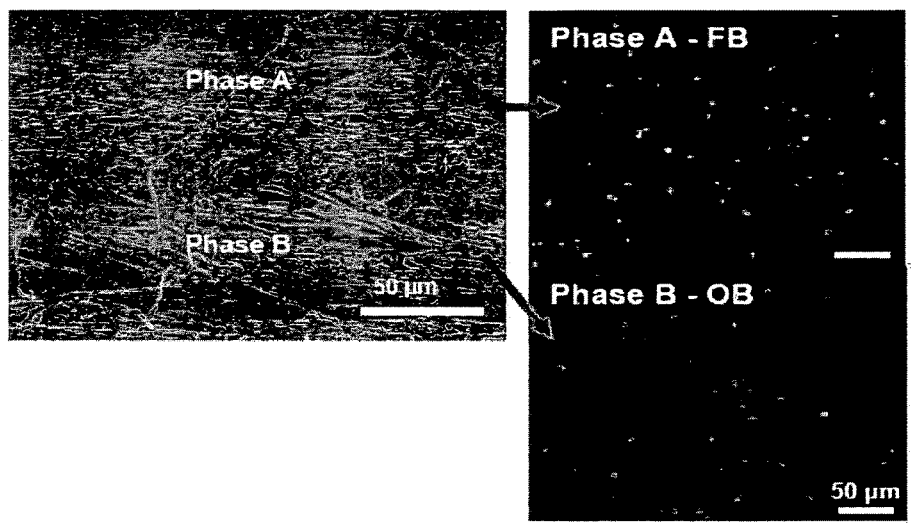
FIG. 15 shows co-culture of fibroblasts (FB) and osteoblasts (OB) on a continuous biphasic nanofiber scaffold according to the present invention. Distinct cellular regions were obtained on the nanofiber scaffold with fibroblasts (green, DiO) and osteoblasts (red, DiI) attached only on Phase A and Phase B, respectively, as indicated by fluorescence confocal microscopy (20×).

To demonstrate the feasibility of co-culture on the biphasic nanofiber scaffold, bovine osteoblasts and fibroblasts derived from explant culture were labeled with Vybrant dyes (green:D\O=fibroblasts, red:D\\=osteoblasts). The fibroblasts were then seeded on Phase A (PLGA) and osteoblasts on Phase B (PLGA-HA, 5%), and allowed to attach for 15 minutes before adding media. Cell distribution on each nanofiber scaffold phase, as well as the cross-section, were imaged at day 1 using fluorescence confocal microscopy. As seen in FIG. 15, with the biphasic design, fibroblasts remained in Phase A' while osteoblasts were localized to Phase B. These results demonstrate the feasibility of co-culture and suggest that the phase-specific cell distribution may lead to multi-tissue formation.

Disclosed herein is the design and systematic in vitro evaluation of a novel biomimetic, biodegradable nanofiber scaffold for soft tissue repair, augmentation, or replacement, such as, e.g., for functional rotator cuff repair. The present invention discloses that nanofiber organization has a significant effect on human rotator cuff fibroblast response, with the structural anisotropy of the aligned and isotropy of the unaligned nanofiber scaffold directly guiding cell attachment and matrix deposition. Controlled cell response resulted in a more physiologically relevant matrix for, e.g., rotator cuff repair on the biomimetic nanofiber scaffold. Moreover, physiologically relevant nanofiber scaffold mechanical properties were maintained in vitro. Our results demonstrate that the novel nanofiber scaffold has significant potential for enabling tendon regeneration and offers a functional tissue engineering solution for soft tissue repair, augmentation, or replacement, such as, e.g., rotator cuff repair.

Example 1.1: Nanofiber Scaffold Fabrication

Figure 19:
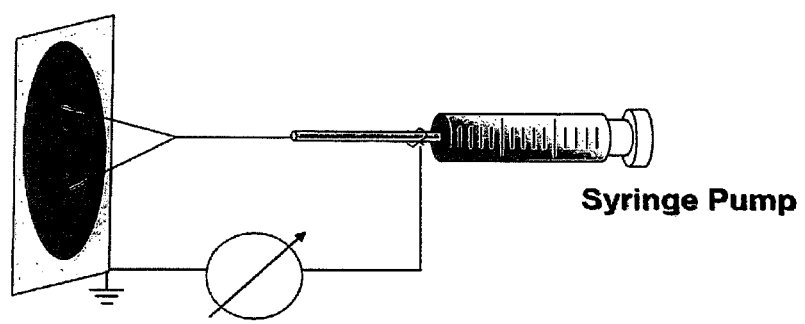
FIG. 19 is a schematic depicting the electrospinning process according to the present invention.

Poly(D, L-lactide-co-glycolide) co-polymer (85:15 PLGA, Mw>>123.6 kDa; Lakeshore Biomaterials, Birmingham, Ala.) nanofiber scaffolds were produced via electrospinning (Matthews, 2002; Formhals, 1934; Reneker, 1996). Briefly, a 35% (v/v) solution of PLGA was prepared in an organic solvent mixture consisting of 55% N.N-dimethylformamide (Sigma-Aldrich, St. Louis, Mo.) and 10% ethyl alcohol. The polymer solution was loaded in a 5 mL syringe with a 18.5-G stainless steel blunt tip needle and electrospun at 8-10 kV using a custom designed electrospinning device. Both aligned and unaligned nanofiber scaffolds were fabricated. For unaligned nanofiber scaffolds, the collecting surface consisted of a stationary plate, while a rotating mandrel having a diameter of 2 inches and a length of 20 inches, which mandrel rotated at 20 m/s was utilized to produce aligned nanofiber scaffolds. The polymer solution was deposited using a syringe pump (Harvard Apparatus, Holliston, Mass.; 1 mL/hour) with the distance between the needle and the collecting target distance (air gap distance) set at 10.5 cm. See, FIGS. 19 and 20. As shown in FIG. 20, the drum surface velocity may be varied by changing the gear in the pump, which provides control over fiber orientation and alignment.

Example 1.2: Nanofiber Scaffold Characterization

The structural and material properties of the nanofiber scaffolds were characterized post fabrication. Specifically, nanofiber morphology and diameter were imaged by Scanning Electron Microscopy (SEM, 5 kV, FEI Quanta 600, FEI Co. Hillsboro, Oreg.). The nanofiber scaffolds were sputter coated with palladium prior to SEM analysis in order to reduce charging effects. Fiber diameter was quantified by image analysis of SEM micrographs (n=3, 2000×) using NIH ImageJ (version 1.34s, Bethesda, Md.). In addition, nanofiber scaffold porosity and pore diameter (n=5) were determined by mercury porosimetry (Micromeritics Autopore III, Norcross, Ga.) following published protocols (Lu, 2003). In this method, the construct porosity was determined by measuring the volume of mercury infused into the structure during analysis. Nanofiber scaffold permeability (n=5) was directly determined using a custom designed device (51 Albro, 2006; Weiss, 2006), by first measuring the pressure difference and then calculating permeability via Darcy's Law:

$$K = Qh/A\Delta P$$

$A\Delta P$ where k is nanofiber scaffold permeability ($m^4/N\ s$), Q is the fluid flow rate through nanofiber scaffold (300 mL/hr), $\Delta P$ is the pressure difference (N/m), h is the thickness of nanofiber scaffold (m) and A is the nanofiber scaffold surface area ($m^2$).

The mechanical properties of the as-fabricated aligned and unaligned nanofiber scaffolds were evaluated under uniaxial tensile testing (Li, 2002). Briefly, the nanofiber scaffolds (6 cm×1 cm) were secured with custom clamps and mounted on an Instron (Model 8841, Norwood, Mass.) with an average sample gauge length of 3 cm. The samples were tested to failure at a strain rate of 5 mm/min, and the aligned nanofiber scaffolds were tested along the long axis of the aligned fibers. Both the yield stress and ultimate tensile stress were determined, and nanofiber scaffold elastic modulus was calculated from the linear region of the stress-strain curve.

Example 1.3: In Vitro Culture of Human Tendon Fibroblasts on Nanofiber Scaffolds Cells and Cell Culture Human rotator cuff fibroblast-like cells were obtained from explant cultures of tissue samples obtained as surgical waste following rotator cuff repair surgery (exempted from IRB approval). For this study, the cells were derived exclusively from female patients (n=3, aged 65 to 70 years). The tissue samples were maintained in Dulbecco's modified Eagle medium (DMEM) supplemented with 10% fetal bovine serum, 1% non-essential amino acids, 1% penicillin/streptomycin and 1% amphotericin B. Only cells obtained from the second and third migration were used in order to ensure a relatively homogeneous cell population (54). All media and supplements were purchased from Mediatech (Herndon, Va.).

Cell Seeding on Nanofiber Scaffolds

Prior to cell seeding and to prevent nanofiber scaffold contraction (Spalazzi, 2008), the ends of aligned and unaligned nanofiber scaffolds were secured to nanofiber scaffold holders using a sterile adhesive (Fisher Scientific, Pittsburgh, Pa.). The nanofiber scaffolds were sterilized by UV irradiation (30 minutes/side) and to promote cell adhesion, the nanofiber scaffolds were pre-incubated in fully supplemented media at 37° C. and 5% $CO_2$ for 16 hours. Human rotator cuff fibroblasts were seeded on the nanofiber scaffolds (1 cm×1 cm cell seeding area) at a density of $3 \times 10^4$ cells/$cm^2$. The cells were allowed to attach on the nanofiber scaffolds for 15 minutes, after which fully supplemented media was added to each culture well. Cells were cultured on the aligned and unaligned nanofiber scaffolds for two weeks, and the effects of nanofiber organization on cell morphology, attachment, proliferation and matrix production were determined at days 1, 7 and 14. In addition, the effects of in vitro culture on nanofiber scaffold mechanical properties were also determined over the two week period. Both monolayer culture of the human tendon fibroblasts and acellular nanofiber scaffolds (aligned as well as unaligned) served as controls.

Cell Viability and Attachment Morphology

Cell attachment morphology on the nanofiber scaffolds (n=3/group) were evaluated by SEM (FEI Quanta 600, FEI Co. Hillsboro, Oreg.) at days 1, 7 and 14. The samples were first rinsed with 0.1 M sodium cacodylate buffer (Sigma-Aldrich) and fixed in Karnovsky's fixative (Karsenty, 1965; Langley, 1999) for 24 hours at 4° C., and subsequently dehydrated with an ethanol series. The nanofiber scaffolds were coated with palladium prior to SEM analysis to reduce charging effects. Cell viability as well as attachment morphology were evaluated by Live/Dead staining (Molecular Probes, Eugene, Oreg.) imaged using confocal microscopy. Specifically, the samples (n=3/group) were rinsed twice with PBS and stained following the manufacturers suggested protocol. The samples were then imaged with a laser scanning confocal microscope (Olympus Fluoview IX70, Center Valley, Pa.) at wavelengths of 488 nm and 568 nm.

Gene Expression

Gene expression was measured by reverse transcriptase polymerase chain reaction (RT-PCR) at days 1, 3 and 14. The nanofiber scaffolds were first rinsed with PBS and total RNA was isolated using the Trizol extraction method (Invitrogen, Carlsbad, Calif.). The isolated RNA was reverse-transcribed into complementary DNA (cDNA) using the Superscript First-Strand Synthesis System (Invitrogen), and the cDNA product was then amplified using recombinant Taq DNA polymerase (Invitrogen). Expression of glyceraldehydes-3-phosphate dehydrogenase (GAPDH) (GAPDH sense, 5'-GGCGATGCTGGCGCTGAGTA-3' (SEQ ID NO:1); antisense, 5'-ATCCACAGTCTTCTGGGTGG-3' (SEQ ID NO:2)), integrin α2 (sense, 5'-CAGAATTTG-GAACGGGACTT-3' (SEQ ID NO:3); antisense, 5'-CAG-GTAGGTCTGCTGGTTCA-3' (SEQ ID NO:4)), integrin α5 (sense, 5'-GTGGCCTTCGGTTTACAGTC-3' (SEQ ID NO:5); antisense, 5'-AATAGCACTGCCTCAGGCTT-3' (SEQ ID NO:6)), integrin αV (sense, 5'-GATGGACCAAT-GAACTGCAC-3' (SEQ ID NO:7); antisense, 5'-TTGGCA-GACAATCTTCAAGC-3" (SEQ ID NO:8)), collagen I (sense, 5'-TGCTGGCCAACTATGCCTCT-3' (SEQ ID NO:9); antisense, 5' TTGCACAATGCTCTGATC-3' (SEQ ID NO:10)) and collagen III (sense, 5'-CCAAACTCTATCT-GAAATCC-3' (SEQ ID NO: 11); antisense, 5'-GGACT-CATAGAATACAATCT-3' (SEQ ID NO: 12)) were determined. All genes were amplified for 30 cycles in a thermocycler (Eppendorf Mastercycler gradient, Brinkmann, Westbury, N.Y.).

Quantitative Analysis of Cell Attachment on Nanofiber Scaffolds

The effects of nanofiber organization (aligned vs. unaligned) on fibroblast attachment and alignment on the nanofiber scaffolds over time were quantified following the methods of Costa et al. (Costa, 2003). Specifically, confocal microscopy images (1024×1024 pixel resolution, n=3) of both fibroblasts seeded on the nanofiber scaffolds and acellular nanofiber scaffolds at days 1, 7 and 14 were analyzed using circular statistics software customized for measurement of fiber alignment (Fiber3). The circular statistics parameters determined include mean vector angle ($-90° \leq \theta \leq 90°$; 0° indicates horizontal orientation) which represents the average fiber alignment in the matrix, mean vector length ($0 \leq r < 1$) which ranges from zero for a randomly distributed sample to unity for a perfectly aligned sample, and angular deviation (0-40.5°) which characterizes the dispersion of the non-Gaussian angle distribution of the nanofibers. Specifically, angular deviation (0-40.5°) which characterizes the dispersion of the non-Gaussian angle distribution of the nanofibers. Specifically, angular deviation of 0° is, in general, found in a perfectly aligned sample, while 40.5° is indicative of random distribution.

Cell Proliferation

Cell proliferation (n=5) was determined at days 1, 3, 7 and 14 by measuring total DNA content using the PicoGreen double-stranded DNA assay (Molecular Probes) following the manufacturers suggested protocol. At designated time points, each nanofiber scaffold was rinsed twice with PBS, then treated with 0.1% Triton X solution (Sigma-Aldrich) and homogenized by sonication (Kontes, Vineland, N.J.) in order to remove adhered cells from the nanofiber scaffold. Sample fluorescence was measured with a microplate reader (Tecan, Research Triangle Park, N.C.), at the excitation and emission wavelengths of 485 on and 535 nm, respectively. The total number of cells in the sample was determined by converting the amount of DNA per sample to cell number using the conversion factor of 8 pg DNA/cell (Li, 2002).

Cell Matrix Production

The elaboration of types I and III collagen (n=3/group) by fibroblasts seeded on the aligned and unaligned nanofiber scaffolds were evaluated by immunohistochemistry at days 7 and 14. Briefly, the samples were rinsed twice with PBS, fixed with 10% neutral buffered formalin for 24 hours at room temperature. Monoclonal antibodies for type I collagen (1:20 dilution) and type III collagen (1:100) were purchased from EMD Chemicals (Calbiochem, San Diego, Calif.) and Sigma-Aldrich, respectively. Before staining for type III collagen, the samples were treated with 1% hyaluronidase for 30 minutes at 37° C. and incubated with primary antibody overnight. Following a PBS wash, biotinylated secondary antibody and Streptavidin conjugate (LSAB2 System-HRP, DakoCytomation, Carpinteria, Calif.) were added. Positive staining with the colorimetric substrate (AEC Substrate Chromogen, DakoCytomation) was indicated by the formation of brown precipitates and visualized with an inverted light microscope (Ziess Axiovert 25, Zeiss, Germany). At day 7, alignment of the collagen type I produced by the human fibroblasts was also evaluated using the circular statistics software (Fiber3) described above.

Example 1.4: Mechanical Properties of the Fibroblast-Seeded Nanofiber Scaffolds

The effects of in vitro fibroblast culture on the mechanical properties of the aligned and unaligned nanofiber scaffolds were determined at days 1, 7 and 14. The human rotator cuff fibroblasts were grown on both types of nanofiber scaffolds (6 cm×1 cm) at a density of $3×10^4$ cells/$cm^2$ in fully supplemented media at 37° C. and 5% CO2. For the control groups, the aligned and unaligned nanofiber scaffolds without cells (acellular) were incubated in fully supplemented DMEM and analyzed at days 1, 7 and 14. At each designated time point, the samples were rinsed twice with PBS, and then tested to failure under uniaxial tension following the protocol described for the as-fabricated nanofiber scaffolds. The elastic modulus, yield stress and ultimate tensile stress of the samples (n=5) were determined.

Example 1.5: Statistical Analysis

Results are presented in the form of mean±standard deviation, with n equal to the number of samples analyzed.

One-way analysis of variance (ANOVA) was performed to determine the effects of fiber organization of the as-fabricated nanofiber scaffolds on material and mechanical properties. Two-way ANOVA was used to determine nanofiber scaffold fiber organization and temporal effects on cellular alignment and cell proliferation. Additionally, two-way ANOVA was performed to determine the effects of cellularity and culture time on nanofiber scaffold tensile mechanical properties. The Tukey-Kramer post-hoc test was utilized for all pair-wise comparisons and statistical significance was attained at $p<0.05$. All statistical analyses were performed using JMP statistical software (SAS Institute, Cary, N.C.).

Example 1.6: Chondrocytes on the Nanofiber-Based Scaffold

One objective of this experiment is to evaluate the response of chondrocytes on PLGA and PLGA-HA nanofiber-based scaffolds.

It has been that chondrocyte-like cells were observed at the interface during in vivo tendon-to-bone healing. (Sano et al., 2002; Koike et al., 2005, 2006). The second objective of this experiment is to identify an optimal nano-HA concentration for the formation of a calcified fibrocartilage-like matrix. It is hypothesized that chondrocytes cultured on the PLGA nanofiber scaffold would form a fibrocartilage-like ECM and that scaffold mineral content would regulate chondrocyte response.

Experimental Procedure

Aligned PLGA and PLGA-HA nanofiber scaffolds are produced by electrospining as discussed supra (Chun, 1995, Reneker & Chun, 1996; Moffat, at al., 2007) (PLGA (85:15)+dimethylformamide+ethanol (35% PLGA); PLGA-HA (10% and 15% HA nanoparticles, 100-150 nm, Nanocerox).

The Scaffold characterized according to the Table 4:

TABLE 4

Scaffold Characterization Measures

| Parameter | Method of Measurement |
|---|---|
| Surface and Bulk Properties | |
| Surface roughness: | Atomic Force Microscopy (AFM, contact mode, pyramidal tip, k = 0.03 N/m, n = 9) |
| Fiber Diameter: | Scanning Electron Microscopy (SEM, 2 kV, 4000×) + image analysis (Image J, n = 30) |
| Mineral Content: | Thermogravimetric analysis (TGA) (25° C.-600° C., 5° C./min, n = 5) |
| Mineral Chemistry: | Fourier Transform Infrared Spectroscopy (FTIR) (200 scans, 4 $cm^{-1}$, n = 2) |
| Elemental Composition: | Energy Dispersive X-ray Analysis (EDAX) (10 kV, 4000×, n = 2) |
| Mechanical Properties | |
| Tension: | Instron, displacement rate = 5 mm/min, n = 5 |
| Compression: | Instron, displacement rate = 2 µm/s, tare load = 10 g, n = 5 |

Figure 72:
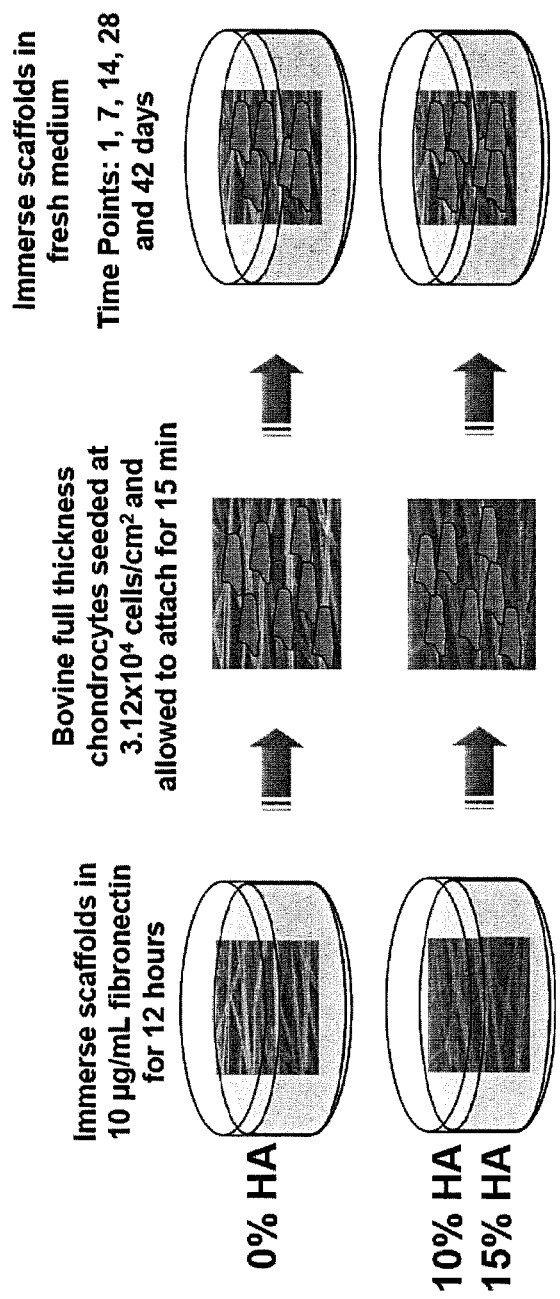
FIG. 72 shows in vitro cell cultuer experimental design for Example 1.6.

The Experiment is set up according to FIG. 72 and as follows:

The Control Group: 0% HA scaffold (PLGA); Experimental Groups: 10% and 15% HA Scaffols (PLGA-HA) Medium: 10% ITS+premix, 10% FES, 40 µg/mL L-proline, 100 µg/mL sodium pyruvate, 0.1 µM dexamethasone, 50 µg/mL ascorbic acid, 1% antifungal.

Scaffold Characterization—Mineral Content

Figure 73:
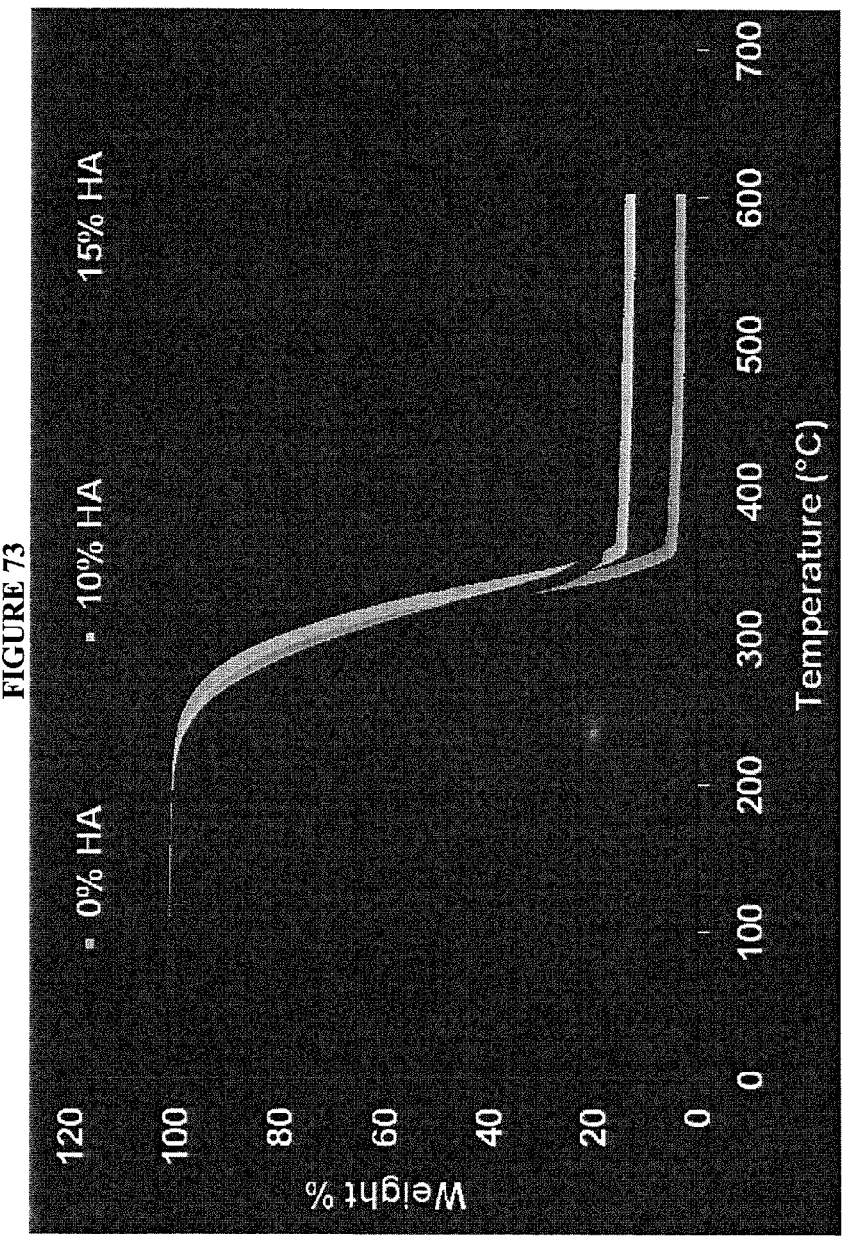
FIG. 73 shows the mineral content of the 0% HA, 10% HA and 15% HA scaffold in Example 1.6.

TGA confirmed the amount of mineral incorporated into the scaffold. Significantly higher mineral content was found for the 15% HA group as compared to the 10% HA scaffolds (*p<0.05) (Table 5, FIG. 73)

TABLE 5

Scaffold Characterization - Mineral Content

| Scaffold | Thermogravimetric Analysis (TGA) Weight % (n = 5) |
|---|---|
| 0% HA | 2.99 ± 0.32 |
| 10% HA | 12.69 ± 0.76* |
| 15% HA | 17.91 ± 0.63* |

Scaffold Characterization—Composition and Chemistry

Figures 11, 11A, 11B, 11C:
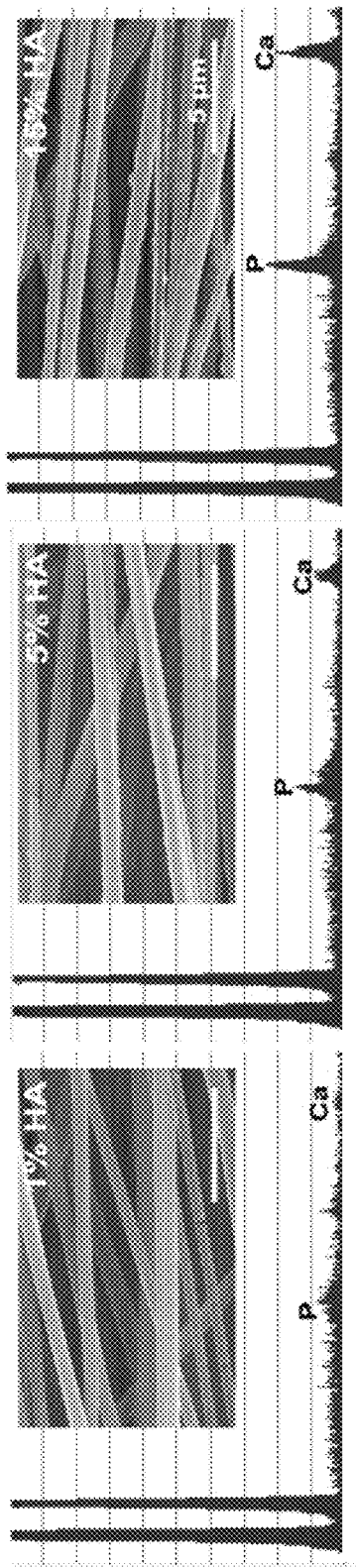
FIGS. 11A-11C show that calcium and phosphorous peaks acquired through EDAX analysis confirmed incorporation of hydroxyapatite (HA) into the PLGA nanofibers. Fiber roughness was found to increase with increasing hydroxyapatite content (1% (FIG. 11A), 5% (FIG. 11B), and 15% (FIG. 11C) HA) as shown by scanning electron microscopy.

The results indicate that Ca and P peak intensity increased with mineral content (FIGS. 11A-11C)

Figure 74:
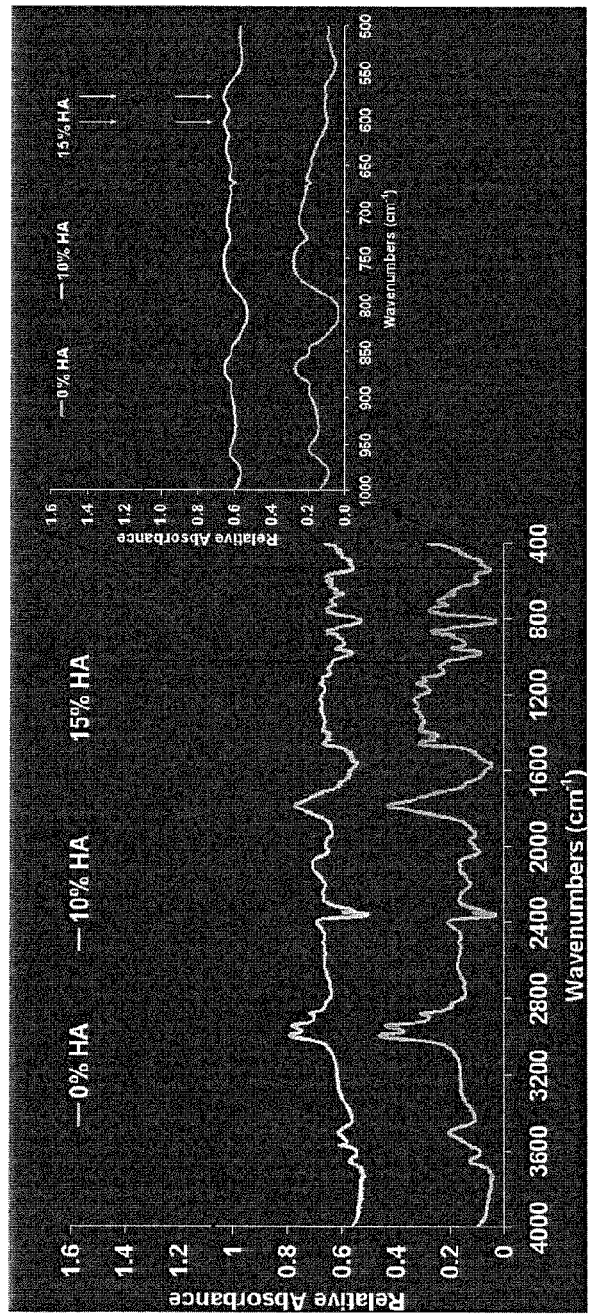
FIG. 74 shows mineral chemistry of incorporated HA in Example 1.6 as determined by FTIR.
Figures 75, 75A:
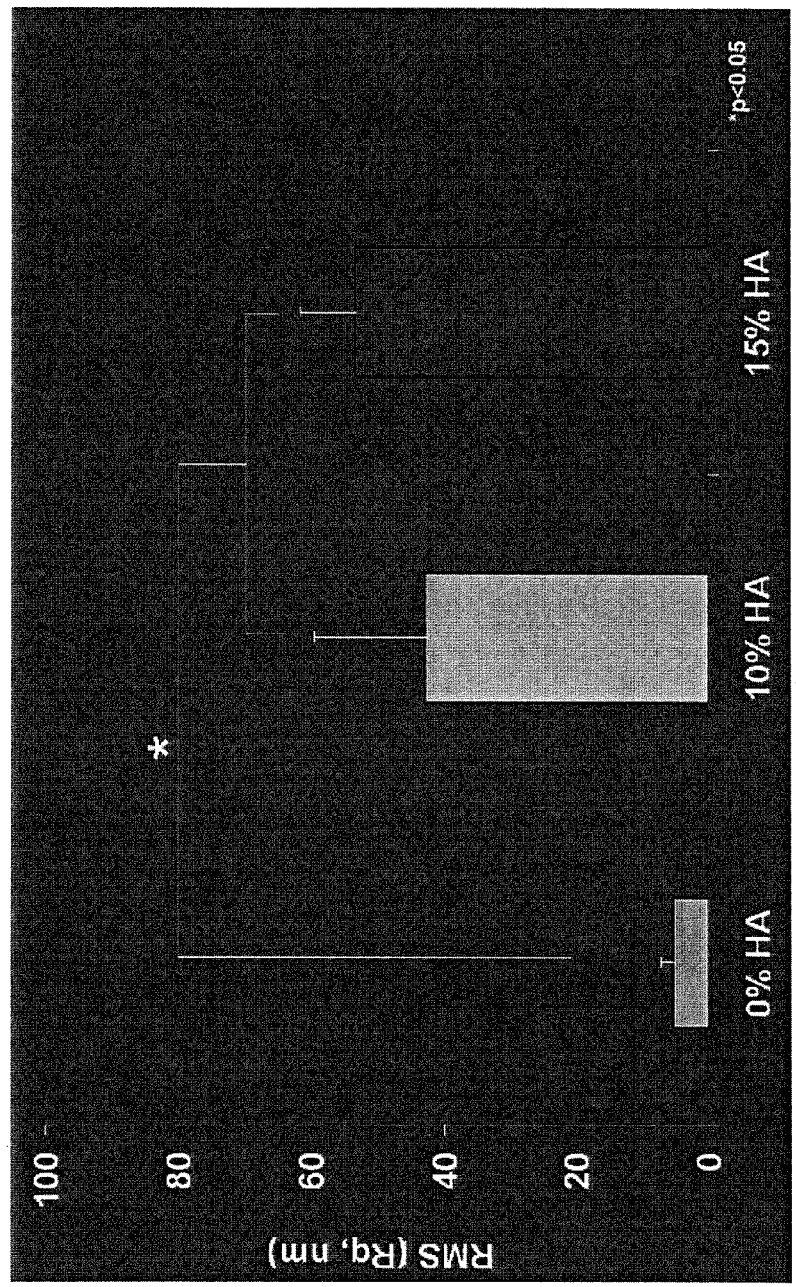
FIG. 75A shows the surface roughness of the 0% HA, 10% HA and the 15% HA nanofiber-based scaffold in Example 1.6.
Figures 76, 76A:
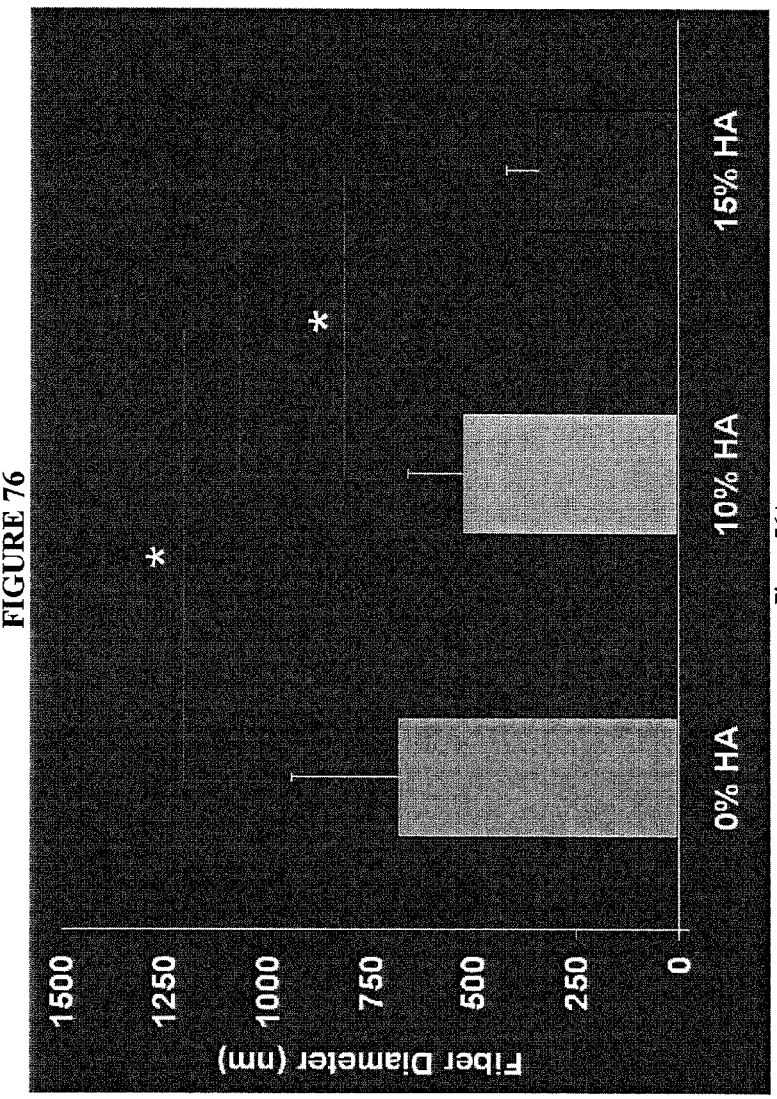

Mineral chemistry of incorporated HA is confirmed by FTIR: The results show phosphate bending vibration peaks at 605 cm$^{-1}$ and 560 cm$^{-1}$. This is indicative of crystalline calcium phosphate. (FIG. 74)

Scaffold Characterization—Surface Roughness and Fiber Diameter

AFM analysis revealed an increase in fiber surface roughness with mineral content (FIGS. 75A-D)

Scaffold Characterization—Fiber Diameter

Nanofiber diameter decreased with increasing mineral content (FIGS. 76A-D)

Scaffold Characterization—Scaffold Mechanical Properties

Figures 77, 77A:
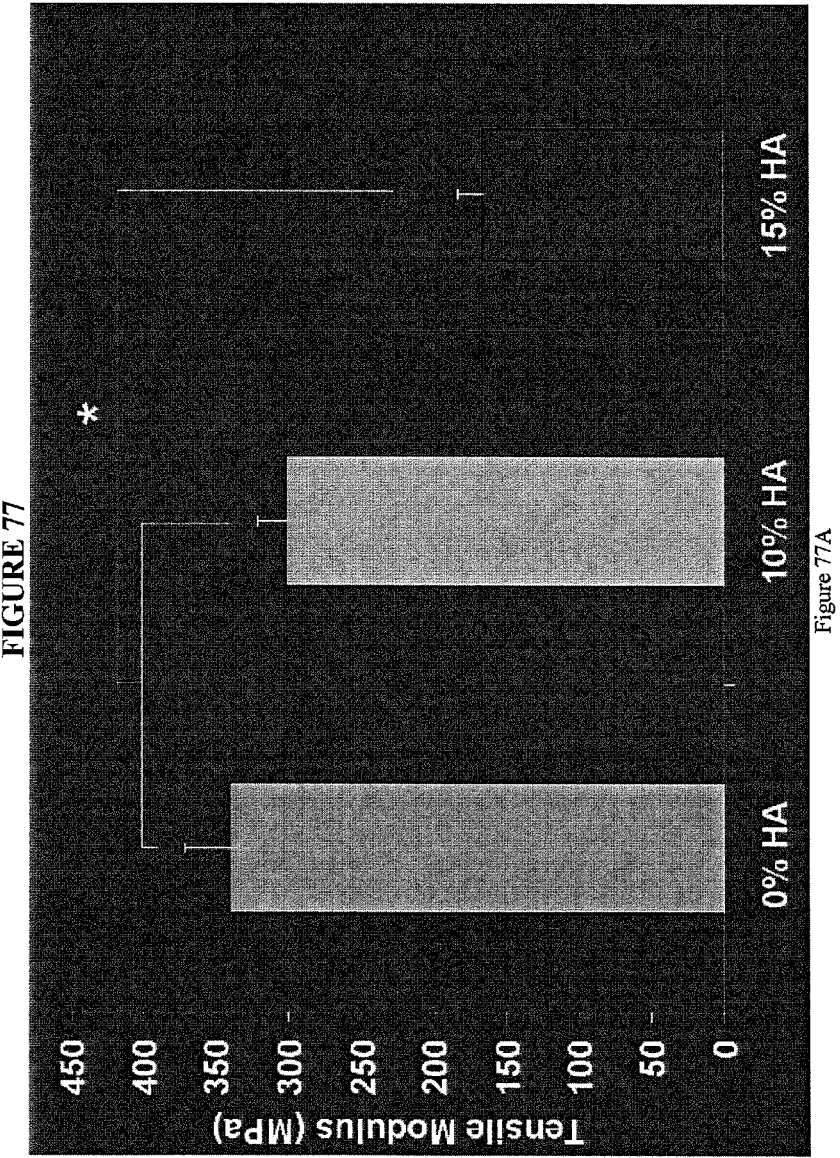
FIG. 77A shows tensile modulus decreasing with increasing mineral content in Example 1.6.

Tensile modulus decreased with increasing mineral content. Significant decrease for 15% HA case was observed. This finding is in range of values reported for modulus of human supraspinatus tendon (Itoi et al., 1995) (FIG. 77A, *p<0.05).

Figure 77B:
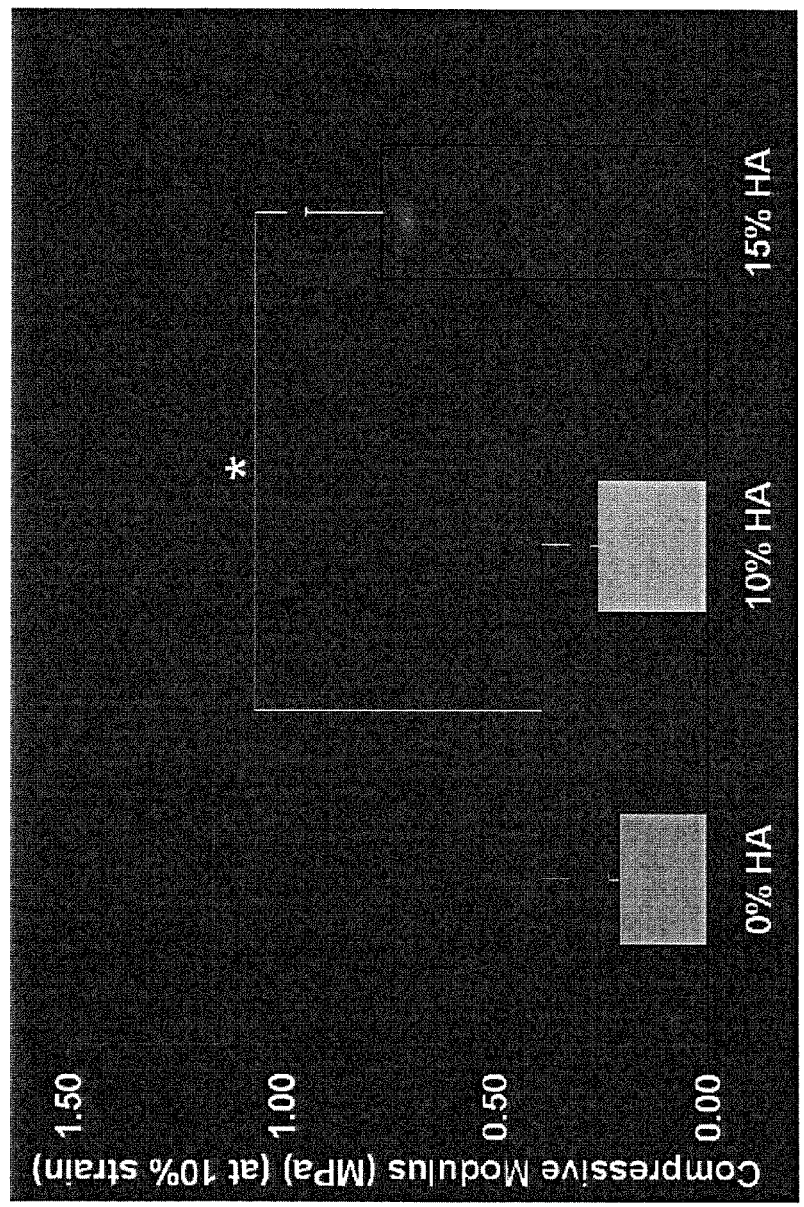
FIG. 77B shows compressive modulus increasing with increasing mineral content in Example 1.6.

Compressive modulus increased with increasing mineral content. There was a significant increase for 15% HA case. This finding is in range of values reported for modulus of direct insertion sites (Moffat et al., PNAS, 2008) (FIG. 77B, *p<0.05).

Cell Morphology and Growth

Figures 78, 78A:
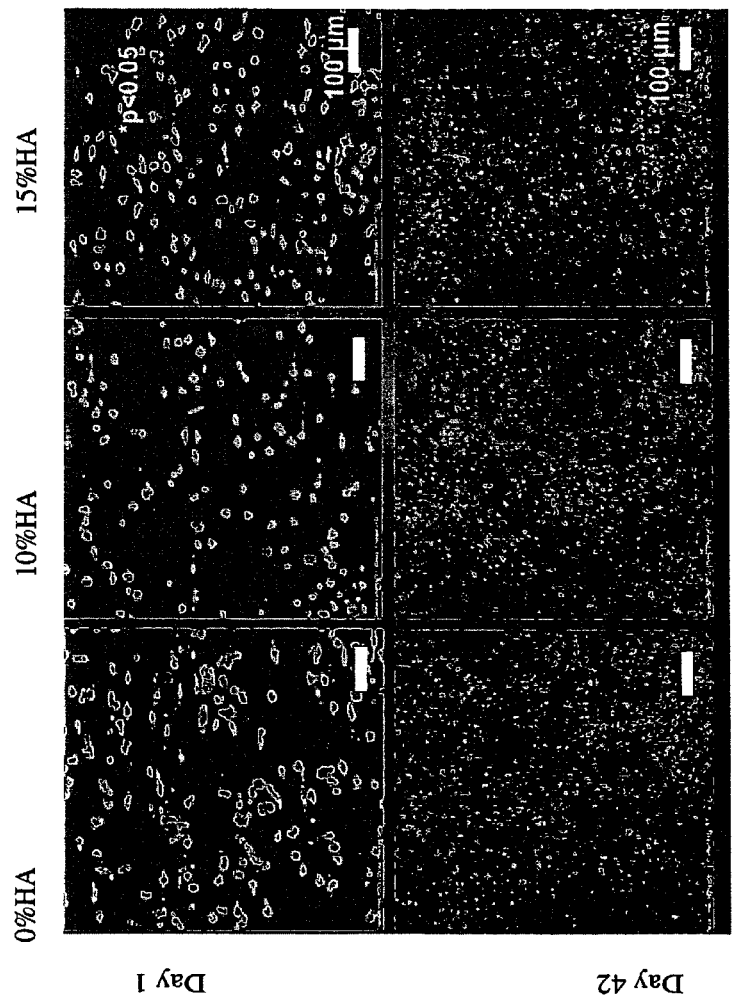
FIG. 78A shows that cell morphology is heterogenous with both elongated and spherical cells observed in Example 1.6.

Cell morphology is heterogenous with both elongated and spherical cells observed (FIG. 78A)

Figures 78, 78B:
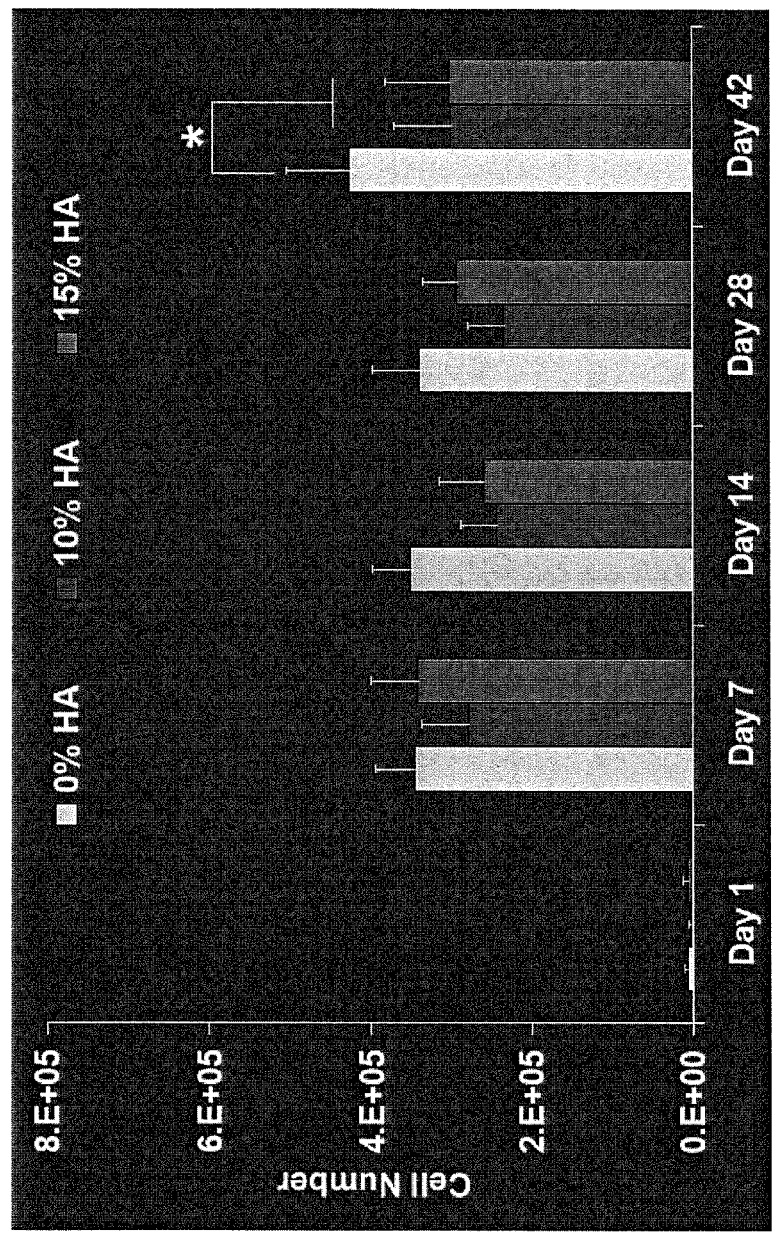
FIG. 78B shows cell proliferation (Cell number) from Day 1-Day 42 in Example 1.6.

There is also significant cell proliferation within 1 week of culture with the highest cell number on 0% HA (PLGA) scaffolds at day 42. (FIG. 78B)

Chondrocyte Collagen Deposition

Figures 79, 79A:
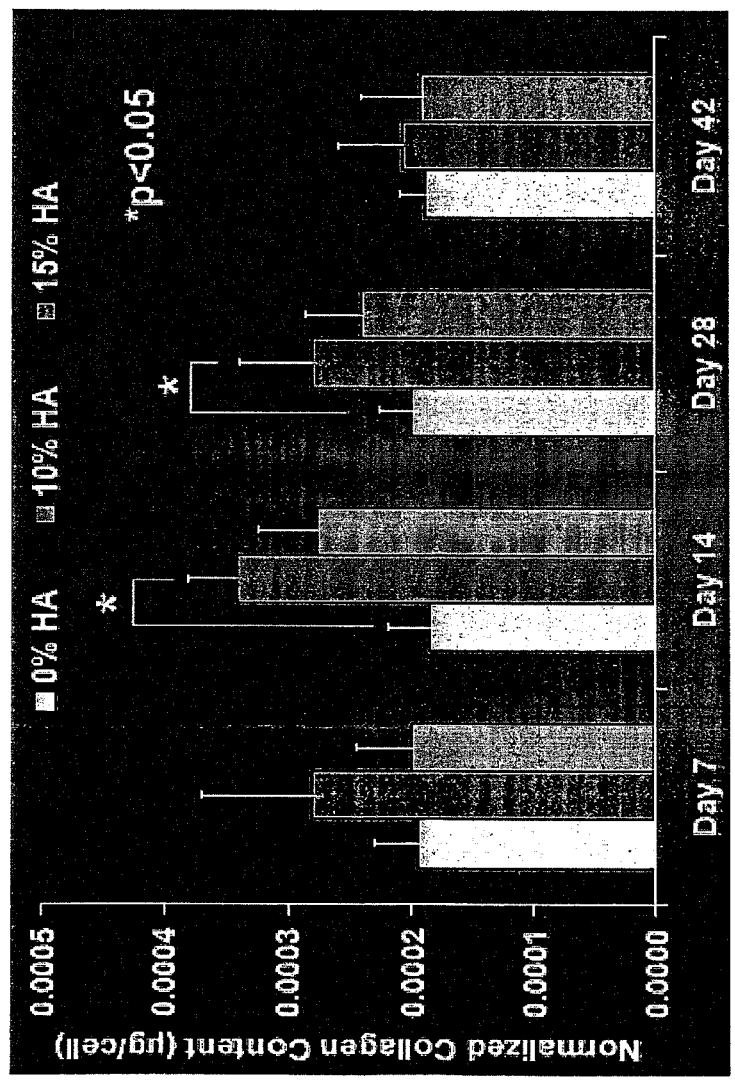
FIG. 79A shows normalized collagen content from Day 7-Day 42 in Example 1.6.

Collagen deposition increased over time on PLGA-HA and is significantly higher on the PLGA-HA. (FIG. 79A)

Figure 79B:
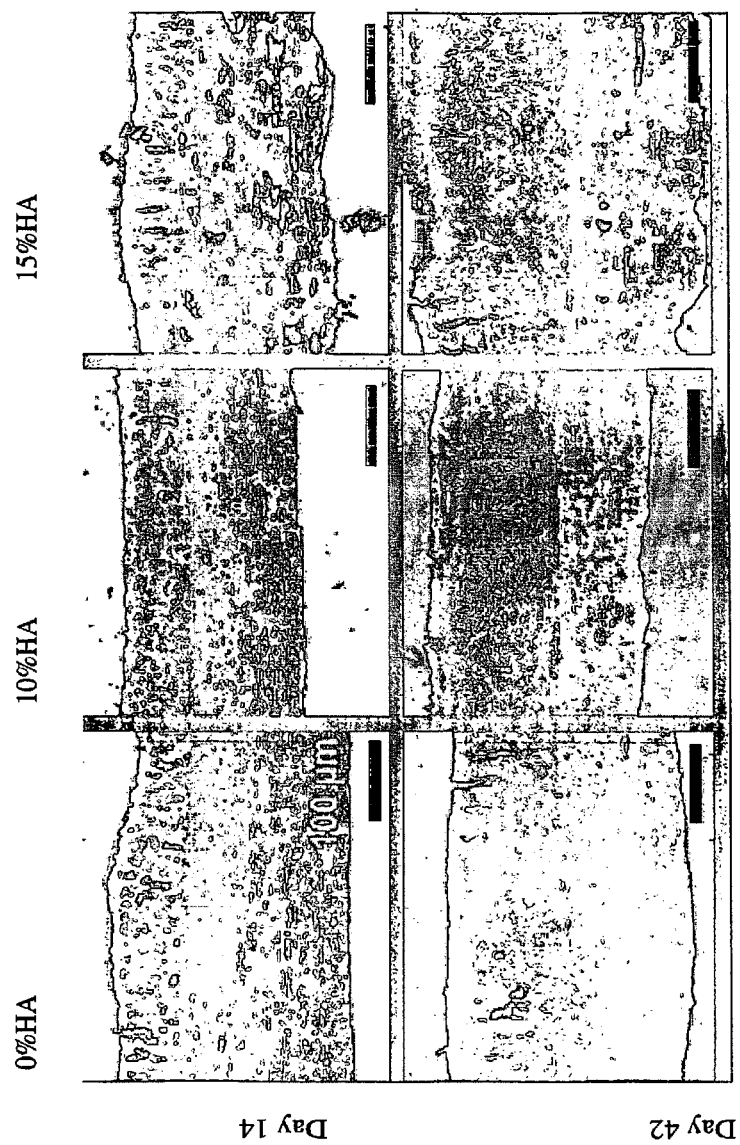
FIG. 79B shows chondrocyte collagen deposition with Picrosirius Red Stain (20×, bar=100 μm)

Dense collagen matrix is observed at day 14 for all groups with enhanced matrix infiltration on PLGA-HA scaffolds. (FIG. 79B)

Regional distribution of collagen is found at day 42.

Nanofiber-Guided Collagen Alignment

Nanofiber scaffold organization guided collagen production with aligned collagen matrix distributed throughout the scaffolds.

Figure 80:
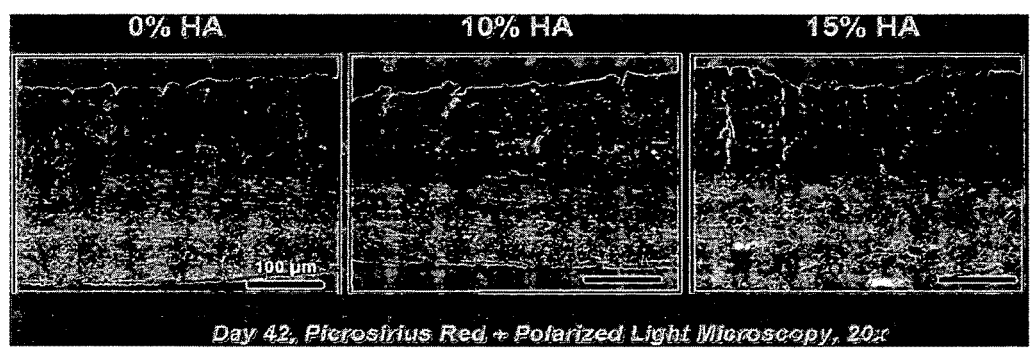
FIG. 80 shows nanofiber-guided collagen alignment with Picrosirius Red Stain on Day 42 (Picrosirius Red+Polarized Light Microscopy, 20×).

Enhanced collagen alignment was found on the PLGA scaffold as compared to the PLGA-HA groups. (FIG. 80)

Collagen Deposition

Figure 81:
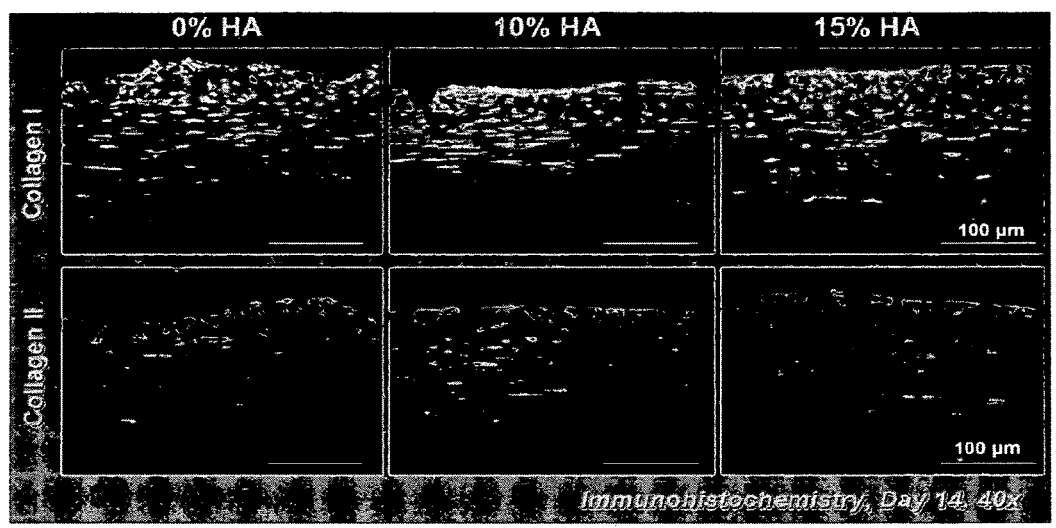
FIG. 81 shows that the nanofiber scaffolds in Example 1.6 supported collagen I and II production. (Immunohistochemistry, Day 14, 40×)

Nanofiber scaffold supported collagen I and II production. In addition, collagen deposition is evident throughout the entire scaffold (FIG. 81).

Chondrocyte GAG Deposition

Figures 82, 82A:
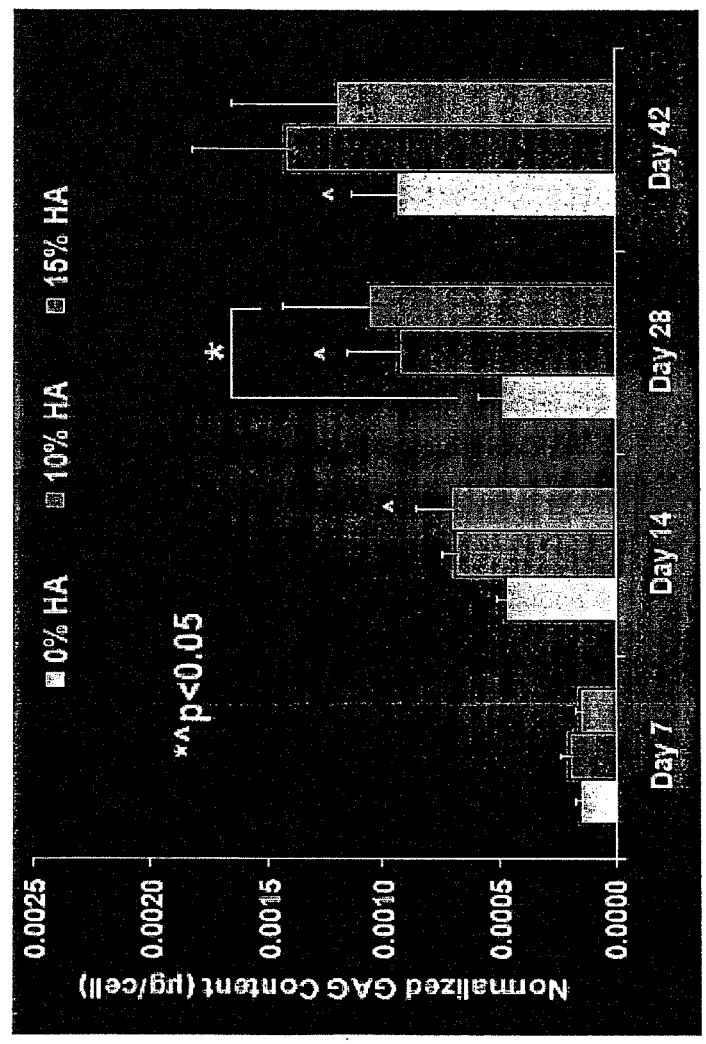
FIG. 82A shows the Normalized GAG content from Day 7 to Day 42.
Figure 82B:
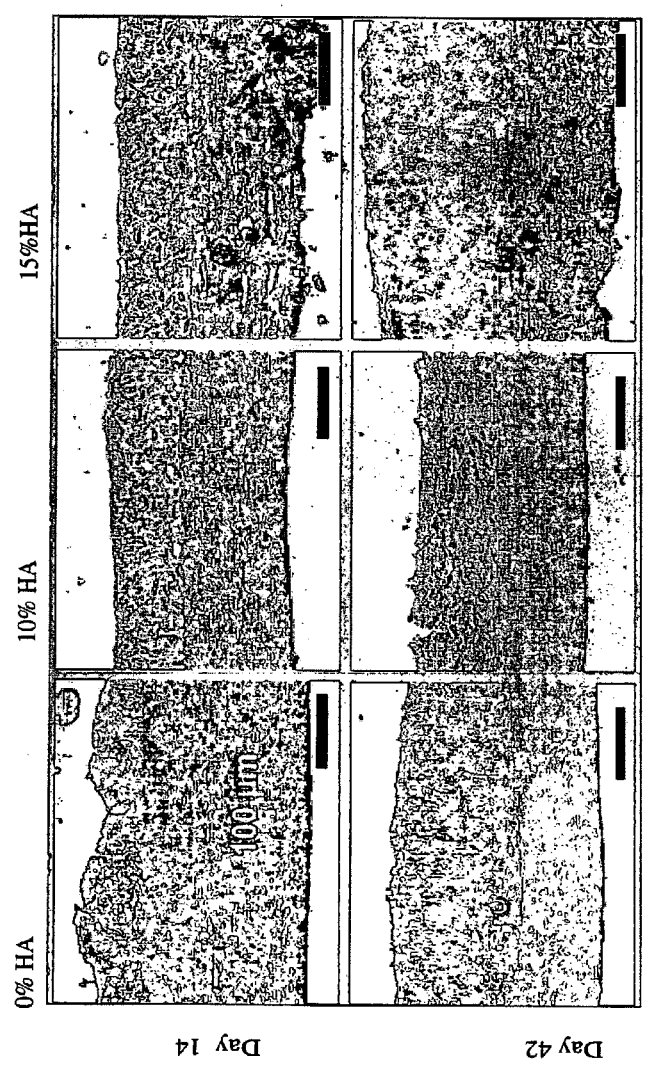
FIG. 82B shows chondrocyte GAG Deposition (Alcian Blue stain, 20×, bar=100 μm)

GAG synthesis increased over time for all groups and is significantly higher on PLGA-HA by day 28. Enhanced GAG matrix deposition and infiltration is also observed on the PLGA-HA. (FIG. 82A-B).

Calcified Matrix Deposition

Figure 83:
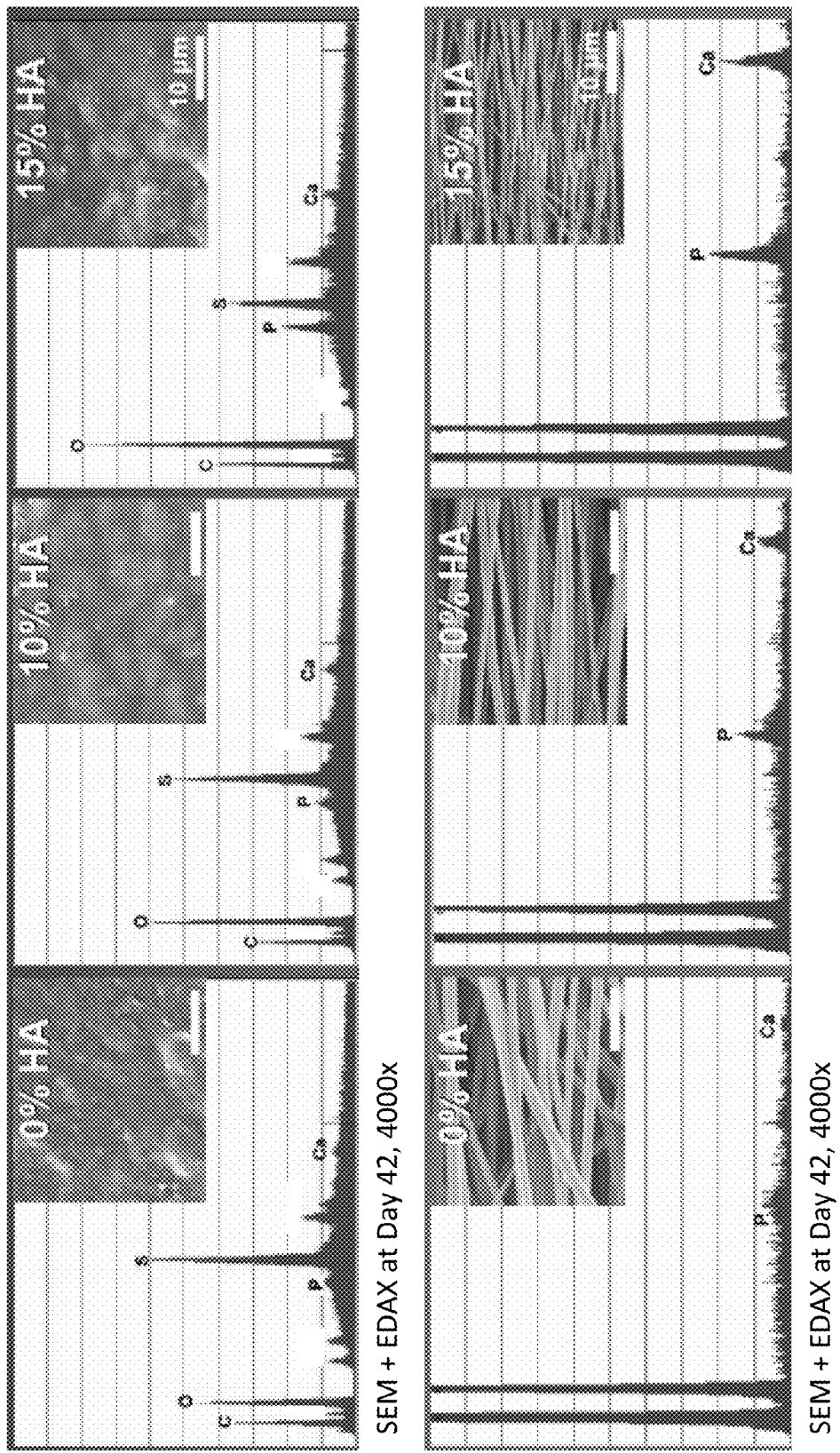
FIG. 83 shows calcified matrix deposition in Example 1.6.

Calcified, protein-rich matrix detected on the PLGA-HA as nanofibers degraded over time. High intensity sulfur peak associated with protein deposition. Ca—P peak intensity ratio differed between the 10% and the 15% HA groups. (FIG. 83)

Chondrocyte Hypertrophy and Matrix Maturation

Figures 84, 84A:
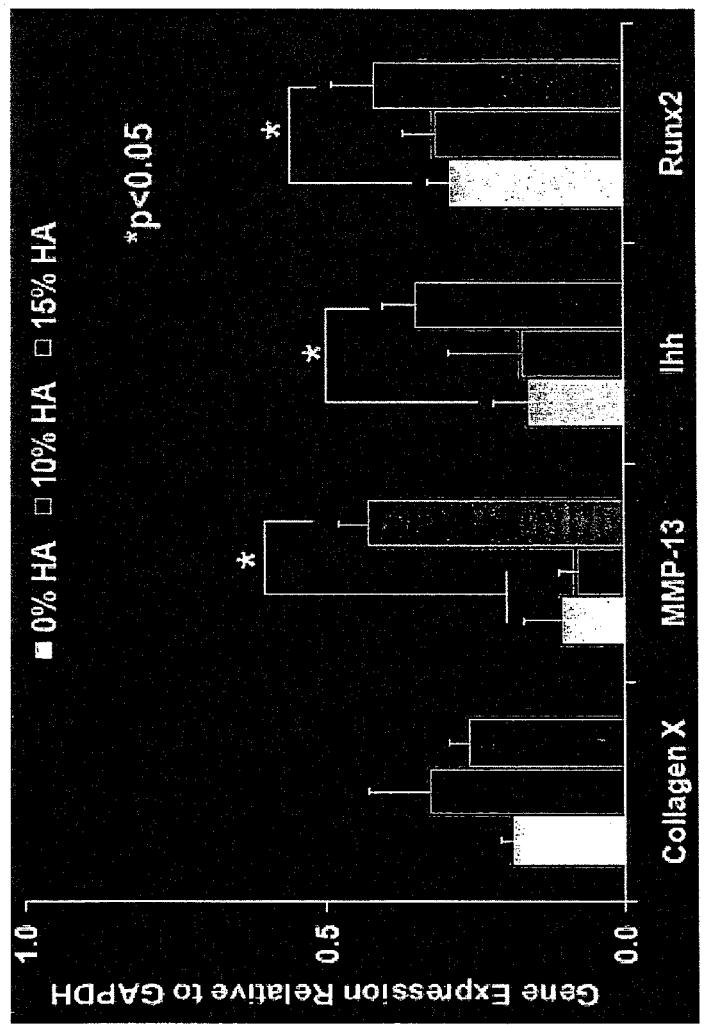
FIG. 84A shows Gene Expression Relative to GAPDH for Collagen X, MMP-13, Ihh and Runx2 for the 0%, 10% and 15% HA nanofiber scaffolds in Example 1.6.

Significantly higher MMP-13, Ihh and Runx2 expression was found on PLGA-HA (15%) at day 3. (FIG. 84A)

Figure 84B:
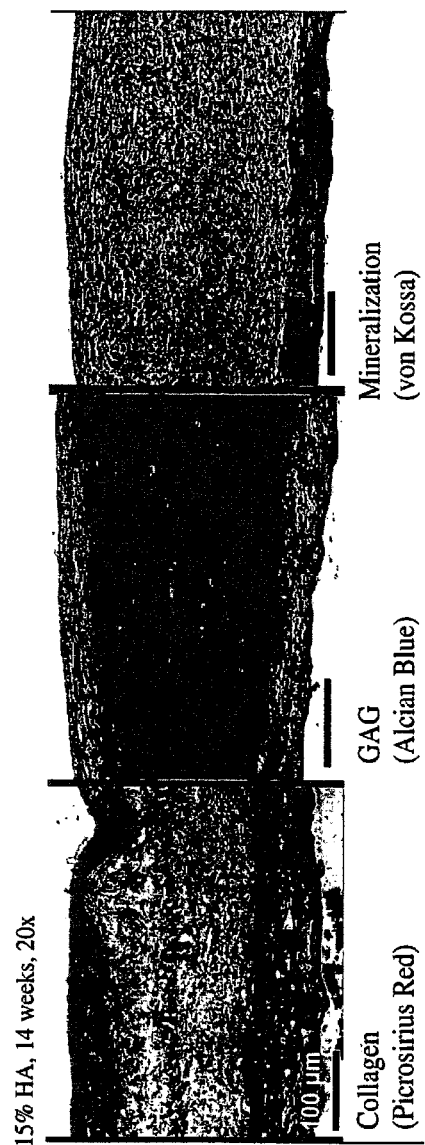
FIG. 84B shows sided by side comparison of collagen (Picrosirius Red), GAG (Alcian Blue), and Mineralization (von Kossa) images for the 15% HA scaffold (14 weeks, 20×).

Matrix heterogeneity was also observed: nanofiber degradation, collagen-rich at periphery and along border of scaffold, GAG-rich at center of matrix, and uniform mineral distribution. (FIG. 84B)

Discussion

It was found that BOTH the PLGA and PLGA-HA supported: chondrocyte attachment and proliferation, synthesis of a collagen- and GAG-rich matrix, deposition of both types I and II collagen and matrix deposition guided by nanofiber alignment. These findings are indicative of the production of a fibrocartilage-like matrix mimicking that of the native tendon-bone insertion.

It was also found that nanofiber compressive mechanical properties increased with addition of HA. A similar trend was observed for the non-calcified and calcified regions of the native insertion. (Moffat et al., PNAS, 2008)

In addition, designed gradient of mechanical properties exhibited by PLGA and PLGA-HA nanofiber scaffolds were found to have minimized the formation of stress concentrations and mediated load transfer between tendon and bone.

HA content was found to affect characterization of PLGA-HA nanofibers. Similar to reported chondrocyte studies with mineral (Kandel et al., 2006; Boskey et al., 1984, Boskey, 1992; Jubeck et al., 2008), HA was found to increase proteoglycan and collagen production. Enhanced matrix infiltration was also found on 15% HA. Further, up-regulation of hypertrophic markers was found on the 15% HA. Finally, compressive mechanical properties of 15% HA similar to those of the native calcified fibrocartilage was found. (Moffat, et al., PEAS, 2008)

Overall, these results demonstrate the potential for: 1) chondrocyte-mediated formation of the non-calcified fibrocartilage interface region on PLGA and 2) chondrocyte-mediated formation of the calcified interface region on the PLGA-HA (15% HA).

Example 2: PLGA-BG Composite Scaffold and Co-Cultures of Different Cell Types

To address the challenge of graft fixation to subchondral bone, a normal and functional interface may be engineered between the ligament and bone. This interface, according to one exemplary embodiment, was developed from the co-culture of osteoblasts and ligament fibroblasts on a multi-phased scaffold system with a gradient of structural and functional properties mimicking those of the native insertion zones to result in the formation of a fibrocartilage-like interfacial zone on the scaffold. Variations in mineral content from the ligament proper to the subchondral bone were examined to identify design parameters significant in the development of the multi-phased scaffold. Mineral content (Ca—P distribution, Ca/P ratio) across the tissue-bone interface was characterized. A multi-phased scaffold with a biomimetic compositional variation of Ca—P was developed and effects of osteoblast-ligament fibroblast co-culture on the development of interfacial zone specific markers (proteoglycan, types II and X collagen) on the scaffold were examined.

Figure 25:
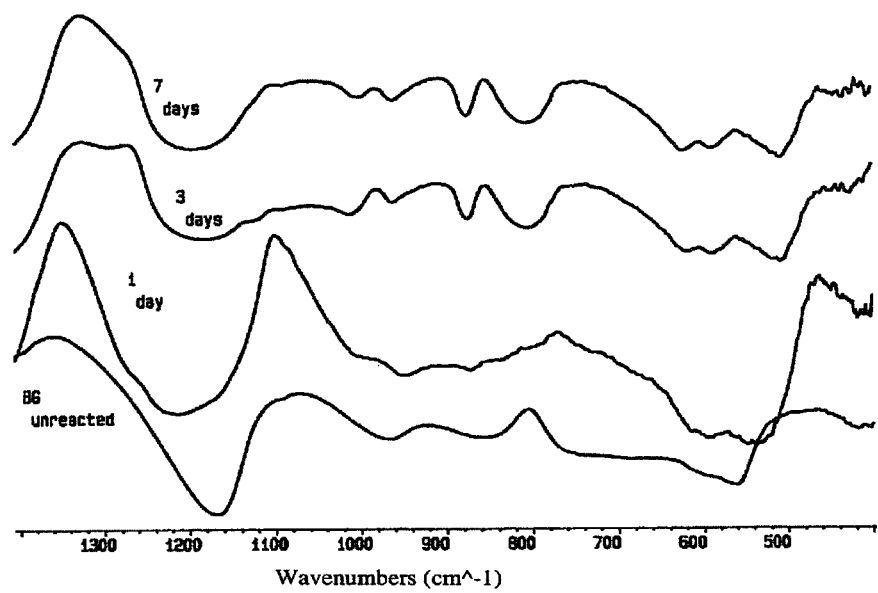
FIG. 25A shows a scanning electron microscopy (SEM) image of Ca—P nodules on BG surface (3 days in SBF). Nodules are about 1 μm in size initially, and grew as immersion continued (15,000×).
FIG. 25B shows an Energy-Dispersive X-ray Analysis (EDXA) spectrum of BG surfaces immersed in SBF for 3 days. The relative Ca/P ratio is approximately equal to 1.67.
FIG. 25C shows a Fourier Transform InfraRed (FTIR) Spectra of bioactive glass (BG) immersed in simulated body fluid (SBF) for up to 7 days, with the presence of an amorphous calcium phosphate (Ca—P) layer at 1 day, and of crystalline layer at 3 days.

The insertion sites of bovine ACL to bone (see FIGS. 23A-23C) were examined by SEM. Pre-skinned bovine tibial-femoral joints were obtained. The intact ACL and attached insertion sites were excised with a scalpel and transferred to 60 mm tissue culturing dishes filled with Dulbecco's Modified Eagle Medium (DMEM) (see FIGS. 24A and 24B). After isolation, the samples were fixed in neutral formalin overnight, and imaged by environmental SEM (FEI Quanta Environmental SEM) at an incident energy of 15 keV. ACL attachment to the femur exhibited an abrupt insertion of the collagen bundle into the cartilage/subchondral bone matrix. Examination of collagen bundle revealed that the surface was ruffled and small collagen fibrils can be seen. When a cross section was imaged, three distinct zones at the insertion site were evident: ligament (L), fibrocartilage (FC), and subchondral bone (B). The interface region spans proximally 200 µm. These cross section views showed the insertion of Sharpey fiber into the fibrocartilage (see FIGS. 25A-25C). Mineralized fibrocartilage was not distinguishable with regular cartilage from these images.

The insertion sites of bovine ACL to bone were examined by scanning electron microscopy (SEM). Bovine tibial-femoral joints were obtained. The intact ACL and attached insertion sites were excised with a scalpel and transferred to 60 mm tissue culturing dishes filled with Dulbecco's Modified Eagle Medium (DMEM). After isolation, the samples were fixed in neutral formalin overnight, and imaged by environmental SEM (FEI Quanta Environmental SEM) at 15 keV.

Figure 8:
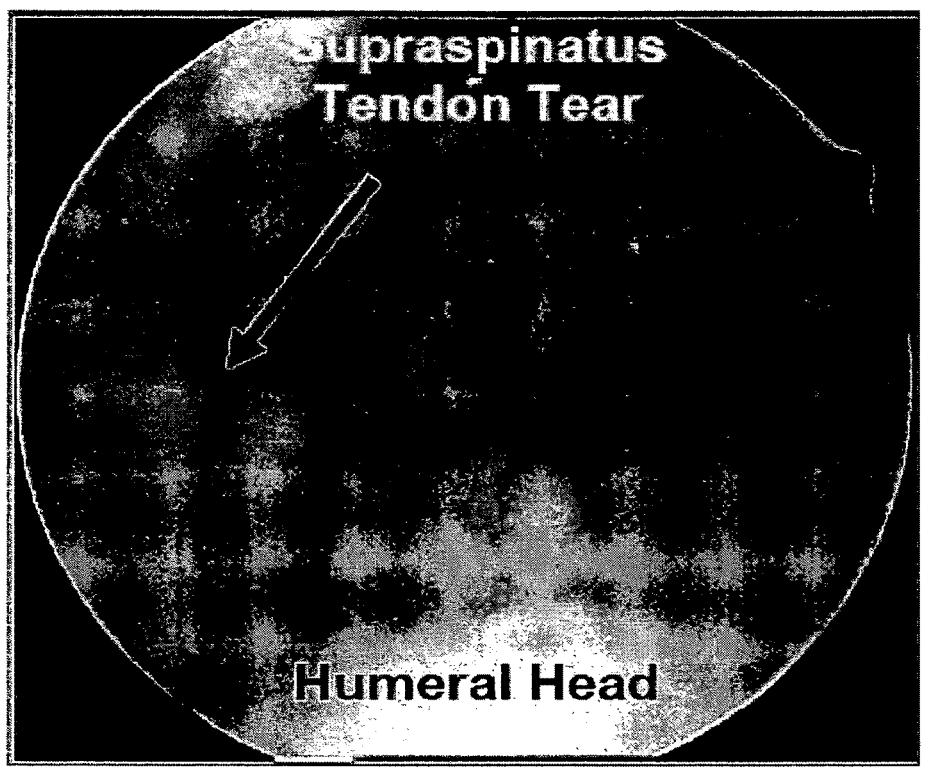
FIG. 8 shows an arthroscopic image of a torn supraspinatus tendon in the right shoulder, posterior view.
Figures 26, 26A, 26B:
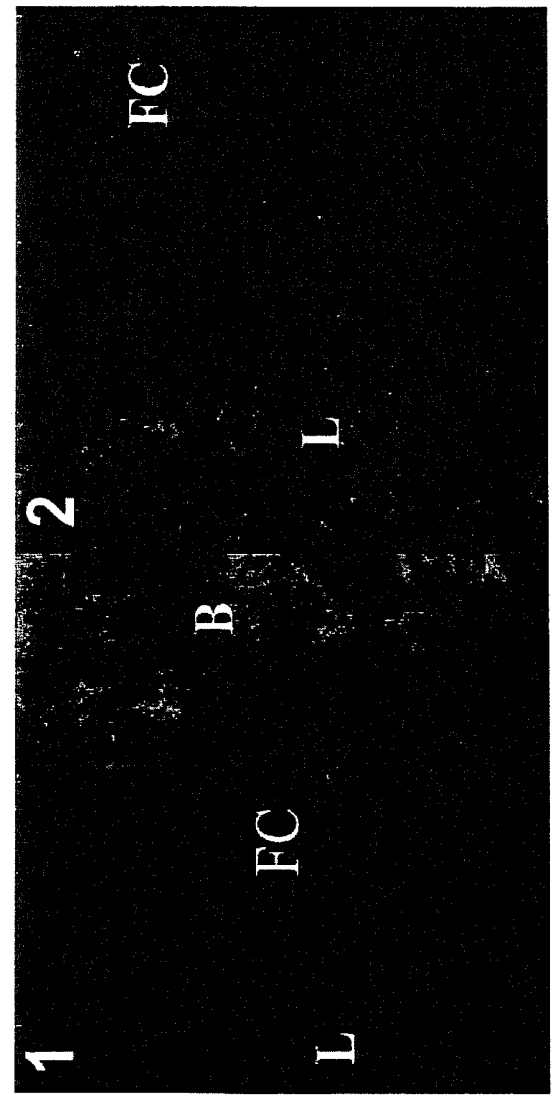
FIGS. 26A-26B show ESEM images of Bovine ACL insertion site (1 and 2), including a cross section of the ACL-femur insertion site, ACL fiber (L) left, fibrocartilage region (FC) middle, and sectioned bone (B) right (FIG. 26A: 250×.

ACL attachment to the femur exhibited an abrupt insertion of the collagen bundle into subchondral bone. When a cross section was imaged (see FIGS. 26A and 26B), three distinct zones at the insertion site were evident: ligament (L), fibrocartilage (FC), and subchondral bone (B). Sharpey fiber insertion into the fibrocartilage (see FIG. 8A) was observed. The bovine interface region spans proximally 600 µm. Examination of the interface using energy dispersive X-ray analysis (EDAX, FEI Company) enable the mineralized and non-mineralized FC zones to be distinguished. A zonal difference in Ca and P content was measured between the ligament proper and the ACL-femoral insertion (see Table 6).

TABLE 6

| Region Analyzed | Ca | P | Ca/P Ratio | S |
|---|---|---|---|---|
| Ligament | 1.69 | 2.98 | 0.57 | 3.71 |
| Insertion | 5.13 | 5.93 | 0.87 | 19.50 |

Figure 28:
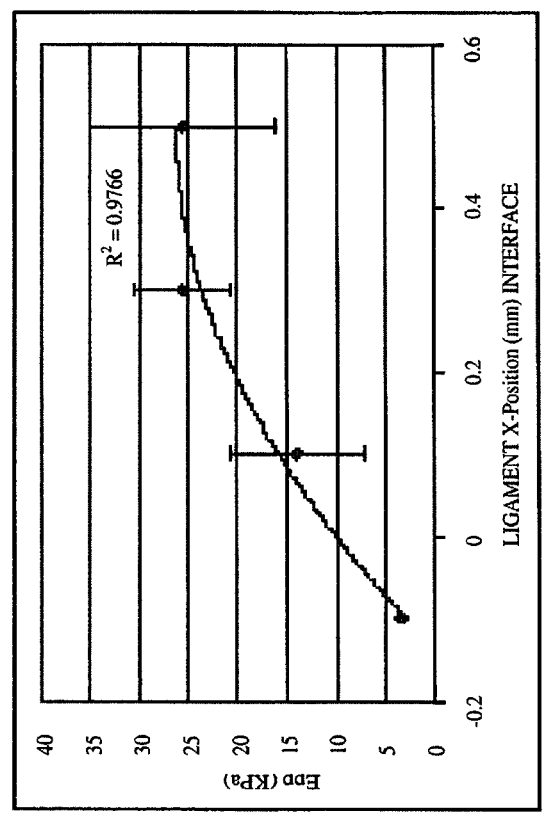
FIG. 28 shows apparent modulus versus indentation X-position across sample.

At the insertion zone (see FIGS. 27A and 27B), higher Ca and P peak intensities were observed, accompanied by an increase in Ca/P ratio as compared to the ligament region. Higher sulfur content due to the presence of sulfated proteoglycans at the FC region was also detected. The zonal difference in Ca—P content was correlated with changes in stiffness across the interface. Nanoindentation measurements were performed using atomic force microscopy (AFM, Digital Instruments). An increasing apparent modulus was measured as the indentation testing position moved from the ligament region into the transition zone (see FIG. 28).

Figure 29:
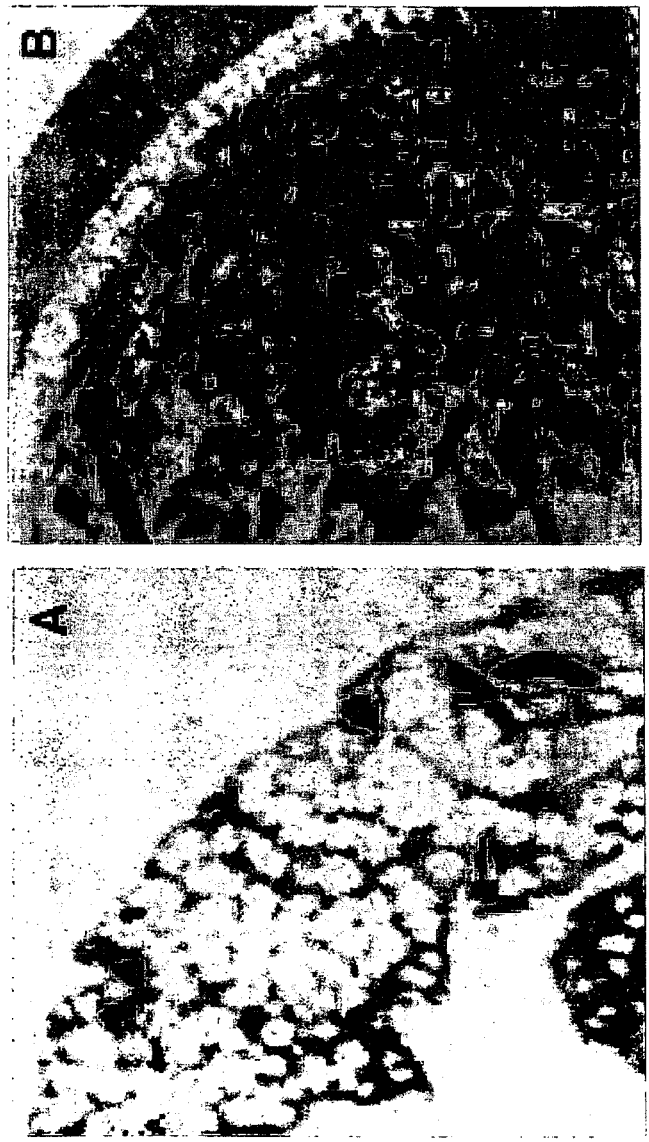
FIGS. 29A-29B show X-Ray computed axial tomography (CT) scans of discs made of poly-lactide-co-glycolide (PLAGA) 50:50 and BG submerged in SBF for 0 days (FIG. 29A) and 28 days.

Ca—P distribution on polylactide-co-glycolide (50:50) and 45S5 bioactive glass composite disc (PLAGA-BG) after incubation in a simulated body fluid (SBF) was evaluated using µCT (µCT 20, Scanco Medical, Bassersdorf, Switzerland) following the methods of Lin et al. The sample was loaded into the system, scanned at 20 mm voxel resolution and an integration time of 120 ms. FIGS. 29A and 29B compare the amount of calcified region (dark areas) observed on the PLAGA-BG disc as a function of incubation time in SBF (from day 0 to day 28). Using custom image analysis software, it was determined that at day 0, the mineralized region corresponded to 0.768% of the total disc (quartered) area, and at day 28, the mineralized region corresponded to 12.9% of the total area. Results demonstrate the Ca—P distribution on scaffolds measured by pCT analysis.

The scaffold system developed for the experiments was based on a 3-D composite scaffold of ceramic and biodegradable polymers. A composite system has been developed by combining poly-lactide-co-glycolide (PLAGA) 50:50 and bioactive glass (BG) to engineer a biodegradable, three-dimensional composite (PLAGA-BG) scaffold with improved mechanical properties. This composite was selected as the bony phase of the multi-phased scaffold as it has unique properties suitable as a bone graft.

A significant feature of the composite was that it was osteointegrative, i.e., able to bond to bone tissue. No such calcium phosphate layer was detected on PLAGA alone, and currently, osteointegration was deemed a significant factor in facilitating the chemical fixation of a biomaterial to bone tissue. A second feature of the scaffold was that the addition of bioactive glass granules to the PLAGA matrix results in a structure with a higher compressive modulus than PLAGA alone.

The compressive properties of the composite approach those of trabecular bone. In addition to being bioactive, the PLAGA-BG lends greater functionality in vivo compared to the PLAGA matrix alone. Moreover, the combination of the two phases serves to neutralize both the acidic byproducts produced during polymer degradation and the alkalinity due to the formation of the calcium phosphate layer. The composite supports the growth and differentiation of human osteoblast-like cells in vitro.

The polymer-bioactive glass composite developed for the experiments was a novel, three-dimensional, polymer-bioactive biodegradable and osteointegrative glass composite scaffold. The morphology, porosity and mechanical properties of the PLAGA-BG construct have been characterized. BG particle reinforcement of the PLAGA structure resulted in an approximately two-fold increase in compressive modulus ($p<0.05$). PLAGA-BG scaffold formed a surface Ca—P layer when immersed in an electrolyte solution (see FIG. 30A), and a surface Ca—P layer was formed. No such layer was detected on PLAGA controls. EDXA spectra confirmed the presence of Ca and P (see FIG. 30B) on the surface. The Ca, P peaks were not evident in the spectra of PLAGA controls.

In vitro formation of a surface Ca—P layer indicates PLAGA-BG composite's osteointegrative potential in vivo. The growth and differentiation of human osteoblast-like cells on the PLAGA-BG scaffolds were also examined. The composite promoted osteoblast-like morphology and stained positive for alkaline phosphatase, and promoted synthesis to a greater extent of Type I collagen synthesis than tissue culture polystyrene controls.

Figure 31:
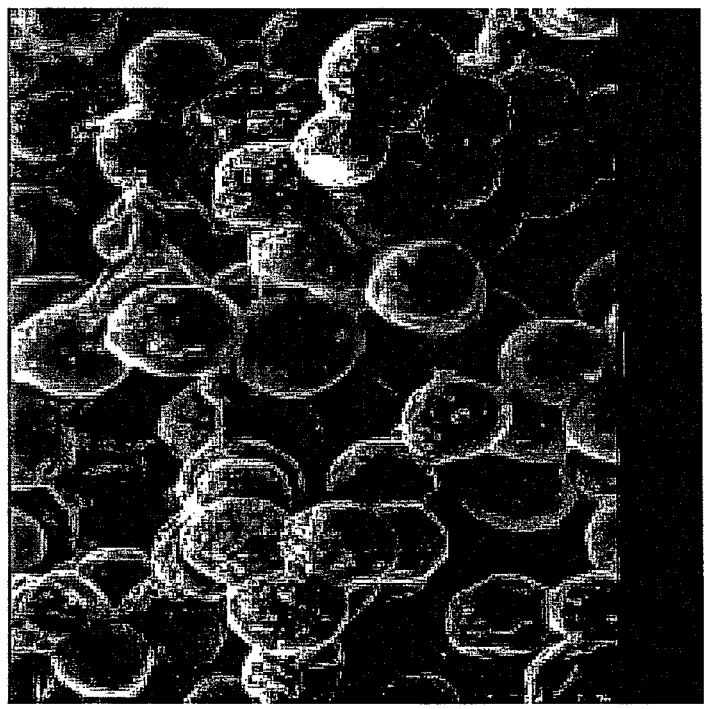
FIG. 31 shows osteoblast grown on PLAGA-BG, 3 weeks.

The porous, interconnected network of the scaffold was maintained after 3 weeks of culture (see FIG. 31). Mercury porosimetry (Micromeritics Autopore III, Micromeritics, Norcross, Ga.) was used to quantify the porosity, average pore diameter and total surface area of the composite construct. The construct porosity was determined by measuring the volume of mercury infused into the structure during analysis. In addition, the construct (n=6) was tested under compression. BG particle reinforcement of the PLAGA structure resulted in approximately two-fold increase in compressive modulus (see Table 7, p<0.05).

TABLE 7

| Scaffold Type | Average Porosity | Pore Diameter (μm) | Elastic Modulus (Mpa) | Compressive Strength (Mpa) |
| --- | --- | --- | --- | --- |
| PLAGA | 31% | 116 | 26.48 ± 3.47 | 0.53 ± 0.07 |
| PLAGA-BG | 43% | 89 | 51.34 ± 6.08 | 0.42 ± 0.05 |

Porosity, pore diameter, and mechanical properties of the scaffold may be variable as a function of microsphere diameter and BG content. The growth and differentiation of human osteoblast-like cells on the PLAGA-BG scaffolds were also examined. The composite supported osteoblast-like morphology and stained positive for alkaline phosphatase.

The porous, interconnected network of the scaffold was maintained after 3 weeks of culture (see FIG. 31). The synthesis of type I collagen was found to be the highest on the composite, as compared to the PLAGA and tissue culture polystyrene (TCPS) controls (n=3, p<0.05) (see FIG. 32).

The effects of bovine osteoblast and fibroblast co-culture on their individual phenotypes were examined. The cells were isolated using primary explant culture. The co-culture was established by first dividing the surfaces of each well in a multi-well plate into three parallel sections using sterile agarose inserts. ACL cells and osteoblasts were seeded on the left and right surfaces respectively, with the middle section left empty. Cells were seeded at 50,000 cells/section and left to attach for 30 minutes prior to rinsing with PBS. The agarose inserts were removed at day 7, and cell migration into the interface was monitored. Control groups were fibroblasts alone and osteoblasts alone.

In time, both ACL fibroblasts and osteoblasts proliferated and expanded beyond the initial seeding areas. These cells continued to grow into the interfacial zone, and a contiguous, confluent culture was observed. All three cultures expressed type I collagen over time. The co-culture group expressed type Il collagen at day 14, while the control fibroblast did not. Type X collagen was not expressed in these cultures, likely due to the low concentration of β-GP used. Alizarin Red S stain intensity was the highest for the osteoblast control, (see FIG. 33C) followed by the co-cultured group (see FIG. 33B). Positive ALP staining was also observed for osteoblast control and co-culture groups (see FIGS. 33F and 33E respectively).

Figure 34:
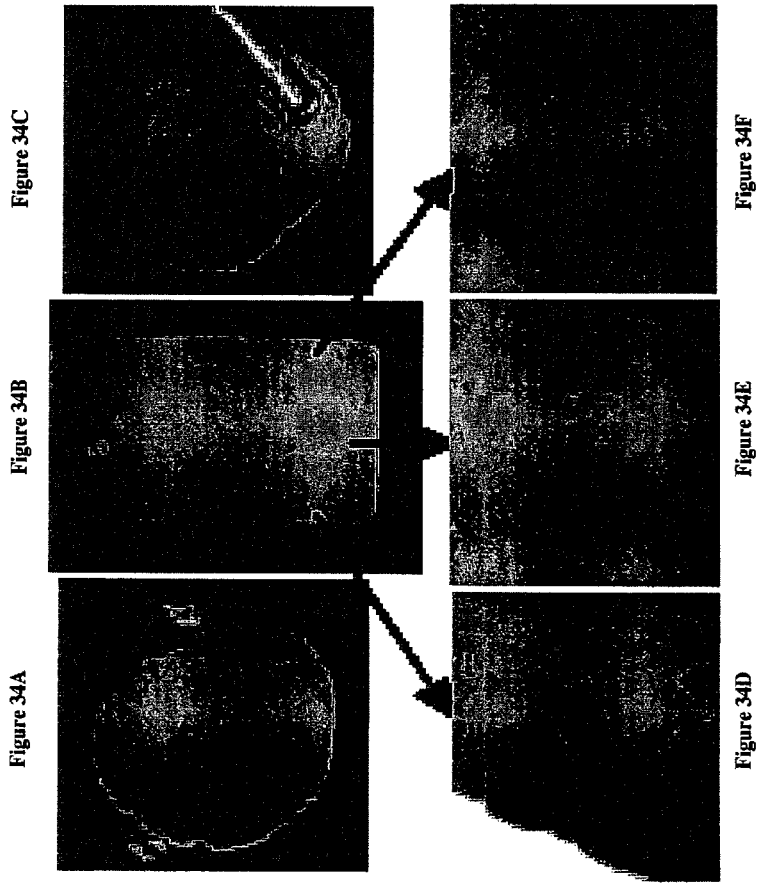
FIGS. 34A-34F show images of multiphase scaffold (FIGS. 34A-34C) and blow-ups of respective sections (FIGS. 34D-34F).

Scaffold of four continuous, graded layers with different sizes of microspheres was formulated (see FIGS. 34A-347F). Layered inhomogeneity was pre-designed into the scaffold. Due to differences in packing efficiency between different sizes of microspheres, the porosity of the scaffold decreases from layers of large microsphere to those consisting of small microspheres. PLAGA-BG composite microspheres were produced via the emulsion method. Three layers of PLAGA-BG microspheres of different diameters (250-300, 300-355, 355-500 μg, from top to bottom) were used, shown in FIGS. 34A-34F. Microsphere layers were sintered at 70° C. for 20 hours.

Figure 35:
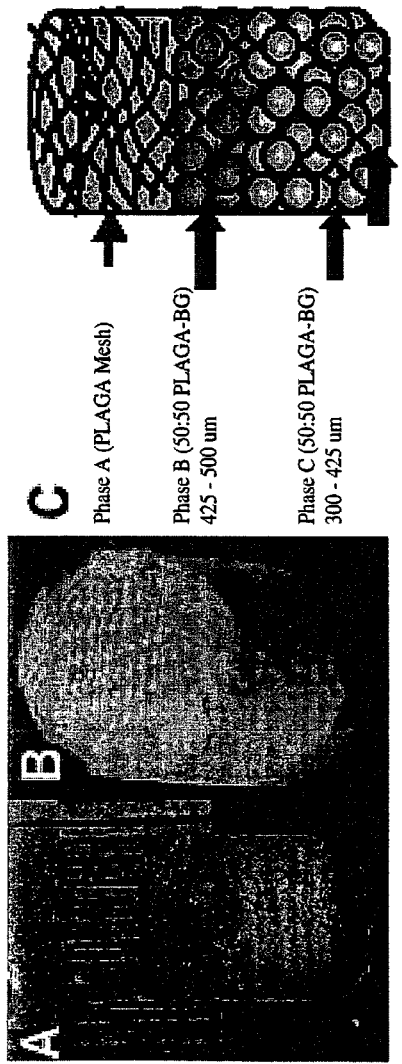
FIGS. 35A-35C show multiphasic scaffolds for co-culture of ligament fibroblasts and osteoblasts.

Image analysis confirmed that pore size increased from bottom to top of scaffold. For the growth of ACL fibroblasts on the scaffold, another type of multi-phased scaffold was fabricated using a PLAGA mesh (Ethicon, N.J.) and two layers of PLAGA-BG microspheres. The layers were sintered in three stages in a Teflon mold. First the mesh was cut into small pieces and sintered in the mold for more than 20 hours at 55° C. A layer of PLAGA-BG microspheres with diameter of 425-500 μm was then added to the mold. This layer was sintered for more than 20 hours at 75° C. The final layer consisted of PLAGA-BG microspheres with diameter greater than 300 μm. The scaffolds and three distinct regions were readily observed (see FIGS. 35A-35C).

Kinetics of Ca—P layer formation on BG surfaces was related to changes in surface zeta potential in a simulated body fluid (SBF). The chemical and structural changes in BG surface Ca—P layer were characterized using Fourier transform infrared spectroscopy (FTIR), SEM and energy dispersive x-ray analysis (EDXA). FTIR provides information on the degree of crystallinity (amorphous vs. crystalline) of the Ca—P layer formed (see FIG. 24A-24B) as well as the functional groups present on BG surface (carbonated Ca—P layer versus non-carbonated, protein adsorption, etc.). FTIR is much more surface sensitive than X-ray diffraction in detecting the Ca—P crystalline structures when the surface layer is only several microns in thickness. SEM combined with EDXA is a powerful tool in relating elemental composition to specific surface morphology and distributions (see FIGS. 25B and 25C). EDXA provides a direct calculation of Ca/P ratio (Ca/P=1.67 for bone mineral and crystalline Ca—P layer) when appropriate standards are used. FTIR, SEM, and EDXA are complimentary techniques which together provide quantitative data on the crystallinity, composition of and functional groups pertaining to the Ca—P layer.

Figure 36:
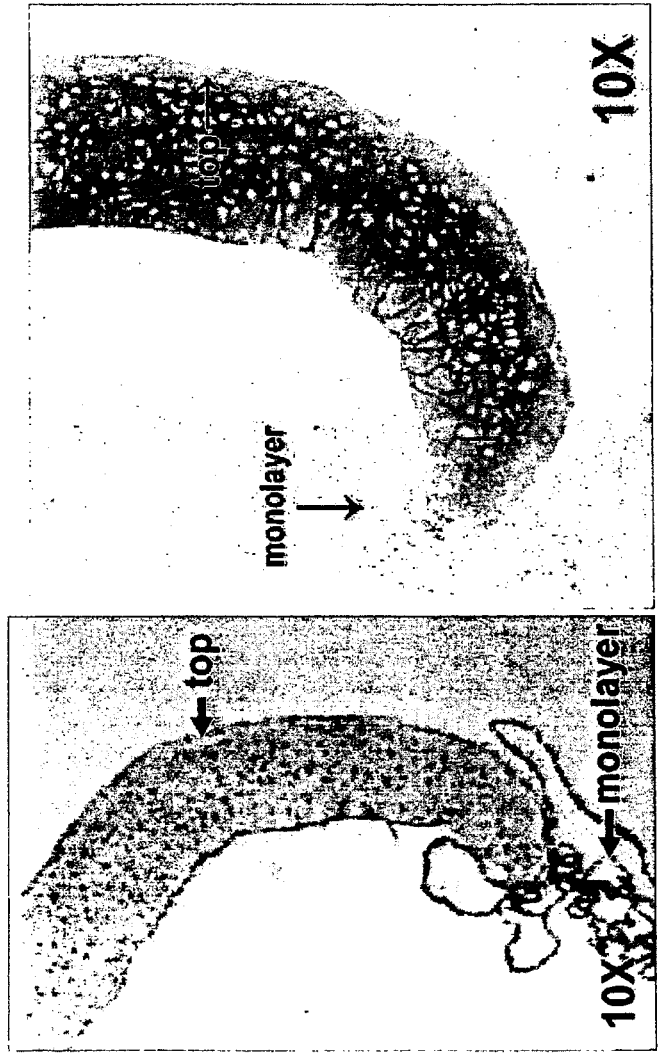
FIGS. 36A-36D show Micromass co-culture samples of osteoblasts and chondrocytes after 14 days.
Figures 36C, 36D:
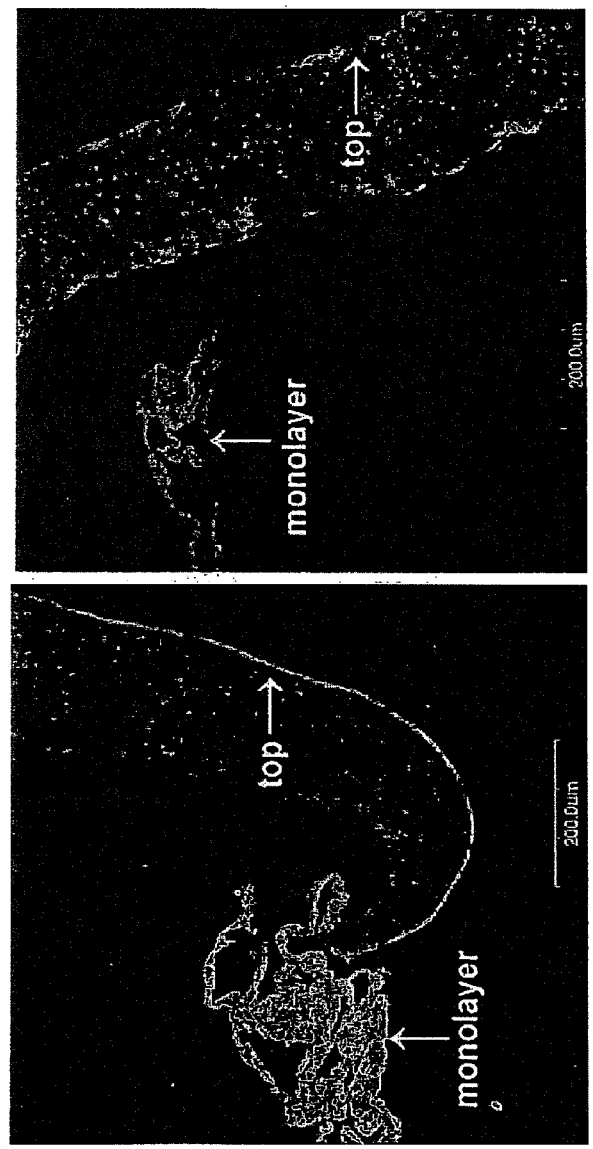

We evaluated the effects of co-culturing on the growth and phenotypic expression of osteoblasts and chondrocytes. Osteoblasts were seeded directly on high density chondrocyte micromasses. Specific effects of co-culture on the expression of chondrogenic markers were observed primarily at the top surface interaction zone instead of within the micromass. Alcian blue staining (see FIG. 36B) revealed characteristic peri-cellular sulfated glycosaminoglycans (GAG) deposition by chondrocytes. GAG deposition was found largely within the micromass, instead of at the co-culture zone where elongated osteoblasts and chondrocytes were located. Sulfated GAG was not detected in the predominantly osteoblast monolayer surrounding the micromass. Surface chondrocytes may have de-differentiated due to co-culturing with osteoblasts. The expression of type I collagen was observed to be distributed mainly on the top surface of the co-cultured mass (FIG. 36C), where osteoblasts were located. Type I was also found at the primarily osteoblastic monolayer surrounding the micromass (see FIG. 36C, left). No type I collagen expression was observed in the chondrocyte-dominated center and bottom surface of the micromass. High expression of type Ii collagen was observed within the micromass (see FIG. 36D).

As types I and Il collagen were detected at the surface, it is possible that due to co-culture, chondrocytes and osteoblasts were forming an osteochondral-like interface at the surface interaction zone. Alizarin Red (ALZ) staining revealed that there was limited mineralization in the co-cultured group, while the osteoblast control stained increasingly positive for calcium. It is likely that co-culture with chondrocytes may have delayed osteoblast mineralization. Preliminary PCR results (see FIGS. 37A and 37B) showed that the 7 day co-culture group expressed types II and X collagen, as detected by RT-PCR.

Summary of Results

Effects of media additives on the growth and mineralization of osteoblasts and human ACL fibroblasts (hACL) were examined. During mineralization, ALP reacted with β-glycerophosphate (βGP) and the phosphate product was utilized for mineralization. Concentrations (0, 1.0, 3.0, 5.0 mM) effects were examined over time. No significant change in cell number was observed for the concentration levels of βGP investigated. At 1.0 mM, a significant difference between 1-day and 7-day samples (p<0.05) was observed. No differences were found between 1.0 mM and 3.0 mM cultures. ALZ stains for the osteoblast cultures were more intense for 3.0 mM than for 1.0 mM. Ectopic mineralization was observed for hACL cultures at 3.0 mM suggesting a potential change in cell phenotype.

Figures 38, 38A, 38B:
FIGS. 38A-38B show SEM images of cellular attachment to PLAGA-BG scaffold after 30 min.
Figures 38C, 38D, 38E:
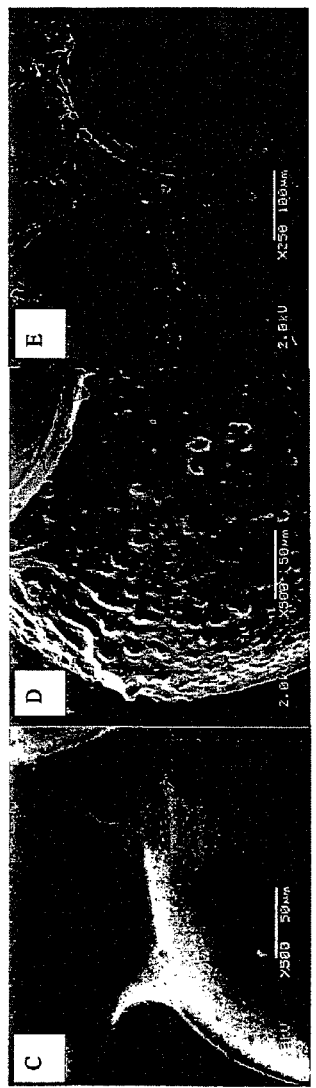
FIGS. 38C-38E show cellular attachment to PLAGA-BG scaffolds.

Interaction of osteoblasts and chondrocytes on a 3-D composite scaffold during co-culture was examined. Scaffolds seeded with only osteoblasts or chondrocytes at the same densities served as controls. Both short-term and long-term co-culture experiments were conducted. Extensive SEM analysis revealed that significant interactions occurred between osteoblasts and chondrocytes during co-culture. Differences in cellular attachment were observed between the chondrocyte control scaffolds and the co-cultured scaffolds. On the co-cultured scaffolds, focal adhesions were evident between the spherical chondrocytes and the surface, indicated by the arrow in FIG. 38B.

No comparable focal adhesions were observed on the chondrocyte controls at the same time point. Chondrocyte morphology changed over time as it assumed a spherical morphology in the first 8 hours, and then spread on the surface of the microspheres (see FIG. 33C). The nodules on the surface of the microspheres correspond to the flattened chondrocytes. These nodules were likely chondrocytes instead of calcium phosphate nodules, since calcium phosphate nodules were approximately 1-5 μm in diameter at the culture duration observed and these nodules were about 10 μm, approximately the diameter of an ovoid cell. After 7 days of culture, the co-culture group exhibited extensive matrix production (see FIG. 33E) and expansion on the scaffold.

Examination of the ACL-bone interface confirmed existence of a mineral gradient across the insertion zone and correlation to changes in material properties. Multi-phased scaffolds with controlled morphology and porosity were fabricated. The osteochondral graft developed from co-culture on PLAGA-BG and hydrogel scaffold supported growth of multiple matrix zones with varied GAG and mineral content. BMSCs differentiated into ligament fibroblast and produced a functional extracellular matrix when cultured with growth factors on a fiber-based scaffold. Mineral content, distribution, and chemistry at the interface and on the scaffold were quantifiable using a complimentary set of surface analysis techniques (FTIR, SEM, EDAX, μCT). Electron microscopy examination of the ACL-bone interface revealed insertion zone including three different regions: ligament, fibrocartilage-like zone, and bone. Co-culture of osteoblasts and ligament fibroblasts on 2-D and 3-D scaffolds resulted in changes in cell morphology and phenotype. Type X collagen, an interfacial zone marker, was expressed during co-culture. Multi-phased scaffold with layered morphology and inhomogenous properties were designed and fabricated. FTIR, SEM and EDXA are complimentary techniques which collectively provided qualitative and quantitative information on the Ca—P layer and composition of the calcium phosphate surface.

Figure 39:
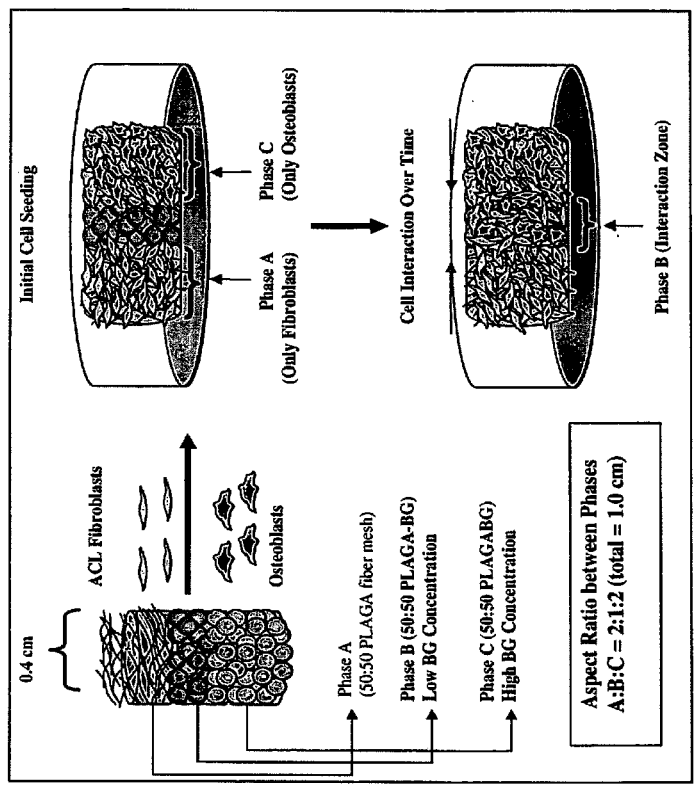
FIG. 39 shows a multi-phased scaffold (for in vitro co-culture of osteoblast and ligament fibroblast cells).

Example 3: Biomimetic, Inhomogenous Triphasic Scaffold and Osteoblast-Fibroblast Co-Culture on the Scaffold A multi-phased scaffold system with inhomogenous properties (FIG. 39) was designed and evaluated for its ability to support the growth and differentiation of multiple cell types. Effects of osteoblast-ligament fibroblast co-culture on a development of interfacial zone specific markers (proteoglycan, types II and X collagen) on the scaffold were examined.

The contiguous scaffold included three sequential phases (A-C), with Phase A (polymer fiber mesh with no Ca—P) intended for ligament culture, and Phase C (polymer-ceramic composite with high Ca—P) for bone formation. Phase 9 (polymer-ceramic composite, lower Ca—P than Phase C), the intermediate region, was where an interfacial zone developed due to the interaction of these two cell types. The scaffolds were fabricated from PLAGA 50:50, and the same polymer was used throughout. The three phases were sintered together past a polymer glass transition temperature to form a multi-phased scaffold. The aspect ratio between the phases of the sintered cylindrical scaffold was as follows: A:B:C=2:1:2, and the as-made, complete construct was 1.0 cm in length and 0.40 cm in diameter (see FIG. 39).

The mineral gradient was created by incorporating different concentrations of bioactive glass (BG) particles during the microsphere synthesis process. BG weight percentage was correlated to the Ca—P content of the interface by comparative EDXA analysis of the Ca—P surface developed through immersion in a simulated body fluid following a well-characterized method to create Ca—P layer on bioactive glass surfaces as described by Lu et al. (2000) and incorporated by reference herein.

When a specific BG weight percentage was correlated with the Ca—P distribution and Ca/P ratio of either the bone or the cartilage region as described above, scaffolds were fabricated based on this weight percentage.

The three phases of the scaffold were inhomogeneous in properties, with zonal differences in mineral content and matrix morphology (see Table 8).

TABLE 8

| | Phase A (Ligament) | Phase B (Interface) | Phase C (Bone) |
| --- | --- | --- | --- |
| Composition | PLGA 50:50 (no BG) | PLGA 50:50/ BG (lower) | PLAGA 50:50/ BG (Higher) |
| Porosity/Pore Diameter | 40% 100 μm | 40% 100 μm | 40% 100 μm |
| Matrix Morphology | Fiber Mesh | Microsphere Based | Microsphere Based |

The differences mimic the ACL-bone interface and facilitate the growth of different tissues. Phase C has a high mineral content compared to Phase A. While the three phases share the same polymer composition, they differ in weight percentage of BG. A positive correlation exists between scaffold stiffness and mineral content of the phase.

The three phases also differ in morphology, with Phase A composed of a porous fibrous mesh, and Phases B and C made of microsphere-based porous scaffold. Post-fabrication characterization of the scaffold included porosity, average pore size, total surface area, as well as mechanical properties under compression. Scaffold porosity was held constant at 40% with a pore diameter of 100 µm, with focus on the effect of mineral content on cellular response as a more relevant parameter in controlling fibroblast phenotype or dedifferentiation into chondrocytes. Growth and differentiation of osteoblasts and ligament fibroblasts co-cultured on the scaffold were examined. Osteoblasts were seeded on Phase C while ligament fibroblasts were seeded on Phase A.

The growth and differentiation of cells on the scaffold was monitored as a function of culturing time (1, 3, 7, 14, 21 days). Cell proliferation, ligament phenotypic expression (fibronectin, type I, III, Il collagen synthesis, laminin, fibronectin) and osteoblast phenotype (alkaline phosphatase, type I collagen, osteocalcin, mineralization) were examined. Expression of interface-specific markers such as proteoglycans, types Il and X collagen were determined to assess changes in fibroblast phenotype.

The three phases of the scaffold differed in composition and morphology, while the same porosity and pore diameter were maintained. Focus was placed on the mineral content of the scaffold for two reasons: 1) it is a more relevant parameter for consideration of the varied mineral distribution within the ACL-bone interface; and 2) mineral content was utilized to direct fibroblast phenotype change or dedifferentiation into chondrocytes.

A component of the polymer ceramic composite scaffold was polylactide (PLA) which degrades via hydrolysis into lactic acid, which may contribute to changes in ligament fibroblast phenotype. Increased mineralization by ligament fibroblasts was observed with increasing concentration of β-glycerophosphate, a media additive commonly used in osteoblast cultures.

The effects of co-culture were evaluated in conjunction with scaffold mineral content. Multiple cell types were considered because the insertion site was made up of four zones, each dominated by a specific cell type. Cell to cell interactions played a significant role in dictating the formation of the interface between ligament and bone. Examination of osteoblast and ligament fibroblast co-cultures established that both cell types proliferated and expanded beyond the initial seeding areas, and that a contiguous and confluent culture was observed at the interface after two weeks. Preliminary studies revealed that co-culture and/or interactions with chondrocytes may have delayed osteoblast-mediated mineralization. Type X collagen was found in the osteoblast-chondrocyte co-cultured samples.

Example 4: Development of a Biodegradable, Porous, Polymer Bioactive Glass Composite Possessing Improved Mechanical Properties and Osteointegrative Potential An objective of the experiments (described below) was to develop a three-dimensional (3-D), porous composite of polylactide-co-glycolide (PLAGA) and 45S5 bioactive glass (MG) that is biodegradable, bioactive, and suitable as a scaffold for bone tissue engineering (PLAGA-BG composite). Additional objectives of the study were to examine the mechanical properties of a PLAGA-BG matrix, evaluate the response of human osteoblast-like cells to the PLAGA-BG composite, and evaluate the ability of the composite to form a surface calcium phosphate layer in vitro. Structural and mechanical properties of PLAGA-BG were measured, and the formation of a surface calcium phosphate layer was evaluated by surface analysis methods. The growth and differentiation of human osteoblast-like cells on PLAGA-BG were also examined. The addition of bioactive glass granules to the PLAGA matrix resulted in a structure with higher compressive modulus than PLAGA alone. Moreover, the PLAGA-BA composite was found to be a bioactive material, as it formed surface calcium phosphate deposits in a simulated body fluid (SBF), and in the presence of cells and serum proteins. The composite supported osteoblast-like morphology, stained positively for alkaline phosphatase, and supported higher levels of Type I collagen synthesis than tissue culture polystyrene controls. A biodegradable, porous, polymer bioactive glass composite possessing improved mechanical properties and osteointegrative potential compared to biodegradable polymers of poly(lactic acid-glycolic acid) alone was successfully developed.

PLAGA-BG Composite Disc and Microsphere Fabrication and Characterization

Figure 40:
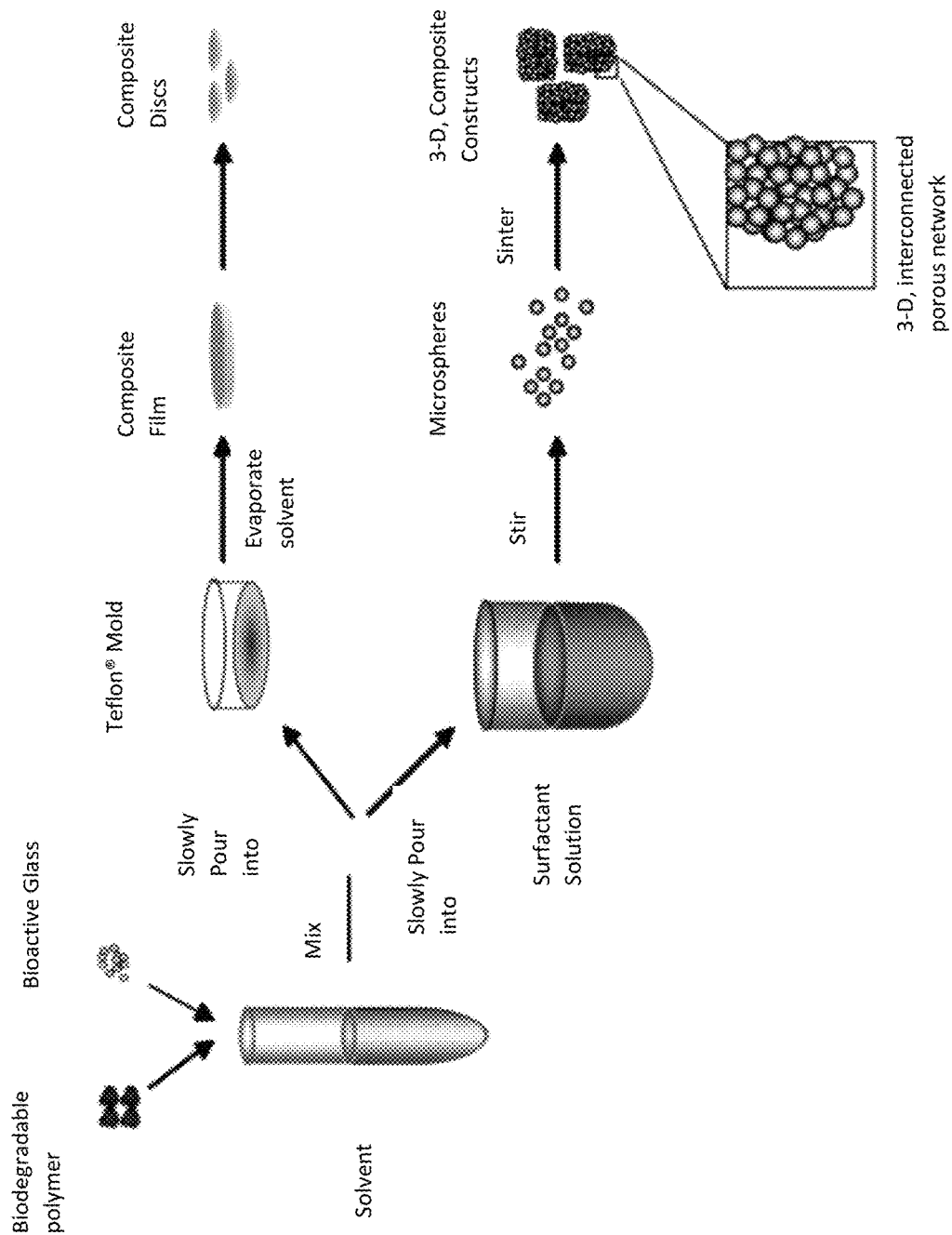
FIG. 40 shows a schematic diagram depicting a fabrication process of a composite (PLAGA-BG) of PLACA and BG, in thin film form and as a 3-D, porous scaffold.

Polylactide-co-glycolide 50:50 co-polymer (PLAGA, Mw approximately equal to 50,000, American Cyanamide, Sunnyvale, Calif.) and 45S5 bioactive glass (BG, MO-SCI Corporation, Rolla, Mo.) granules were used to fabricate the composite (PLAGA-BG) discs and microspheres. FIG. 40 is a schematic of the synthesis process of some forms of PLAGA-BG composite used in this study. Specifically, PLAGA-BG discs were formed through the traditional solvent-casting process, where PLAGA and BG granules were first mixed according to a polymer to ceramic weight ratio of 1:3 and dissolved in methylene chloride. The solution was then slowly poured into a Teflon mold and allowed to cool overnight in a −20° C. freezer. The resultant polymer-ceramic film was bored into 1-cm wide and 0.1-mm thick discs. The discs were then dried overnight to remove any residual solvent (Lyph-lock 12, PLAGA-BG composite microspheres were formed through a water-oil-water emulsion. Specifically, PLAGA granules were first dissolved in methylene chloride, and BG particles (<40 µm) were added to achieve a 25% mixture. The mixture was then poured into a 1% polyvinyl alcohol (Polysciences, Warrington, Pa.) solution. The suspension was stirred constantly, and the spheres were allowed to harden in the polyvinyl alcohol solution. The resultant microspheres were then washed, vacuum filtered, and dried at room temperature. Next, the composite microspheres were sifted using a mechanical sifter to a final size range of 100-200 µm. The cylindrical construct, averaging 0.5 cm in width and 1.0 cm in height, was fabricated by heating the microspheres at 70° C. for 20 hours in a stainless-steel mold.

Before in vitro evaluations, the morphology, porosity and mechanical properties of the PLAGA-BG construct were determined. Pore interconnectivity, morphology, and the bonding of microspheres within the construct was examined by scanning electron microscopy (SEM, Amray 1830-D4), at an acceleration voltage of 20 keV. Elemental composition of the composite surface was determined by energy-dispersive X-ray analysis (EDXA). Mercury porosimetry (Micromeritics Autopore III, Micromeritics, Norcross, Ga.) was used to measure the porosity, average pore diameter, and total surface area of the composite construct. In this method, the construct porosity was determined by measuring the volume of mercury infused into the structure during analysis. In addition, the construct (n=6) was tested under compression using the Instron Servohydrolic System 8500 (Instron, Canton, Mass.), with a ramp speed of 0.02 cm/s. The compressive strength and elastic modulus of the construct were determined. PLAGA scaffolds without BG served as controls.

The composite discs were immersed for 1, 7, and 14 days in a simulated body fluid (SBF) whose ion concentration is similar to that of extracellular fluid. PLAGA discs without BG served as controls. A surface area to volume ratio of 1.0 cm' was maintained for all immersions. The pH of the solution as a function of immersion time was measured. Perfect sink conditions were maintained during the immersion study. SEM (Amray 1830-D4) and EDXA were used to monitor the formation of a Ca—P layer on composite films.

Seeding Human Osteosarcoma Cells on the PLAGA-BG Composite Scaffold

Human osteosarcoma cells (SaOS-2) were cultured in Medium 199 (M199, Sigma Chemicals, St. Louis, Mo.), supplemented with 10% fetal bovine serum (Life Technologies, Rockville, Md.), L-glutamine, and antibiotics. The cells were grown to confluence at 37° C. and 5% $CO_2$. Under these conditions, the osteoblastic phenotype of SaOS-2 was maintained for up to at least four weeks of culture, with positive expression of alkaline phosphatase, type I collagen, osteocalcin, and formation of mineralized cultures.

SaOS-2 cells were seeded on the porous, PLAGA-BG scaffolds (n=3) at the density of $5\times10^4$ cells/$cm^2$, and were cultured in 12-well plates (Fisher Scientific, Fair Lawns, N.J.) for up to 3 weeks. PLAGA alone and tissue culture polystyrene (TCPS) served as control groups. Once the cells have grown to confluence, at two weeks from the start of culture, mineralization medium containing 3.0 mM of β-glycerophosphate and 10 µg/ml of L-ascorbic acid Cell adhesion and growth morphology on the 3-D construct were monitored using SEM (20 keV). Alkaline phosphatase staining was performed at each culturing time point, using a standard histochemical assay. The samples were indubated for 30 min with Napthol AS-Bi (Sigma), phosphate salt, N,N-dimethyl formamide (Sigma), and Fast Red (Sigma) at 37° C. The samples were then fixed in 2% paraformaldehyde for 30 min at 4° C. The synthesis of type I collagen by SaOS-2 cells was quantified using a modified ELISA.

The formation of mineralized nodules was examined by SEM-EDXA. Mineralization was further ascertained using Alizarin Red S staining for calcium. Briefly, the samples were washed with deionized $H_2O$, fixed with 2% paraformaldehyde and incubated in 2% Alizarin Red S solution for 5 min. The samples were then washed with deionized water and viewed under the microscope.

Summary of Results:

Data in the graphs are presented in the form of mean±standard deviation (mean±SD), with n equal to the number of samples analyzed per immersion treatment. One-way analyses of variance (ANOVA) and the Student's t-test were used to compare the mechanical testing data (n=6), porosimetry results (n=3), as well as the collagen synthesis data (n=3). Statistical significance was evaluated at the p<0.05.

SEM examination of the PLAGA-BG discs revealed a homogenous distribution of the MG particles within the PLAGA phase. In addition, the composites in disc form as well as microsphere form were visually more opaque than PLAGA alone, largely because of the addition of BG.

Sintering of the microspheres resulted in a well-integrated structure, with the microspheres joined at the contact necks. SEM analysis revealed that a 3-D, interconnected porous network was found throughout the composite construct. Elemental analysis using EDXA showed that the composite surface was largely made up of C, Na, Si, Ca, and P before any immersions.

The result from structural characterizations of the as-fabricated composite scaffold are summarized in the following Table 9.

TABLE 9

| Scaffold Type | Average Porosity | Pore Diameter (µm) | Elastic Modulus (Mpa) | Compressive Strength (Mpa) |
|---|---|---|---|---|
| PLAGA | 31% | 116 | 26.48 ± 3.47 | 0.53 ± 0.07 |
| PLAGA-BG | 43% | 89 | 51.34 ± 6.08 | 0.42 ± 0.05 |

BG particle-reinforcement of the PLAGA structure resulted in a near two-fold increase in compressive modulus. The structural and mechanical properties of the scaffold can be systematically optimized by varying microsphere and scaffold fabrication parameters. Porosimetry analysis revealed that the 3-D composite measured an average porosity of 43%, with a mean pore diameter of 89 µm. The PLAGA control scaffold exhibited 31% total porosity and a mean pore diameter of 116 µm. The PLAGA-BG composite possessed a higher elastic modulus (51.336±6.080 MPa versus 26.479±3.468 MPa) than the control PLAGA scaffold. Although the means were different, the compressive strength of the composite at 0.417±0.054 MPa was not statistically different from that of the PLAGA control (0.533±0.068 MPa), at p<0.05.

The bioactivity of the composite was determined by monitoring the formation of a calcium phosphate layer on the composite discs in a simulated body fluid (SBF). The composite was found to be bioactive because it formed a calcium phosphate layer on its surface after immersion in SBF for 7 days. SEM-EDXA results showed that an amorphous calcium-phosphate layer was found on the composite surface after 7 days of immersion, whereas no such layer was detected on the control polymer without bioactive glass particles for the same duration. In particular, polymer-ceramic composite (PLAGA-BG) which were immersed in simulated SBF for 14 days formed a surface calcium phosphate layer (Ca, P presence confirmed by X-ray analysis as summarized in FIG. 41). No such layer was found on the PLAGA control without 45S5 bioactive glass. The composite (PLAGA-BG) surface was covered with calcium phosphate nodules after 14 days of immersion. In contrast, the PLAGA control surface, after immersion for 14 days in SBF, did not form a calcium phosphate layer, but began to exhibit surface pores formed due to the degradation of the polymer.

Figure 41:
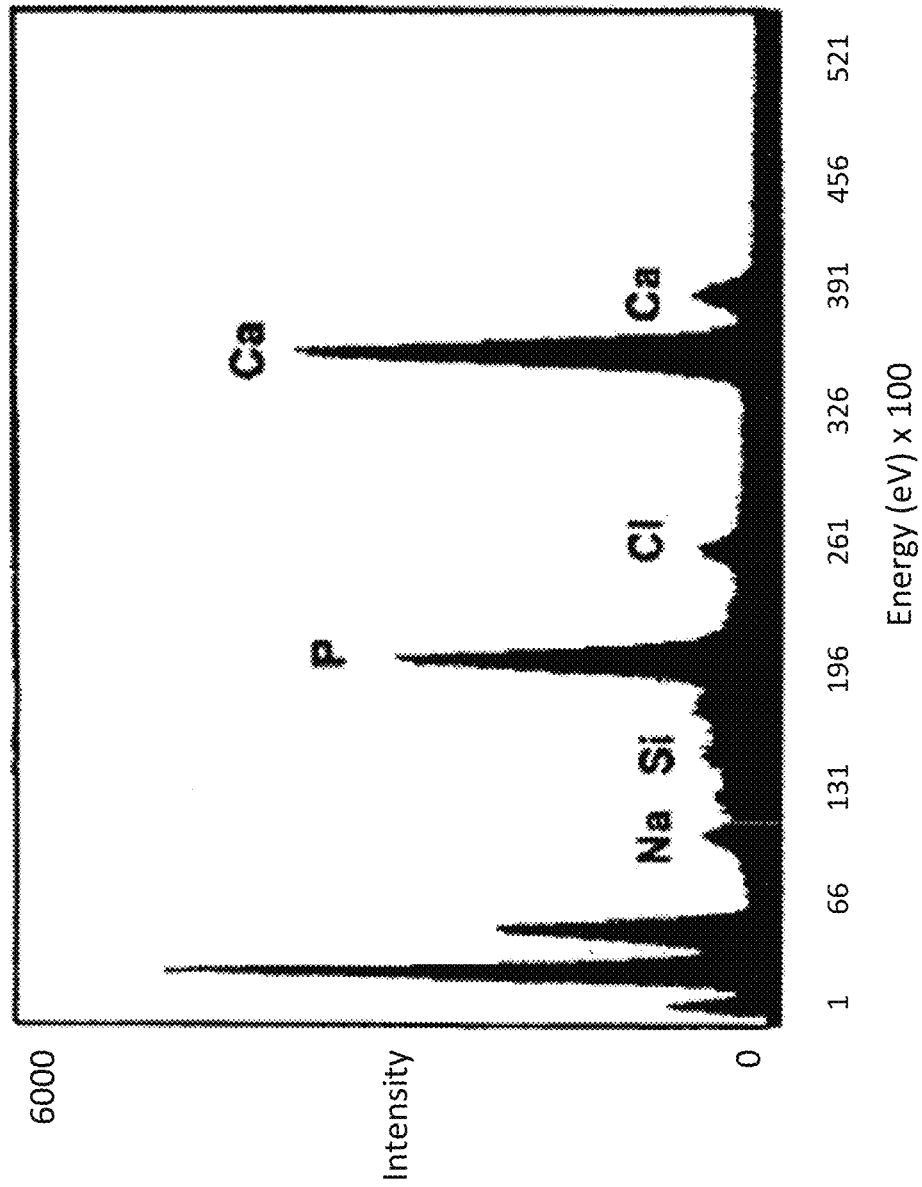
FIG. 41 shows EDXA spectra of the PLAGA-BG composite immersed in SBF for 14 days.

FIG. 41 shows EDXA spectra of the PLAGA-BG composite immersed in a SBF for 14 days. The composite surface still contained C. Si, Ca, and P, whereas the Cl peak was detected after immersion in SBF. A surface calcium phosphate layer has formed on the PLAGA-BG composite surface. The Ca and P peaks were not found in the spectra of PLAGA controls.

The microsphere-based, porous, PLAGA-BG composite supported the growth and phenotypic expression of human osteoblast-like cells. Media pH variation was measured for the full duration (3 weeks) of cell culture with PLAGA-BG and PLAGA, and physiological pH (7.3-7.7) was maintained in all cultures for up to 3 weeks. There was no significant change in solution pH after 2 weeks of culture with osteoblast-like cells, and culture media was exchanged every other day to remove metabolic products and supply fresh nutrients to the cells. Extensive cellular growth was detected on the scaffold surface as well as within the PLAGA-BG composite. In addition, the porous network of the scaffold was maintained even after 3 weeks of culture. In many areas, cellular growth had bridged two or more microspheres while maintaining the porous structure. SEM analysis revealed the synthesis of collagen-like fibers by the SaOS-2 cells. All cultures stained positively for the synthesis of alkaline phosphatase, although a much higher intensity of stain was observed in cultures with the PLAGA-BG scaffold than for PLAGA cultures.

Figure 32:
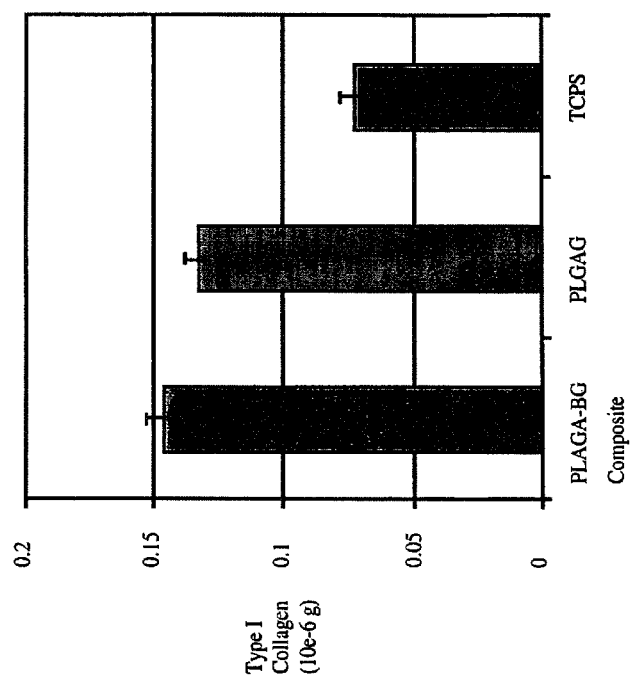
FIG. 32 shows a comparison of the expression of type I collagen by human osteoblast-like cells cultured on the PLAGA-BG composite versus on tissue culture polystyrene (TOPS) controls and on PLAGA alone. Shows higher type I collagen type synthesis on PLAGA-BG.

As shown in FIG. 32, the synthesis of type I collagen by SaOS-2 cells increased with culturing time, with the highest amount found on PLAGA-BG composite (0.146±0.006 µg), as compared to PLAGA (0.132±0.006 µg), and TCPS controls (0.073±0.005 µg). The expression of type I collagen by SaOS-2 cells cultured on the composite was significantly higher than cells grown on TCPS controls, (p<0.05). There was a trend towards higher Type I collagen synthesis on the PLAGA-BG composite compared to PLAGA alone, but this was not found to be significant. (p=0.06) The formation of a mineralized matrix was confirmed by positive staining with Alizarin Red S and elemental analysis in which Ca and P were detected on PLAGA-BG scaffolds cultured with SaOS-2 cells. Alizarin stain intensity increased with culturing time. The mineralized nodules were not observed on PLAGA or TCPS controls after 2 weeks of culture, before the addition of the mineralization medium. After 1 week of culturing with the mineralization medium, mineralization as reflected in staining intensity, was much less on the control substrates than on PLAGA-BG.

SEM and EDXA analyses confirmed the formation of calcium phosphate nodules on the composite surface after only 3 days of culture, before the addition of the mineralization medium. These calcium phosphate nodules are similar in size and shape as observed on PLAGA-BG discs in the SBF. In time, the Ca—P nodules increased in size and formed larger aggregates, indicating that the PLAGABG composite was bioactive in vitro. The relative Ca to P peak ratio of the deposits decreased as a function of culturing time. These results collectively suggest that the composite was bioactive, and was capable of forming a surface calcium phosphate layer.

Example 5: ACL-Bone Interface Regeneration Through Biomimetic Scaffold Design and Co-Culture of Osteoblasts and Fibroblasts The degree of graft integration is a significant factor governing clinical success and it is believed that interface regeneration significantly improves the long term outcome. The approach of this set of experiments was to regenerate the ACL-bone interface through biomimetic scaffold design and the co-culture of osteoblasts and fibroblasts. The interface exhibits varying cellular, chemical, and mechanical properties across the tissue zones, which can be explored as scaffold design parameters. This study describes the design and testing of a multi-phased, continuous scaffold with controlled heterogeneity for the formation of multiple tissues. The continuous scaffold consists of three phases: Phase A for soft tissue, Phase C for bone, and Phase B for interface development. Each phase was designed with optimal composition and geometry suitable for the tissue type to be regenerated. Fibroblasts were seeded on Phase A and osteoblasts were seeded on Phase C, and the interactions of osteoblasts and fibroblasts (ACL and hamstring tendon) during co-cultures on the scaffolds were examined in vitro.

Phases A, B and C consist of poly(lactide-co-glycolide) (PLAGA, 10:90) woven mesh, PLAGA (85:15) microspheres, and PLAGA(85:15)/Bioactive Glass (45S5.BG) composite microspheres, respectively. The microspheres were formed via a double emulsion method, and the continuous multi-phased scaffolds were formed by sintering above the polymer glass transition temperature. Scaffold porosity and pore diameter were determined by porosimetry (Micromeritics, n=3) and the samples were tested under uniaxial compression (MTS 810, n=5) at 1.3 mm/min up to 5% strain with 10 N preload.

Bovine and human osteoblasts (bOB and hOB), and bovine ACL fibroblasts (bFB) and human hamstring tendon fibroblasts (hFB) were obtained through explant culture. In experiment I, bOB and bFB ($5 \times 10^5$ cells each/scaffold) were co-cultured on the scaffold, and cell viability, attachment, migration and growth were evaluated by electron and fluorescence microscopy. The bOB were pre-labeled with CM-DiI, and both cell types were labeled with calcein AM (Molecular Probes) prior to imaging. Matrix production and mineralization were determined by histology. After ascertaining cell viability on the scaffolds, a more extensive experiment using hOB and hFB was conducted in which cell proliferation and differentiation and above analyses were investigated. The mechanical properties of the seeded scaffolds were also measured as a function of culture time.

Compression testing of scaffolds indicated an average modulus of 120±20 MPa and yield strength of 2.3 MPa. The intrusion volume, porosity and pore diameter data are summarized in Table 10 below.

TABLE 10

|  | Intrusion Volume (µL) | Porosity (%) | Mode Pore Diameter (µm) |
| --- | --- | --- | --- |
| Phase A | 41 ± 8 | 58 ± 5 | 73 ± 11 |
| Phase B | 28 ± 7 | 34 ± 4 | 75 ± 7 |
| Phase C | 12.5 | 25.7 | 83 |

The fibroblasts and osteoblasts were localized primarily at the two ends of the scaffolds after initial seeding, with few cells found in Phase B. After 28 days, both cell types migrated into Phase B (FIG. 42B), and extensive cell growth was observed in Phases A and C (FIGS. 42A and 42C).

Extensive collagen-rich matrix production was found throughout the three phases at day 28 (FIGS. 42D-E).

The biomimetic, multi-phased scaffolds supported the growth and ECM production of both osteoblasts and fibroblasts. After 28 days of culture, collagen production was evident in all three phases and mineralized matrix was found in the bone and interface regions. Osteoblast and fibroblast interaction at the interface (Phase B) suggests that these cells may play a significant role in the development of a functional insertion site. These findings demonstrate that this novel scaffold is capable of simultaneously supporting the growth of multiple cell types and can be used as a model system to regenerate the soft tissue to bone interface. Additional studies can focus on scaffold optimization and the development of the interface on the novel scaffold.

Example 6: Two Triphasic Scaffolds for Interface Tissue Engineering

This set of experiments is directed to the development of a multi-phased scaffold with controlled heterogeneity for interface tissue engineering. This continuous scaffold is comprised of three phases with Phase A designed for ligament formation, Phase C for bone, and Phase B for interface development. The design objective was to formulate a scaffold that is able to support the growth and differentiation of both osteoblasts and ligament fibroblasts. Two design parameters were varied among the three phases: mineral (Ca/P) content and geometry. This study introduces a 3-D biomimetic substrate for interface development. The interaction of osteoblasts and ACL fibroblasts during co-culture on the multi-phased scaffold were examined. An objective of the study was to demonstrate that both cell types proliferate and elaborate a collagen like matrix on the 3-D scaffolds.

Two types of scaffolds were fabricated. The first type is comprised entirely of microspheres formed via a double emulsion method. Phase A consists of poly(lactide-co-glycolide) 50:50 (PLAGA), Phase C of PLAGA/Bioactive glass (PLAGA-BG) composite microspheres, and Phase B contains a mixture of PLAGA and PLAGA-BG. For the second type of scaffold which has a different geometry and degradation rate, Phase A consists of PLAGA (10:90) woven mesh, Phase C of PLAGA 85:15/BG microspheres, and Phase B contains PLAGA (85:15) microspheres. The continuous multi-phased scaffolds were formed by sintering above the glass transition temperature.

Bovine osteoblasts and ACL fibroblasts were obtained from explant cultures of tissue isolated from neonatal calves. The cells were cultured in Dulbecco's Modified Eagles Medium (DMEM, Mediatech), supplemented with 10% fetal bovine serum, L-glutamine, and 1% penicillin/streptomycin (Mediatech).

Scaffolds were sterilized by ethylene oxide and fibroblasts were seeded at a density of $5 \times 10^5$ cell/scaffold onto Phase A, while osteoblasts were seeded at $5 \times 10^5$ cell/scaffold on Phase C. Phase B was left unseeded and the migration of osteoblasts and fibroblasts into this interfacial region was examined. The osteoblasts were labeled with CM-DiI cell tracer (Molecular Probes), and their location was tracked with respect to fibroblasts and each phase of the scaffold. The scaffolds were cultured in supplemented DMEM for up to 28 days. Ascorbic acid (10 μg/mL) and 3 mM β-glycerophosphate were added to the cultures at day 7.

Cell migration, attachment and growth were examined using scanning electron microscopy (5 kV, JEOL 5600LV). Cell viability and migration were evaluated by fluorescence microscopy (Zeiss Axiovert 40) using calcein AM tracer (Molecular Probes). Matrix production and mineralization were determined via histology. The samples were fixed, embedded and sectioned, after which Trichrome, von Kossa and Picrosirius Red stains were performed.

Figures 43, 43A, 43B, 43C, 43D:
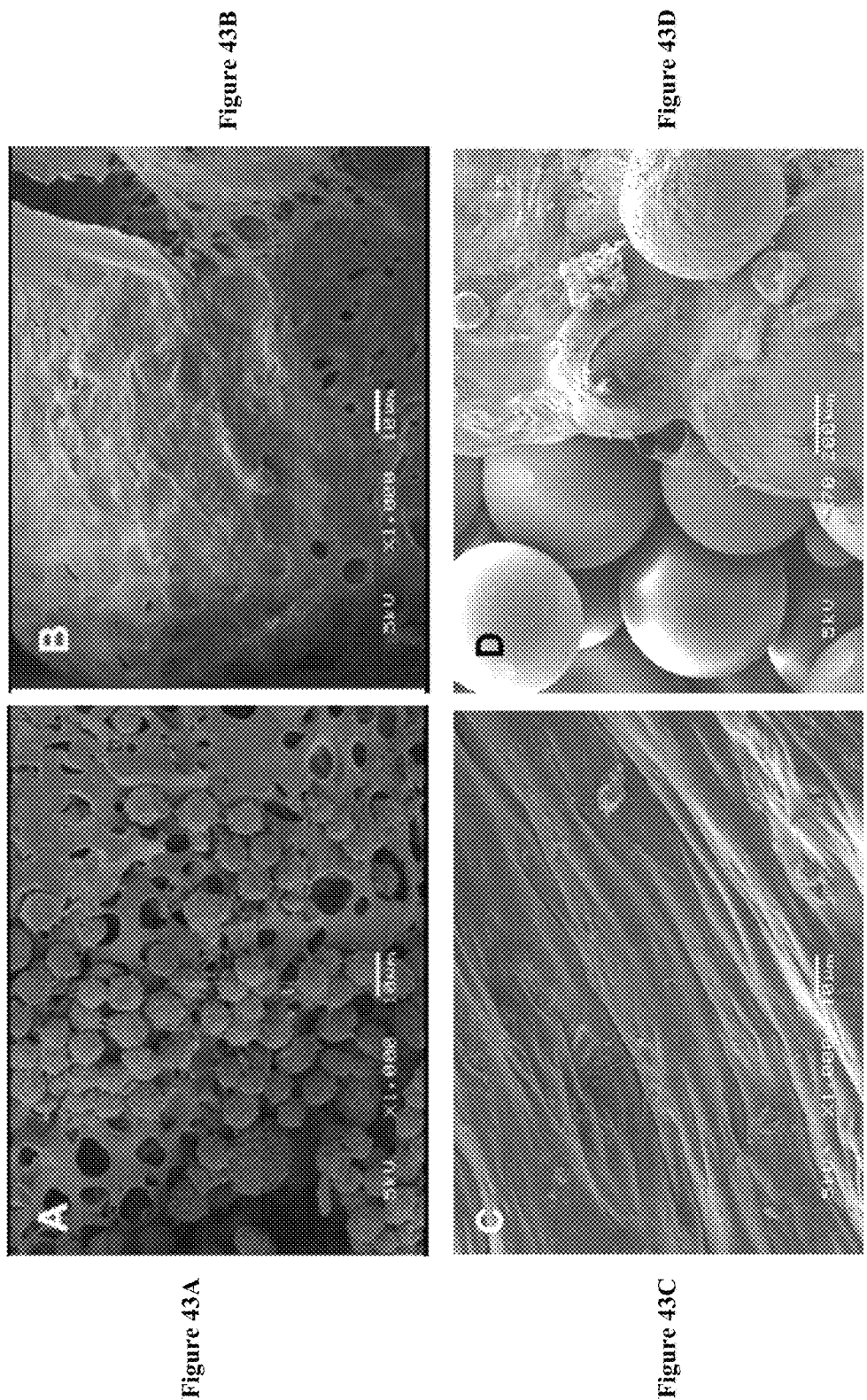
FIGS. 43A-43D show SEM images, another set of experiments.
Figure 44:
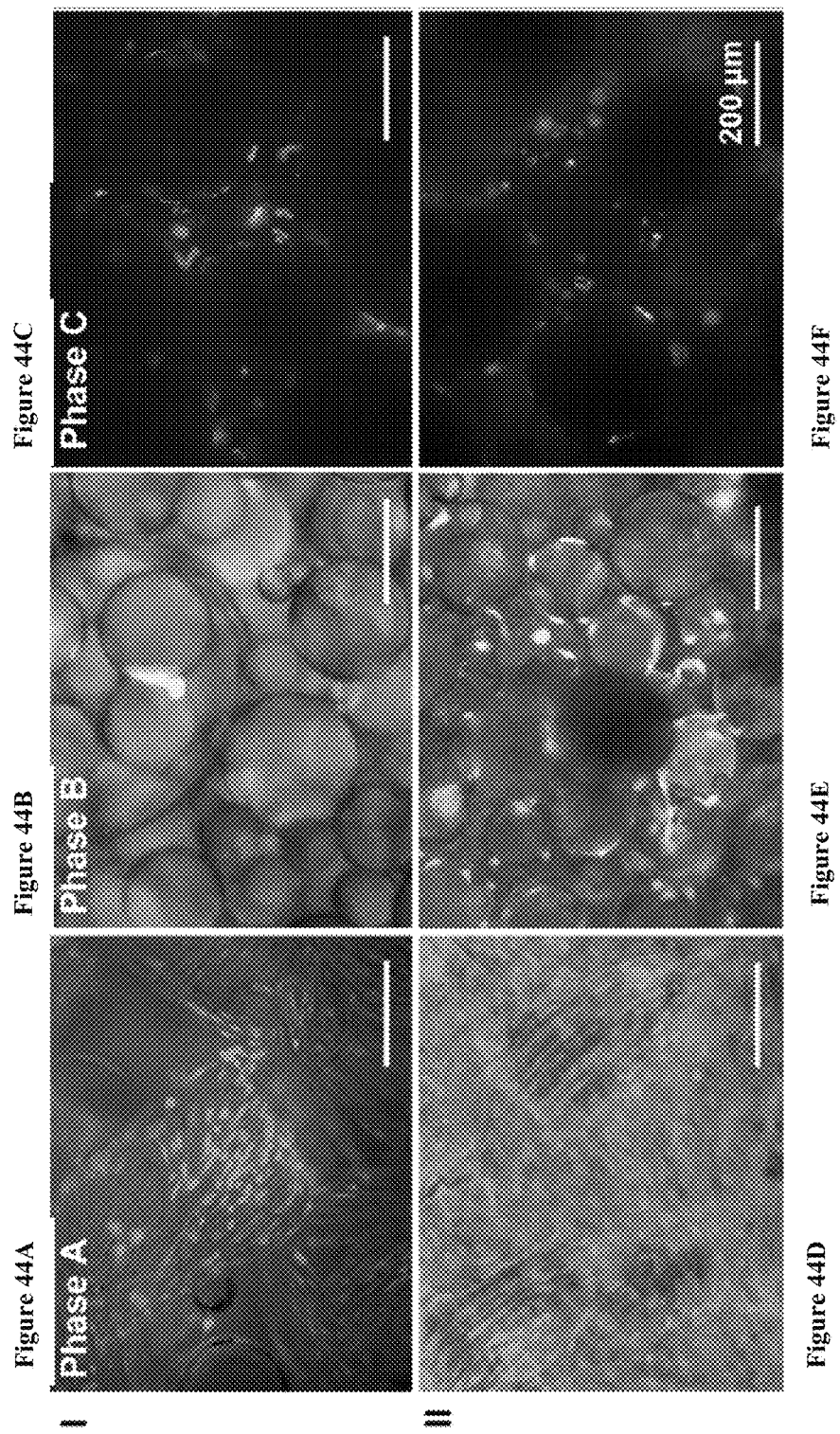
FIGS. 44A-44F show fluorescence microscopy images.
Figure 45:
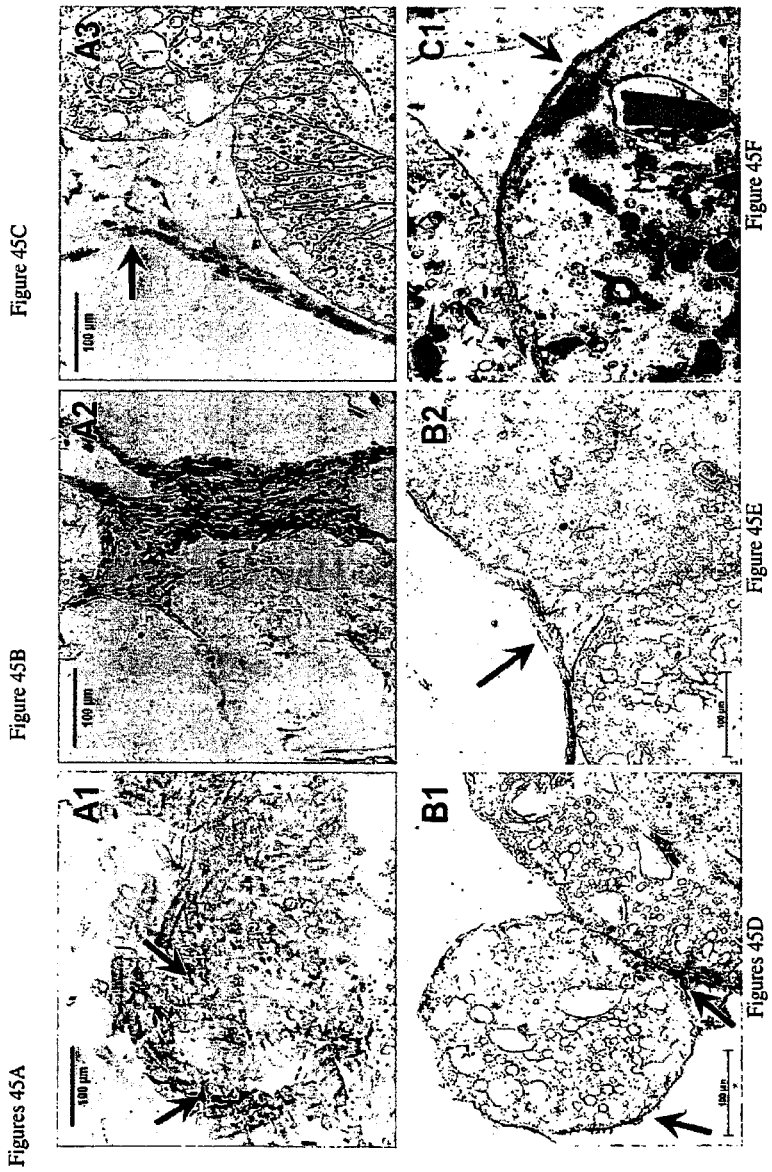
FIGS. 45A-45C show Trichrom images (Day 0, ×10) of Phase A, Phase B and Phase C, respectively.
FIGS. 45D-45E show Picrosirius Red images of Phase B and Phase C, respectively.
FIG. 45F shows a von Kossa image of Phase C.

At day 0, SEM analysis showed that a large number of cells attached to Phase A and C of the scaffolds (FIG. 43A). Fluorescence microscopy revealed that fibroblasts and osteoblasts were localized primarily at opposite ends of the scaffolds after initial seeding, with very few cells found in Phase B (FIGS. 44A-C). At day 28, SEM analysis revealed that both cell types elaborated extracellular matrix (ECM) on Phases A and C (FIGS. 43B and 43C) with some matrix formation observed in Phase B (FIG. 43D). Fibroblasts were found largely in Phase A and osteoblasts in Phase C (FIGS. 44D and 44F), with a mixture of cell types found in Phase B (FIG. 44E).

Figure 49A:
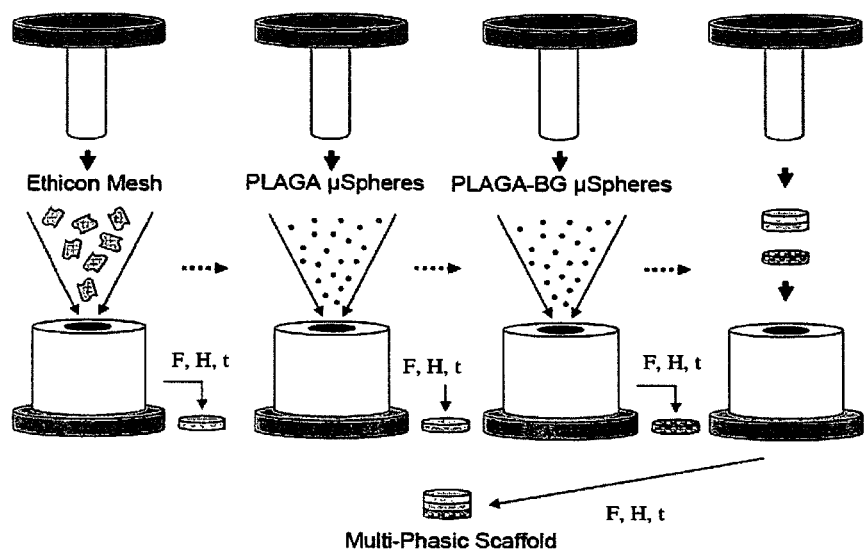
FIG. 49A schematically shows a method for producing multiphasic scaffolds, in another set of experiments. First Ethicon PLAGA mesh is cut into small pieces and inserted into a mold. By applying compression force (F) and heating (H) at 150° C. for time (t)=20 hours, the mesh segments are sintered into a mesh scaffold, which is removed from the mold. Next, PLAGA microspheres are inserted into the mold, sintered, then removed as a second scaffold. The same process is performed for the PLAGA-BG microspheres. Finally, Phases A and B are joined by solvent evaporation, then all three scaffolds are inserted into the mold and sintered together, forming the final multiphasic scaffold.
Figure 49B:
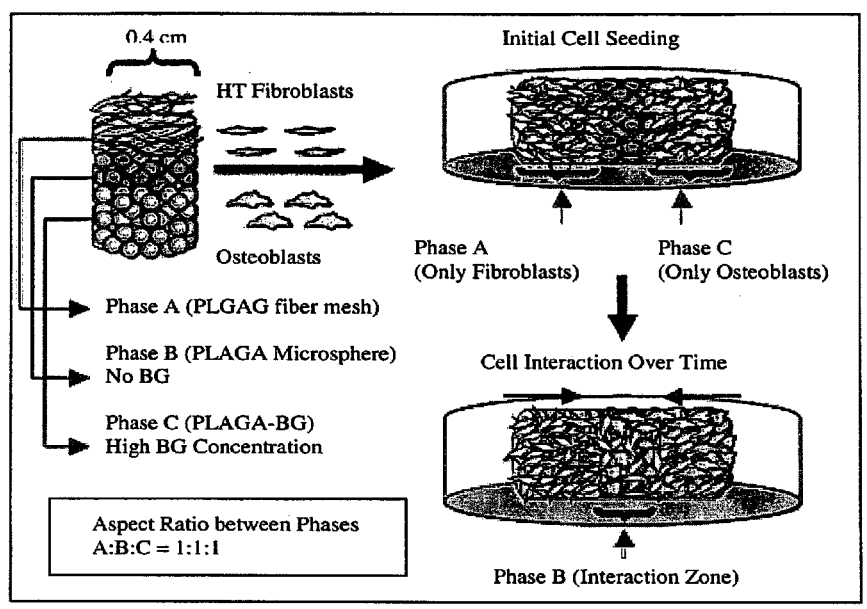
FIG. 49B shows a schematic of a fibroblast-osteoblast co-culture experimental design.

Histological analyses confirmed cell migration into Phase B and matrix production throughout the three phases of the scaffold at day 28 (FIGS. 49A-49C). The collagen-rich matrix (FIGS. 49D and 49E) seen in all three phases and osteoblast-mediated mineralization were observed on the surface of the PLAGA-BG microspheres (FIG. 49F, see arrow).

The biomimetic, multi-phased scaffolds supported the growth and ECM production by both osteoblasts and fibroblasts. After 28 days of culture, collagen production was evident in all three phases and mineralized matrix was found in the bone and interface regions only. Osteoblast and fibroblast interaction at the interface (Phase B) suggests that these cells may serve a significant role in the development of a functional insertion site. The results demonstrate that this novel scaffold is capable of simultaneously supporting the growth of multiple matrix zones. Additional studies can examine the effects of cell-cell interactions at the interface region and optimize the scaffold for clinical utilization.

Example 7: A Novel Micro-Co-Culture Model and Examination of Osteoblasts-Fibroblasts Interaction in a Micro-Co-Culture It is believed that fibroblasts and osteoblasts interactions play a significant role in interface formation. In vivo, fibroblasts and osteoblasts form a fibrocartilage layer within the bone tunnel. Since the natural interface spans less than 400 pm, a novel micro-co-culture model was developed that utilizes microfluidics to exert spatial control in cell distribution. This can be used to determine how cell-cell interactions may regulate interface remodeling locally at the micro-scale. The fabrication parameters of this model were optimized and initial osteoblastic and fibroblastic responses were examined.

Channels were designed having a bimodal non-intersecting serpentine geometry with 200 μm features. The design was implemented on silicon wafers using SU-8 25 (Microchem) photoresist and a mold patterned using Polydimethylsiloxane (PDMS, Dupont). In this design, osteoblast and fibroblast channels were first separated by PDMS, which was later removed to allow cell to cell interactions.

In order to optimize the channel depth for subsequent co-culture studies, the spin-coating durations (30, 45, 60 and 90 s) were varied. Cell seeding time was optimized by incubating the cells within the channels for 1, 3, 6, and 24 hours prior to removal of the PDMS followed by live-dead staining.

Bovine primary osteoblasts and fibroblasts were obtained from explant cultures. The cells were grown in supplemented DMEM (10% FBS, 1% NEAA and 1% antibiotics) at 37° C. and 5% $CO_2$. Osteoblast or fibroblast suspension ($20 \times 10^6$ cells/ml) was perfused into its respective microchannels. Cells were allowed to attach for 1 hour prior to PDMS removal. Cell migration was tracked by labeling fibroblasts with CM-DiI and osteoblasts with CFDA-SE (Molecular Probes) prior to seeding.

Analyses were performed at days 1, 2, and 6 following PDMS removal. Alkaline Phosphatase (ALP) activity was ascertained with fast-blue stain (Sigma), while type-1 collagen deposition was examined by immunohistochemistry.

Figure 46:
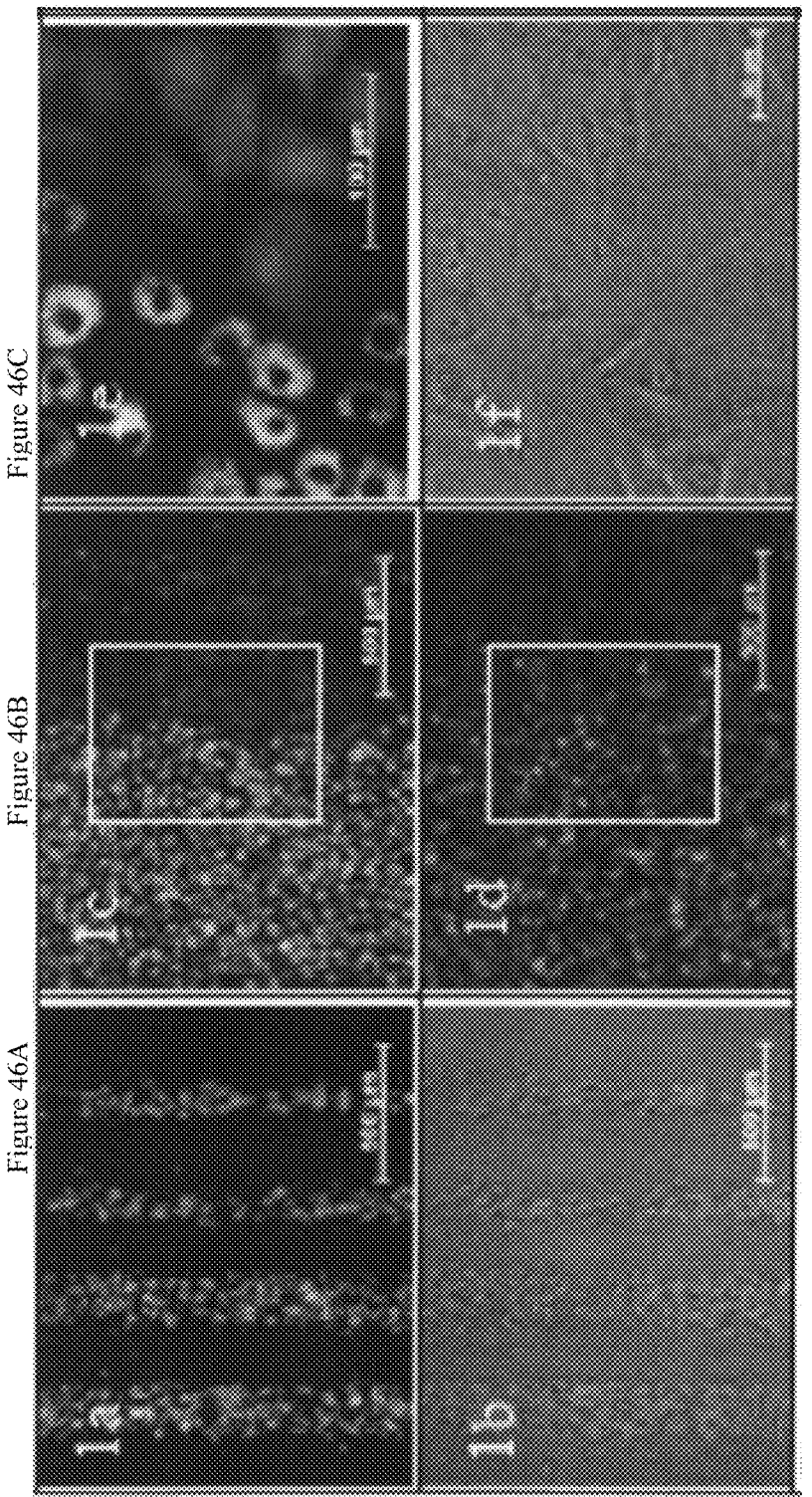
Figures 46G, 46H, 46I:
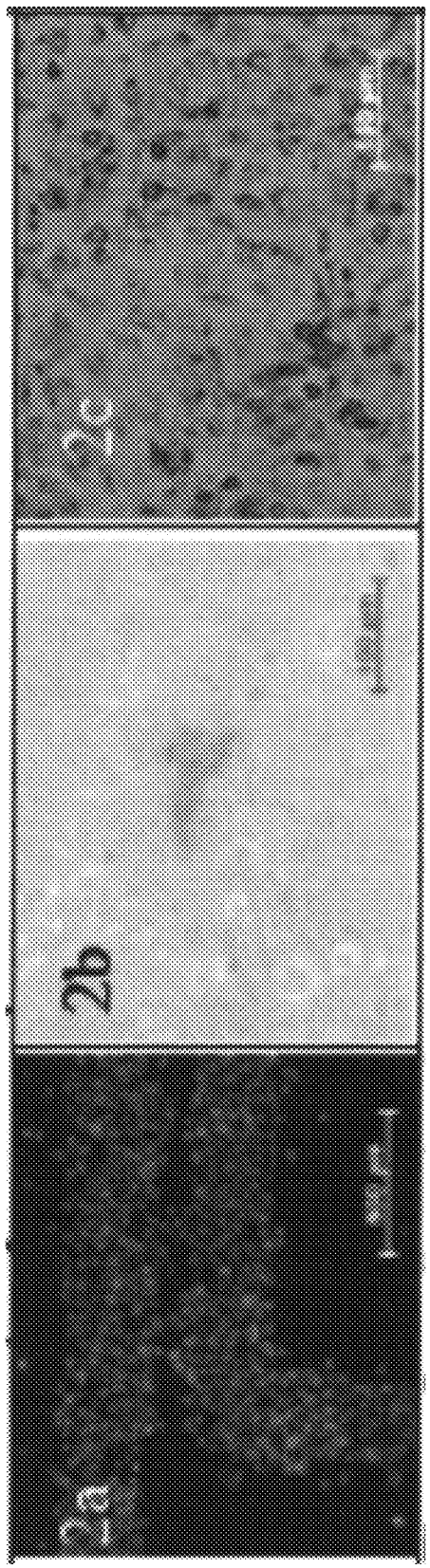
FIGS. 46G-46I show stained images.

A spin-coating duration of 30 seconds was chosen to balance channel depth and uniformity. Based on the cell viability, the optimal cell attachment time within the channels was 1 hour (FIG. 46-2*a*). Both cell types migrated and proliferated beyond their initial seeding zone (FIGS. 30-1*a* through 46-1*d*) and grew into physical contact by day 1 (FIGS. 46-1*e* and 46-1*f*). Local confluency and cross-migration were observed at day 2. ALP activity was observed in the osteoblast region (FIG. 46-2*b*), while type-1 collagen was found in all regions (FIG. 46-2*c*).

A successful micro-co-culture model was developed and initial examination of the interactions between osteoblasts and fibroblasts in a micro-co-culturing environment was performed. Cells proliferated beyond the initial seeding region and maintained their phenotypes as indicated by ALP activity of osteoblasts and type-1 collagen deposition of both cell types. The cell-to-cell cross-migration at day 2 offered a host of homotypic and heterotypic cell interactions. Micropatterning of cells offers an unique opportunity to control the local micro-environment and permit the in-depth examination of cell-cell interactions. This understanding can aid in the identification of mechanisms driving interface formation.

Figure 47:
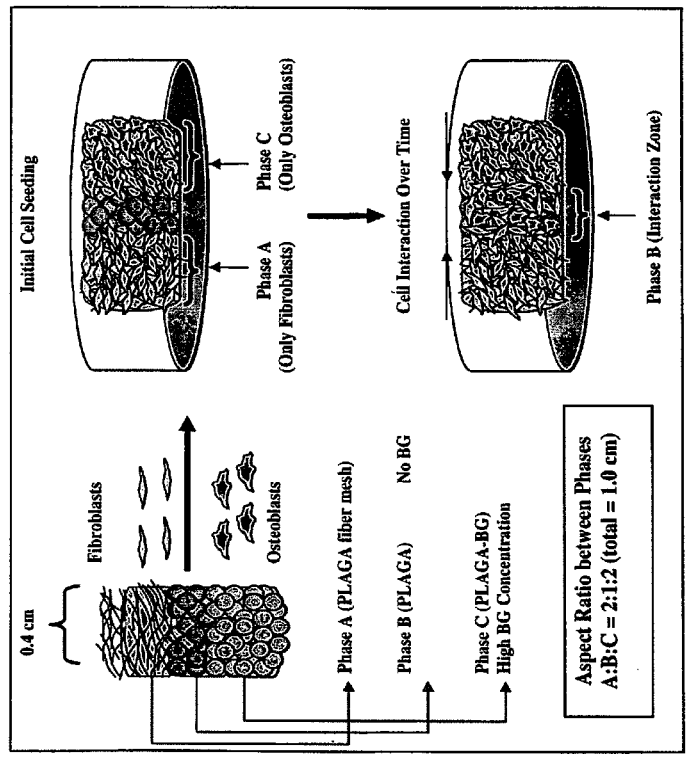
FIG. 47 shows a schematic of the experimental design, in another set of experiments, for in vitro evaluations of human osteoblasts and fibroblasts co-cultured on multi-phased scaffolds.

Example 8: In Vitro Evaluations of Human Osteoblasts and Fibroblasts Co-Cultured on Multi-Phased Scaffolds This set of experiments was directed to in vitro evaluations of human osteoblasts and fibroblasts co-cultured on multi-phased scaffolds. A schematic of the experimental design for the in vitro study is shown in FIG. 47. Phase A (mesh) was seeded with human hamstring tendon fibroblast cell suspension. Phase C was seeded with osteoblasts. Cell interaction in the interfacial Phase B was monitored over time. Acellular scaffolds served as controls.

Cell proliferation in Phases A, B, and C during 35 days of human hamstring tendon fibroblast and osteoblast co-culture on multiphased scaffolds is shown in FIG. 48A. A general trend of increasing cell number was observed in each phase over time. Data demonstrates that all three phases of the scaffold support cellular viability and proliferation. A higher number of cells were seeded on phase A due to its inherently larger surface area compared to phase C.

Mechanical testing data for multiphased scaffolds seeded with human hamstring tendon fibroblasts and human osteoblasts over 35 days of culture (n=4) is graphically shown in FIGS. 48B and 48C. Scaffolds were tested in uniaxial compression. Compressive modulus (FIG. 48B) and yield strength (FIG. 48C) were calculated from the resulting stress-strain curves. Both cell seeded (C) and acellular (AC) scaffolds were examined at days 0, 7, 21, and 35.

Compared to the acellular controls, the cell seeded scaffolds degraded slower and better maintained their structural integrity over time. The yield strength of the acellular scaffold decreased over 35 days, while the seeded scaffolds maintained its yield strength.

Example 9: Triphasic Scaffold Fabrication and Evaluation of Human Hamstring Tendon Fibroblasts and Trabecular Bone Osteoblasts Seeded on the Triphasic Scaffold The scaffold designed for this study consisted of three phases and were fabricated in four stages (FIG. 49A). First, Phase A was formed from polyglactin 10:90 poly(lactide-co-glycolide) (PLGA) mesh sheets (Vicryl VKML, Ethicon). Mesh sheets were cut into small segments (approximately 5 mm×5 mm) and inserted into cylindrical molds (7.44 mm diameter). Molds were heated to 150° C. for 20 hours to sinter the segments together to form a cylindrical mesh scaffold. The next phase (Phase B) consisted of 100% 85:15-poly(DL-lactide-co-glycolide) (PLAGA, Alkermes Medisorb, $M_w$26 123.6 kDa) microspheres formed by a water/oil/water emulsion. Briefly, 1 g PLAGA was dissolved in 10 mL methylene chloride (EM Science, Gibbstown, N.J.) and poured into a mixing 1% PVA surfactant solution (Sigma Chemicals, St. Louis, Mo.). Microspheres were mixed for 4 hours, recovered by filtration, allowed to dry in a fume hood overnight, then vacuum desiccated for 24 hours. To form the PLAGA microsphere phase, about 0.075 g microspheres were inserted into the same molds as used previously, and sintered at 55° C. for 5 hours. The last phase (Phase C) consisted of composite microspheres formed from an 80:20 ratio of PLAGA and 45S5 bioactive glass (BG, MO-SCI Corporation, Rolla, Md.). Again, microspheres were formed by emulsion, except with 0.25 g bioactive glass suspended in a solution of 1 g PLAGA in 10 mL methylene chloride. Microspheres (28-30 mg/scaffold) were sintered in the same molds at 55° C. for five hours. After all three phases were sintered separately, Phases A and B were joined by methylene chloride solvent evaporation, and then sintered to Phase C for 10 hours at 55° C. in the same molds. Subsequently, scaffolds were sterilized with ethylene oxide. Final scaffold dimensions are detailed in FIGS. 32-4A and 32-4B.

Human osteoblast-like cells and hamstring tendon fibroblasts were obtained from explant culture of tissue isolated from humerus trabecular bone and hamstring tendon respectively. Trabecular bone was rinsed with PBS, then cultured in Dulbecco's Modified Eagle's Medium (DMEM, Mediatech, Herndon, Va., USA) supplemented with 10% fetal bovine serum, 1% non essential amino acids, and 1% penicillin/streptomycin (Mediatech, Herndon, Va.), and incubated at 37° C. in a 5% $CO_2$ incubator to allow for cell migration. Hamstring tendon obtained from excess tissue utilized for hamstring tendon ACL reconstruction autografts was minced and cultured in similarly supplemented DMEM. The first migrations of cells were discarded to obtain a more uniform cell distribution. Second migration, passage 2 osteoblast-like cells and second and third migration, passage 5 hamstring tendon fibroblasts were utilized for the co-culture experiment.

Scaffold dimensions were measured prior to cell seeding and before and after EtO sterilization. Phase thickness was calculated by image analysis, while phase diameter was determined using a digital caliper. Scaffold porosity and pore diameter (Phases A and B: n=3; Phase C: n=1) were determined by mercury porosimetry (Micromeritics Autopore III and Autopore IV 9500, Micromeritics, Norcross, Ga.). The porosity data were utilized to determine cell seeding densities and cell suspension volumes for Phases A and C, with the volumes calculated such that fibroblasts suspension remains in Phase A and osteoblasts suspension in Phase C.

Hamstring tendon fibroblasts were seeded at a density of 250,000 cells/scaffold in a volume of 40.7 μL/scaffold on Phase A (FIG. 49B). After allowing the fibroblasts to attach to the scaffolds for 20 minutes, the scaffolds were rotated upside down so that Phase C faced upwards. Subsequently, 75,000 osteoblast-like cells were seeded per scaffold in a volume of 12.5 μl. After allowing the osteoblasts to attach to the scaffold for 20 minutes, the scaffolds were covered with DMEM supplemented with 10% FBS, 1% NEAA, and 1% penicillin/streptomycin, and incubated at 37° C. and 5% $CO_2$. Ascorbic acid at a concentration of 20 μg/mL was added beginning at day 7. Media was exchanged every two days. Scaffolds were cultured in 6-well plates and covered with 7 ml of supplemented media per scaffold to minimize pH fluctuations due to rapid poly(glycolic acid) degradation.

Cell attachment, migration, and proliferation on the multiphased scaffolds were examined using SEM (5 kV, JEOL 5600LV) at days 7, 21, and 35. The scaffolds were fixed with Karnovsky's glutaraldehyde fixative, and stored at 4° C. for 24 hours. The samples were then rinsed with Hank's buffered salt solution two times, and serially dehydrated with ethanol. Cross-sections of the scaffold phases were mounted on an aluminum post and gold-coated prior to analysis.

Extracellular matrix production and mineralization were determined via histology at day 35. Scaffolds were rinsed two times with room temperature PBS. The scaffolds were then covered with 10% neutral buffered formalin and stored at 4° C. Samples were plastic embedded using a modification of a procedure developed by Erben. The scaffolds were first suspended in 2% agarose (low gelling temperature, cell culture grade, Sigma, St. Louis, Mo.), then serially dehydrated with ethanol and cleared with xylene substitute (Surgipath, Sub-X, Richmond, Ill.). Following dehydration, samples were embedded in poly(methyl methacrylate) (Polysciences, Inc., Warrington, Pa.) and sectioned into 10 µm slices. The scaffold sections were stained with either hematoxylin and eosin, von Kossa or Picrosirius Red stains and imaged with light microscopy.

At days 1, 7, 21, and 35, scaffolds were rinsed twice with PBS and subsequently the three phases were separated. Each phase was then stored in 0.1% Triton-X at −80° C. Cellular proliferation in each phase was determined by means of PicoGreen DNA quantitation assay. In addition, cellular phenotype for mineralization was evaluated using a quantitative alkaline phosphatase (ALP) assay.

At days 0, 7, 21, and 35, seeded and acellular scaffolds were tested under uniaxial compression (MTS 810, n=4). The crosshead speed was 1.3 mm/min, and the scaffolds were compressed up to 35-40% strain. A 10 N preload was applied prior to testing. The effects of scaffold degradation and extracellular matrix production on scaffold compressive modulus were examined.

Mercury porosimetry data for each phase are summarized in Table 11 shown below.

TABLE 11

| | Pore Area (mm$^2$) | Intrusion Volume (µL) | Porosity (%) | Mode Pore Diameter (µm) |
|---|---|---|---|---|
| Phase A (n = 3) | 6000 ± 800 | 41 ± 8 | 58 ± 5 | 73 ± 11 |
| Phase B (n = 3) | 2400 ± 500 | 28 ± 7 | 34 ± 4 | 75 ± 7 |
| Phase C (n = 1) | 706.3 | 12.5 | 25.7 | 83 |

Figure 50A:
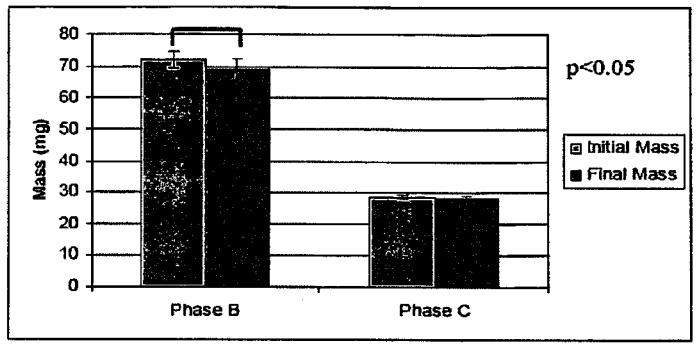
FIG. 50A, shows graphically a comparison of microsphere initial mass and final mass after undergoing a sintering process.
Figure 50B:
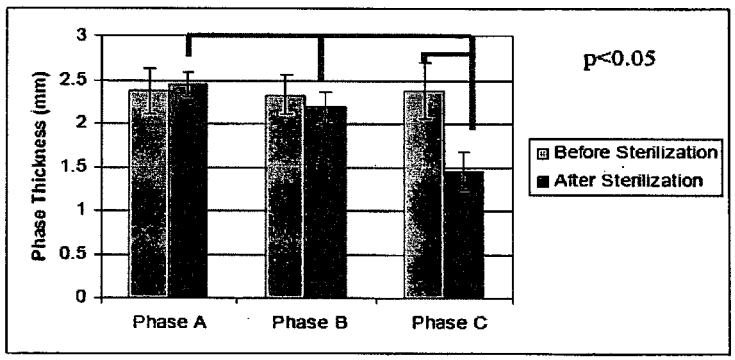
FIGS. 50B-50C: show graphically scaffold phase thicknesses and diameters, in the experiments of FIG. 49.
Figure 50C:
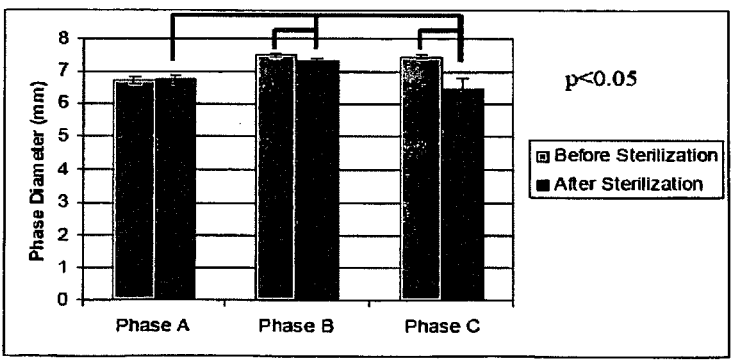

Scaffold dimensions are shown in FIGS. 50B and 50C. The thickness of Phase C decreased significantly (p<0.05) due to contraction during the EtO sterilization (FIG. 50B). In addition, the thicknesses of all phases were significantly different from each other after sterilization. Scaffold diameters also varied due to contraction during sintering, in the case of Phase $A_1$ and contraction of Phase C during sterilization. The diameters of Phases B and C decreased significantly after sterilization, and the diameters of all phases were significantly different from each other after sterilization (p<0.05). During the scaffold fabrication process, microspheres are lost between weighing and filling the molds. This loss is mainly due to static charge accumulation in one or more of the microspheres, weighing paper, or mold, which prevents a small percentage of the microspheres from entering the molds. PLAGA-BG microspheres for Phase C generally experience a 2.1±1.4% loss in mass, while the PLAGA microspheres for Phase B suffer a loss of 4.0±1.8% (FIG. 50A). Composite microspheres are generally more statically charged than the PLAGA microspheres; however, the stainless steel mold, used more often for the composite microspheres, dissipates charge buildup more readily than the PTFE mold, which is used more often for the PLAGA microspheres, possibly explaining why there is a significant loss for Phase B (p<0.05). Mesh for Phase A is not susceptible to this loss.

Compressive modulus and yield strength were obtained for seeded and acellular control scaffolds at days 0, 7, 21, and 35 of culture. A rapid decrease in compressive modulus was observed following day 0, possibly due to rapid initial polymer degradation. By day 35, the seeded scaffolds exhibited a greater compressive modulus (FIG. 51A) and yield strength (FIG. 51B), possibly due to cellular extracellular matrix and mineralization compensating loss of scaffold strength due to polymer degradation.

In this experiment, the cell types were switched from bovine ACL fibroblasts and trabecular bone osteoblast-like cells to human hamstring tendon fibroblasts and trabecular bone osteoblasts due to the increased clinical relevance of these new cell types. This experiment aimed to acquire quantitative data about cell proliferation and migration throughout the three phases, as well as cellular alkaline phosphatase activity in each phase of the scaffold.

Based on the previous experiment performed with bovine cells, it is apparent that the biomimetic, multi-phased scaffolds support the growth and ECM production of both osteoblasts and fibroblasts. After 28 days of culture, collagen production was evident in all three phases and mineralized matrix was found in the bone and interface regions. Osteoblast and fibroblast interaction at the interface (Phase B) suggests that these cells may play a significant role in the development of a functional insertion site. These findings demonstrate that this novel scaffold is capable of simultaneously supporting the growth of multiple cell types and can be used as a model system to regenerate the soft tissue to bone interface.

Additional studies can focus on scaffold optimization and the development of the interface on the novel scaffold.

Example 10: Electrospun PLACA Meshes in the Multi-Phased Scaffold Design

The objective of the set of experiments was to incorporate electrospun PLAGA meshes into the multi-phased scaffold design, substituting the Ethicon mesh phase, and allowing the entire scaffold to be made in-house.

Electrospinning, short for electrostatic spinning, is a relatively new term that describes a principle first discovered in the first half of the 20th century (see, for example, U.S. Pat. Nos. 1,975,504, 2,160,962, 2,187,306, 2,323,025 and 2,349,950 to Formhals, the entire contents of which are incorporated herein by reference). Electrostatic spinning involves the fabrication of fibers by applying a high electric potential to a polymer solution. The material to be electrospun, or dissolved into a solution in the case of polymers, is loaded into a syringe or spoon, and a high potential is applied between the solution and a grounded substrate. As the potential is increased, the electrostatic force applied to the polymer solution overcomes surface tension, distorting the solution droplet into a Taylor cone from which a jet of solution is ejected toward the grounded plate. The jet splays into randomly oriented fibers, assuming that the solution has a high cohesive strength, linked to polymer chain molecular weight, to prevent droplets from forming instead of fibers in a process known as electrospraying. These fibers have diameters ranging from nanometer scale to greater than 1 µm and are deposited onto the grounded substrate or onto objects inserted into the electric field forming a non-woven mesh. Mesh characteristics can be customized by altering electrospinning parameters. For example, fiber diameter and morphology can be altered, including the formation of beads along the fibers, by controlling applied voltage and polymer solution surface tension and viscosity. Also, fiber orientation can be controlled by rotating the grounded substrate. This high degree of customizability and ability to use many different materials, such as biodegradable polymers and silks, grant this fabrication method a high potential in the development of materials for biomedical application. Management of fiber diameter allows surface area to be controlled, and polymers with different degradation rates can be combined in various ratios to control fiber degradation, both of which are significant in drug delivery applications. Also, controlling the orientation of fiber deposition grants a degree of control over cell attachment and migration. Moreover, the ability to electrospin fiber meshes onto non-metal objects placed in the electric field enables the fabrication of multiphasic scaffold systems.

Here, in order to obtain precise parameters for the mesh fibers, including fiber diameter, morphology, and alignment, the effects of processing parameters on fiber characteristics were studied. A variable-speed rotating drum was designed and constructed to serve as a substrate for aligned fibers, and Theological experiments were performed on the polymer solutions to determine the effect of polymer concentration on solution viscosity and the subsequent effect of solution viscosity on fiber diameter and morphology.

In addition to determining the speed of each gear, the effect of each speed on fiber alignment was determined qualitatively. A 30% v/v PLAGA solution was prepared with 60% dimethylformamide and 10% ethanol, and this solution was electrospun onto the rotating drum at each of the four speed settings. The resulting meshes were examined by scanning electron microscopy (JEOL 5600LV).

The relationship between polymer concentration (Alkermes 85:15 PLAGA) and solution viscosity was determine by means of a Theological study. Three concentrations of polymer were tested—20%, 30%, and 40% v/v—in dimethylformamide (DMF) and ethanol. The composition of each solution is listed in Table 12 shown below.

TABLE 12

|   | PLGA | DMF | EtOH |
|---|------|-----|------|
| 1 | 20%  | 70% | 10%  |
| 2 | 30%  | 60% | 10%  |
| 3 | 40%  | 50% | 10%  |

Solutions were analyzed using an Advanced Rheometer AR 200Ot. There was variability in the viscosity measurements (n=1) at different strain rates due to the evaporation of solvent during testing. The geometry used for the viscosity measurements was a 25 mm stainless steel disc. A solvent trap was not used since it is not designed to fit with this geometry and a prior trial using the solvent trap with another geometry resulted in poor results, possibly because water from the solvent trap seal interacted with the polymer solution. Additional trials can use a solvent trap to obtain consistent and reliable values for viscosity. For the present study, averages were taken of the viscosity measurements taken at strain rates tested after the equipment had equilibrated. As a result, there are standard deviations for the viscosity measurements even with an n of 1.

The surface velocity of the rotating drum was seen to increase with increased pulley positions from gear 1 to gear 4, as shown in Table 13 below. The degree of fiber alignment increased with increasing drum velocity, as seen in the SEMs of each mesh (see FIGS. 52A-D).

TABLE 13

| Gear | RPM | Vs (m/s) |
|------|-----|----------|
| $1^{st}$ | 23.3 | 7.4 |
| $2^{nd}$ | 29.5 | 9.4 |

TABLE 13-continued

| Gear | RPM | Vs (m/s) |
|------|-----|----------|
| $3^{rd}$ | 46.2 | 15 |
| $4^{th}$ | 63.4 | 20 |

It was found that (as expected) the degree of fiber orientation increased with increasing drum rotational velocity. The image was analyzed and a histogram of fiber angles was generated against the horizontal axis of the image at regular interval across the image. Thus, the degree of alignment of the fibers can be quantified. It is desirable to control the degree of fiber alignment in the electrospun meshes so that the extracellular environment found at the interface can be mimicked. By producing biomimetic scaffolds, it was intended to direct cell growth to reproduce the tissue inhomogeneity found at the native ACL insertions. In addition to controlling the fiber alignment, it is desirable to control fiber diameter and morphology. It was previously determined that substituting 10% of the DMF in the polymer solutions with ethanol reduces the surface tension of the solution and results in a significant reduction in the number of beads formed along the fibers when electrospinning PLAGA. This effect was also observed by Fong et al., who reduced the number of beads in electrospun polyethylene oxide) (PEO) meshes by the addition of ethanol. Surface tension of the polymer solution acts to form spheres during the electrospinning process. By reducing the solution surface tension, the formation of spheres is less favorable and straighter fibers result. Fong et al. also determined that the addition of ethanol increased the viscosity of the PEO:water solutions, which also favors the formation of straight fibers, and results in increased fiber diameter. Deitzel et al. also have demonstrated a relationship between PEO:water solution viscosity and fiber diameter, with fiber diameter increasing with increasing viscosity according to a power law. A relationship between solution viscosity and concentration of polymer can be determined in order to understand how PLAGA:N, N-DMF viscosity affects fiber diameter and morphology. The effect of solution viscosity on fiber diameter and morphology can be determined by spinning the various solutions and examining the resulting meshes by SEM. Other variables can affect the fiber parameters. By changing the percentage of polymer, the surface tensions of the polymer solutions also change in addition to the viscosity. Therefore, in addition to testing the viscosities of each solution, the surface tension of each solution are measured. It is desirable to keep all variables constant except for viscosity in order to truly determine the effect of solution viscosity on fiber characteristics. However, the interrelation of many of the electrospinning parameters complicates the process.

A PLAGA mesh was electrospun directly onto a microsphere scaffold.

This is one way to incorporate the mesh. In addition, the scaffolds can be secured to the drum and aligned fibers electrospin directly onto the scaffolds.

However, because of the high rotational velocities, it is difficult to secure the scaffolds and prevent them from flying off the drum when it begins rotating. Alternatively, aligned fiber meshes can simply be spun separately, and then later sintered to the microsphere scaffolds. For example, aligned fiber meshes can be electrospun onto aluminum foil, then wrapped around a rod with multiple mesh sheets sintered together to obtain a hollow cylinder of aligned fibers.

Figure 52:
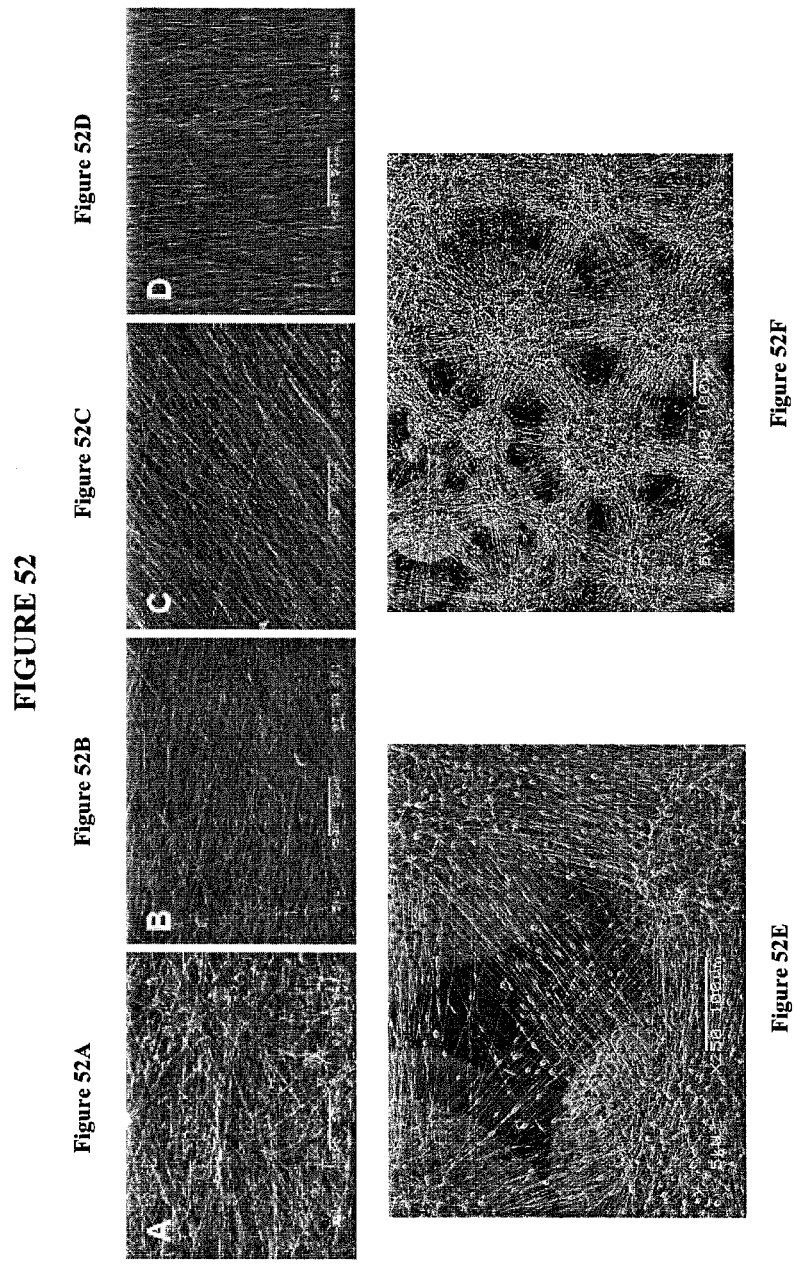
Figure 53:
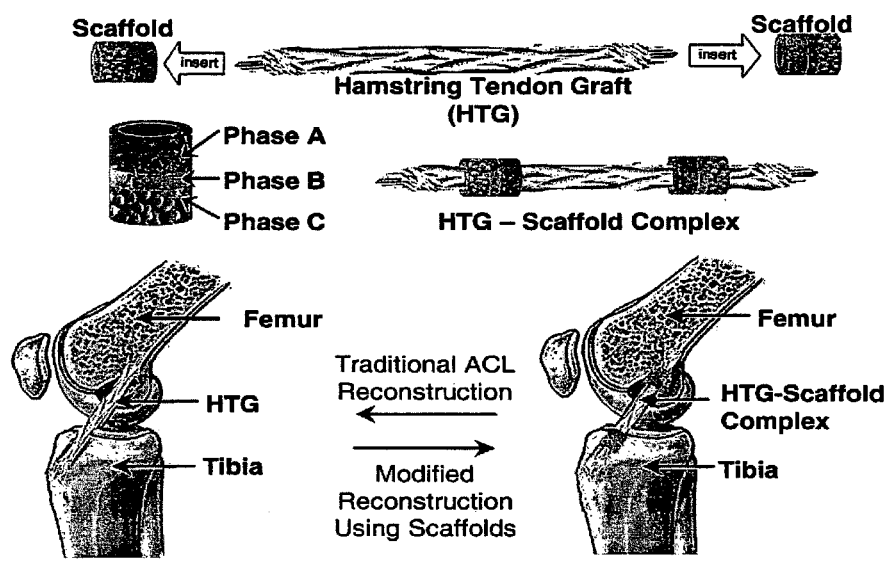
FIG. 53 schematically shows an exemplary multi-phased scaffold as a hamstring tendon graft collar which can be implemented during ACL reconstruction surgery to assist with hamstring tendon-to-bone healing.

FIGS. 52E and 52F show scanning electron microscopy (SEM) images of another embodiment of multi-phased scaffold, with 85:15 PLAGA electrospun mesh joined with PLAGA:BG composite microspheres.

Example 11: A Fully Synthetic Implantable Scaffold

With reference to FIG. 55, the fully synthetic implantable scaffold according to the present invention may be made according to the following procedure. A synthetic graft (Phase A) is made using conventional techniques from any suitable bioresorbable and/or biodegradable synthetic polymer material, such as for example, aliphatic polyesters, poly(amino acids), copoly(ether-esters), polyalkylenes oxalates, polyamides, poly(iminocarbonates), polyorthoesters, polyoxaesters, polyamidoesters, poly(ε-caprolactone)s, polyanhydrides, polyarylates, polyphosphazenes, polyhydroxyalkanoates, polysaccharides, degradable polyurethanes, and biopolymers, and a blend of two or more of the preceding polymers. For example, the synthetic graft may be made from at least one of a poly(lactide-co-glycolide), poly(lactide) and poly(glycolide).

Phases B and C of the scaffold are made from any suitable material as previously defined herein. For example, phase C may be constructed of a polymer-ceramic composite with high Ca—P and phase B may be constructed of a polymer only or a polymer-ceramic composite with a lower Ca—P than phase C.

The fully synthetic scaffold is assembled by first attaching Phase B to both ends of Phase A using conventional techniques, such as sintering or solvent evaporation. The Phase C is attached to the free end of each respective Phase B, again using conventional techniques, such as sintering or solvent evaporation. Thus formed, the scaffold is a multi-phased, biodegradable, and osteointegrative composite having the structure: Phase C-Phase B-Phase A-Phase B-Phase C.

As previously described, each phase of the scaffold may be further treated to initiate, promote, and enhance integration of the scaffold with anatomical environment to which it is delivered. Such treatment may include seeding appropriate phases of the scaffold with appropriate cell types (e.g., seeding a phase C which will be inserted into bone with osteoblasts, osteoblast-like cells, and/or stem cells or seeding phase C, which will be attached to soft tissue with fibroblasts, chondrocytes and/or stem cells), treating appropriate phases of the scaffold with a medicament, such as for example anti-infectives, antibiotics, bisphosphonate, hormones, analgesics, anti-inflammatory agents, growth factors, angiogenic factors, chemotherapeutic agents, anti-rejection agents, and RGD peptides.

The fully synthetic implantable scaffold according to the present invention may be used in any ligament or tendon repair or reconstruction. Preferably, the fully synthetic implantable scaffold according to the present invention is used to repair or reconstruct anterior cruciate ligaments.

Example 12: The Triphasic Scaffold for Use as Graft Collar or Interference Screw Clinically, the hamstring tendon graft is mechanically fixed extra-articularly by looping the graft around a transfemoral pin in the femoral bone tunnel, while a screw with a washer or a staple is used to fix the graft to the tibia. Interference screws have been used in the bone tunnel, but with limited success due to graft laceration and poor fixation strength. With mechanical fixation, the fibrocartilage interface is not regenerated after ACL reconstruction. A non-physiologic, fibrovascular scar tissue is instead formed within the bone tunnel as part of the healing process. The presence of this partially mineralized layer within the tunnel renders the graft-bone fixation site the weakest point mechanically (Rodeo, 2006). This problem is exacerbated by the active lifestyle of ACL injury patients (15-35 years old), which necessitates higher fixation strength and expedited healing. Thus, graft-to-bone fixation remains a significant clinical problem.

The subject approach to addressing the challenge of biological fixation is original and represents a significant departure from the conventional focus on tendon-to-bone healing within the bone tunnel. It is emphasized here that the native anatomical fibrocartilage interface is orthogonal to the subchondral bone and continuous with surrounding articular cartilage. In addition, the neo-fibrocartilage formed within the bone tunnel represents the mechanical weak link for tendon-to-bone integration. Biological fixation therefore requires that the anatomical fibrocartilage insertion is regenerated between graft and bone, accompanied by the complete mineralization of the tendon within the bone tunnel.

It is envisioned that the triphasic scaffold may be used clinically as either as a graft collar or an interference screw during ACL reconstruction surgery. The ultimate goal is to facilitate the formation of the anatomic fibrocartilage interface directly on the soft tissue graft. As a graft collar, the scaffold will be fabricated as a hollow cylinder through which the ACL graft can be inserted. As shown in FIG. 62, the collar can be sutured or secured to the ends of the tendon graft. Fixation is achieved by inserting the collar-graft complex into the bone tunnel, with Phase C positioned inside the bone tunnel, Phase B flush with articular cartilage, and only Phase A directly exposed to the joint cavity. It is anticipated that the designed heterogeneity and optimized interaction between MSC-derived cells will induce the formation of a fibrocartilage interface directly onto the graft. Graft integration within the bone tunnel will be facilitated by Phase C, the osteointegrative polymer-ceramic composite, and with the eventual addition of growth factors (e.g., bone morphogenetic proteins), which will induce osteointegration and mineralization of the tendon graft within the bone tunnel.

Figure 63:
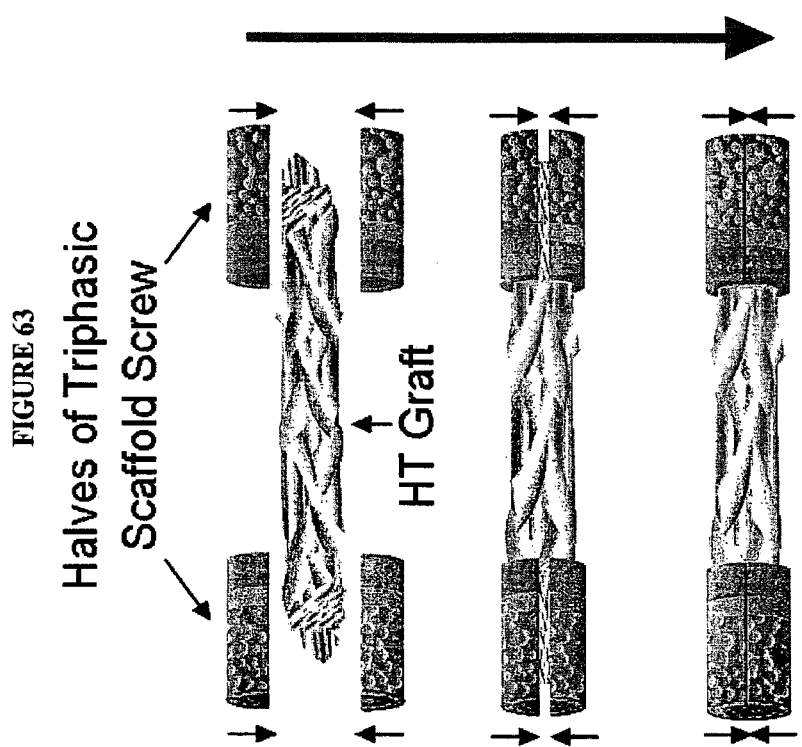
FIG. 63 shows clinical application as a bioactive interference screw.

For use as an interference screw, the triphasic scaffold can be fabricated as matching portions of the hollow cylinder, with each portion containing the three scaffold phases. As shown in FIG. 63, the two matching portions will encase the soft tissue graft on all sides. The relative position of each phase of the triphasic scaffold would be in the anatomical position, i.e., with Phase A (soft tissue) exposed to the joint cavity, Phase B (fibrocartilage interface) flush with articular cartilage, and Phase C (bone) encased within the bone tunnel. There are several advantages to this novel interference screw design: 1) the biomimetic triphasic screw design enables the regeneration of the relevant tissue types on the scaffold system, 2) the partitioned design permits the application of mechanical loading to the graft, which has been known to induce fibrocartilage formation, and 3) the tendon graft is in contact with the triphasic scaffold on all sides. Any applied mechanical and chemical stimulation would be uniformly experienced by the graft.

The optimal outcome scenario post-degradation of the screw or graft collar is to have a completely mineralized tissue within the bone tunnel, accompanied by the formation of a physiologically equivalent fibrocartilage insertion directly outside the bone.

For ligament tissue engineering, the triphasic scaffold may be coupled with synthetic grafts for ACL replacement. The future design of ACL replacement grafts must take into consideration the integration of the graft with bone. In this integrative ACL prosthesis design, the ACL prosthesis will contain three regions, a bony end consisting of Phase C, followed by Phase 8, then by polymer fiber-based ACL portion. The triphasic scaffold can also be incorporated into any existing ACL prosthesis design, as the soft tissue graft shown in FIGS. 62 and 63 can easily be replaced by any synthetic ACL reconstruction scaffold. For example, in the case of a degradable polymer-based ACL prosthesis (Cooper, 2005), the triphasic scaffold can be sintered onto the polymer scaffold and implanted for ACL reconstruction.

One common feature in the above examples of clinical application is the focus on engineering soft tissue-to-bone integration ex vivo, which would reduce the complexity of graft reconstruction to just bone-to-bone integration in vivo. This is more feasible clinically as it is much more difficult to integrate soft tissue with bone compared to bone-to-bone integration.

Extensive characterization of the chemical and mechanical properties of the interface (Wang, 2006; Spalazzi, 2006; Moffat, 2005) has been conducted and novel in vitro co-culture (Wang, 2005) and tri-culture (Wang, 2006) models have been developed to examine the role of cell-cell interactions in interface formation. In combination with knowledge of in vivo models of tendon-bone healing (Rodeo, 1993; Kawamura, 2005), there is a solid foundation and clear rationale for the described approach.

From a broader impact perspective, this approach is also unique in that previous tissue engineering methods have focused predominantly on the design of a single type of tissue (e.g., only ligament or bone) on a scaffold with uniform properties, when the application may have involved more than one tissue type. Moreover, the novel scaffold design and co-culture methods described here can be applied to treat other clinical conditions (e.g., rotator cuff, osteoarthritis) and will enable the design of a new generation of integrative fixation devices. The described studies will also provide fundamental insights into the mechanism of soft tissue-bone interface regeneration.

Figure 64:
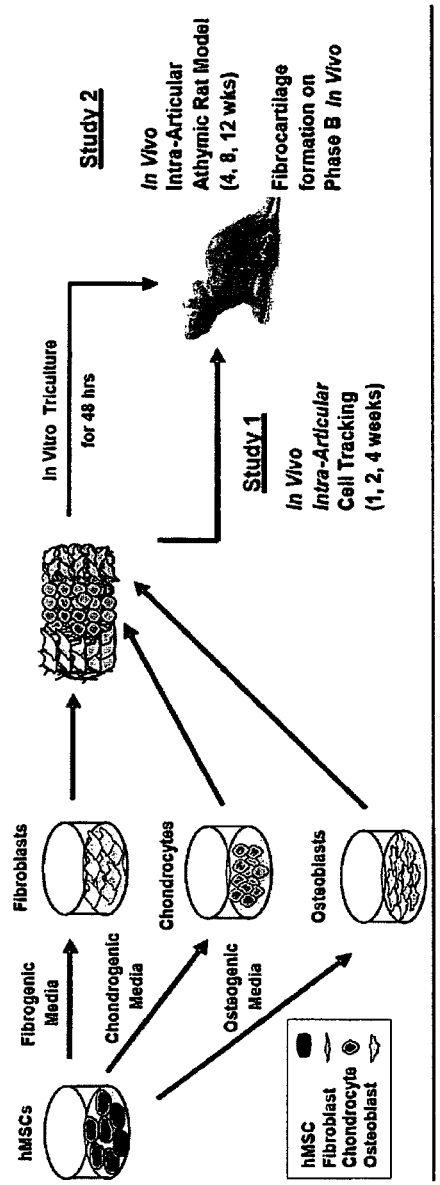
FIG. 64 shows schematic summary of experimental approach.

Clinical feasibility of the scaffold was determined by testing the hypothesis that the biomimetic matrix heterogeneity engineered on the triphasic scaffold will be maintained in vivo in an intra-articular model. A summary schematic of this research approach is presented below in FIG. 64. It was determined that modifications to the scaffold design were necessary to achieve distinct cell and matrix regions in vivo.

Scaffold Design Optimization

Based on the outcomes of in vitro and in vivo co-culture and tri-culture experiments, the multi-phased scaffold design has been improved upon, with the goal of localizing the interface-relevant cells within Phase B without compromising the scaffold design requirements (higher porosity and pore diameter) necessary for Phase A. Specifically, a degradable cell barrier between adjacent phases has been incorporated. This barrier is based on a polylactide-co-glycolide (PLGA) electrospun nanofiber mesh (FIG. 65-I), which, based on porosimetry analysis, has an average pore diameter of 5.2±0.9 µm. This nanofiber mesh will prevent unwanted cell migration and gel infiltration into Phase A or Phase C. Cell localization is important as 3-D co-culture results demonstrate that cell-specific distribution is required for the development of the biomimetic, controlled matrix distribution on the multi-phased scaffold.

Figure 65:
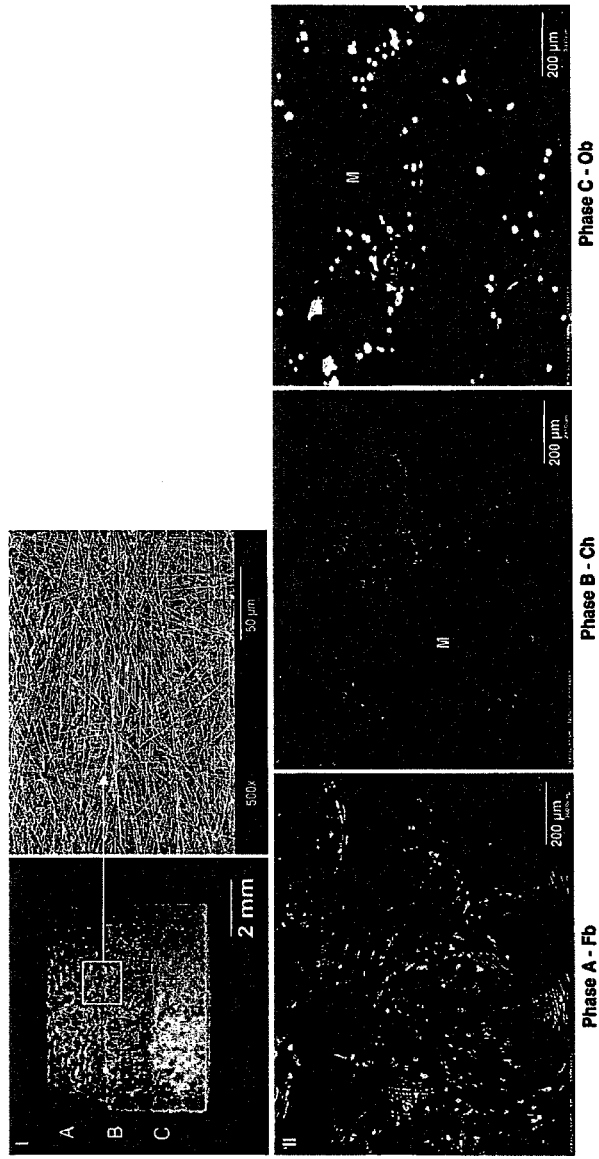
FIG. 65: I. Multi-phased scaffold design with nanofiber mesh sintered between phases to localize cell seeding. II. Tracking of fibroblasts (Phase A), chondrocytes (Phase B) and osteoblasts (Phase C) on the multi-phased scaffold (Day 1, 10×). Phase specific cell distribution was maintained, which successfully localized fibroblasts (Fb), chondrocytes (CH) and osteoblasts (Ob) on Phase A, B and C, respectively.

Preliminary cell tracking results of fibroblasts and osteoblasts tri-cultured with chondrocytes loaded in hydrogel for 24 hours on the modified scaffold are shown in FIG. 65-II. Fibroblasts, chondrocytes, and osteoblasts were detected only in their respective phases as determined by fluorescence confocal microscopy. The nanofiber mesh served as an effective barrier to gel infiltration and unwanted cell cross-migration. It is anticipated that the mesh will degrade over time, having ensured the establishment of cell-specific regions in tri-culture.

Mechano-Actuve Scaffold Induces Remodeling and Expression of Fibrocartilage Markers on Tendon Grafts Based on the hypothesis that mechanical loading, in addition to multiphasic scaffold design and heterotypic cellular interactions, will be required for interface generation, this experiment focuses on the design and evaluation of a novel mechano-active scaffold that is capable of applying compression to tendon grafts and inducing metaplasia of tendon into fibrocartilage. Specifically the novel scaffold system combines a degradable graft collar with nanofiber meshes fabricated from poly(latic-co-glycolic acid) (PLGA). One objective of the experiment is to characterize the contractile properties of the nanofiber mesh as well as the mesh and scaffold complex. A second objective of the experiment is to evaluate the effect of scaffold induced compression on fibrocartilage development on tendon graft, focusing on matrix remodeling and the development of fibrocartilage-related markers.

First, aligned nanofiber meshes were fabricated by electrospinning. A viscous polymer solution consisting of 35% poly(D,L-lactic-co-glycolic acid) 85:15 (PLGA, I.V.=0.70 dL/g, Lakeshore Biomaterials, Birmingham, Ala.), 55% N,N-dimethylformamide (Sigma, St. Louis, Mo.), and 10% ethanol (Commercial Alcohol, Inc., Toronto, Ontario) was loaded into a syringe fitted with an 18-gauge needle (Becton Dickinson, Franklin Lakes, N.J.). Aligned fibers were obtained using an aluminum drum with an outer diameter of 10.2 cm rotating with a surface velocity of 20 m/2. A constant flow rate of 1 mL/hr was maintained using a syringe pump (Harvard Apparatus, Holliston, Mass.), and an electrical potential was applied between the needle and the grounded substrate (distance=10 cm) using a high voltage DC power supply (Spellman, Hauppauge, N.Y., 8-10 kV). Fiber morphology, diameter and alignment of the as-fabricated mesh samples were analyzed using scanning electron microscopy (SEM). The samples were sputter-coated with gold (LVC-76, Plasma Sciences, Lorton, Va.) and subsequently imaged (JSM 5600LV, JEOL, Tokyo, Japan) at an accelerating voltage of gkV.

The nanofiber mesh exhibited a high degree of alignment with an average fiber diameter of 0.9±0.4 pin. Anisotropic mesh contractile behavior was observed in the mesh, with significantly higher contraction found in the direction of nanofiber alignment. Specifically, the mesh contracted over 57% along the aligned fiber direction (y-axis) by 2 hours, with less than 13% reduction in the x-axis. Mesh contraction continued over time, exhibiting over 70% contraction in the y-axis and 20% in the x-axis by 24 hours and stabilizing thereafter, with no significant differences found between the 24- and 72-hour groups.

The said nanofiber is then wrapped around a tendon graft collar based on a sintered microsphere scaffold fabricated following published methods. In addition, patellar tendon grafts were isolated from neonatal bovine tibiofemoral joints obtained from a local abattoir. The compression of the nanofiber mesh, the graft collar scaffold with nanofiber mesh, the tendon with nanofiber mesh, and finally the tendon graft with the graft collar scaffold and the nanofiber mesh were evaluated. Further, the effects of compression on graft cellularity, organization, matrix content, and cell phenotype were evaluated.

It was found that complex of nanofiber mesh and graft collar was able to apply a physiological range of compressive loading on the tendons. Moreover scaffold-mediated compression promoted matrix remodeling, maintained graft glycosaminoglycan content and induced gene expression for fibrocartilage markers, including type II collagen, aggrecan core protein, and TGF-β.

Mesenchymal Stem Cells and Differentiation into Interface-Relevant Cell Populations The experiments will also utilize fibroblasts, chondrocytes, and osteoblasts derived from adult mesenchymal stem cells (MSCs) originated from human bone marrow. The MSCs are chosen because they are ideal for tissue engineering applications. These cells can be harvested from the patient prior to surgery, expanded, and pre-differentiated into desired cell types, and then seeded onto 3-D scaffolds. In addition to being autologous, MSCs can differentiate into fibroblasts (Pittenger, 1999; Moreau, 2005), chondrocytes (Pittenger, 1999; Meinel, 2004), and osteoblasts (Pittenger, 1999; Mauney, 2005) which are the relevant cell types found at the soft tissue-bone interface. This versatility will simplify the tissue harvest process to a single procedure instead of the normal three required to obtain the three types of cells. Successful implementation of MSC-derived cells will significantly enhance the clinical feasibility and translational potential of the triphasic scaffold.

Specifically, MSCs purchased from Cambrex will be pre-differentiated into fibroblasts (Fb), chondrocytes (Ch), and osteoblasts (Ob) based on well-established protocols. The fibrogenic media will contain 1 ng/mL of basic fibroblast growth factor, 5 ng/mL of transforming growth factor-beta (TGF-β3) and 50 µg/ml of L-Ascorbic Acid-2-Phosphate (AA) (Moreau, 2005; Altman, 2002). The chondrogenic media will contain 5 ng/mL TGF-β3, 0.1 mM non-essential amino acids, 50 µg/ml AA, 10 nM dexamethasone (Dex), and 5 µg/ml of insulin16). The osteogenic media will contain 10 nM Dex, 10 mM of β-glycerophosphate, and 50 µg/ml AA (Mauney, 2005).

Intra-Articular ACL Reconstruction Model

Figure 66:
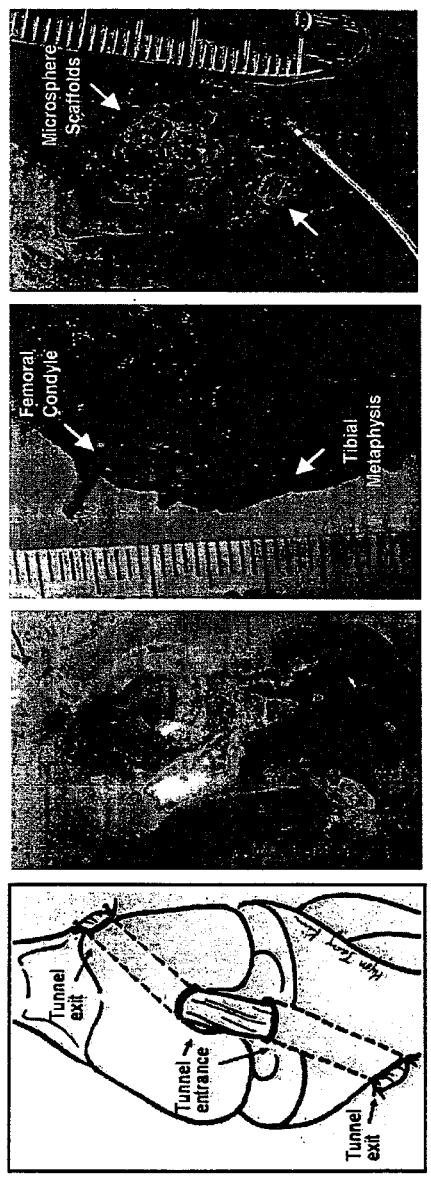

The study will use male athymic rats (Charles River Laboratories, mean weight 300 grams) to demonstrate unilateral ACL reconstruction (Rodeo, 2006) using a flexor digitorum longus tendon graft from the ipsilateral limb, as shown in FIG. 66-I. The rats will be anesthetized with a mixture of ketamine hydrochloride 80 mg/kg and xylazine 5 mg/kg, administered intraperitoneally. Ampicillin 25 mg/kg subcutaneous injection will be used for antibiotic prophylaxis. After appropriate anesthesia, the rat will be prepared for sterile surgery. The flexor digitorum longus tendon will be harvested via a longitudinal incision made on the medial aspect of the distal leg and ankle. The full length of the flexor digitorum longus tendon (average length 20 mm) will be harvested. An incision will be made over the rat knee, and a lateral parapatellar arthrotomy will be performed. The ACL, PCL, MCL, and LCL will be excised. Sectioning these ligaments causes minimal trauma to the knee and is not expected to affect the overall biologic response that will already occur from the knee arthrotomy. Using a needle with outer diameter of 2.5 mm, a bone tunnel will be made in the proximal tibia and the distal femur, entering the joint at the attachment sites of the ACL. We will measure the total length of the femur-tendon-tibia complex to determine the amount of displacement required to apply 1% and 10% strain.

The triphasic scaffold fabricated in the form of the graft collar will be used for implantation. After incorporating the graft collar onto the flexor tendon graft, the graft-scaffold complex will be passed through the bone tunnels to replace the ACL. Both ends of the grafted tendon will be secured to the surrounding periosteum at the extra-articular tunnel exit sites at the distal femur and well as proximal tibia using 4-0 Ethibond suture. Post-operative activity will be controlled using an external fixator that we have designed and fabricated for rat knees (Rodeo, 2006).

Cell Tracking In vivo

Figure 67:
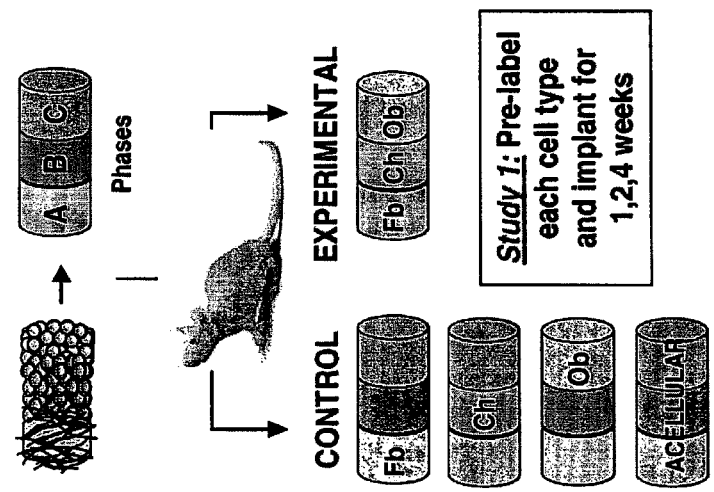
FIG. 67: In vivo model. I. Schematic of reconstruction model. II. Reconstruction using flexor tendon graft. III. Bone tunnel formed in the femur and tibia. IV. Microsphere scaffold inserted into the two bone tunnels.

A further objective of these experiments is to track the three types of implanted cell populations in vivo and to determine their presence over a 4-week implantation period. Cell Labeling—After pre-differentiation of MSCs into Fb, Ch, and Ob, cells will be seeded based on the optimal cell seeding density (cells/cm$^3$) on their designated phase of the triphasic scaffold based on results from Phase I. As shown in FIG. 65, the Fb will be pre-labeled with Vybrant DiD dye (green), Ch with Vybrant DiO (red), and Ob with Vybrant DiI (yellow). All dyes can be purchased from Molecular Probes. The pre-label cells will be seeded on their respective phases of the triphasic scaffold collar, and tricultured for 2 days following established protocols (Spalazzi, 2006). As summarized in FIG. 67, the scaffold (n=3 per group) will be implanted for 1, 2, and 4 weeks, and the presence of the cells will be tracked over time and correlated to the formation of fibrocartilage tissue on the triphasic scaffold. At each time point, the scaffold collar+graft complex will be excised and cryosectioned for fluorescence microscopy (cell imaging) and histological analysis (fibrocartilage formation). Specifically, development of interface-relevant markers will be determined: proteoglycan and mineral deposition, as well as immunohistochemistry for collagen types I, II, III, IX, and X. Acellular scaffolds and unoperated contralateral insertion sites will serve as additional controls. A total of 45 animals (15 per time point) will be needed for this experiment.

In vivo Evaluation for Interface Regeneration

Figure 68:
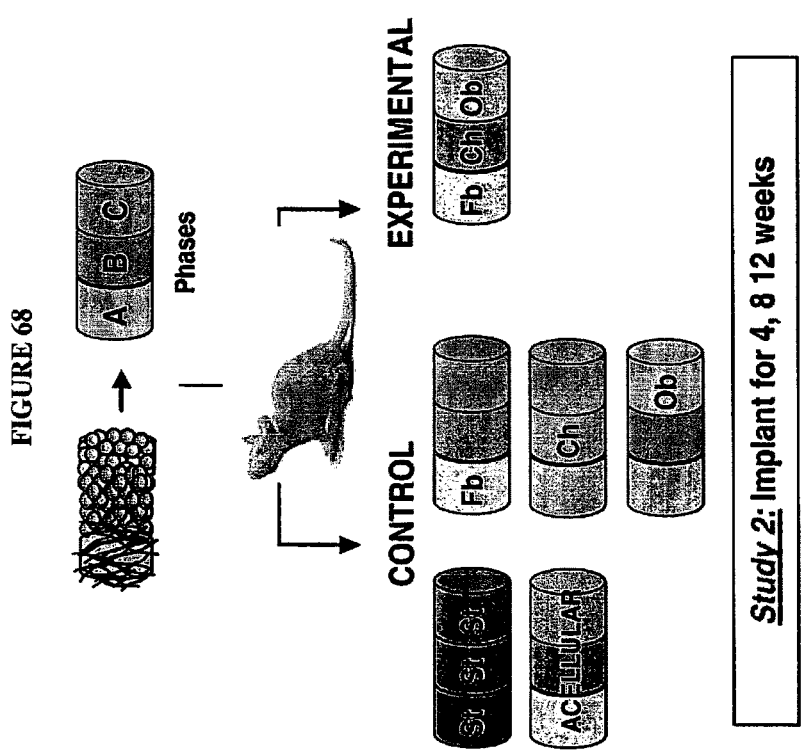
FIG. 68 shows Experimental design for interface regeneration on the tri-cultured triphasic scaffold in an intraarticular ACL reconstruction model.

This experiment further focuses on interface regeneration on the tri-cultured, triphasic scaffold in an intra-articular ACL reconstruction model. Specifically, MSC-derived fibroblasts, chondrocytes and osteoblasts will be seeded on their respective phases of the triphasic scaffold, and cultured in vitro for 2 days (Spalazzi, 2006). The scaffold will be implanted following the experimental design outlined in FIG. 68. Each animal will receive one scaffold (randomly selected) and will be sacrificed at 4, 8, and 12 weeks. Outcomes will be evaluated using histomorphometric, micro-CT, and biomechanical analyses. Quantitative histomorphometric measurements will be made using the Bioquant Image Analysis system (R&M Biometrics, Inc., Nashville, Tenn.) available in the Analytical Microscopy Laboratory (Director, Dr. S. Doty). The implant evaluation methods successfully utilized in the previously described in vivo studies will also be used here. Specifically, the development of a fibrocartilage-like tissue and interfacial markers (n=3) will be determine. Scaffold mechanical properties (n=6) will also be determined over time. Mineralization (total bone mineral content, bone volume fraction, and mineral distribution) will be analyzed by micro-CT prior to mechanical testing, so an additional sample is not needed. A push-out test (Knowles, 1992) will be performed on week 12 samples (tri-culture only, n=6) in order to determine the osteointegration potential of Phase C within the bone tunnel.

A total of 168 male athymic nude rats (54 animals each for weeks 4 & 8, and 60 animals for week 12) will be used in this experiment.

Expected Outcomes

It is anticipated that for the in vivo cell tracking experiment, all three cell types will persist at the implantation site for up to 4 weeks, and that the seeded chondrocytes will contribute to the formation of a fibrocartilage-like region on the interface phase (Phase B) of the triphasic scaffold. For the in vivo evaluation of interface regeneration experiment, it is expected that an interface-like region will form on the scaffold post-ACL reconstruction.

In these experiments, the formation of a fibrocartilage-like tissue on the interface phase of the triphasic scaffold has been focused on for several reasons. The long term role of the scaffold as a graft collar is to induce fibrocartilage formation on the reconstructed graft. After establishing the stability of the triphasic scaffold in the intra-articular model, and the viability of application of controlled mechanical stimulation to induce fibrocartilage formation on the graft, the next stage of the project will focus on the application of controlled chemical stimulation to induce fibrocartilage formation on the graft. For example, phase-specific growth factor delivery can be incorporated to provide chemical stimuli for interface regeneration. It is however critical to first establish the feasibility of the tri-culture, triphasic scaffold in a physiologically relevant intra-articular model.

REFERENCES

The following documents, as well as those cited within this specification, are specifically incorporated by reference to the extent that they provide or teach exemplary methodology, techniques and/or compositions supplemental to those employed herein.

1. Abate, J A, Fadale, P D, Hulstyn, M J & Walsh, W R, (1998) "Initial fixation strength of polylactic acid interference screws in anterior cruciate ligament reconstruction," *Arthroscopy* 14:278-284.
2. Albro, M B, Chahine, N O, Caligaris, M, Wei, V I, Likhitpanichkul, M, Ng, K W, Hung, C T & Ateshian, G A, (2007) "Osmotic loading of spherical gels: a biomimetic study of hindered transport in the cell protoplasm," *J. Biomech. Eng.* 129:503.
3. Allum, R L, (2001) "BASK Instructional Lecture 1: graft selection in anterior cruciate ligament reconstruction," *Knee* 8:69-72.
4. Altman, G H, at al. (2002) "Advanced bioreactor with controlled application of multidimensional strain for tissue engineering," *Journal of Biomechanical Engineering* 124:742-749.
5. Altman, G H, et al., (2002) "Silk matrix for tissue engineered anterior cruciate ligaments,", 23:4131-4141.
6. American Academy of Orthopaedic Surgeons, (1997) "Arthoplasty and Total Joint Replacement Procedures: United States 1990 to 1997," (Report, United States).
7. Anderson, K, et al., (2001) "Augmentation of tendon healing in an intraarticular bone tunnel with use of a bone growth factor," *Am. J Sports Med.* 29:689-698.
8. Badami, A S, Kreke, M R, Thompson, M S, Riffle, J S & Goldstein, A S, (2006) "Effect of fiber diameter on spreading, proliferation, and differentiation of osteoblastic cells on electrospun poly(lactic acid) substrates," *Biomaterials*, 27:596.
9. Badylak, S F (2002) "The extracellular matrix as a nanofiber scaffold for tissue reconstruction," *Semin. Cell Dev. Biol.* 13:377.
10. Baker, B M and Mauck, R L, (2007) "The effect of nanofiber alignment on the maturation of engineered meniscus constructs," *Biomaterials*, 28:1967.
11. Bashur, C A, Dahlgren, L A & Goldstein, A S (2006) "Effect of fiber diameter and orientation on fibroblast morphology and proliferation on electrospun poly(D,L-lactic-co-glycolic acid) meshes," *Biomaterials*, 27:5681.
12. Batycky, R P, Hanes, J, Langer, R & Edwards, D A, (1997) "A theoretical model of erosion and macromolecular drug release from biodegrading microspheres," *Pharmaceutical Sciences* 86:1464-1477.
13. Bellincampi, L D, Closkey, R F, Prasad, R, Zawadsky, J P & Dunn, M G, (1998) "Viability of fibroblast-seeded ligament analogs after autogenous implantation," *J. Orthop. Res.* 16:414-420.
14. Benjamin, M, Evans, E J, CoPP, L, (1986) "The histology of tendon attachments to bone in man," *J Anat.* 149:89-100.
15. Benjamin, M, Evans, E J, Rao, R D, Findlay, J A & Pemberton, D J, (1991) "Quantitative differences in the histology of the attachment zones of the meniscal horns in the knee joint of man," *J. Anat.* 177:127-134.
16. Benjamin, M, Kumai, T, Milz, S, Boszczyk, B M, Boszczyk, A A, Ralphs, J R, (2002) "The skeletal attachment of tendon-tendon "entheses"," *Comp Biochem. Physiol A. Mol. Integr. Physiol.* 133(4):931-945.
17. Benjamin, M, Ralphs, J R (1998) "Fibrocartilage in tendons and ligaments—an adaptation to compressive load," *J. Anat.* 193(Pt 4):481-494.
18. Berg, E E, (1996) "Autograft bone-patella tendon-bone plug comminution with loss of ligament fixation and stability," *Arthroscopy* 12:232-235.
19. Beynnon, B D, et al., (1996) "A sagittal plane model of the knee and cruciate ligaments with application of a sensitivity analysis," *J. Biomech. Eng.* 118:227-239.
20. Beynnon, B D, at al., (1997) "The effect of functional knee bracing on the anterior cruciate ligament in the weightbearing and nonweightbearing knee," *Am. J. Sports Med.* 25:353-359.
21. Beynnon, B D, et al., (2002) "Anterior Cruciate Ligament Replacement: Comparison of Bone-Patellar Tendon-Bone Grafts with Two-Strand Hamstring Grafts," *J Bone Joint Surg Am*, 84-A:1503-1513.
22. Blevins, F T, Djurasovic, M, Flatow, E L, Vogel, K G (1997) "Biology of the rotator cuff tendon," *Orthop. Clin. North Am.* 28(1):1-16.
23. Blickenstaff, K R. Grana, W A & Egle, D, (1997) "Analysis of a semitendinosus autograft in a rabbit model," *Am. J. Sports Med.* 25:554-559.
24. Bolton, C W & Bruchman, W C, (1985) "The GORE-TEX expanded polytetrafluoroethylene prosthetic ligament. An in vitro and in vivo evaluation," *Clin. Orthop.* 202-213.
25. Bonfield, W, (1988) "Composites for bone replacement," *J. Biomed. Eng.* 10:522-526.
26. Borden, M, Attawia, M, Khan, Y & Laurencin, C T, (2002) "Tissue engineered microsphere-based matrices for bone repair: design and evaluation," *Biomaterials*, 23:551-559.
27. Boskey, A L, et al., (1996) "The mechanism of beta-glycerophosphate action in mineralizing chick limb-bud mesenchymal cell cultures," *J. Bone Min. Res.* 11:1694-1702.
28. Brady, G A, Eisinger, M, Arnoczky, S P & Warren, R F, (1988) "In vitro fibroblast seeding of prosthetic anterior cruciate ligaments. A preliminary study," *Am. J. Sports Med.* 16:203-208.

29. Brand, J, Jr., Weiler, A, Caborn, D N, Brown, C H, Jr. & Johnson, D L (2000) "Graft fixation in cruciate ligament reconstruction," *Am. J. Sports Med.* 28:761-774.
30. Brody, G A, Eisinger, M, Arnoczky, S P & Warren, R F, (1988) "In vitro fibroblast seeding of prosthetic anterior cruciate ligaments. A preliminary study," *Am. J. Sports Med.* 16:203-208.
31. Bromage, T G, Smolyar, I, Doty, S B, Holton, E & Zuyev, A N, (1998) "Bone growth rate and relative mineralization density during space flight," *Scanning* 20:238-239.
32. Burkart, A, Imhoff, A B & Roscher, E, (2000) "Foreign-body reaction to the bioabsorbable suretac device," *Arthroscopy,* 16:91-95.
33. Butler, D L, Goldstein, S A & Guilak, F, (2000) "Functional tissue engineering: the role of biomechanics," *J. Biomech. Eng.* 122:570-575.
34. Chen, C H, et al., (2003) "Enveloping the tendon graft with periosteum to enhance tendon-bone healing in a bone tunnel: A biomechanical and histologic study in rabbits," *Arthroscopy* 19:290-296.
35. Cheung, H S & McCarty, D J, (1985) "Mitogenesis induced by calcium-containing crystals. Role of intracellular dissolution," *Exp. Cell Res.* 157:63-70.
36. Christenson, E M, et al. (2007) "Nanobiomaterial applications in orthopedics," *J. Orthop. Res.* 25:11-22.
37. Chun I, et al. (1995) "Fine Fibres Spun By Electrospinning Process From Polymer Solution And Polymer Melts." Dissertation, The University of Akron.
38. Clark, J M & Sidles, J A, (1990) "The interrelation of fiber bundles in the anterior cruciate ligament," *J. Orthop. Res.* 8:180-188.
39. Codman, E, (1934) "The Shoulder, Rupture of the Supraspinatus Tendon and Other Lesions In or About the Subacromial Bursa," Thomas Todd, BostoN.
40. Cole, B J, ElAttrache, N S & Anbari, A, (2007) "Arthroscopic rotator cuff repairs: an anatomical and biomechanical rationale for different suture-anchor repair configurations," *Arthroscopy* 23:662-669.
41. Coons, D A and Alan, B F, (2006) "Tendon graft substitutes-rotator cuff patches," *Sports Med. Arthrosc.* 14:185-190.
42. Cooper J A at al., (2005) "Fiber-based tissue-engineered scaffold for ligament replacement: design considerations and in vitro evaluation" *Biomaterials,* 26(13):1523-1532.
43. Cooper, J A, (2002) "Design, optimization and in vivo evaluation of a tissue-engineered anterior cruciate ligament replacement," Drexel University (Thesis/Dissertation) (2002).
44. Cooper, J A, Lu, H H & Laurencin, C T, (2000) "Fiber-based tissue engineering scaffold for ligament replacement: design considerations and in vitro evaluation," Proceedings of 5th World Biomaterial Congress, 208 (Abstract).
45. Costa, K D, Lee, E J & Holmes, J W, (2003) "Creating alignment and anisotropy in engineered heart tissue: role of boundary conditions in a model three-dimensional culture system," *Tissue Eng.* 9:567-577.
46. Courtney, T, Sacks, M S, Stankus, J, Guan, J & Wagner, W R, (2006) "Design and analysis of tissue engineering scaffolds that mimic soft tissue mechanical anisotropy," *Biomaterials,* 27:3631-3638.
47. Currey, J D, (1988) "The effect of porosity and mineral content on the Young's modulus of elasticity of compact bone," *J Biomech,* 21(2):131-139.
48. Curtis, A and Wilkinson, C, (1997) "Topographical control of cells," *Biomaterials,* 18:1573-1583.
49. Daniel, D M, et al., (1994) "Fate of the ACL-injured patient. A prospective outcome study," *Am. J. Sports Med.* 22:632-644.
50. Deitzel et al., (2001) "Controlled deposition of electrospun poly(ethylene oxide) fibers," *Polymer,* 42(19):8163-8170.
51. Deitzel at al., (2002) "Electrospinning of Nanofibers with Specific Surface Chemistry," *Polymer,* 43(3): 1025-1029.
52. Dejardin, L M, Arnoczky, S P, Ewers, B J, Haut, R C & Clarke, R B (2001) "Tissue engineered rotator cuff tendon using porcine small intestine submucosa. Histologic and mechanical evaluation in dogs," *Am. J. Sports Med.* 29:175-184.
53. Delon, I & Brown, N H (2007) "Integrins and the actin cytoskeleton," *Curr. Opin. Cell Biol.* 19:43-50.
54. DeOrio, J K and Cofield, R H, (1984) "Results of a second attempt at surgical repair of a failed initial rotator-cuff repair," *J. Bone Joint Surg. Am.* 66:563.
55. Derwin, K A, Baker, A R, Spragg, R K, Leigh, D R & Iannotti, J P, (2006) "Commercial extracellular matrix scaffolds for rotator cuff tendon repair. Biomechanical, biochemical, and cellular properties," *J. Bone Joint Surg. Am.* 88:2665.
56. Drost, M R, Willems, P, Snijders, H, Huyghe, J M, Janssen, J D & Huson, A, (1995) "Confined compression of canine annulus fibrosus under chemical and mechanical loading," *J. Biomech. Eng.* 11: 390.
57. Ducheyne, P, (1987) "Bioceramics: material characteristics versus in vivo behavior," *J. Biomed. Matls. Res.* 21:219-236.
58. Dunn, M G, Liesch, J B, Tiku, M L, Maxian, S H & Zawadsky, J P, (1994) "The Tissue Engineering Approach to Ligament Reconstruction," *Matls. Res. Soc.* 331:13-18.
59. El-Amin, S F, et al., (2001) "Human osteoblast integrin expression on degradable polymeric materials for tissue engineered bone," *J. Orthop. Res,* 20(1):20-28.
60. Engelmayr, G C, Jr., Papworth, G D, Watkins, S C, Mayer, J E, Jr. & Sacks, M S, (2006) "Guidance of engineered tissue collagen orientation by large-scale scaffold microstructures," *J. Biomech.* 39:1819.
61. Erben, R G, (1997) "Embedding of Bone Samples in Methylmethacrylate: An Improved Method Suitable for Bone Histomorphometry, Histochemistry, and Immunohistochemistry" *J. Histochem. Cytochem.* 45:307-314.
62. Ferguson, V L, Bushby, A J., Boyde, A, (2003) "Nanomechanical properties and mineral concentration in articular calcified cartilage and subchondral bone," *J. Anat.* 203(2):191-202.
63. Fleming, B, Beynnon, B, Howe, J, McLeod, W & Pope, M, (1992) "Effect of tension and placement of a prosthetic anterior cruciate ligament on the anteroposterior laxity of the knee," *J. Orthop. Res.* 10:177-186.
64. Fleming, B C, Abate, J A, Peura, G D & Beynnon, B D, (2001) "The relationship between graft tensioning and the anterior-posterior laxity in the anterior cruciate ligament reconstructed goat knee," *J. Orthop. Res.* 19:841-844.
65. Fong et al., (1999) "Beaded nanofibers formed during electrospinning" *Polymer,* 40:4585-4592.
66. Formhals, A, (1934) "Process and Apparatus for Preparing Artificial Threads," U.S. Pat. No. 1,975,504, issued October, 1934.
67. Fridrikh et al., (2003) "Controlling the fiber diameter during electrospinning" *Physical Review Letter,* 90:144502.
68. Fu, F H, Bennett, C H, Ma, C B, Menetrey, J & Lattermann, C, (2000) "Current trends in anterior cruciate 68. ligament reconstruction. Part II. Operative procedures and clinical correlations," *Am. J. Sports Med.* 28:124-130.
69. Fujihara, K, Kotaki, M & Ramakrishna, S (2005) "Guided bone regeneration membrane made of polycaprolactone/calcium carbonate composite nanofibers," *Biomaterials,* 26:4139.
70. Fujikawa, K, Iseki, F & Seedhom, B B, (1989) "Arthroscopy after anterior cruciate reconstruction with the Leeds-Keio ligament," *J. Bone Joint Surg. Br.* 71:566-570.
71. Fung, Y C, (1972) "Stress-strain-history relations of soft tissues in simple elongation. In Biomechanics: Its Foundations and Objectives," Fung, Y C, Perrone, N, Anliker, M, eds., Prentice-Hall: San Diego, pp. 181-208.
72. Galatz, L M, Ball, C M, Teefey, S A, Middleton, M D & Yamaguchi, K, (2004) "The outcome and repair integrity of completely arthroscopically repaired large and massive rotator cuff tears," *J. Bone Joint Surg. Am.* 86-A:219.
73. Gao, J & Messner, K, (1996) "Quantitative comparison of soft tissue-bone interface at chondral ligament insertions in the rabbit knee joint," *J. Anat.* 188:367-373.
74. Gao, J, Rasanen, T, Persliden, J & Messner, K, (1996) "The morphology of ligament insertions after failure at low strain velocity: an evaluation of ligament entheses in the rabbit knee," *J. Anat.* 189:127-133.
75. Garcia, A J (2005) "Get a grip: integrins in cell-biomaterial interactions," *Biomaterials,* 26:7525.
76. Garreta, E, Gasset, D, Semino, C & Borros, S, (2007) "Fabrication of a three-dimensional nanostructured biomaterial for tissue engineering of bone," *Biomol. Eng.* 24:75.
77. Gartsman, G M (2001) "All arthroscopic rotator cuff repairs," *Orthop. Clin. North Am.* 32:501.
78. Gartsman, G M, (1997) "Massive, irreparable tears of the rotator cuff. Results of operative debridement and subacromial decompression," *J. Bone Joint Surg. Am.* 79:715.
79. Gazielly, D F, Gleyze, P & Montagnon, C (1994) "Functional and anatomical results after rotator cuff repair," *CHn. Orthop. Relat. Res*, (304):43-53.
80. Gerber, C, Schneeberger, A G, Perren, S M & Nyffeler, R W, (1999) "Experimental rotator cuff repair. A preliminary study," *J. Bone Joint Surg. Am.* 81:1281.
81. Glass-Brudzinski, J, Perizzolo, D & Brunette, D M (2000) "Effects of substratum surface topography on the organization of cells and collagen fibers, in collagen gel cultures," *J. Biomed. Mater. Res.* 61:608.
82. Gotlin, R S & Huie, G, (2000) "Anterior cruciate ligament injuries. Operative and rehabilitative options," *Phys. Med. Rehabil. Clin. N. Am.* 11:895-928.
83. Goulet, F, et al., (2000) "Principles of Tissue Engineering," Lanza, R P, Langer, R & Vacanti, J P (eds.), pp. 639-645 Academic Press.
84. Grana, W A, Egle, D M, Mahnken, R & Goodhart, C W, (1994) "An analysis of autograft fixation after anterior cruciate ligament reconstruction in a rabbit model," *Am. J. Sports Med.* 22:344-351.
85. Gregoire, M, Orly, I, Kerebel, L M & Kerebel, B, (1987) "In vitro effects of calcium phosphate biomaterials on fibroblastic cell behavior," *Biol. Cell,* 59:255-260.
86. Harner, C D, et al., (1999) "Quantitative analysis of human cruciate ligament insertions," *Arthroscopy* 15:741-749 (1999).
87. Hench, L L, (1991) "Bioceramics: from concept to clinic," *J. Am. Cera. Soc.* 74(7):1487-1510.
88. Hynes, R O (1992) "Integrins: versatility, modulation, and signaling in cell adhesion," *Cell,* 69:11.
89. Hynes, R O (2002) "Integrins: bidirectional, allosteric signaling machines," *Cell,* 110:673.
90. Itoi, E, Berglund, L J, Grabowski, J J, Schultz, F M, Growney, E S, Morrey, B F & An K N (1995) "Tensile properties of the supraspinatus tendon," *J. Orthop. Res.* 13:578.
91. Jackson, D W, (1992) American Academy of Orthopaedic Surgeon Bulletin, 40:10-11.
92. Jackson, D W, et al., (1991) *Trans. Orhtop. Res. Soc.* 16:208 (Abstract).
93. Jackson, D W, et al., (1993) "A comparison of patellar tendon autograft and allograft used for anterior cruciate ligament reconstruction in the goat model," *Am. J. Sports Med.* 21:176-185.
94. Jackson, D W, Grood, E S, Arnoczky, S P, Butler, D L & Simon, T M, (1987) "Cruciate reconstruction using freeze dried anterior cruciate ligament allograft and a ligament augmentation device (LAD). An experimental study in a goat model," *Am. J. Sports Med.* 15:528-538.
95. Jiang, J, Nicoll, S B & Lu, H H, (2003) "Effects of Osteoblast and Chondrocyte Co-Culture on Chondrogenic and Osteoblastic Phenotype In vitro," *Trans. Orhtop. Res. Soc.* 49 (Abstract).
96. Johnson, R J, (1982) "The anterior cruciate: a dilemma in sports medicine," *Int. J. Sports Med.* 3:71-79.
97. Joshi, M D, Suh, J K, Marui, T & Woo, S L (1995) "Interspecies variation of compressive biomechanical properties of the meniscus," *J. Biomed. Mater. Res.* 29:823.
98. Karsenty, G. (1965) "A formaldehyde-glutaraldehyde fixative of high osmolality for use in electron microscopy," *J. Cell. Biol.* 27:137A.
99. Kawamura S et al., (2005) ORS.
100. Kim et al., (2003) *Biomaterials.*
101. Knowles J C, et al., (1992) *Biomaterials,* 13(8):491-496.
102. Koike, et al., (2006) "Delay of supraspinatus repair by up to 12 weeks does not impair enthesis formation: A quantitative histologic study in rabbits." *Journal of Orthopaedic Research.* 24(2):202-210.
103. Koike, Y, Trudel, G, Uhthoff, H K, (2005) "Formation of a new enthesis after attachment of the supraspinatus tendon: A quantitative histologic study in rabbits," *J. Orthop. Res.* 23(6):1433-1440.
104. Kumagai, J, Sarkar, K, Uhthoff, H K, Okawara, Y, Ooshima, A. (1994) "Immunohistochemical distribution of type I, II and ITI collagens in the rabbit supraspinatus tendon insertion," *J. Anat.* 185(Pt. 2):279-284.
105. Kurosaka, M, Yoshiya, S & Andrish, J T, (1987) "A biomechanical comparison of different surgical techniques of graft fixation in anterior cruciate ligament reconstruction," *Am. J Sports Med.* 15:225-229.
106. Kurzweil, P R, Frogameni, A D & Jackson, D W, (1995) "Tibial interference screw removal following anterior cruciate ligament reconstruction," *Arthroscopy* 11L:289-291.
107. Kwan, M K, Wayne, J S, Woo, S L, Field, F P, Hoover, J & Meyers, M, (1989) "Histological and biomechanical assessment of articular cartilage from stored osteochondral shell allografts," *J. Orthop. Res.* 7:637.
108. Langley, S M, Chai, P J, Miller, S E, Mault, J R, Jaggers, J J, Tsui, S S, Lodge, A J, Lefurgey, A & Ungerleider, R M. (1999) "Intermittent perfusion protects the brain during deep hypothermic circulatory arrest," *Ann. Thorac. Surg.* 68:4.
109. Lannotti, J P, Codsi, M J, Kwon, Y W, Derwin, K, Ciccone, J & Brems, J J (2006) "Porcine small intestine submucosa augmentation of surgical repair of chronic two-tendon rotator cuff tears. A randomized, controlled trial," *J. Bone Joint Surg. Am.* 88:1238.
110. Larson, R P, (1994) "The Crucial Ligaments: Diagnosis and Treatment of Ligamentous Injuries About the Knee," John, A. Jr. & Feagin, J. A. (eds.), pp. 785-796 Churchill Livingstone, N.Y.
111. Latridis, J C, Setton, L A, Foster, R J, Rawlins, B A, Weidenbaum, M & Mow, V C (1998) "Degeneration affects the anisotropic and nonlinear behaviors of human anulus fibrosus in compression," *J. Biomech.* 31:535.
112. Lee, C H, Shin, H J, Cho, I H, Kang, Y M, Kim, I A, Park, K D & Shin, J W (2005) "Nanofiber alignment and direction of mechanical strain affect the ECM production of human ACL fibroblast," *Biomaterials* 26:1261.
113. LeRoux, M A and Setton, L A (2002) "Experimental and biphasic FEM determinations of the material properties and hydraulic permeability of the meniscus in tension," *J. Biomech. Eng.* 124:315.
114. Li, W J, Danielson, K G, Alexander, P G & Tuan, R S "Biological response of chondrocytes cultured in three-dimensional nanofibrous poly(epsilon-caprolactone) scaffolds," *J. Biomed. Mater. Res. A*67:1105.
115. Li, W J, Laurencin, C T, Caterson, E J, Tuan, R S & Ko, F K (2002) "Electrospun nanofibrous structure: a novel scaffold for tissue engineering," *J. Biomed. Mater. Res.* 60:613.
116. Li, W J, Mauck, R L, Cooper, J A, Yuan, X & Tuan, R S (2007) "Engineering controllable anisotropy in electrospun biodegradable nanofibrous scaffolds for musculoskeletal tissue engineering," *J. Biomech.* 40:1686.
117. Li, W J, Tuli, R, Okafor, C, Derfoul, A, Danielson, K G, Hall, D J & Tuan, R S (2005) "A three-dimensional nanofibrous scaffold for cartilage tissue engineering using human mesenchymal stem cells," *Biomaterials* 26:599.
118. Liu, S H, et al., (1997) "Morphology and matrix composition during early tendon to bone healing," *Clinical Orthopaedics & Related. Research.* 253-260.
119. Loeser, R F, Sadiev, S, Tan, L & Goldring, M B (2000) "Integrin expression by primary and immortalized human chondrocytes: evidence of a differential role for $\alpha 1\beta 1$ and $\alpha 2\beta 1$ integrins in mediating chondrocyte adhesion to types II and VI collagen," *Osteoarthritis. Cartilage.* 8:96.
120. Loh, J C, et al., (2003) "Knee stability and graft function following anterior cruciate ligament reconstruction: Comparison between 11 o'clock and 10 o'clock femoral tunnel placement," *Arthroscopy,* 19:297-304.
121. Lu, H H, Cooper, J A, Jr., Manuel, S, Freeman, J W, Attawia, M A, Ko, F R & Laurencin, C T (2005) "Anterior cruciate ligament regeneration using braided biodegradable scaffolds: in vitro optimization studies," *Biomaterials* 26:4805.
122. Lu, H H, Cooper, J A, Ko, F A, Attawia, M A & Laurencin, C T, (2001)"Effect of polymer scaffold composition on the morphology and growth of anterior cruciate ligaments cells," *Society for Biomaterials Proceedings* (Abstract).
123. Lu, H H, El Amin, S F, Scott, K D & Laurencin, C T, "Three dimensional, bioactive, biodegradable, polymer bioactive glass composite scaffolds with improved mechanical properties support collagen synthesis and mineralization of human osteoblast-like cells in vitro," *J. Biomed. Matls. Res.* 64A:465-474.
124. Lu, H H, et al., (2003) "Evaluation of Optimal Parameters in the Co-Culture of Human Anterior Cruciate Ligament Fibroblasts and Osteoblasts for Interface Tissue Engineering," ASME 2003 Summer Bioengineering Conference (Abstract).
125. Lu, H H, Pollack, S R & Ducheyne, P, "45S5 bioactive glass surface charge variations and the formation of a surface calcium phosphate layer in a solution containing fibronectin," *J. Biomed. Matls. Res.* 54:454-461.
126. Lu, H H, Pollack, S R & Ducheyne, P, "Temporal zeta potential variations of 45S5 bioactive glass immersed in an electrolyte solution," *J. Biomed. Matls. Res.* 51:80-87.
127. Ma, Z, Kotaki, M, Inai, R & Ramakrishna, S (2005) "Potential of nanofiber matrix as tissue engineering scaffolds" *Tissue Eng.* 11:101.
128. Mansat, P, Cofield, R H, Kersten, T E & Rowland, C M (1997) "Complications of rotator cuff repair. Orthop," *Clin. North Am.* 28:205.
129. Markolf, K L, et al., (2002) "Effects of femoral tunnel placement on knee laxity and forces in an anterior cruciate ligament graft," *J. Orthop. Res.* 20:1016-1024.
130. Matthews, J A, Wnek, G E, Simpson, D G & Nowlin, G L (2002) "Electrospinning of Collagen Nanofibers," *Biomacromolecules,* 3:232.
131. Matthews, L S, Soffer, S R, (1989) "Pitfalls in the use of interference screws for anterior cruciate ligament reconstruction: brief report," *Arthroscopy,* 5:225-226.
132. Matyas, J R, Anton, M G, Shrive, N G & Frank, C B, (1995)"Stress governs tissue phenotype at the femoral insertion of the rabbit MCL," *J. Biomech.* 28:147-157.
133. Mauney J R, et al., (2005) "In vitro and in vivo evaluation of differentially demineralized cancellous bone scaffolds combined with human bone marrow stromal cells for tissue engineering" *Biomaterials* 26(16):3173-3185.
134. Mazzocca, A D, Millett, P J, Guanche, C A, Santangelo, S A & Arciero, R A (2005) "Arthroscopic single-row versus double-row suture anchor rotator cuff repair." *Am. J. Sports Med.* 33:1861.
135. McCarthy, D M, Tolin, B S, Schwendeman, L, Friedman, M J & Woo, S L, (1993) "The Anterior Cruciate Ligament: Current and Future Concepts," Douglas, W. & M D Jackson (eds.) Raven Press, New York.
136. Meinel L, at al., (2004) *Biotechnol Bioeng,* 88:379-391.
137. Messner, K, (1997) "Postnatal development of the cruciate ligament insertions in the rat knee. Morphological evaluation and immunohistochemical study of collagens types I and II," *Acta Anatomica,* 160:261-268.
138. Moffat K L, et al., (2005) ISTL-V.
139. Moffat, et al. (2008) "Characterization of the structure-function relationship at the ligament-to-bone interface." PNAS. 105(23):7947-7952.
140. Moffat, K L, Sun, W S, Chahine, N O, Pena, P E, Doty, S B, Hung, C T, Ateshian, G A, Lu, H H, (2006) "Characterization of the Mechanical Properties and Mineral Distribution of the Anterior Cruciate Ligament-to-Bone Insertion Site," *Conf. Proc. IEEE Eng. Med. Biol. Soc.* 1:2366-2369.
141. Moore, P B & Dedman, J R., (1982) "Calcium binding proteins and cellular regulation," *Life Sci.* 31:2937-2946.
142. Moreau J E, et al., (2005) *J Orthop Res,* 23:164-174.
143. Murugan, R, & Ramakrishna, S (2007) "Design strategies of tissue engineering scaffolds with controlled fiber orientation," *Tissue Eng.* 13:1845.
144. Nerurkar, N L, Elliott, D M & Mauck, R L, (2007) "Mechanics of oriented electrospun nanofibrous scaffolds for annulus fibrosus tissue engineering," *J. Orthop. Res.* 25:1018.

145. Nicoll, S B, Wedrychowska, A, Smith, N R & Bhatnagar, R S, (2001) "Modulation of proteoglycan and collagen profiles in human dermal fibroblasts by high density micromass culture and treatment with lactic acid suggests change to a chondrogenic phenotype," *Connect. Tissue Res.* 42:59-69.

146. Niyibizi, C, Sagarrigo, V C, Gibson, G & Kavalkovich, K,
(1996) "Identification and immunolocalization of type X collagen at the ligament-bone interface," *Biochem. Biophys. Res. Commun.* 222:584-589.

147. Noyes, F R & Barber-Westin, S D, (1996) "Revision anterior cruciate ligament surgery: experience from Cincinnati," *Clin. Orthop.* 116-129).

148. Noyes, F R, Mangine, R E & Barber, S, (1987) "Early knee motion after open and arthroscopic anterior cruciate ligament reconstruction," *Am. J. Sports Med.* 15:149-160.

149. Noyes, F R, Mangine, R E & Barber, S, (1987) "Early knee motion after open and arthroscopic anterior cruciate ligament reconstruction," *Am. J. Sports Med.* 15:149-160.

150. O'Brien, F J, Harley, B A, Waller, M A, Yannas, I V, Gibson, L J & Prendergast, P J (2007) "The effect of pore size on permeability and cell attachment in collagen scaffolds for tissue engineering," *Technol. Health Care,* 15:3.

151. Ozaki, J, Fujimoto, S, Masuhara, K, Tamai, S & Yoshimoto, S (1986) "Reconstruction of chronic massive rotator cuff tears with synthetic materials," *CHn. Orthop. Relat. Res.* (202):173-83.

152. Panni, A S, Milano, G, Lucania, L & Fabbriciani, C, (1997)
"Graft healing after anterior cruciate ligament reconstruction in rabbits," *Clin. Orthop.* 203-212.

153. Park, M C, Cadet, E R, Levine. W N, Bigliani, L U & Ahmad, C S (2005) "Tendon-to-bone pressure distributions at a repaired rotator cuff footprint using transosseous suture and suture anchor fixation techniques," *Am. J. Sports Med.* 33:1154.

154. Park, M C, Tibone, J E, ElAttrache, N S, Ahmad, C S, Jun, B J & Lee, T Q, (2007) "Part II: Biomechanical assessment for a footprint-restoring transosseous-equivalent rotator cuff repair technique compared with a double-row repair technique," *J. Shoulder Elbow Surg.* 16:469.

155. Pena, F, Grontvedt, T, Brown, G A, Aune, A K & Engebretsen, L, (1996) "Comparison of failure strength between metallic and absorbable interference screws. Influence of insertion torque, tunnel-bone block gap, bone mineral density, and interference," *Am. J. Sports Med.* 24:329-334.

156. Petersen, W & Tillmann, B, (1999) "Structure and vascularization of the cruciate ligaments of the human knee joint," *Anat. Embryol. (Berl).* 200:325-334.

157. Pham, Q P, Sharma, U & Mikos, A G (2006) "Electrospinning of polymeric nanofibers for tissue engineering applications: a review," *Tissue Eng.* 12:1197.

158. Pham, Q P, Sharma, U & Mikos, A G, (2006) "Electrospun poly(epsilon-caprolactone) microfiber and multilayer nanofiber/microfiber scaffolds: characterization of scaffolds and measurement of cellular infiltration," *Biomacromolecules,* 7:2796.

159. Pittenger M F, et al., (1999) *Science,* 284:143-147.

160. Post, M, (1985) "Rotator cuff repair with carbon filament. A preliminary report of five cases," *Clin. Orthop. Relat. Res.* (196):154-158.

161. Radhakrishnan, P, Lewis, N T, Mao, J J, (2004) "Zone-specific micromechanical properties of the extracellular matrices of growth plate cartilage," *Ann. Biomed. Eng.* 32(2):284-291.

162. Reneker, D H and Chun, I, (1996) "Nanometer diameter fibres of polymer, produced by electrospinning," *Nanotechnology,* 7:216.

163. Robertson, D B, Daniel, D M & Biden, E, (1986) "Soft tissue fixation to bone," *Am. J. Sports Med.* 14:398-403.

164. Rodeo, S A, Arnoczky, S P., Torzilli, P A, Hidaka, C. Warren, R F, (1993) "Tendon-healing in a bone tunnel. A biomechanical and histological study in the dog." *J Bone Joint Surg Am.* 75(12):1795-1803.

165. Rodeo, S A, et al., (2006) ORS, 2006.

166. Rodeo, S A, Suzuki, K, Deng, X H, Wozney, J & Warren, R P, (1999) "Use of recombinant human bone morphogenetic protein-2 to enhance tendon healing in a bone tunnel," *Am. J. Sports Med.* 27:476-488.

167. Rokito, A S, Zuckerman; J D, Gallagher, M A & Cuomo, F, (1996) "Strength after surgical repair of the rotator cuff," *J. Shoulder Elbow Surg.* 5:12.

168. Romeo, A A, Hang, D W, Bach, B R, Jr. & Shott, S (1999) "Repair of full thickness rotator cuff tears. Gender, age, and other factors affecting outcome," *CHn. Orthop. Relat. Res.* (367):243-55.

169. Safran, M R, & Harner, C D, (1996) "Technical considerations of revision anterior cruciate ligament surgery," *Clin. Orthop.* 50-64.

170. Sagarriga, V C, Kavalkovich, K, Wu, J & Niyibizi, C, (1996) "Biochemical analysis of collagens at the ligament-bone interface reveals presence of cartilage-specific collagens," *Arch. Biochem. Biophys.* 328:135-142.

171. Sahoo, S, Ouyang, H, Goh, J C, Tay, T E & Toh, S L, (2006) "Characterization of a novel polymeric scaffold for potential application in tendon/ligament tissue engineering." *Tissue Eng.* 12:91.

172. Sano, et al. (2002) "Experimental fascial autografting for the supraspinatus tendon defect: Remodeling process of the grafted fascia and the insertion into bone." Journal of Shoulder and Elbow Surgery. 11(2):166-173.

173. Scapinelli, R & Little, K. (1970) "Observations on the mechanically induced differentiation of cartilage from fibrous connective tissue," *J. Pathol.* 101:85-91.

174. Schafer, et al., (2000) "In vitro generation of osteochondral composites," *Biomaterials,* 21:2599-2606.

175. Schafer, et al., (2002) "Tissue-engineered composites for the repair of large osteochondral defects," *Arthritis Rheum.* 46:2524-2534.

176. Schlegel, T F, Hawkins, R J, Lewis, C W, Motta, T & Turner, A S, (2006) "The effects of augmentation with Swine small intestine submucosa on tendon healing under tension: histologic and mechanical evaluations in sheep." *Am. J. Sports Med.* 34:275.

177. Sclamberg, S G, Tibone, J E, Itamura, J M & Kasraeian, S,
(2004) "Six-month magnetic resonance imaging follow-up of large and massive rotator cuff repairs reinforced with porcine small intestinal submucosa." *J. Shoulder Elbow Surg.* 13:538.

178. Shellock, F G, Mink, J H., Curtin, S & Friedman, M J, (1992) "M R imaging and metallic implants for anterior cruciate ligament reconstruction: assessment of ferromagnetism and artifact," *J. Magn. Reson. Imaging,* 2:225-228.

179. Shin et al., (2001) "Experimental characterization of electrospinning: the electrically forced jet and instabilities," *Polymer,* 42(25):09955-09967.

180. Singhvi, R, Kumar, A, Lopez, G P, Stephanopoulos, G N, Wang, D I, Whitesides, G M & Ingber, D E, (1994) "Engineering cell shape and function." *Science*, 264:696.
181. Sittinger, et al., (1994) "Engineering of cartilage tissue using bieresorbable polymer carriers in perusion culture," *Biomaterials*, 15(6):451-456.
182. Soslowsky, L J, Thomopoulos, S, Tun, S, Flanagan, C L, Keefer, C C, Mastaw, J & Carpenter, J E, (2000) "Neer Award 1999. Overuse activity injures the supraspinatus tendon in an animal model: a histologic and biomechanical study." *J. Shoulder Elbow Surg.* 9:79.
183. Spalazzi J P, et al., (2006) "Development of Controlled Matrix Heterogeneity on a Triphasic Scaffold for Orthopedic Interface Tissue Engineering" Tissue Engineering, 12(12):3497-3508, 2006.
184. Spalazzi J P, et al., (2006) "Elastographic Imaging of Strain Distribution In The Anterior Cruciate Ligament and at the Ligament-Bone Insersions" *J Orthop Res*, 24(10): 2001-2010.
185. Spalazzi, J P, Dionisio, K L, Jiang, J & Lu, H H, (2003) "Chondrocyte and Osteoblast Interaction on a Degradable Polymer Ceramic Scaffold," ASME 2003 Summer Bioengineering Conference (Abstract)(2003).
186. Spalazzi, J P, Vyner, M C, Jacobs, M T, Moffat, E L, Rich, C G & Lu, H H, (2008) "Mechanoactive Scaffold Induces Tendon Remodeling and Expression of Fibrocartilage Markers." *CHn. Orthop. Relat. Res.* 466(8):1938-1948.
187. Stankus, J J, Guan, J, Fujimoto, K & Wagner, W R, (2006) "Microintegrating smooth muscle cells into a biodegradable, elastomeric fiber matrix." *Biomaterials*, 27:735.
188. Steiner, M E, Hecker, A T, Brown, C H, Jr. & Hayes, W C, (1994)"Anterior cruciate ligament graft fixation. Comparison of hamstring and patellar tendon grafts," *Am. J. Sports Med.* 22:240-246.
189. Sui, G, Yang, X, Mei, F, Hu, X, Chen, G, Deng, X, & Ryu, S, (2007) "Poly-L-lactic acid/hydroxyapatite hybrid membrane for bone tissue regeneration," *J. Biomed Mater Res A.* 82(2):445-54.
190. Teixeira, A I, Abrams, G A, Bertics, P J, Murphy, C J & Nealey, P F, (2003) "Epithelial contact guidance on well-defined micro- and nanostructured substrates." *J. Cell. Sci.* 116:1881.
191. Tempelhof, S, Rupp, S & Seil, R, (1999) "Age-related prevalence of rotator cuff tears in asymptomatic shoulders." *J. Shoulder Elbow Surq.* 8:296.
192. Thomas, N P, Turner, I G & Jones, C B, (1987) "Prosthetic anterior cruciate ligaments in the rabbit. A comparison of four types of replacement," *J. Bone Joint Surg. Br.* 69:312-316.
193. Thomopoulos, S, et al., (2002) "The localized expression of extracellular matrix components in healing tendon insertion sites: an in situ hybridization study," *J. Orthop. Res.* 20:454-463.
194. Thomopoulos, S, Fomovsky, G M, Chandran, P L & Holmes, J W, (2007) "Collagen fiber alignment does not explain mechanical anisotropy in fibroblast populated collagen gels." *J. Biomech. Eng.* 129:642.
195. Thomopoulos, S, Marquez, J P, Weinberger, B, Birman, V & Genin, G M, (2006) "Collagen fiber orientation at the tendon to bone insertion and its influence on stress concentrations." *J. Biomech.* 39:1842.
196. Thomopoulos, S, Williams, G R, Gimbel J A, Favata, M & Soslowsky, L J, (2003) "Variations of biomechanical, structural, and compositional properties along the tendon to bone insertion site." *J. Orthop. Res.* 21:413.
197. Vitale, M A, Vitale, M G, Zivin, J G, Braman, J P, Bigliani, L U & Flatow, E L, (2007) "Rotator cuff repair: an analysis of utility scores and cost-effectiveness. J. Shoulder." *Elbow. Surg.* 16:181.
198. Wang I N E and Lu H H, ORS, 2005.
199. Wang I N E, et al., (2006) "Age-dependent changes in matrix composition and organization at the ligament-to-bone insertion," *J Orthop Res*, 24(8):1745-1755.
200. Wang, I N E, Shan, J, Choi, R, Oh, S, Kepler, C K, Chen, F H, Lu, H H, (2007) "Role of osteoblast-fibroblast interactions in the formation of the ligament-to-bone interface." *J Orthop Res*, 25(12):1609-1620.
201. Wang, J H, Jia, F, Gilbert, T W & Woo, S L, (2003) "Cell orientation determines the alignment of cell-produced collagenous matrix." *J. Biomech.* 36:97.
202. Wei, X & Messner, K, (1996) "The postnatal development of the insertions of the medial collateral ligament in the rat knee," *Anat. Embryol. (Berl)* 193:53-59.
203. Weiler, A, Hoffmann, R F, Bail, H J, Rehm, O & Sudkamp, N P, (2002) "Tendon healing in a bone tunnel. Part II: Histologic analysis after biodegradable interference fit fixation in a model of anterior cruciate ligament reconstruction in sheep," *Arthroscopy*, 18:124-135.
204. Weiler, A, Windhagen, H J, Raschke, M J, Laumeyer, A & Hoffmann, R F, (1998) "Biodegradable interference screw fixation exhibits pull-out force and stiffness similar to titanium screws," *Am. J. Sports Med.* 26:119-126.
205. Weiss, J A and Maakestad, B J, (2006) "Permeability of human medial collateral ligament in compression transverse to the collagen fiber direction." *J. Biomech.* 39:276.
206. Williams, G R, Jr., Rockwood, C A, Jr., Bigliani, L U, Iannotti, J P & Stanwood, W, (2004) "Rotator cuff tears: why do we repair them?" *J. Bone Joint Surg. Am.* 86-A: 2764.
207. Woo, S L, Gomez, M A, Seguchi, Y, Endo, C M & Akeson, W H, (1983) "Measurement of mechanical properties of ligament substance from a bone-ligament-bone preparation," *J. Orthop. Res.* 1:22-29.
208. Woo, S L, Maynard, J, Butler, D L, Lyon, R M, Torzilli, P A, Akeson, W H, Cooper, R R, Oakes, B, (1988) "Ligament, Tendon, and Joint Capsule Insertions to Bone. In Injury and Repair of the Musculosketal Soft Tissues." Woo, S L, Bulkwater, J A, eds., American Academy of Orthopaedic Surgeons: Savannah, Ga., pp. 133-166.
209. Woo, S L, Newton, P O, MacKenna, D A & Lyon, R M, (1992) "A comparative evaluation of the mechanical properties of the rabbit medial collateral and anterior cruciate ligaments," *J. Biomech.* 25:377-386.
210. Wu H, et al., (2003) "Fabrication of Complex Three-Dimensional Microchannel Systems in PDMS," *J. Am. Chem. Soc. Jan.* 15, 2003; 125(2):554-559.
211. Wuthier, R E, (1993) "Involvement of cellular metabolism of calcium and phosphate in calcification of avian growth plate cartilage," *J. Nutr.* 123:301-309.
212. Wutticharoenmongkol, P, Sanchavanakit, N, Pavasant, P, & Supaphol, P (2006) "Novel bone scaffolds of electrospun polycaprolactone fibers filled with nanoparticles. J. Nanosci Nanotechnol." 6(2):514-22.
213. Xu, et al., (2004) "Aligned biodegradable nanofibrous structure: a potential scaffold for blood vessel engineering" *Biomaterials*, 25(5):877-886.
214. Yahia, L, (1997) "Ligaments and Ligamentoplasties," Springer Verlag, Berlin Heidelberg.
215. Yamanaka, K and Matsumoto, T (1994) "The joint side tear of the rotator cuff. A followup study by arthrography." *CHn. Orthop. Relat. Res.* 304:68-73.

216. Yang, F, Murugan, R, Wang, S & Ramakrishna, S, (2005) "Electrospinning of nano/micro scale poly(L-lactic acid) aligned fibers and their potential in neural tissue engineering." *Biomaterials,* 26:2603.
217. Yin, L & Elliott, D M (2004) "A biphasic and transversely isotropic mechanical model for tendon: application to mouse tail fascicles in uniaxial tension." *J. Biomech.* 37:907.
218. Yoshimoto, H, Shin, Y M, Terai, H, Vacanti, J P, (2003) "A biodegradable nanofiber scaffold by electrospinning and its potential for bone tissue engineering." *Biomaterials,* 24(12):2077-2082.
219. Yoshiya, S, Nagano, M, Kurosaka, M, Muratsu, H & Mizuno, K, (2000) "Graft healing in the bone tunnel in anterior cruciate ligament reconstruction," *Clin. Orthop.* 278-286.
220. Zhong, S, Teo, W E, Zhu, X, Beuerman, R W, Ramakrishna, S & Yung, L Y, (20060 "An aligned nanofibrous collagen scaffold by electrospinning and its effects on in vitro fibroblast culture." *J. Biomed. Mater. Res. A*79:456.

What is claimed is:

1. A scaffold apparatus for fixing musculoskeletal soft tissue to bone in a subject, said scaffold apparatus comprising (i) a graft collar and (ii) a polymer-fiber nanofiber mesh wrapped around the graft collar so as to apply compressive mechanical loading to the graft collar.

2. The scaffold apparatus of claim 1, wherein an outer surface of the graft collar is wrapped in its entirety by the polymer-fiber nanofiber mesh.

3. The scaffold apparatus of claim 1, wherein the graft collar is biphasic.

4. The scaffold apparatus of claim 3, wherein the biphasic graft collar includes a first phase comprising a material which promotes growth and proliferation of chondrocytes, and a second phase adjacent to the first phase comprising a material which promotes the growth and proliferation of osteoblasts.

5. The scaffold apparatus of claim 1, wherein the nanofiber mesh comprises polylactide-co-glycolide (PLGA).

6. The scaffold apparatus of claim 1, wherein the nanofiber mesh is electrospun.

7. The scaffold apparatus of claim 1, wherein the scaffold apparatus is coupled to a soft tissue graft.

8. The apparatus of claim 7, wherein the soft tissue graft is a graft for a ligament of the subject.

9. The apparatus of claim 8, wherein the ligament is an anterior cruciate ligament of the subject.

10. An graft-fixation apparatus comprising the scaffold apparatus of claim 1.

11. The apparatus of claim 10, wherein the graft fixation apparatus is an interference screw.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Primer directed to human GAPDH

<400> SEQUENCE: 1
ggcgatgctg gcgctgagta                                                    20

<210> SEQ ID NO 2
<211> LENGTH: 20
<212> TYPE: DNA
<213> ORGANISM: Artificial Sequence
<220> FEATURE:
<223> OTHER INFORMATION: Primer directed to human GAPDH

<400> SEQUENCE: 2
atccacagtc ttctgggtgg                                                    20

<210> SEQ ID NO 3
<211> LENGTH: 20
<212> TYPE: DNA
<213> ORGANISM: Artificial Sequence
<220> FEATURE:
<223> OTHER INFORMATION: Primer directed to human integrin alpha-2

<400> SEQUENCE: 3
cagaatttgg aacgggactt                                                    20

<210> SEQ ID NO 4
<211> LENGTH: 20
<212> TYPE: DNA
<213> ORGANISM: Artificial Sequence
<220> FEATURE:
<223> OTHER INFORMATION: Primer directed to human integrin alpha-2

<400> SEQUENCE: 4
caggtaggtc tgctggttca                                                    20

<210> SEQ ID NO 5
<211> LENGTH: 20
<212> TYPE: DNA
<213> ORGANISM: Artificial Sequence
<220> FEATURE:
<223> OTHER INFORMATION: Primer directed to human integrin alpha-5

<400> SEQUENCE: 5
gtggccttcg gtttacagtc                                                    20
```

```
<210> SEQ ID NO 6
<211> LENGTH: 20
<212> TYPE: DNA
<213> ORGANISM: Artificial Sequence
<220> FEATURE:
<223> OTHER INFORMATION: Primer directed to human integrin alpha-5

<400> SEQUENCE: 6
aatagcactg cctcaggctt                                              20

<210> SEQ ID NO 7
<211> LENGTH: 20
<212> TYPE: DNA
<213> ORGANISM: Artificial Sequence
<220> FEATURE:
<223> OTHER INFORMATION: Primer directed to human integrin alpha-V

<400> SEQUENCE: 7
gatggaccaa tgaactgcac                                              20

<210> SEQ ID NO 8
<211> LENGTH: 20
<212> TYPE: DNA
<213> ORGANISM: Artificial Sequence
<220> FEATURE:
<223> OTHER INFORMATION: Primer directed to human integrin alpha-V

<400> SEQUENCE: 8
ttggcagaca atcttcaagc                                              20

<210> SEQ ID NO 9
<211> LENGTH: 20
<212> TYPE: DNA
<213> ORGANISM: Artificial Sequence
<220> FEATURE:
<223> OTHER INFORMATION: Primer directed to human collagen I

<400> SEQUENCE: 9
tgctggccaa ctatgcctct                                              20

<210> SEQ ID NO 10
<211> LENGTH: 18
<212> TYPE: DNA
<213> ORGANISM: Artificial Sequence
<220> FEATURE:
<223> OTHER INFORMATION: Primer directed to human collgen I

<400> SEQUENCE: 10
ttgcacaatg ctctgatc                                                18

<210> SEQ ID NO 11
<211> LENGTH: 20
<212> TYPE: DNA
<213> ORGANISM: Artificial Sequence
<220> FEATURE:
<223> OTHER INFORMATION: Primer directed to human collagen III

<400> SEQUENCE: 11
ccaaactcta tctgaaatcc                                              20

<210> SEQ ID NO 12
<211> LENGTH: 20
<212> TYPE: DNA
<213> ORGANISM: Artificial Sequence
<220> FEATURE:
<223> OTHER INFORMATION: Primer directed to human collagen III
```

```
<400> SEQUENCE: 12
ggactcatag aatacaatct                                                    20
```